US009409947B2

(12) United States Patent
Myasoedov et al.

(10) Patent No.: US 9,409,947 B2
(45) Date of Patent: Aug. 9, 2016

(54) METHOD FOR PRODUCING A RECOMBINANT PEPTIDE AND RESULTANT PEPTIDE

(71) Applicant: "IVIX" Ltd., Moscow (RU)

(72) Inventors: Nikolay Fedorovich Myasoedov, Moscow (RU); Lyudmila Alexandrovna Andreeva, Moscow (RU); Dmitriy Viktorovich Golikov, Moscow (RU)

(73) Assignee: "IVIX" LTD., Moscow (RU)

( * ) Notice: Subject to any disclaimer, the term of this patent is extended or adjusted under 35 U.S.C. 154(b) by 0 days.

(21) Appl. No.: 14/388,080

(22) PCT Filed: May 28, 2013

(86) PCT No.: PCT/RU2013/000433
§ 371 (c)(1),
(2) Date: Sep. 25, 2014

(87) PCT Pub. No.: WO2013/151467
PCT Pub. Date: Oct. 10, 2013

(65) Prior Publication Data
US 2015/0111837 A1    Apr. 23, 2015

(30) Foreign Application Priority Data
Mar. 28, 2012    (RU) ................ 2012111965

(51) Int. Cl.
| C07K 7/06 | (2006.01) |
| A61K 38/08 | (2006.01) |
| C07K 5/103 | (2006.01) |
| C07K 5/08 | (2006.01) |
| C07K 5/10 | (2006.01) |
| A61K 38/00 | (2006.01) |

(52) U.S. Cl.
CPC ............. *C07K 7/06* (2013.01); *C07K 5/0802* (2013.01); *C07K 5/1002* (2013.01); *C07K 5/1013* (2013.01); *A61K 38/00* (2013.01); *A61K 38/08* (2013.01)

(58) Field of Classification Search
None
See application file for complete search history.

(56) References Cited

U.S. PATENT DOCUMENTS

| 5,932,548 | A | 8/1999 | Deghenghi |
| 5,955,421 | A | 9/1999 | Deghenghi |
| 6,211,156 | B1 | 4/2001 | Argiolas et al. |
| 2009/0111161 | A1 | 4/2009 | Jones et al. |
| 2010/0095987 | A1 | 4/2010 | Jones et al. |
| 2010/0190722 | A1 | 7/2010 | Bevec et al. |
| 2010/0197572 | A1 | 8/2010 | Bevec et al. |
| 2010/0204143 | A1 | 8/2010 | Bevec et al. |
| 2010/0204148 | A1 | 8/2010 | Bevec et al. |
| 2010/0210534 | A1 | 8/2010 | Bevec |
| 2010/0210567 | A1 | 8/2010 | Bevec |
| 2010/0273700 | A1 | 10/2010 | Bevec et al. |
| 2010/0286028 | A1 | 11/2010 | Bevec et al. |
| 2011/0081711 | A1 | 4/2011 | Jones et al. |
| 2012/0129791 | A1 | 5/2012 | Myasoedov et al. |

FOREIGN PATENT DOCUMENTS

| CN | 101302246 | 11/2008 |
| EA | 013948 | 8/2010 |
| EA | 200900804 | 8/2010 |
| RU | 1124544 | 1/1995 |
| RU | 2 058 791 | 4/1996 |
| RU | 2 155 065 | 8/2000 |
| RU | 2 264 823 | 1/2004 |
| RU | 2 252 779 | 5/2005 |
| RU | 2 290 195 | 12/2006 |
| RU | 2 404 793 | 11/2010 |
| RU | 2411249 C2 * | 2/2011 |
| WO | WO 94/22460 | 10/1994 |
| WO | WO 01/34171 | 5/2001 |
| WO | WO 2009/033678 | 3/2009 |
| WO | WO 2009/058679 | 5/2009 |
| WO | WO 2013151467 A2 * | 10/2013 | ............... C07K 7/06 |

OTHER PUBLICATIONS

Shevchenko et al., "Synthesis of Tritium-Labeled Selank", Radiochemistry, 2006, vol. 48, No. 3, pp. 296-300.*
UniProtKB/Swiss-Prot: Q8WTQ1.2; D104A_HUMAN; Jul. 2015; pp. 1-3.*
Semple et al., "Duplication and selection in the evolution of primate _-defensin genes", Genome Biology, 2003, pp. R31.1-R31.11.*
Patil et al., "Cross-species analysis of the mammalian _-defensin gene family: presence of syntenic gene clusters and preferential expression in the male reproductive tract", Comparative Genomics, 2005, pp. 5-17.*
GenScript Peptide Calculator, Peptide Sequence TKP, obtained from https://www.genscript.com on Aug. 21, 2015.*
UniProtKB/Swiss-Prot: Q8WTQ1.2, 2015, pp. 1-3.*
Semion et al., "Antinociceptive action of the SP14 tetrapeptide and of some tuftsin analogs", Pol. J. Pharmacol Pharm., 1990, pp. 393-401.*
Dagan et al., "Tuftsin Analogues: Synthesis, Structure-Function Relationships, and Implications for Specificity of Tuftsin's Bioactivity", Journal of Medicinal Chemistry, 1986, pp. 1961-1968.*
Andreeva et al., "The Perspectives of Development of New Peptide Preparations for Clinical Use Which Have Anti-Infective and Immune-Modulating Activity", Infekc. immun., 2011, pp. 171-176.*
Nair et al., "Interactions of Radiolabeled Tuftsin with Human Neutrophils", Immunochemistry, 1978, pp. 901-907.*
Chipens et al., "Elongated and Cyclic Analogues of Tuftsin and Rigin", Peptides, Proceedings of the Sixteeth European Peptide Symposium, 1981, pp. 445-450.*
Ashmarin et al., "A Comparative Analysis of the Distribution of Glyprolines after Their Administration by Different Ways", Russian Journal of Bioorganic Chemistry, 2008, pp. 415-420.*

(Continued)

*Primary Examiner* — Lianko Garyu
(74) *Attorney, Agent, or Firm* — Troutman Sanders LLP

(57) ABSTRACT

The invention relates to peptides with the following general formula:

A-Thr-Lys-Pro-B-C-D-X, where:

A—0, Met, Met (O), Thr, Ala, His, Phe, Lys, Gly
B—0, Gly, Asp, Trp, Gln, Asn, Tyr, Pro, Arg
C—0, Arg, Phe, Tyr, Gly, His, Pro, Lys
D—0, Val, Gly, Tyr, Trp, Phe, His
X—OH, OCH$_3$, NH$_2$,
where 0 is no amino acid residue, provided that if A≠0, then B and/or C and/or D≠0, if B≠0, then C and/or D≠0,
excluding the peptides Phe-Thr-Lys-Pro-Gly (SEQ ID NO: 1), Thr-Lys-Pro-Pro-Arg (SEQ ID NO: 2), Thr-Lys-Pro-Arg-Gly (SEQ ID NO: 3).

36 Claims, 3 Drawing Sheets

(56) References Cited

OTHER PUBLICATIONS

Mezö et al.,"Synthesis, Conformation, and Immunoreactivity of New Carrier Molecules Based on Repeated Tuftsin-Like Sequence", Biopolymers, 2004, p. 645-656.*

Pavlov, T., "Anti-Ulcer Effects of Selank and Its Fragments", Abstract of Ph.D. Thesis, Moscow 2006, pp. 1-44.

Zolotarev et al., "Evenly Tritium-Labeled Peptides in Study of Peptide in Vivo and in Vitro Biodegradation", Russian Journal of Bioorganic Chemistry, 2006, vol. 32, No. 2, pp. 166-173. (corresponds to the Russian-language reference Zolotarev et al., Ravnomerno mechenie tritium peptide v issledovaniyah poi h biodegradacii in vivo i in vitro, Biooorganicheskaya Khimiya, 2006, 32(2):183-191.).

Arletti, et al. "Sexual impotence is associated with a reduced production of oxytocin and with an increased production of opioid peptides in the paraventricular nucleus of male rats" Neuroscience Letters 1997, 233:65-68.

Ashmarin, et al. "Natural and hybrid ("chimeric") stable regulatory glyproline peptides" Pathophysiology 2005, 11:179-185.

Cantor, et al. "Chronic fluoxetine inhibits sexual behavior in the male rat: reversal with oxytocin" Psychopharmacology 1999, 144:355-362.

Czabak-Garbacz, et al. "Influence of long-term treatment with tuftsin analogue TP-7 on the anxiety-phobic states and body weight" Pharmacological Reports 2006, 58:562-567.

Diamond et al. Co-administration of low doses of intranasal PT-141, a melanocortin receptor agonist, and sildenafil to men with erectile dysfunction results in an enhanced erectile response, Urology, 2005, 65(4):755-759.

English-language abstract of Chinese Patent Publication No. CN101302246; Database WPI, Week 200912, Thompson Scientific, London, GB; AN 2009-B41118 XP002686138, & CN 101 302 246 A (Inst Toxicant & Medicament Acad Military) Nov. 12, 2008 Abstract.

International Preliminary Report on Patentability dated Dec. 6, 2011, which issued during prosecution of International Application No. PCT/RU2010/000285.

International Search Report dated Sep. 18, 2013, which issued during prosecution of International Application No. PCT/RU2013/000433, which corresponds to the present application.

International Search Report dated Sep. 23, 2010, which issued during prosecution of International Application No. PCT/RU2010/000285.

Kolomin, et al. "Expression of inflammation-related genes in mouse spleen under tuftsin analog Selank" Regulatory Peptides 2011, 170:18-23.

Kozlovskaya, et al. "A Comparative Study of the Effect of Tuftsin Fragments on Passive Avoidance Learning Characteristics" Pharmaceutical Chemistry Journal 2001, 35(3):121-123. (Translation of C12).

Kozlovskaya, et al. "Comparison study of series of tuftsin's fragments of short-time and durable action on the index of conditional reactions of passive avoidance" Chimiko-pharmac. Zh. 35 (2001), 3-5.

Kozlovskaya, et al. "Selank and short peptides of the Tuftsin Family in the Regulation of Adaptive Behavior in Stress" Neuroscience and Behavioral Physiology 2003, 33(9): 853-860. (Translation of C14).

Kozlovskaya, et al. "Selanc and Small peptides of Tuftsin derivatives in regulation of adaptive regulation of adaptive behavior of animal in stress" Ross. Fiziol. Zh. I. M. Sechenova. 88 (2002), 751-761.

Kumar et al. "Sexual Behaviour in Normal and Neurotic Females" Indian J. Psychiat. 1984, 26(3):213-218.

Semenova, et al. "Use of Selank to Correct Measures of Integrative Brain Activity and Biogenic Amine Levels in Adult Rats Resulting from Antenatal Hypoxia" Neuroscience and Behavioral Physiology 2008, 38(2):203-207 (Translated from Rossiiskii Fiziologicheskii Zhurnal imeni I. M. Sechenova, vol. 92, No. 11, pp. 1332-1338, 2006).

Seredinin et al., "The Study of Anxiolytic Activity of Tuftsin Analogue in Inbred Mice With Different Types of Emotional-Stress Reaction" Institute of Pharmacology, Russian Academy of Medical Sciences, Moscow, Zhurnal VND, 1998, 48(1):153-160.(English Translation of the full article provided).

Sollertinskaya, et al. "Compensatory and Antiamnestic Effects of Heptapeptide Selank in Monkeys" Journal of Evolutionary Biochemistry and Physiology 2008, 44(3):332-340.

Supplementary European Search Report dated Nov. 15, 2012, which issued during prosecution of EP 10783644.7.

* cited by examiner

METHOD FOR PRODUCING A RECOMBINANT PEPTIDE AND RESULTANT PEPTIDE

CROSS REFERENCE TO RELATED APPLICATIONS

This application is a U.S. National Phase Application under 35 U.S.C. §371 of International Patent Application No. PCT/RU2013/000433 filed May 28, 2013, which claims priority to Russian Patent Application No. 2012111965 filed Mar. 28, 2012. The International Application was published on Oct. 10, 2013, as International Publication No. WO 2013/151467 under PCT Article 21(2). The entire contents of these applications are hereby incorporated by reference.

SEQUENCE LISTING

The instant application contains a Sequence Listing which has been submitted electronically in ASCII format and is hereby incorporated by reference in its entirety. Said ASCII copy, created on Dec. 8, 2014, is named 246273.000002_SL.txt and is 559,963 bytes in size.

FIELD OF INVENTION

The invention relates to the field of biochemistry and concerns of recombinant method for production of peptides and the resulting peptides. In particular, the invention relates to peptides with the following general formula:

A-Thr-Lys-Pro-B-C-D-X, where:
A—0, Met, Met (O), Thr, Ala, His, Phe, Lys, Gly
B—0, Gly, Asp, Trp, Gln, Asn, Tyr, Pro, Arg
C—0, Arg, Phe, Tyr, Gly, His, Pro, Lys
D—0, Val, Gly, Tyr, Trp, Phe, His
X—OH, OCH$_3$, NH$_2$,
where 0 is no amino acid residue, provided that if A≠0, then B and/or C and/or D≠0, if B≠0, then C and/or D≠0, excluding the peptides Phe-Thr-Lys-Pro-Gly (SEQ ID NO: 1), Thr-Lys-Pro-Pro-Arg (SEQ ID NO: 2), Thr-Lys-Pro-Arg-Gly (SEQ ID NO: 3).

BACKGROUND OF THE INVENTION

It is known that small peptides exhibit extremely high activity, stimulating self-healing in the organs where a disturbance occurred. As it is commonly known, smaller peptides were initially derived from animal tissues, and later they learned to produce them in laboratory conditions.

Medicinal products containing peptides are capable of restoring damaged body cells, returning lost functions to the affected organ, and rejuvenating it. Medicinal products containing peptides were developed more than three decades ago; since that time, hundreds of experiments have been performed, which proved the efficacy of peptides in treatment and prevention of diseases of various body systems, as well as individual organ- and all-body rejuvenation.

In the body, peptides serve as information messengers: they transfer information from one cell to another, so that everything could be done well and on time. If one cell functions properly, then the corresponding organ operates well. If a malfunction occurs, it affects the whole organ, leading to a disease. Clearly, it is possible to treat the disease by introducing missing substances into the body, but this approach would completely 'spoil' the cell, and it would stop functioning properly. Therefore, it is necessary to send peptide messengers to the cell, which will make it function, so that the body would heal itself. Each organ has a supply of reserve stem cells. If this supply is spent evenly, one lives to the age of 100-110. Peptides are the same for all mammals. Therefore, if a calf peptide is introduced to a human, their body will take it as native molecule. The main problem was to find how to isolate peptides from animal organs. This technology was invented by Prof. Vladimir Morozov and Prof. Vyacheslav Havinson in Military Medical Academy as early as in 1971. Medicinal products were developed, and then, based on them, dietary supplements were made, because dietary supplements are easy to use. In their studies of aging processes and methods to influence it, employees of St. Petersburg Institute of Gerontology concluded that introduction of peptides into the diet of experimental group of mice increased their life expectancy by 30-38%. Later, studies of peptides were performed on the elderly in Kiev Institute of Gerontology and in St. Petersburg. This showed almost 2-fold reduction of mortality rate, indicating high geroprotective activity of peptides. Long-term study and use of peptide medicinal products showed their high efficacy in patients of different age groups; however, particular efficacy was observed in elderly (over 50 years old). Absolute advantage of peptide bioregulators is absence of any adverse reactions. Within 26 years, more than 15 min. people with various pathologies received such products. Their efficacy averaged to 75-95%. Peptide deficit, developing with age and pathologic changes, significantly accelerates tissue wear and body aging. The fact is that an adequate functioning of cells and tissues requires adequate amounts of peptides, which, in turn, support optimal gene operation. Peptides, functioning in cells specific for them, are synthesized there. Therefore, in pathological changes, as well as with age, cell functioning is disrupted; hence, peptide reproduction is affected as well. Consequently, cell function is affected secondarily. Thus, degeneration of tissues progresses, which eventually is manifested clinically. So, application of small peptides is one of the major innovations in medicine and can significantly slow down the rate of aging by stimulating cell proliferation and tissue regeneration, as well as enhancing cell life span. Another important advantage of peptides is their antitumor action. Currently, the use of peptides is the best and uncompromising solution in revitalization (body rejuvenation) and cancer prevention, because it allows to rejuvenate cells and tissues not only by regulation and synchronization of all cyclic processes, but also by increasing the capacity of cell division without atypia (atypia is an incorrect cell structure, or abnormality).

Of course, at the present stage of art, small peptide production from animal tissues is impractical, since this method is very expensive, not to mention the humanity of the production process.

A modern and advanced production method comprises using recombinant microorganisms. Most convenient microorganism is *E. coli*. Commercial strains of *E. coli*, suitable for use in laboratory conditions, such as *E. coli* K12, *E. coli* 0104, are known in the prior art. These and similar known *E. coli* strains can be used to obtain strains producing small peptides claimed. A nucleic acid, encoding the corresponding target small peptide, can be integrated in any known strain, suitable for use in the laboratory conditions. Vectors, such as bacterial plasmids, viruses, virions, hybrid vectors containing phage DNA, and plasmids, are used to insert DNA into a host cell. These vectors include, for example, cosmids and phasmids.

Furthermore, it is possible to produce peptides by conventional chemical synthesis.

Proposed peptides solve the problem of expanding the range of tools for stimulation of reproductive and sexual function and treatment of reproductive and sexual dysfunction, which remains relevant now. Currently, pathogenetic treatment of such pathologies is performed using psychotherapy, antidepressants, anxiolytics, adaptogens, as well as vitamins, common plant-based stimulants, and diet supplements. Such treatment is long, inefficient and accompanied by many side effects.

One of the most effective classes of physiologically active substances, suitable for production of stimulants of reproductive and sexual function, is peptides, which, as endogenous substances, have virtually no negative side effects.

Our own research showed that heptapeptide Selank with the general formula of Thr-Lys-Pro-Arg-Pro-Gly-Pro (SEQ ID NO: 2680), a synthetic analog of the endogenously produced peptide Tuftsin, can be used as a tool for prevention and treatment of reproductive and sexual dysfunction (Patent of Russian Federation No 2404793). However, the synthesis of heptapeptide Selank is multistage, which greatly increases the cost of medicinal products based on it; moreover, it is exposed to intense proteolysis in the body, which reduces its stimulating effect on prevention and treatment of reproductive and sexual dysfunction.

DISCLOSURE OF INVENTION

The aim of the invention is to expand the range of tools with reproductive- and sexual-function stimulating activity.

Technical result, achieved when implementing the present invention, is an increase in efficacy of prevention and treatment of reproductive and sexual dysfunction, reduction in duration of course therapy, and cost reduction of medications, where peptides with the following general formula are proposed as a medicinal product:

A-Thr-Lys-Pro-B-C-D-X, where:

A—0, Met, Met (O), Thr, Ala, His, Phe, Lys, Gly
B—0, Gly, Asp, Tip, Gln, Asn, Tyr, Pro, Arg
C—0, Arg, Phe, Tyr, Gly, His, Pro, Lys
D—0, Val, Gly, Tyr, Trp, Phe, His
X—OH, OCH$_3$, NH$_2$,
where 0 means no amino acid residue.

Provided that if A≠0, then B and/or C and/or D≠0; if B≠0, then C and/or D≠0, excluding peptides Phe-Thr-Lys-Pro-Gly (SEQ ID NO: 1), Thr-Lys-Pro-Pro-Arg (SEQ ID NO: 2), Thr-Lys-Pro-Arg-Gly (SEQ ID NO: 3).

Selection of amino acid residues at positions A, B, C, D, and X is based on a bioinformatic analysis of amino acid residue frequency at corresponding positions of N-terminal and C-terminal amino acid residues in the database [EROP-Moscow (erop.inbi.ras.ru/) Zamyatin A. A. EROP-Moscow: Specialized data bank for endogenous regulatory oligopeptides, Protein Sequence and Data Analysis, 4(1), 49-52, 1991; Zamyatnin A. A. et al., The EROP-Moscow oligopeptide database. Nucleic Acids Research, 34(Database issue), D261-D266, 2006]. Selection of these amino acid residues was performed based on the criterion of greater than 50% incidence of an amino acid residue at that position. This sample of amino acid residues was experimentally confirmed by synthesis of individual peptides and their test for stimulation of reproductive- and sexual-function activity in models in vivo. Pharmacophore position in a peptide is determined experimentally. It is known that any peptide is exposed to peptidases and breaks down into specific fragments. For this purpose, following Selank heptapeptide fragments were synthesized: Thr-Lys (SEQ ID NO: 2678), Thr-Lys-Pro (SEQ ID NO: 5), Pro-Gly-Pro (SEQ ID NO: 2677), Arg-Pro-Gly-Pro (SEQ ID NO: 2676), Pro-Arg-Pro-Gly-Pro (SEQ ID NO: 2675), and their activity was studied. Results are provided in Table 4. In this analysis, pharmacophore was determined: it is Thr-Lys-Pro (SEQ ID NO: 5). It was shown that attachment of individual experimentally identified amino acid residues to the C-terminus maintained the peptide's activity (stimulating reproductive and sexual function) provided that the number of amino acid residues in the peptide is 3 or more than 4, as shown by studies (Table 5, Example 10). Tetrapeptides do not have reproductive and sexual-function stimulating activity.

Mentioned technical result is achieved by directed synthesis of various peptides with the general formula A-Thr-Lys-Pro-B-C-D-X (except tetrapeptides) and by using these peptides as a stimulant of reproductive and sexual function for prevention and treatment of reproductive and sexual dysfunction. Our own research showed that synthesized peptides, i.e. Thr-Lys-Pro tripeptide (SEQ ID NO: 5), Thr-Lys-Pro-Arg-Pro pentapeptide (SEQ ID NO: 6), and Thr-Lys-Pro-Arg-Pro-Phe hexapeptide (SEQ ID NO: 7), corresponding to the general formula A-Thr-Lys-Pro-B-C-D-X, can be recommended as stimulants of reproductive and sexual function.

All peptides with the general formula A-Thr-Lys-Pro-B-C-D-X (except tetrapeptides), recommended as stimulants of reproductive and sexual function, have a common pattern, i.e. Thr-Lys-Pro tripeptide molecule is present in their molecular structure.

Thr-Lys-Pro-Arg-Pro-Gly-Pro (SEQ ID NO: 2680) heptapeptide (Selank) was used as a control. Results of conducted studies showed that peptides with the general formula A-Thr-Lys-Pro-B-C-D-X (except tetrapeptides) have reproductive- and sexual-function stimulating activity and can be used as medicinal products for prevention and treatment of reproductive and sexual dysfunction.

Some peptides of the general formula A-Thr-Lys-Pro-B-C-D-X are shown in Table 1.

TABLE 1

| X-OH | X-OCH$_3$ | X-NH$_2$ | SEQ ID NO |
|---|---|---|---|
| Thr-Lys-Pro | Thr-Lys-Pro | Thr-Lys-Pro | 5 |
| Thr-Lys-Pro-Arg-His | Thr-Lys-Pro-Arg-His | Thr-Lys-Pro-Arg-His | 8 |
| Thr-Lys-Pro-Phe-His | Thr-Lys-Pro-Phe-His | Thr-Lys-Pro-Phe-His | 9 |
| Thr-Lys-Pro-Tyr-His | Thr-Lys-Pro-Tyr-His | Thr-Lys-Pro-Tyr-His | 10 |
| Thr-Lys-Pro-Gly-His | Thr-Lys-Pro-Gly-His | Thr-Lys-Pro-Gly-His | 11 |
| Thr-Lys-Pro-His-His | Thr-Lys-Pro-His-His | Thr-Lys-Pro-His-His | 12 |

TABLE 1-continued

| X-OH | X-OCH₃ | X-NH₂ | SEQ ID NO |
|---|---|---|---|
| Thr-Lys-Pro-Lys-His | Thr-Lys-Pro-Lys-His | Thr-Lys-Pro-Lys-His | 13 |
| Thr-Lys-Pro-Gly-His | Thr-Lys-Pro-Gly-His | Thr-Lys-Pro-Gly-His | 14 |
| Thr-Lys-Pro-Gly-Arg-His | Thr-Lys-Pro-Gly-Arg-His | Thr-Lys-Pro-Gly-Arg-His | 15 |
| Thr-Lys-Pro-Gly-Phe-His | Thr-Lys-Pro-Gly-Phe-His | Thr-Lys-Pro-Gly-Phe-His | 16 |
| Thr-Lys-Pro-Gly-Tyr-His | Thr-Lys-Pro-Gly-Tyr-His | Thr-Lys-Pro-Gly-Tyr-His | 17 |
| Thr-Lys-Pro-Gly-His-His | Thr-Lys-Pro-Gly-His-His | Thr-Lys-Pro-Gly-His-His | 18 |
| Thr-Lys-Pro-Gly-Pro-His | Thr-Lys-Pro-Gly-Pro-His | Thr-Lys-Pro-Gly-Pro-His | 19 |
| Thr-Lys-Pro-Gly-Lys-His | Thr-Lys-Pro-Gly-Lys-His | Thr-Lys-Pro-Gly-Lys-His | 20 |
| Thr-Lys-Pro-Asp-His | Thr-Lys-Pro-Asp-His | Thr-Lys-Pro-Asp-His | 21 |
| Thr-Lys-Pro-Asp-Arg-His | Thr-Lys-Pro-Asp-Arg-His | Thr-Lys-Pro-Asp-Arg-His | 22 |
| Thr-Lys-Pro-Asp-Phe-His | Thr-Lys-Pro-Asp-Phe-His | Thr-Lys-Pro-Asp-Phe-His | 23 |
| Thr-Lys-Pro-Asp-Tyr-His | Thr-Lys-Pro-Asp-Tyr-His | Thr-Lys-Pro-Asp-Tyr-His | 24 |
| Thr-Lys-Pro-Asp-His-His | Thr-Lys-Pro-Asp-His-His | Thr-Lys-Pro-Asp-His-His | 25 |
| Thr-Lys-Pro-Asp-Pro-His | Thr-Lys-Pro-Asp-Pro-His | Thr-Lys-Pro-Asp-Pro-His | 26 |
| Thr-Lys-Pro-Asp-Lys-His | Thr-Lys-Pro-Asp-Lys-His | Thr-Lys-Pro-Asp-Lys-His | 27 |
| Thr-Lys-Pro-Trp-His | Thr-Lys-Pro-Trp-His | Thr-Lys-Pro-Trp-His | 28 |
| Thr-Lys-Pro-Trp-Arg-His | Thr-Lys-Pro-Trp-Arg-His | Thr-Lys-Pro-Trp-Arg-His | 29 |
| Thr-Lys-Pro-Trp-Phe-His | Thr-Lys-Pro-Trp-Phe-His | Thr-Lys-Pro-Trp-Phe-His | 30 |
| Thr-Lys-Pro-Trp-Tyr-His | Thr-Lys-Pro-Trp-Tyr-His | Thr-Lys-Pro-Trp-Tyr-His | 31 |
| Thr-Lys-Pro-Trp-His-His | Thr-Lys-Pro-Trp-His-His | Thr-Lys-Pro-Trp-His-His | 32 |
| Thr-Lys-Pro-Trp-Pro-His | Thr-Lys-Pro-Trp-Pro-His | Thr-Lys-Pro-Trp-Pro-His | 33 |
| Thr-Lys-Pro-Trp-Lys-His | Thr-Lys-Pro-Trp-Lys-His | Thr-Lys-Pro-Trp-Lys-His | 34 |
| Thr-Lys-Pro-Gln-His | Thr-Lys-Pro-Gln-His | Thr-Lys-Pro-Gln-His | 35 |
| Thr-Lys-Pro-Gln-Arg-His | Thr-Lys-Pro-Gln-Arg-His | Thr-Lys-Pro-Gln-Arg-His | 36 |
| Thr-Lys-Pro-Gln-Phe-His | Thr-Lys-Pro-Gln-Phe-His | Thr-Lys-Pro-Gln-Phe-His | 37 |
| Thr-Lys-Pro-Gln-Tyr-His | Thr-Lys-Pro-Gln-Tyr-His | Thr-Lys-Pro-Gln-Tyr-His | 38 |
| Thr-Lys-Pro-Gln-His-His | Thr-Lys-Pro-Gln-His-His | Thr-Lys-Pro-Gln-His-His | 39 |
| Thr-Lys-Pro-Gln-Pro-His | Thr-Lys-Pro-Gln-Pro-His | Thr-Lys-Pro-Gln-Pro-His | 40 |
| Thr-Lys-Pro-Gln-Lys-His | Thr-Lys-Pro-Gln-Lys-His | Thr-Lys-Pro-Gln-Lys-His | 41 |
| Thr-Lys-Pro-Asn-His | Thr-Lys-Pro-Asn-His | Thr-Lys-Pro-Asn-His | 42 |
| Thr-Lys-Pro-Asn-Arg-His | Thr-Lys-Pro-Asn-Arg-His | Thr-Lys-Pro-Asn-Arg-His | 43 |
| Thr-Lys-Pro-Asn-Phe-His | Thr-Lys-Pro-Asn-Phe-His | Thr-Lys-Pro-Asn-Phe-His | 44 |
| Thr-Lys-Pro-Asn-Tyr-His | Thr-Lys-Pro-Asn-Tyr-His | Thr-Lys-Pro-Asn-Tyr-His | 45 |
| Thr-Lys-Pro-Asn-His-His | Thr-Lys-Pro-Asn-His-His | Thr-Lys-Pro-Asn-His-His | 46 |
| Thr-Lys-Pro-Asn-Pro-His | Thr-Lys-Pro-Asn-Pro-His | Thr-Lys-Pro-Asn-Pro-His | 47 |
| Thr-Lys-Pro-Asn-Lys-His | Thr-Lys-Pro-Asn-Lys-His | Thr-Lys-Pro-Asn-Lys-His | 48 |
| Thr-Lys-Pro-Tyr-His | Thr-Lys-Pro-Tyr-His | Thr-Lys-Pro-Tyr-His | 49 |
| Thr-Lys-Pro-Tyr-Arg-His | Thr-Lys-Pro-Tyr-Arg-His | Thr-Lys-Pro-Tyr-Arg-His | 50 |

TABLE 1-continued

| X-OH | X-OCH$_3$ | X-NH$_2$ | SEQ ID NO |
|---|---|---|---|
| Thr-Lys-Pro-Tyr-Phe-His | Thr-Lys-Pro-Tyr-Phe-His | Thr-Lys-Pro-Tyr-Phe-His | 51 |
| Thr-Lys-Pro-Tyr-Tyr-His | Thr-Lys-Pro-Tyr-Tyr-His | Thr-Lys-Pro-Tyr-Tyr-His | 52 |
| Thr-Lys-Pro-Tyr-His-His | Thr-Lys-Pro-Tyr-His-His | Thr-Lys-Pro-Tyr-His-His | 53 |
| Thr-Lys-Pro-Tyr-Pro-His | Thr-Lys-Pro-Tyr-Pro-His | Thr-Lys-Pro-Tyr-Pro-His | 54 |
| Thr-Lys-Pro-Tyr-Lys-His | Thr-Lys-Pro-Tyr-Lys-His | Thr-Lys-Pro-Tyr-Lys-His | 55 |
| Thr-Lys-Pro-Arg-His | Thr-Lys-Pro-Arg-His | Thr-Lys-Pro-Arg-His | 56 |
| Thr-Lys-Pro-Arg-Arg-His | Thr-Lys-Pro-Arg-Arg-His | Thr-Lys-Pro-Arg-Arg-His | 57 |
| Thr-Lys-Pro-Arg-Phe-His | Thr-Lys-Pro-Arg-Phe-His | Thr-Lys-Pro-Arg-Phe-His | 58 |
| Thr-Lys-Pro-Arg-Tyr-His | Thr-Lys-Pro-Arg-Tyr-His | Thr-Lys-Pro-Arg-Tyr-His | 59 |
| Thr-Lys-Pro-Arg-His-His | Thr-Lys-Pro-Arg-His-His | Thr-Lys-Pro-Arg-His-His | 60 |
| Thr-Lys-Pro-Arg-Pro-His | Thr-Lys-Pro-Arg-Pro-His | Thr-Lys-Pro-Arg-Pro-His | 61 |
| Thr-Lys-Pro-Arg-Lys-His | Thr-Lys-Pro-Arg-Lys-His | Thr-Lys-Pro-Arg-Lys-His | 62 |
| Met-Thr-Lys-Pro-His | Met-Thr-Lys-Pro-His | Met-Thr-Lys-Pro-His | 63 |
| Met-Thr-Lys-Pro-Arg-His | Met-Thr-Lys-Pro-Arg-His | Met-Thr-Lys-Pro-Arg-His | 64 |
| Met-Thr-Lys-Pro-Phe-His | Met-Thr-Lys-Pro-Phe-His | Met-Thr-Lys-Pro-Phe-His | 65 |
| Met-Thr-Lys-Pro-Tyr-His | Met-Thr-Lys-Pro-Tyr-His | Met-Thr-Lys-Pro-Tyr-His | 66 |
| Met-Thr-Lys-Pro-Gly-His | Met-Thr-Lys-Pro-Gly-His | Met-Thr-Lys-Pro-Gly-His | 67 |
| Met-Thr-Lys-Pro-His-His | Met-Thr-Lys-Pro-His-His | Met-Thr-Lys-Pro-His-His | 68 |
| Met-Thr-Lys-Pro-Lys-His | Met-Thr-Lys-Pro-Lys-His | Met-Thr-Lys-Pro-Lys-His | 69 |
| Met-Thr-Lys-Pro-Gly-His | Met-Thr-Lys-Pro-Gly-His | Met-Thr-Lys-Pro-Gly-His | 70 |
| Met-Thr-Lys-Pro-Gly-Arg-His | Met-Thr-Lys-Pro-Gly-Arg-His | Met-Thr-Lys-Pro-Gly-Arg-His | 71 |
| Met-Thr-Lys-Pro-Gly-Phe-His | Met-Thr-Lys-Pro-Gly-Phe-His | Met-Thr-Lys-Pro-Gly-Phe-His | 72 |
| Met-Thr-Lys-Pro-Gly-Tyr-His | Met-Thr-Lys-Pro-Gly-Tyr-His | Met-Thr-Lys-Pro-Gly-Tyr-His | 73 |
| Met-Thr-Lys-Pro-Gly-His-His | Met-Thr-Lys-Pro-Gly-His-His | Met-Thr-Lys-Pro-Gly-His-His | 74 |
| Met-Thr-Lys-Pro-Gly-Pro-His | Met-Thr-Lys-Pro-Gly-Pro-His | Met-Thr-Lys-Pro-Gly-Pro-His | 75 |
| Met-Thr-Lys-Pro-Gly-Lys-His | Met-Thr-Lys-Pro-Gly-Lys-His | Met-Thr-Lys-Pro-Gly-Lys-His | 76 |
| Met-Thr-Lys-Pro-Asp-His | Met-Thr-Lys-Pro-Asp-His | Met-Thr-Lys-Pro-Asp-His | 77 |
| Met-Thr-Lys-Pro-Asp-Arg-His | Met-Thr-Lys-Pro-Asp-Arg-His | Met-Thr-Lys-Pro-Asp-Arg-His | 78 |
| Met-Thr-Lys-Pro-Asp-Phe-His | Met-Thr-Lys-Pro-Asp-Phe-His | Met-Thr-Lys-Pro-Asp-Phe-His | 79 |
| Met-Thr-Lys-Pro-Asp-Tyr-His | Met-Thr-Lys-Pro-Asp-Tyr-His | Met-Thr-Lys-Pro-Asp-Tyr-His | 80 |
| Met-Thr-Lys-Pro-Asp-His-His | Met-Thr-Lys-Pro-Asp-His-His | Met-Thr-Lys-Pro-Asp-His-His | 81 |
| Met-Thr-Lys-Pro-Asp-Pro-His | Met-Thr-Lys-Pro-Asp-Pro-His | Met-Thr-Lys-Pro-Asp-Pro-His | 82 |
| Met-Thr-Lys-Pro-Asp-Lys-His | Met-Thr-Lys-Pro-Asp-Lys-His | Met-Thr-Lys-Pro-Asp-Lys-His | 83 |
| Met-Thr-Lys-Pro-Trp-His | Met-Thr-Lys-Pro-Trp-His | Met-Thr-Lys-Pro-Trp-His | 84 |
| Met-Thr-Lys-Pro-Trp-Arg-His | Met-Thr-Lys-Pro-Trp-Arg-His | Met-Thr-Lys-Pro-Trp-Arg-His | 85 |
| Met-Thr-Lys-Pro-Trp-Phe-His | Met-Thr-Lys-Pro-Trp-Phe-His | Met-Thr-Lys-Pro-Trp-Phe-His | 86 |
| Met-Thr-Lys-Pro-Trp-Tyr-His | Met-Thr-Lys-Pro-Trp-Tyr-His | Met-Thr-Lys-Pro-Trp-Tyr-His | 87 |
| Met-Thr-Lys-Pro-Trp-His-His | Met-Thr-Lys-Pro-Trp-His-His | Met-Thr-Lys-Pro-Trp-His-His | 88 |

TABLE 1-continued

| X-OH | X-OCH₃ | X-NH₂ | SEQ ID NO |
|---|---|---|---|
| Met-Thr-Lys-Pro-Trp-Pro-His | Met-Thr-Lys-Pro-Trp-Pro-His | Met-Thr-Lys-Pro-Trp-Pro-His | 89 |
| Met-Thr-Lys-Pro-Trp-Lys-His | Met-Thr-Lys-Pro-Trp-Lys-His | Met-Thr-Lys-Pro-Trp-Lys-His | 90 |
| Met-Thr-Lys-Pro-Gln-His | Met-Thr-Lys-Pro-Gln-His | Met-Thr-Lys-Pro-Gln-His | 91 |
| Met-Thr-Lys-Pro-Gln-Arg-His | Met-Thr-Lys-Pro-Gln-Arg-His | Met-Thr-Lys-Pro-Gln-Arg-His | 92 |
| Met-Thr-Lys-Pro-Gln-Phe-His | Met-Thr-Lys-Pro-Gln-Phe-His | Met-Thr-Lys-Pro-Gln-Phe-His | 93 |
| Met-Thr-Lys-Pro-Gln-Tyr-His | Met-Thr-Lys-Pro-Gln-Tyr-His | Met-Thr-Lys-Pro-Gln-Tyr-His | 94 |
| Met-Thr-Lys-Pro-Gln-His-His | Met-Thr-Lys-Pro-Gln-His-His | Met-Thr-Lys-Pro-Gln-His-His | 95 |
| Met-Thr-Lys-Pro-Gln-Pro-His | Met-Thr-Lys-Pro-Gln-Pro-His | Met-Thr-Lys-Pro-Gln-Pro-His | 96 |
| Met-Thr-Lys-Pro-Gln-Lys-His | Met-Thr-Lys-Pro-Gln-Lys-His | Met-Thr-Lys-Pro-Gln-Lys-His | 97 |
| Met-Thr-Lys-Pro-Asn-His | Met-Thr-Lys-Pro-Asn-His | Met-Thr-Lys-Pro-Asn-His | 98 |
| Met-Thr-Lys-Pro-Asn-Arg-His | Met-Thr-Lys-Pro-Asn-Arg-His | Met-Thr-Lys-Pro-Asn-Arg-His | 99 |
| Met-Thr-Lys-Pro-Asn-Phe-His | Met-Thr-Lys-Pro-Asn-Phe-His | Met-Thr-Lys-Pro-Asn-Phe-His | 100 |
| Met-Thr-Lys-Pro-Asn-Tyr-His | Met-Thr-Lys-Pro-Asn-Tyr-His | Met-Thr-Lys-Pro-Asn-Tyr-His | 101 |
| Met-Thr-Lys-Pro-Asn-His-His | Met-Thr-Lys-Pro-Asn-His-His | Met-Thr-Lys-Pro-Asn-His-His | 102 |
| Met-Thr-Lys-Pro-Asn-Pro-His | Met-Thr-Lys-Pro-Asn-Pro-His | Met-Thr-Lys-Pro-Asn-Pro-His | 103 |
| Met-Thr-Lys-Pro-Asn-Lys-His | Met-Thr-Lys-Pro-Asn-Lys-His | Met-Thr-Lys-Pro-Asn-Lys-His | 104 |
| Met-Thr-Lys-Pro-Tyr-His | Met-Thr-Lys-Pro-Tyr-His | Met-Thr-Lys-Pro-Tyr-His | 105 |
| Met-Thr-Lys-Pro-Tyr-Arg-His | Met-Thr-Lys-Pro-Tyr-Arg-His | Met-Thr-Lys-Pro-Tyr-Arg-His | 106 |
| Met-Thr-Lys-Pro-Tyr-Phe-His | Met-Thr-Lys-Pro-Tyr-Phe-His | Met-Thr-Lys-Pro-Tyr-Phe-His | 107 |
| Met-Thr-Lys-Pro-Tyr-Tyr-His | Met-Thr-Lys-Pro-Tyr-Tyr-His | Met-Thr-Lys-Pro-Tyr-Tyr-His | 108 |
| Met-Thr-Lys-Pro-Tyr-His-His | Met-Thr-Lys-Pro-Tyr-His-His | Met-Thr-Lys-Pro-Tyr-His-His | 109 |
| Met-Thr-Lys-Pro-Tyr-Pro-His | Met-Thr-Lys-Pro-Tyr-Pro-His | Met-Thr-Lys-Pro-Tyr-Pro-His | 110 |
| Met-Thr-Lys-Pro-Tyr-Lys-His | Met-Thr-Lys-Pro-Tyr-Lys-His | Met-Thr-Lys-Pro-Tyr-Lys-His | 111 |
| Met-Thr-Lys-Pro-Arg-His | Met-Thr-Lys-Pro-Arg-His | Met-Thr-Lys-Pro-Arg-His | 112 |
| Met-Thr-Lys-Pro-Arg-Arg-His | Met-Thr-Lys-Pro-Arg-Arg-His | Met-Thr-Lys-Pro-Arg-Arg-His | 113 |
| Met-Thr-Lys-Pro-Arg-Phe-His | Met-Thr-Lys-Pro-Arg-Phe-His | Met-Thr-Lys-Pro-Arg-Phe-His | 114 |
| Met-Thr-Lys-Pro-Arg-Tyr-His | Met-Thr-Lys-Pro-Arg-Tyr-His | Met-Thr-Lys-Pro-Arg-Tyr-His | 115 |
| Met-Thr-Lys-Pro-Arg-His-His | Met-Thr-Lys-Pro-Arg-His-His | Met-Thr-Lys-Pro-Arg-His-His | 116 |
| Met-Thr-Lys-Pro-Arg-Pro-His | Met-Thr-Lys-Pro-Arg-Pro-His | Met-Thr-Lys-Pro-Arg-Pro-His | 117 |
| Met-Thr-Lys-Pro-Arg-Lys-His | Met-Thr-Lys-Pro-Arg-Lys-His | Met-Thr-Lys-Pro-Arg-Lys-His | 118 |
| Met(O)-Thr-Lys-Pro-His | Met(O)-Thr-Lys-Pro-His | Met(O)-Thr-Lys-Pro-His | 119 |
| Met(O)-Thr-Lys-Pro-Arg-His | Met(O)-Thr-Lys-Pro-Arg-His | Met(O)-Thr-Lys-Pro-Arg-His | 120 |
| Met(O)-Thr-Lys-Pro-Phe-His | Met(O)-Thr-Lys-Pro-Phe-His | Met(O)-Thr-Lys-Pro-Phe-His | 121 |
| Met(O)-Thr-Lys-Pro-Tyr-His | Met(O)-Thr-Lys-Pro-Tyr-His | Met(O)-Thr-Lys-Pro-Tyr-His | 122 |
| Met(O)-Thr-Lys-Pro-Gly-His | Met(O)-Thr-Lys-Pro-Gly-His | Met(O)-Thr-Lys-Pro-Gly-His | 123 |
| Met(O)-Thr-Lys-Pro-His-His | Met(O)-Thr-Lys-Pro-His-His | Met(O)-Thr-Lys-Pro-His-His | 124 |
| Met(O)-Thr-Lys-Pro-Lys-His | Met(O)-Thr-Lys-Pro-Lys-His | Met(O)-Thr-Lys-Pro-Lys-His | 125 |
| Met(O)-Thr-Lys-Pro-Gly-His | Met(O)-Thr-Lys-Pro-Gly-His | Met(O)-Thr-Lys-Pro-Gly-His | 126 |

TABLE 1-continued

| X-OH | X-OCH₃ | X-NH₂ | SEQ ID NO |
|---|---|---|---|
| Met(O)-Thr-Lys-Pro-Gly-Arg-His | Met(O)-Thr-Lys-Pro-Gly-Arg-His | Met(O)-Thr-Lys-Pro-Gly-Arg-His | 127 |
| Met(O)-Thr-Lys-Pro-Gly-Phe-His | Met(O)-Thr-Lys-Pro-Gly-Phe-His | Met(O)-Thr-Lys-Pro-Gly-Phe-His | 128 |
| Met(O)-Thr-Lys-Pro-Gly-Tyr-His | Met(O)-Thr-Lys-Pro-Gly-Tyr-His | Met(O)-Thr-Lys-Pro-Gly-Tyr-His | 129 |
| Met(O)-Thr-Lys-Pro-Gly-His-His | Met(O)-Thr-Lys-Pro-Gly-His-His | Met(O)-Thr-Lys-Pro-Gly-His-His | 130 |
| Met(O)-Thr-Lys-Pro-Gly-Pro-His | Met(O)-Thr-Lys-Pro-Gly-Pro-His | Met(O)-Thr-Lys-Pro-Gly-Pro-His | 131 |
| Met(O)-Thr-Lys-Pro-Gly-Lys-His | Met(O)-Thr-Lys-Pro-Gly-Lys-His | Met(O)-Thr-Lys-Pro-Gly-Lys-His | 132 |
| Met(O)-Thr-Lys-Pro-Asp-His | Met(O)-Thr-Lys-Pro-Asp-His | Met(O)-Thr-Lys-Pro-Asp-His | 133 |
| Met(O)-Thr-Lys-Pro-Asp-Arg-His | Met(O)-Thr-Lys-Pro-Asp-Arg-His | Met(O)-Thr-Lys-Pro-Asp-Arg-His | 134 |
| Met(O)-Thr-Lys-Pro-Asp-Phe-His | Met(O)-Thr-Lys-Pro-Asp-Phe-His | Met(O)-Thr-Lys-Pro-Asp-Phe-His | 135 |
| Met(O)-Thr-Lys-Pro-Asp-Tyr-His | Met(O)-Thr-Lys-Pro-Asp-Tyr-His | Met(O)-Thr-Lys-Pro-Asp-Tyr-His | 136 |
| Met(O)-Thr-Lys-Pro-Asp-His-His | Met(O)-Thr-Lys-Pro-Asp-His-His | Met(O)-Thr-Lys-Pro-Asp-His-His | 137 |
| Met(O)-Thr-Lys-Pro-Asp-Pro-His | Met(O)-Thr-Lys-Pro-Asp-Pro-His | Met(O)-Thr-Lys-Pro-Asp-Pro-His | 138 |
| Met(O)-Thr-Lys-Pro-Asp-Lys-His | Met(O)-Thr-Lys-Pro-Asp-Lys-His | Met(O)-Thr-Lys-Pro-Asp-Lys-His | 139 |
| Met(O)-Thr-Lys-Pro-Trp-His | Met(O)-Thr-Lys-Pro-Trp-His | Met(O)-Thr-Lys-Pro-Trp-His | 140 |
| Met(O)-Thr-Lys-Pro-Trp-Arg-His | Met(O)-Thr-Lys-Pro-Trp-Arg-His | Met(O)-Thr-Lys-Pro-Trp-Arg-His | 141 |
| Met(O)-Thr-Lys-Pro-Trp-Phe-His | Met(O)-Thr-Lys-Pro-Trp-Phe-His | Met(O)-Thr-Lys-Pro-Trp-Phe-His | 142 |
| Met(O)-Thr-Lys-Pro-Trp-Tyr-His | Met(O)-Thr-Lys-Pro-Trp-Tyr-His | Met(O)-Thr-Lys-Pro-Trp-Tyr-His | 143 |
| Met(O)-Thr-Lys-Pro-Trp-His-His | Met(O)-Thr-Lys-Pro-Trp-His-His | Met(O)-Thr-Lys-Pro-Trp-His-His | 144 |
| Met(O)-Thr-Lys-Pro-Trp-Pro-His | Met(O)-Thr-Lys-Pro-Trp-Pro-His | Met(O)-Thr-Lys-Pro-Trp-Pro-His | 145 |
| Met(O)-Thr-Lys-Pro-Trp-Lys-His | Met(O)-Thr-Lys-Pro-Trp-Lys-His | Met(O)-Thr-Lys-Pro-Trp-Lys-His | 146 |
| Met(O)-Thr-Lys-Pro-Gln-His | Met(O)-Thr-Lys-Pro-Gln-His | Met(O)-Thr-Lys-Pro-Gln-His | 147 |
| Met(O)-Thr-Lys-Pro-Gln-Arg-His | Met(O)-Thr-Lys-Pro-Gln-Arg-His | Met(O)-Thr-Lys-Pro-Gln-Arg-His | 148 |
| Met(O)-Thr-Lys-Pro-Gln-Phe-His | Met(O)-Thr-Lys-Pro-Gln-Phe-His | Met(O)-Thr-Lys-Pro-Gln-Phe-His | 149 |
| Met(O)-Thr-Lys-Pro-Gln-Tyr-His | Met(O)-Thr-Lys-Pro-Gln-Tyr-His | Met(O)-Thr-Lys-Pro-Gln-Tyr-His | 150 |
| Met(O)-Thr-Lys-Pro-Gln-His-His | Met(O)-Thr-Lys-Pro-Gln-His-His | Met(O)-Thr-Lys-Pro-Gln-His-His | 151 |
| Met(O)-Thr-Lys-Pro-Gln-Pro-His | Met(O)-Thr-Lys-Pro-Gln-Pro-His | Met(O)-Thr-Lys-Pro-Gln-Pro-His | 152 |

TABLE 1-continued

| X-OH | X-OCH₃ | X-NH₂ | SEQ ID NO |
|---|---|---|---|
| Met(O)-Thr-Lys-Pro-Gln-Lys-His | Met(O)-Thr-Lys-Pro-Gln-Lys-His | Met(O)-Thr-Lys-Pro-Gln-Lys-His | 153 |
| Met(O)-Thr-Lys-Pro-Asn-His | Met(O)-Thr-Lys-Pro-Asn-His | Met(O)-Thr-Lys-Pro-Asn-His | 154 |
| Met(O)-Thr-Lys-Pro-Asn-Arg-His | Met(O)-Thr-Lys-Pro-Asn-Arg-His | Met(O)-Thr-Lys-Pro-Asn-Arg-His | 155 |
| Met(O)-Thr-Lys-Pro-Asn-Phe-His | Met(O)-Thr-Lys-Pro-Asn-Phe-His | Met(O)-Thr-Lys-Pro-Asn-Phe-His | 156 |
| Met(O)-Thr-Lys-Pro-Asn-Tyr-His | Met(O)-Thr-Lys-Pro-Asn-Tyr-His | Met(O)-Thr-Lys-Pro-Asn-Tyr-His | 157 |
| Met(O)-Thr-Lys-Pro-Asn-His-His | Met(O)-Thr-Lys-Pro-Asn-His-His | Met(O)-Thr-Lys-Pro-Asn-His-His | 158 |
| Met(O)-Thr-Lys-Pro-Asn-Pro-His | Met(O)-Thr-Lys-Pro-Asn-Pro-His | Met(O)-Thr-Lys-Pro-Asn-Pro-His | 159 |
| Met(O)-Thr-Lys-Pro-Asn-Lys-His | Met(O)-Thr-Lys-Pro-Asn-Lys-His | Met(O)-Thr-Lys-Pro-Asn-Lys-His | 160 |
| Met(O)-Thr-Lys-Pro-Tyr-His | Met(O)-Thr-Lys-Pro-Tyr-His | Met(O)-Thr-Lys-Pro-Tyr-His | 161 |
| Met(O)-Thr-Lys-Pro-Tyr-Arg-His | Met(O)-Thr-Lys-Pro-Tyr-Arg-His | Met(O)-Thr-Lys-Pro-Tyr-Arg-His | 162 |
| Met(O)-Thr-Lys-Pro-Tyr-Phe-His | Met(O)-Thr-Lys-Pro-Tyr-Phe-His | Met(O)-Thr-Lys-Pro-Tyr-Phe-His | 163 |
| Met(O)-Thr-Lys-Pro-Tyr-Tyr-His | Met(O)-Thr-Lys-Pro-Tyr-Tyr-His | Met(O)-Thr-Lys-Pro-Tyr-Tyr-His | 164 |
| Met(O)-Thr-Lys-Pro-Tyr-His-His | Met(O)-Thr-Lys-Pro-Tyr-His-His | Met(O)-Thr-Lys-Pro-Tyr-His-His | 165 |
| Met(O)-Thr-Lys-Pro-Tyr-Pro-His | Met(O)-Thr-Lys-Pro-Tyr-Pro-His | Met(O)-Thr-Lys-Pro-Tyr-Pro-His | 166 |
| Met(O)-Thr-Lys-Pro-Tyr-Lys-His | Met(O)-Thr-Lys-Pro-Tyr-Lys-His | Met(O)-Thr-Lys-Pro-Tyr-Lys-His | 167 |
| Met(O)-Thr-Lys-Pro-Arg-His | Met(O)-Thr-Lys-Pro-Arg-His | Met(O)-Thr-Lys-Pro-Arg-His | 168 |
| Met(O)-Thr-Lys-Pro-Arg-Arg-His | Met(O)-Thr-Lys-Pro-Arg-Arg-His | Met(O)-Thr-Lys-Pro-Arg-Arg-His | 169 |
| Met(O)-Thr-Lys-Pro-Arg-Phe-His | Met(O)-Thr-Lys-Pro-Arg-Phe-His | Met(O)-Thr-Lys-Pro-Arg-Phe-His | 170 |
| Met(O)-Thr-Lys-Pro-Arg-Tyr-His | Met(O)-Thr-Lys-Pro-Arg-Tyr-His | Met(O)-Thr-Lys-Pro-Arg-Tyr-His | 171 |
| Met(O)-Thr-Lys-Pro-Arg-His-His | Met(O)-Thr-Lys-Pro-Arg-His-His | Met(O)-Thr-Lys-Pro-Arg-His-His | 172 |
| Met(O)-Thr-Lys-Pro-Arg-Pro-His | Met(O)-Thr-Lys-Pro-Arg-Pro-His | Met(O)-Thr-Lys-Pro-Arg-Pro-His | 173 |
| Met(O)-Thr-Lys-Pro-Arg-Lys-His | Met(O)-Thr-Lys-Pro-Arg-Lys-His | Met(O)-Thr-Lys-Pro-Arg-Lys-His | 174 |
| Thr-Thr-Lys-Pro-His | Thr-Thr-Lys-Pro-His | Thr-Thr-Lys-Pro-His | 175 |
| Thr-Thr-Lys-Pro-Arg-His | Thr-Thr-Lys-Pro-Arg-His | Thr-Thr-Lys-Pro-Arg-His | 176 |
| Thr-Thr-Lys-Pro-Phe-His | Thr-Thr-Lys-Pro-Phe-His | Thr-Thr-Lys-Pro-Phe-His | 177 |
| Thr-Thr-Lys-Pro-Tyr-His | Thr-Thr-Lys-Pro-Tyr-His | Thr-Thr-Lys-Pro-Tyr-His | 178 |
| Thr-Thr-Lys-Pro-Gly-His | Thr-Thr-Lys-Pro-Gly-His | Thr-Thr-Lys-Pro-Gly-His | 179 |
| Thr-Thr-Lys-Pro-His-His | Thr-Thr-Lys-Pro-His-His | Thr-Thr-Lys-Pro-His-His | 180 |

TABLE 1-continued

| X-OH | X-OCH₃ | X-NH₂ | SEQ ID NO |
|---|---|---|---|
| Thr-Thr-Lys-Pro-Lys-His | Thr-Thr-Lys-Pro-Lys-His | Thr-Thr-Lys-Pro-Lys-His | 181 |
| Thr-Thr-Lys-Pro-Gly-His | Thr-Thr-Lys-Pro-Gly-His | Thr-Thr-Lys-Pro-Gly-His | 182 |
| Thr-Thr-Lys-Pro-Gly-Arg-His | Thr-Thr-Lys-Pro-Gly-Arg-His | Thr-Thr-Lys-Pro-Gly-Arg-His | 183 |
| Thr-Thr-Lys-Pro-Gly-Phe-His | Thr-Thr-Lys-Pro-Gly-Phe-His | Thr-Thr-Lys-Pro-Gly-Phe-His | 184 |
| Thr-Thr-Lys-Pro-Gly-Tyr-His | Thr-Thr-Lys-Pro-Gly-Tyr-His | Thr-Thr-Lys-Pro-Gly-Tyr-His | 185 |
| Thr-Thr-Lys-Pro-Gly-His-His | Thr-Thr-Lys-Pro-Gly-His-His | Thr-Thr-Lys-Pro-Gly-His-His | 186 |
| Thr-Thr-Lys-Pro-Gly-Pro-His | Thr-Thr-Lys-Pro-Gly-Pro-His | Thr-Thr-Lys-Pro-Gly-Pro-His | 187 |
| Thr-Thr-Lys-Pro-Gly-Lys-His | Thr-Thr-Lys-Pro-Gly-Lys-His | Thr-Thr-Lys-Pro-Gly-Lys-His | 188 |
| Thr-Thr-Lys-Pro-Asp-His | Thr-Thr-Lys-Pro-Asp-His | Thr-Thr-Lys-Pro-Asp-His | 189 |
| Thr-Thr-Lys-Pro-Asp-Arg-His | Thr-Thr-Lys-Pro-Asp-Arg-His | Thr-Thr-Lys-Pro-Asp-Arg-His | 190 |
| Thr-Thr-Lys-Pro-Asp-Phe-His | Thr-Thr-Lys-Pro-Asp-Phe-His | Thr-Thr-Lys-Pro-Asp-Phe-His | 191 |
| Thr-Thr-Lys-Pro-Asp-Tyr-His | Thr-Thr-Lys-Pro-Asp-Tyr-His | Thr-Thr-Lys-Pro-Asp-Tyr-His | 192 |
| Thr-Thr-Lys-Pro-Asp-His-His | Thr-Thr-Lys-Pro-Asp-His-His | Thr-Thr-Lys-Pro-Asp-His-His | 193 |
| Thr-Thr-Lys-Pro-Asp-Pro-His | Thr-Thr-Lys-Pro-Asp-Pro-His | Thr-Thr-Lys-Pro-Asp-Pro-His | 194 |
| Thr-Thr-Lys-Pro-Asp-Lys-His | Thr-Thr-Lys-Pro-Asp-Lys-His | Thr-Thr-Lys-Pro-Asp-Lys-His | 195 |
| Thr-Thr-Lys-Pro-Trp-His | Thr-Thr-Lys-Pro-Trp-His | Thr-Thr-Lys-Pro-Trp-His | 196 |
| Thr-Thr-Lys-Pro-Trp-Arg-His | Thr-Thr-Lys-Pro-Trp-Arg-His | Thr-Thr-Lys-Pro-Trp-Arg-His | 197 |
| Thr-Thr-Lys-Pro-Trp-Phe-His | Thr-Thr-Lys-Pro-Trp-Phe-His | Thr-Thr-Lys-Pro-Trp-Phe-His | 198 |
| Thr-Thr-Lys-Pro-Trp-Tyr-His | Thr-Thr-Lys-Pro-Trp-Tyr-His | Thr-Thr-Lys-Pro-Trp-Tyr-His | 199 |
| Thr-Thr-Lys-Pro-Trp-His-His | Thr-Thr-Lys-Pro-Trp-His-His | Thr-Thr-Lys-Pro-Trp-His-His | 200 |
| Thr-Thr-Lys-Pro-Trp-Pro-His | Thr-Thr-Lys-Pro-Trp-Pro-His | Thr-Thr-Lys-Pro-Trp-Pro-His | 201 |
| Thr-Thr-Lys-Pro-Trp-Lys-His | Thr-Thr-Lys-Pro-Trp-Lys-His | Thr-Thr-Lys-Pro-Trp-Lys-His | 202 |
| Thr-Thr-Lys-Pro-Gln-His | Thr-Thr-Lys-Pro-Gln-His | Thr-Thr-Lys-Pro-Gln-His | 203 |
| Thr-Thr-Lys-Pro-Gln-Arg-His | Thr-Thr-Lys-Pro-Gln-Arg-His | Thr-Thr-Lys-Pro-Gln-Arg-His | 204 |
| Thr-Thr-Lys-Pro-Gln-Phe-His | Thr-Thr-Lys-Pro-Gln-Phe-His | Thr-Thr-Lys-Pro-Gln-Phe-His | 205 |
| Thr-Thr-Lys-Pro-Gln-Tyr-His | Thr-Thr-Lys-Pro-Gln-Tyr-His | Thr-Thr-Lys-Pro-Gln-Tyr-His | 206 |
| Thr-Thr-Lys-Pro-Gln-His-His | Thr-Thr-Lys-Pro-Gln-His-His | Thr-Thr-Lys-Pro-Gln-His-His | 207 |
| Thr-Thr-Lys-Pro-Gln-Pro-His | Thr-Thr-Lys-Pro-Gln-Pro-His | Thr-Thr-Lys-Pro-Gln-Pro-His | 208 |
| Thr-Thr-Lys-Pro-Gln-Lys-His | Thr-Thr-Lys-Pro-Gln-Lys-His | Thr-Thr-Lys-Pro-Gln-Lys-His | 209 |
| Thr-Thr-Lys-Pro-Asn-His | Thr-Thr-Lys-Pro-Asn-His | Thr-Thr-Lys-Pro-Asn-His | 210 |
| Thr-Thr-Lys-Pro-Asn-Arg-His | Thr-Thr-Lys-Pro-Asn-Arg-His | Thr-Thr-Lys-Pro-Asn-Arg-His | 211 |
| Thr-Thr-Lys-Pro-Asn-Phe-His | Thr-Thr-Lys-Pro-Asn-Phe-His | Thr-Thr-Lys-Pro-Asn-Phe-His | 212 |
| Thr-Thr-Lys-Pro-Asn-Tyr-His | Thr-Thr-Lys-Pro-Asn-Tyr-His | Thr-Thr-Lys-Pro-Asn-Tyr-His | 213 |
| Thr-Thr-Lys-Pro-Asn-His-His | Thr-Thr-Lys-Pro-Asn-His-His | Thr-Thr-Lys-Pro-Asn-His-His | 214 |
| Thr-Thr-Lys-Pro-Asn-Pro-His | Thr-Thr-Lys-Pro-Asn-Pro-His | Thr-Thr-Lys-Pro-Asn-Pro-His | 215 |
| Thr-Thr-Lys-Pro-Asn-Lys-His | Thr-Thr-Lys-Pro-Asn-Lys-His | Thr-Thr-Lys-Pro-Asn-Lys-His | 216 |
| Thr-Thr-Lys-Pro-Tyr-His | Thr-Thr-Lys-Pro-Tyr-His | Thr-Thr-Lys-Pro-Tyr-His | 217 |
| Thr-Thr-Lys-Pro-Tyr-Arg-His | Thr-Thr-Lys-Pro-Tyr-Arg-His | Thr-Thr-Lys-Pro-Tyr-Arg-His | 218 |

TABLE 1-continued

| X-OH | X-OCH₃ | X-NH₂ | SEQ ID NO |
|---|---|---|---|
| Thr-Thr-Lys-Pro-Tyr-Phe-His | Thr-Thr-Lys-Pro-Tyr-Phe-His | Thr-Thr-Lys-Pro-Tyr-Phe-His | 219 |
| Thr-Thr-Lys-Pro-Tyr-Tyr-His | Thr-Thr-Lys-Pro-Tyr-Tyr-His | Thr-Thr-Lys-Pro-Tyr-Tyr-His | 220 |
| Thr-Thr-Lys-Pro-Tyr-His-His | Thr-Thr-Lys-Pro-Tyr-His-His | Thr-Thr-Lys-Pro-Tyr-His-His | 221 |
| Thr-Thr-Lys-Pro-Tyr-Pro-His | Thr-Thr-Lys-Pro-Tyr-Pro-His | Thr-Thr-Lys-Pro-Tyr-Pro-His | 222 |
| Thr-Thr-Lys-Pro-Tyr-Lys-His | Thr-Thr-Lys-Pro-Tyr-Lys-His | Thr-Thr-Lys-Pro-Tyr-Lys-His | 223 |
| Thr-Thr-Lys-Pro-Arg-His | Thr-Thr-Lys-Pro-Arg-His | Thr-Thr-Lys-Pro-Arg-His | 224 |
| Thr-Thr-Lys-Pro-Arg-Arg-His | Thr-Thr-Lys-Pro-Arg-Arg-His | Thr-Thr-Lys-Pro-Arg-Arg-His | 225 |
| Thr-Thr-Lys-Pro-Arg-Phe-His | Thr-Thr-Lys-Pro-Arg-Phe-His | Thr-Thr-Lys-Pro-Arg-Phe-His | 226 |
| Thr-Thr-Lys-Pro-Arg-Tyr-His | Thr-Thr-Lys-Pro-Arg-Tyr-His | Thr-Thr-Lys-Pro-Arg-Tyr-His | 227 |
| Thr-Thr-Lys-Pro-Arg-His-His | Thr-Thr-Lys-Pro-Arg-His-His | Thr-Thr-Lys-Pro-Arg-His-His | 228 |
| Thr-Thr-Lys-Pro-Arg-Pro-His | Thr-Thr-Lys-Pro-Arg-Pro-His | Thr-Thr-Lys-Pro-Arg-Pro-His | 229 |
| Thr-Thr-Lys-Pro-Arg-Lys-His | Thr-Thr-Lys-Pro-Arg-Lys-His | Thr-Thr-Lys-Pro-Arg-Lys-His | 230 |
| Ala-Thr-Lys-Pro-His | Ala-Thr-Lys-Pro-His | Ala-Thr-Lys-Pro-His | 231 |
| Ala-Thr-Lys-Pro-Arg-His | Ala-Thr-Lys-Pro-Arg-His | Ala-Thr-Lys-Pro-Arg-His | 232 |
| Ala-Thr-Lys-Pro-Phe-His | Ala-Thr-Lys-Pro-Phe-His | Ala-Thr-Lys-Pro-Phe-His | 233 |
| Ala-Thr-Lys-Pro-Tyr-His | Ala-Thr-Lys-Pro-Tyr-His | Ala-Thr-Lys-Pro-Tyr-His | 234 |
| Ala-Thr-Lys-Pro-Gly-His | Ala-Thr-Lys-Pro-Gly-His | Ala-Thr-Lys-Pro-Gly-His | 235 |
| Ala-Thr-Lys-Pro-His-His | Ala-Thr-Lys-Pro-His-His | Ala-Thr-Lys-Pro-His-His | 236 |
| Ala-Thr-Lys-Pro-Lys-His | Ala-Thr-Lys-Pro-Lys-His | Ala-Thr-Lys-Pro-Lys-His | 237 |
| Ala-Thr-Lys-Pro-Gly-His | Ala-Thr-Lys-Pro-Gly-His | Ala-Thr-Lys-Pro-Gly-His | 238 |
| Ala-Thr-Lys-Pro-Gly-Arg-His | Ala-Thr-Lys-Pro-Gly-Arg-His | Ala-Thr-Lys-Pro-Gly-Arg-His | 239 |
| Ala-Thr-Lys-Pro-Gly-Phe-His | Ala-Thr-Lys-Pro-Gly-Phe-His | Ala-Thr-Lys-Pro-Gly-Phe-His | 240 |
| Ala-Thr-Lys-Pro-Gly-Tyr-His | Ala-Thr-Lys-Pro-Gly-Tyr-His | Ala-Thr-Lys-Pro-Gly-Tyr-His | 241 |
| Ala-Thr-Lys-Pro-Gly-His-His | Ala-Thr-Lys-Pro-Gly-His-His | Ala-Thr-Lys-Pro-Gly-His-His | 242 |
| Ala-Thr-Lys-Pro-Gly-Pro-His | Ala-Thr-Lys-Pro-Gly-Pro-His | Ala-Thr-Lys-Pro-Gly-Pro-His | 243 |
| Ala-Thr-Lys-Pro-Gly-Lys-His | Ala-Thr-Lys-Pro-Gly-Lys-His | Ala-Thr-Lys-Pro-Gly-Lys-His | 244 |
| Ala-Thr-Lys-Pro-Asp-His | Ala-Thr-Lys-Pro-Asp-His | Ala-Thr-Lys-Pro-Asp-His | 245 |
| Ala-Thr-Lys-Pro-Asp-Arg-His | Ala-Thr-Lys-Pro-Asp-Arg-His | Ala-Thr-Lys-Pro-Asp-Arg-His | 246 |
| Ala-Thr-Lys-Pro-Asp-Phe-His | Ala-Thr-Lys-Pro-Asp-Phe-His | Ala-Thr-Lys-Pro-Asp-Phe-His | 247 |
| Ala-Thr-Lys-Pro-Asp-Tyr-His | Ala-Thr-Lys-Pro-Asp-Tyr-His | Ala-Thr-Lys-Pro-Asp-Tyr-His | 248 |
| Ala-Thr-Lys-Pro-Asp-His-His | Ala-Thr-Lys-Pro-Asp-His-His | Ala-Thr-Lys-Pro-Asp-His-His | 249 |
| Ala-Thr-Lys-Pro-Asp-Pro-His | Ala-Thr-Lys-Pro-Asp-Pro-His | Ala-Thr-Lys-Pro-Asp-Pro-His | 250 |
| Ala-Thr-Lys-Pro-Asp-Lys-His | Ala-Thr-Lys-Pro-Asp-Lys-His | Ala-Thr-Lys-Pro-Asp-Lys-His | 251 |
| Ala-Thr-Lys-Pro-Trp-His | Ala-Thr-Lys-Pro-Trp-His | Ala-Thr-Lys-Pro-Trp-His | 252 |
| Ala-Thr-Lys-Pro-Trp-Arg-His | Ala-Thr-Lys-Pro-Trp-Arg-His | Ala-Thr-Lys-Pro-Trp-Arg-His | 253 |
| Ala-Thr-Lys-Pro-Trp-Phe-His | Ala-Thr-Lys-Pro-Trp-Phe-His | Ala-Thr-Lys-Pro-Trp-Phe-His | 254 |
| Ala-Thr-Lys-Pro-Trp-Tyr-His | Ala-Thr-Lys-Pro-Trp-Tyr-His | Ala-Thr-Lys-Pro-Trp-Tyr-His | 255 |
| Ala-Thr-Lys-Pro-Trp-His-His | Ala-Thr-Lys-Pro-Trp-His-His | Ala-Thr-Lys-Pro-Trp-His-His | 256 |

TABLE 1-continued

| X-OH | X-OCH₃ | X-NH₂ | SEQ ID NO |
|---|---|---|---|
| Ala-Thr-Lys-Pro-Trp-Pro-His | Ala-Thr-Lys-Pro-Trp-Pro-His | Ala-Thr-Lys-Pro-Trp-Pro-His | 257 |
| Ala-Thr-Lys-Pro-Trp-Lys-His | Ala-Thr-Lys-Pro-Trp-Lys-His | Ala-Thr-Lys-Pro-Trp-Lys-His | 258 |
| Ala-Thr-Lys-Pro-Gln-His | Ala-Thr-Lys-Pro-Gln-His | Ala-Thr-Lys-Pro-Gln-His | 259 |
| Ala-Thr-Lys-Pro-Gln-Arg-His | Ala-Thr-Lys-Pro-Gln-Arg-His | Ala-Thr-Lys-Pro-Gln-Arg-His | 260 |
| Ala-Thr-Lys-Pro-Gln-Phe-His | Ala-Thr-Lys-Pro-Gln-Phe-His | Ala-Thr-Lys-Pro-Gln-Phe-His | 261 |
| Ala-Thr-Lys-Pro-Gln-Tyr-His | Ala-Thr-Lys-Pro-Gln-Tyr-His | Ala-Thr-Lys-Pro-Gln-Tyr-His | 262 |
| Ala-Thr-Lys-Pro-Gln-His-His | Ala-Thr-Lys-Pro-Gln-His-His | Ala-Thr-Lys-Pro-Gln-His-His | 263 |
| Ala-Thr-Lys-Pro-Gln-Pro-His | Ala-Thr-Lys-Pro-Gln-Pro-His | Ala-Thr-Lys-Pro-Gln-Pro-His | 264 |
| Ala-Thr-Lys-Pro-Gln-Lys-His | Ala-Thr-Lys-Pro-Gln-Lys-His | Ala-Thr-Lys-Pro-Gln-Lys-His | 265 |
| Ala-Thr-Lys-Pro-Asn-His | Ala-Thr-Lys-Pro-Asn-His | Ala-Thr-Lys-Pro-Asn-His | 266 |
| Ala-Thr-Lys-Pro-Asn-Arg-His | Ala-Thr-Lys-Pro-Asn-Arg-His | Ala-Thr-Lys-Pro-Asn-Arg-His | 267 |
| Ala-Thr-Lys-Pro-Asn-Phe-His | Ala-Thr-Lys-Pro-Asn-Phe-His | Ala-Thr-Lys-Pro-Asn-Phe-His | 268 |
| Ala-Thr-Lys-Pro-Asn-Tyr-His | Ala-Thr-Lys-Pro-Asn-Tyr-His | Ala-Thr-Lys-Pro-Asn-Tyr-His | 269 |
| Ala-Thr-Lys-Pro-Asn-His-His | Ala-Thr-Lys-Pro-Asn-His-His | Ala-Thr-Lys-Pro-Asn-His-His | 270 |
| Ala-Thr-Lys-Pro-Asn-Pro-His | Ala-Thr-Lys-Pro-Asn-Pro-His | Ala-Thr-Lys-Pro-Asn-Pro-His | 271 |
| Ala-Thr-Lys-Pro-Asn-Lys-His | Ala-Thr-Lys-Pro-Asn-Lys-His | Ala-Thr-Lys-Pro-Asn-Lys-His | 272 |
| Ala-Thr-Lys-Pro-Tyr-His | Ala-Thr-Lys-Pro-Tyr-His | Ala-Thr-Lys-Pro-Tyr-His | 273 |
| Ala-Thr-Lys-Pro-Tyr-Arg-His | Ala-Thr-Lys-Pro-Tyr-Arg-His | Ala-Thr-Lys-Pro-Tyr-Arg-His | 274 |
| Ala-Thr-Lys-Pro-Tyr-Phe-His | Ala-Thr-Lys-Pro-Tyr-Phe-His | Ala-Thr-Lys-Pro-Tyr-Phe-His | 275 |
| Ala-Thr-Lys-Pro-Tyr-Tyr-His | Ala-Thr-Lys-Pro-Tyr-Tyr-His | Ala-Thr-Lys-Pro-Tyr-Tyr-His | 276 |
| Ala-Thr-Lys-Pro-Tyr-His-His | Ala-Thr-Lys-Pro-Tyr-His-His | Ala-Thr-Lys-Pro-Tyr-His-His | 277 |
| Ala-Thr-Lys-Pro-Tyr-Pro-His | Ala-Thr-Lys-Pro-Tyr-Pro-His | Ala-Thr-Lys-Pro-Tyr-Pro-His | 278 |
| Ala-Thr-Lys-Pro-Tyr-Lys-His | Ala-Thr-Lys-Pro-Tyr-Lys-His | Ala-Thr-Lys-Pro-Tyr-Lys-His | 279 |
| Ala-Thr-Lys-Pro-Arg-His | Ala-Thr-Lys-Pro-Arg-His | Ala-Thr-Lys-Pro-Arg-His | 280 |
| Ala-Thr-Lys-Pro-Arg-Arg-His | Ala-Thr-Lys-Pro-Arg-Arg-His | Ala-Thr-Lys-Pro-Arg-Arg-His | 281 |
| Ala-Thr-Lys-Pro-Arg-Phe-His | Ala-Thr-Lys-Pro-Arg-Phe-His | Ala-Thr-Lys-Pro-Arg-Phe-His | 282 |
| Ala-Thr-Lys-Pro-Arg-Tyr-His | Ala-Thr-Lys-Pro-Arg-Tyr-His | Ala-Thr-Lys-Pro-Arg-Tyr-His | 283 |
| Ala-Thr-Lys-Pro-Arg-His-His | Ala-Thr-Lys-Pro-Arg-His-His | Ala-Thr-Lys-Pro-Arg-His-His | 284 |
| Ala-Thr-Lys-Pro-Arg-Pro-His | Ala-Thr-Lys-Pro-Arg-Pro-His | Ala-Thr-Lys-Pro-Arg-Pro-His | 285 |
| Ala-Thr-Lys-Pro-Arg-Lys-His | Ala-Thr-Lys-Pro-Arg-Lys-His | Ala-Thr-Lys-Pro-Arg-Lys-His | 286 |
| His-Thr-Lys-Pro-His | His-Thr-Lys-Pro-His | His-Thr-Lys-Pro-His | 287 |
| His-Thr-Lys-Pro-Arg-His | His-Thr-Lys-Pro-Arg-His | His-Thr-Lys-Pro-Arg-His | 288 |
| His-Thr-Lys-Pro-Phe-His | His-Thr-Lys-Pro-Phe-His | His-Thr-Lys-Pro-Phe-His | 289 |
| His-Thr-Lys-Pro-Tyr-His | His-Thr-Lys-Pro-Tyr-His | His-Thr-Lys-Pro-Tyr-His | 290 |
| His-Thr-Lys-Pro-Gly-His | His-Thr-Lys-Pro-Gly-His | His-Thr-Lys-Pro-Gly-His | 291 |
| His-Thr-Lys-Pro-His-His | His-Thr-Lys-Pro-His-His | His-Thr-Lys-Pro-His-His | 292 |
| His-Thr-Lys-Pro-Lys-His | His-Thr-Lys-Pro-Lys-His | His-Thr-Lys-Pro-Lys-His | 293 |
| His-Thr-Lys-Pro-Gly-His | His-Thr-Lys-Pro-Gly-His | His-Thr-Lys-Pro-Gly-His | 294 |

TABLE 1-continued

| X-OH | X-OCH₃ | X-NH₂ | SEQ ID NO |
|---|---|---|---|
| His-Thr-Lys-Pro-Gly-Arg-His | His-Thr-Lys-Pro-Gly-Arg-His | His-Thr-Lys-Pro-Gly-Arg-His | 295 |
| His-Thr-Lys-Pro-Gly-Phe-His | His-Thr-Lys-Pro-Gly-Phe-His | His-Thr-Lys-Pro-Gly-Phe-His | 296 |
| His-Thr-Lys-Pro-Gly-Tyr-His | His-Thr-Lys-Pro-Gly-Tyr-His | His-Thr-Lys-Pro-Gly-Tyr-His | 297 |
| His-Thr-Lys-Pro-Gly-His-His | His-Thr-Lys-Pro-Gly-His-His | His-Thr-Lys-Pro-Gly-His-His | 298 |
| His-Thr-Lys-Pro-Gly-Pro-His | His-Thr-Lys-Pro-Gly-Pro-His | His-Thr-Lys-Pro-Gly-Pro-His | 299 |
| His-Thr-Lys-Pro-Gly-Lys-His | His-Thr-Lys-Pro-Gly-Lys-His | His-Thr-Lys-Pro-Gly-Lys-His | 300 |
| His-Thr-Lys-Pro-Asp-His | His-Thr-Lys-Pro-Asp-His | His-Thr-Lys-Pro-Asp-His | 301 |
| His-Thr-Lys-Pro-Asp-Arg-His | His-Thr-Lys-Pro-Asp-Arg-His | His-Thr-Lys-Pro-Asp-Arg-His | 302 |
| His-Thr-Lys-Pro-Asp-Phe-His | His-Thr-Lys-Pro-Asp-Phe-His | His-Thr-Lys-Pro-Asp-Phe-His | 303 |
| His-Thr-Lys-Pro-Asp-Tyr-His | His-Thr-Lys-Pro-Asp-Tyr-His | His-Thr-Lys-Pro-Asp-Tyr-His | 304 |
| His-Thr-Lys-Pro-Asp-His-His | His-Thr-Lys-Pro-Asp-His-His | His-Thr-Lys-Pro-Asp-His-His | 305 |
| His-Thr-Lys-Pro-Asp-Pro-His | His-Thr-Lys-Pro-Asp-Pro-His | His-Thr-Lys-Pro-Asp-Pro-His | 306 |
| His-Thr-Lys-Pro-Asp-Lys-His | His-Thr-Lys-Pro-Asp-Lys-His | His-Thr-Lys-Pro-Asp-Lys-His | 307 |
| His-Thr-Lys-Pro-Trp-His | His-Thr-Lys-Pro-Trp-His | His-Thr-Lys-Pro-Trp-His | 308 |
| His-Thr-Lys-Pro-Trp-Arg-His | His-Thr-Lys-Pro-Trp-Arg-His | His-Thr-Lys-Pro-Trp-Arg-His | 309 |
| His-Thr-Lys-Pro-Trp-Phe-His | His-Thr-Lys-Pro-Trp-Phe-His | His-Thr-Lys-Pro-Trp-Phe-His | 310 |
| His-Thr-Lys-Pro-Trp-Tyr-His | His-Thr-Lys-Pro-Trp-Tyr-His | His-Thr-Lys-Pro-Trp-Tyr-His | 311 |
| His-Thr-Lys-Pro-Trp-His-His | His-Thr-Lys-Pro-Trp-His-His | His-Thr-Lys-Pro-Trp-His-His | 312 |
| His-Thr-Lys-Pro-Trp-Pro-His | His-Thr-Lys-Pro-Trp-Pro-His | His-Thr-Lys-Pro-Trp-Pro-His | 313 |
| His-Thr-Lys-Pro-Trp-Lys-His | His-Thr-Lys-Pro-Trp-Lys-His | His-Thr-Lys-Pro-Trp-Lys-His | 314 |
| His-Thr-Lys-Pro-Gln-His | His-Thr-Lys-Pro-Gln-His | His-Thr-Lys-Pro-Gln-His | 315 |
| His-Thr-Lys-Pro-Gln-Arg-His | His-Thr-Lys-Pro-Gln-Arg-His | His-Thr-Lys-Pro-Gln-Arg-His | 316 |
| His-Thr-Lys-Pro-Gln-Phe-His | His-Thr-Lys-Pro-Gln-Phe-His | His-Thr-Lys-Pro-Gln-Phe-His | 317 |
| His-Thr-Lys-Pro-Gln-Tyr-His | His-Thr-Lys-Pro-Gln-Tyr-His | His-Thr-Lys-Pro-Gln-Tyr-His | 318 |
| His-Thr-Lys-Pro-Gln-His-His | His-Thr-Lys-Pro-Gln-His-His | His-Thr-Lys-Pro-Gln-His-His | 319 |
| His-Thr-Lys-Pro-Gln-Pro-His | His-Thr-Lys-Pro-Gln-Pro-His | His-Thr-Lys-Pro-Gln-Pro-His | 320 |
| His-Thr-Lys-Pro-Gln-Lys-His | His-Thr-Lys-Pro-Gln-Lys-His | His-Thr-Lys-Pro-Gln-Lys-His | 321 |
| His-Thr-Lys-Pro-Asn-His | His-Thr-Lys-Pro-Asn-His | His-Thr-Lys-Pro-Asn-His | 322 |
| His-Thr-Lys-Pro-Asn-Arg-His | His-Thr-Lys-Pro-Asn-Arg-His | His-Thr-Lys-Pro-Asn-Arg-His | 323 |
| His-Thr-Lys-Pro-Asn-Phe-His | His-Thr-Lys-Pro-Asn-Phe-His | His-Thr-Lys-Pro-Asn-Phe-His | 324 |
| His-Thr-Lys-Pro-Asn-Tyr-His | His-Thr-Lys-Pro-Asn-Tyr-His | His-Thr-Lys-Pro-Asn-Tyr-His | 325 |
| His-Thr-Lys-Pro-Asn-His-His | His-Thr-Lys-Pro-Asn-His-His | His-Thr-Lys-Pro-Asn-His-His | 326 |
| His-Thr-Lys-Pro-Asn-Pro-His | His-Thr-Lys-Pro-Asn-Pro-His | His-Thr-Lys-Pro-Asn-Pro-His | 327 |
| His-Thr-Lys-Pro-Asn-Lys-His | His-Thr-Lys-Pro-Asn-Lys-His | His-Thr-Lys-Pro-Asn-Lys-His | 328 |
| His-Thr-Lys-Pro-Tyr-His | His-Thr-Lys-Pro-Tyr-His | His-Thr-Lys-Pro-Tyr-His | 329 |
| His-Thr-Lys-Pro-Tyr-Arg-His | His-Thr-Lys-Pro-Tyr-Arg-His | His-Thr-Lys-Pro-Tyr-Arg-His | 330 |
| His-Thr-Lys-Pro-Tyr-Phe-His | His-Thr-Lys-Pro-Tyr-Phe-His | His-Thr-Lys-Pro-Tyr-Phe-His | 331 |
| His-Thr-Lys-Pro-Tyr-Tyr-His | His-Thr-Lys-Pro-Tyr-Tyr-His | His-Thr-Lys-Pro-Tyr-Tyr-His | 332 |

TABLE 1-continued

| X-OH | X-OCH₃ | X-NH₂ | SEQ ID NO |
|---|---|---|---|
| His-Thr-Lys-Pro-Tyr-His-His | His-Thr-Lys-Pro-Tyr-His-His | His-Thr-Lys-Pro-Tyr-His-His | 333 |
| His-Thr-Lys-Pro-Tyr-Pro-His | His-Thr-Lys-Pro-Tyr-Pro-His | His-Thr-Lys-Pro-Tyr-Pro-His | 334 |
| His-Thr-Lys-Pro-Tyr-Lys-His | His-Thr-Lys-Pro-Tyr-Lys-His | His-Thr-Lys-Pro-Tyr-Lys-His | 335 |
| His-Thr-Lys-Pro-Arg-His | His-Thr-Lys-Pro-Arg-His | His-Thr-Lys-Pro-Arg-His | 336 |
| His-Thr-Lys-Pro-Arg-Arg-His | His-Thr-Lys-Pro-Arg-Arg-His | His-Thr-Lys-Pro-Arg-Arg-His | 337 |
| His-Thr-Lys-Pro-Arg-Phe-His | His-Thr-Lys-Pro-Arg-Phe-His | His-Thr-Lys-Pro-Arg-Phe-His | 338 |
| His-Thr-Lys-Pro-Arg-Tyr-His | His-Thr-Lys-Pro-Arg-Tyr-His | His-Thr-Lys-Pro-Arg-Tyr-His | 339 |
| His-Thr-Lys-Pro-Arg-His-His | His-Thr-Lys-Pro-Arg-His-His | His-Thr-Lys-Pro-Arg-His-His | 340 |
| His-Thr-Lys-Pro-Arg-Pro-His | His-Thr-Lys-Pro-Arg-Pro-His | His-Thr-Lys-Pro-Arg-Pro-His | 341 |
| His-Thr-Lys-Pro-Arg-Lys-His | His-Thr-Lys-Pro-Arg-Lys-His | His-Thr-Lys-Pro-Arg-Lys-His | 342 |
| Lys-Thr-Lys-Pro-His | Lys-Thr-Lys-Pro-His | Lys-Thr-Lys-Pro-His | 343 |
| Lys-Thr-Lys-Pro-Arg-His | Lys-Thr-Lys-Pro-Arg-His | Lys-Thr-Lys-Pro-Arg-His | 344 |
| Lys-Thr-Lys-Pro-Phe-His | Lys-Thr-Lys-Pro-Phe-His | Lys-Thr-Lys-Pro-Phe-His | 345 |
| Lys-Thr-Lys-Pro-Tyr-His | Lys-Thr-Lys-Pro-Tyr-His | Lys-Thr-Lys-Pro-Tyr-His | 346 |
| Lys-Thr-Lys-Pro-Gly-His | Lys-Thr-Lys-Pro-Gly-His | Lys-Thr-Lys-Pro-Gly-His | 347 |
| Lys-Thr-Lys-Pro-His-His | Lys-Thr-Lys-Pro-His-His | Lys-Thr-Lys-Pro-His-His | 348 |
| Lys-Thr-Lys-Pro-Lys-His | Lys-Thr-Lys-Pro-Lys-His | Lys-Thr-Lys-Pro-Lys-His | 349 |
| Lys-Thr-Lys-Pro-Gly-His | Lys-Thr-Lys-Pro-Gly-His | Lys-Thr-Lys-Pro-Gly-His | 350 |
| Lys-Thr-Lys-Pro-Gly-Arg-His | Lys-Thr-Lys-Pro-Gly-Arg-His | Lys-Thr-Lys-Pro-Gly-Arg-His | 351 |
| Lys-Thr-Lys-Pro-Gly-Phe-His | Lys-Thr-Lys-Pro-Gly-Phe-His | Lys-Thr-Lys-Pro-Gly-Phe-His | 352 |
| Lys-Thr-Lys-Pro-Gly-Tyr-His | Lys-Thr-Lys-Pro-Gly-Tyr-His | Lys-Thr-Lys-Pro-Gly-Tyr-His | 353 |
| Lys-Thr-Lys-Pro-Gly-His-His | Lys-Thr-Lys-Pro-Gly-His-His | Lys-Thr-Lys-Pro-Gly-His-His | 354 |
| Lys-Thr-Lys-Pro-Gly-Pro-His | Lys-Thr-Lys-Pro-Gly-Pro-His | Lys-Thr-Lys-Pro-Gly-Pro-His | 355 |
| Lys-Thr-Lys-Pro-Gly-Lys-His | Lys-Thr-Lys-Pro-Gly-Lys-His | Lys-Thr-Lys-Pro-Gly-Lys-His | 356 |
| Lys-Thr-Lys-Pro-Asp-His | Lys-Thr-Lys-Pro-Asp-His | Lys-Thr-Lys-Pro-Asp-His | 357 |
| Lys-Thr-Lys-Pro-Asp-Arg-His | Lys-Thr-Lys-Pro-Asp-Arg-His | Lys-Thr-Lys-Pro-Asp-Arg-His | 358 |
| Lys-Thr-Lys-Pro-Asp-Phe-His | Lys-Thr-Lys-Pro-Asp-Phe-His | Lys-Thr-Lys-Pro-Asp-Phe-His | 359 |
| Lys-Thr-Lys-Pro-Asp-Tyr-His | Lys-Thr-Lys-Pro-Asp-Tyr-His | Lys-Thr-Lys-Pro-Asp-Tyr-His | 360 |
| Lys-Thr-Lys-Pro-Asp-His-His | Lys-Thr-Lys-Pro-Asp-His-His | Lys-Thr-Lys-Pro-Asp-His-His | 361 |
| Lys-Thr-Lys-Pro-Asp-Pro-His | Lys-Thr-Lys-Pro-Asp-Pro-His | Lys-Thr-Lys-Pro-Asp-Pro-His | 362 |
| Lys-Thr-Lys-Pro-Asp-Lys-His | Lys-Thr-Lys-Pro-Asp-Lys-His | Lys-Thr-Lys-Pro-Asp-Lys-His | 363 |
| Lys-Thr-Lys-Pro-Trp-His | Lys-Thr-Lys-Pro-Trp-His | Lys-Thr-Lys-Pro-Trp-His | 364 |
| Lys-Thr-Lys-Pro-Trp-Arg-His | Lys-Thr-Lys-Pro-Trp-Arg-His | Lys-Thr-Lys-Pro-Trp-Arg-His | 365 |
| Lys-Thr-Lys-Pro-Trp-Phe-His | Lys-Thr-Lys-Pro-Trp-Phe-His | Lys-Thr-Lys-Pro-Trp-Phe-His | 366 |
| Lys-Thr-Lys-Pro-Trp-Tyr-His | Lys-Thr-Lys-Pro-Trp-Tyr-His | Lys-Thr-Lys-Pro-Trp-Tyr-His | 367 |
| Lys-Thr-Lys-Pro-Trp-His-His | Lys-Thr-Lys-Pro-Trp-His-His | Lys-Thr-Lys-Pro-Trp-His-His | 368 |
| Lys-Thr-Lys-Pro-Trp-Pro-His | Lys-Thr-Lys-Pro-Trp-Pro-His | Lys-Thr-Lys-Pro-Trp-Pro-His | 369 |
| Lys-Thr-Lys-Pro-Trp-Lys-His | Lys-Thr-Lys-Pro-Trp-Lys-His | Lys-Thr-Lys-Pro-Trp-Lys-His | 370 |

TABLE 1-continued

| X-OH | X-OCH₃ | X-NH₂ | SEQ ID NO |
|---|---|---|---|
| Lys-Thr-Lys-Pro-Gln-His | Lys-Thr-Lys-Pro-Gln-His | Lys-Thr-Lys-Pro-Gln-His | 371 |
| Lys-Thr-Lys-Pro-Gln-Arg-His | Lys-Thr-Lys-Pro-Gln-Arg-His | Lys-Thr-Lys-Pro-Gln-Arg-His | 372 |
| Lys-Thr-Lys-Pro-Gln-Phe-His | Lys-Thr-Lys-Pro-Gln-Phe-His | Lys-Thr-Lys-Pro-Gln-Phe-His | 373 |
| Lys-Thr-Lys-Pro-Gln-Tyr-His | Lys-Thr-Lys-Pro-Gln-Tyr-His | Lys-Thr-Lys-Pro-Gln-Tyr-His | 374 |
| Lys-Thr-Lys-Pro-Gln-His-His | Lys-Thr-Lys-Pro-Gln-His-His | Lys-Thr-Lys-Pro-Gln-His-His | 375 |
| Lys-Thr-Lys-Pro-Gln-Pro-His | Lys-Thr-Lys-Pro-Gln-Pro-His | Lys-Thr-Lys-Pro-Gln-Pro-His | 376 |
| Lys-Thr-Lys-Pro-Gln-Lys-His | Lys-Thr-Lys-Pro-Gln-Lys-His | Lys-Thr-Lys-Pro-Gln-Lys-His | 377 |
| Lys-Thr-Lys-Pro-Asn-His | Lys-Thr-Lys-Pro-Asn-His | Lys-Thr-Lys-Pro-Asn-His | 378 |
| Lys-Thr-Lys-Pro-Asn-Arg-His | Lys-Thr-Lys-Pro-Asn-Arg-His | Lys-Thr-Lys-Pro-Asn-Arg-His | 379 |
| Lys-Thr-Lys-Pro-Asn-Phe-His | Lys-Thr-Lys-Pro-Asn-Phe-His | Lys-Thr-Lys-Pro-Asn-Phe-His | 380 |
| Lys-Thr-Lys-Pro-Asn-Tyr-His | Lys-Thr-Lys-Pro-Asn-Tyr-His | Lys-Thr-Lys-Pro-Asn-Tyr-His | 381 |
| Lys-Thr-Lys-Pro-Asn-His-His | Lys-Thr-Lys-Pro-Asn-His-His | Lys-Thr-Lys-Pro-Asn-His-His | 382 |
| Lys-Thr-Lys-Pro-Asn-Pro-His | Lys-Thr-Lys-Pro-Asn-Pro-His | Lys-Thr-Lys-Pro-Asn-Pro-His | 383 |
| Lys-Thr-Lys-Pro-Asn-Lys-His | Lys-Thr-Lys-Pro-Asn-Lys-His | Lys-Thr-Lys-Pro-Asn-Lys-His | 384 |
| Lys-Thr-Lys-Pro-Tyr-His | Lys-Thr-Lys-Pro-Tyr-His | Lys-Thr-Lys-Pro-Tyr-His | 385 |
| Lys-Thr-Lys-Pro-Tyr-Arg-His | Lys-Thr-Lys-Pro-Tyr-Arg-His | Lys-Thr-Lys-Pro-Tyr-Arg-His | 386 |
| Lys-Thr-Lys-Pro-Tyr-Phe-His | Lys-Thr-Lys-Pro-Tyr-Phe-His | Lys-Thr-Lys-Pro-Tyr-Phe-His | 387 |
| Lys-Thr-Lys-Pro-Tyr-Tyr-His | Lys-Thr-Lys-Pro-Tyr-Tyr-His | Lys-Thr-Lys-Pro-Tyr-Tyr-His | 388 |
| Lys-Thr-Lys-Pro-Tyr-His-His | Lys-Thr-Lys-Pro-Tyr-His-His | Lys-Thr-Lys-Pro-Tyr-His-His | 389 |
| Lys-Thr-Lys-Pro-Tyr-Pro-His | Lys-Thr-Lys-Pro-Tyr-Pro-His | Lys-Thr-Lys-Pro-Tyr-Pro-His | 390 |
| Lys-Thr-Lys-Pro-Tyr-Lys-His | Lys-Thr-Lys-Pro-Tyr-Lys-His | Lys-Thr-Lys-Pro-Tyr-Lys-His | 391 |
| Lys-Thr-Lys-Pro-Arg-His | Lys-Thr-Lys-Pro-Arg-His | Lys-Thr-Lys-Pro-Arg-His | 392 |
| Lys-Thr-Lys-Pro-Arg-Arg-His | Lys-Thr-Lys-Pro-Arg-Arg-His | Lys-Thr-Lys-Pro-Arg-Arg-His | 393 |
| Lys-Thr-Lys-Pro-Arg-Phe-His | Lys-Thr-Lys-Pro-Arg-Phe-His | Lys-Thr-Lys-Pro-Arg-Phe-His | 394 |
| Lys-Thr-Lys-Pro-Arg-Tyr-His | Lys-Thr-Lys-Pro-Arg-Tyr-His | Lys-Thr-Lys-Pro-Arg-Tyr-His | 395 |
| Lys-Thr-Lys-Pro-Arg-His-His | Lys-Thr-Lys-Pro-Arg-His-His | Lys-Thr-Lys-Pro-Arg-His-His | 396 |
| Lys-Thr-Lys-Pro-Arg-Pro-His | Lys-Thr-Lys-Pro-Arg-Pro-His | Lys-Thr-Lys-Pro-Arg-Pro-His | 397 |
| Lys-Thr-Lys-Pro-Arg-Lys-His | Lys-Thr-Lys-Pro-Arg-Lys-His | Lys-Thr-Lys-Pro-Arg-Lys-His | 398 |
| Gly-Thr-Lys-Pro-His | Gly-Thr-Lys-Pro-His | Gly-Thr-Lys-Pro-His | 399 |
| Gly-Thr-Lys-Pro-Arg-His | Gly-Thr-Lys-Pro-Arg-His | Gly-Thr-Lys-Pro-Arg-His | 400 |
| Gly-Thr-Lys-Pro-Phe-His | Gly-Thr-Lys-Pro-Phe-His | Gly-Thr-Lys-Pro-Phe-His | 401 |
| Gly-Thr-Lys-Pro-Tyr-His | Gly-Thr-Lys-Pro-Tyr-His | Gly-Thr-Lys-Pro-Tyr-His | 402 |
| Gly-Thr-Lys-Pro-Gly-His | Gly-Thr-Lys-Pro-Gly-His | Gly-Thr-Lys-Pro-Gly-His | 403 |
| Gly-Thr-Lys-Pro-His-His | Gly-Thr-Lys-Pro-His-His | Gly-Thr-Lys-Pro-His-His | 404 |
| Gly-Thr-Lys-Pro-Lys-His | Gly-Thr-Lys-Pro-Lys-His | Gly-Thr-Lys-Pro-Lys-His | 405 |
| Gly-Thr-Lys-Pro-Gly-His | Gly-Thr-Lys-Pro-Gly-His | Gly-Thr-Lys-Pro-Gly-His | 406 |
| Gly-Thr-Lys-Pro-Gly-Arg-His | Gly-Thr-Lys-Pro-Gly-Arg-His | Gly-Thr-Lys-Pro-Gly-Arg-His | 407 |
| Gly-Thr-Lys-Pro-Gly-Phe-His | Gly-Thr-Lys-Pro-Gly-Phe-His | Gly-Thr-Lys-Pro-Gly-Phe-His | 408 |

TABLE 1-continued

| X-OH | X-OCH₃ | X-NH₂ | SEQ ID NO |
|---|---|---|---|
| Gly-Thr-Lys-Pro-Gly-Tyr-His | Gly-Thr-Lys-Pro-Gly-Tyr-His | Gly-Thr-Lys-Pro-Gly-Tyr-His | 409 |
| Gly-Thr-Lys-Pro-Gly-His-His | Gly-Thr-Lys-Pro-Gly-His-His | Gly-Thr-Lys-Pro-Gly-His-His | 410 |
| Gly-Thr-Lys-Pro-Gly-Pro-His | Gly-Thr-Lys-Pro-Gly-Pro-His | Gly-Thr-Lys-Pro-Gly-Pro-His | 411 |
| Gly-Thr-Lys-Pro-Gly-Lys-His | Gly-Thr-Lys-Pro-Gly-Lys-His | Gly-Thr-Lys-Pro-Gly-Lys-His | 412 |
| Gly-Thr-Lys-Pro-Asp-His | Gly-Thr-Lys-Pro-Asp-His | Gly-Thr-Lys-Pro-Asp-His | 413 |
| Gly-Thr-Lys-Pro-Asp-Arg-His | Gly-Thr-Lys-Pro-Asp-Arg-His | Gly-Thr-Lys-Pro-Asp-Arg-His | 414 |
| Gly-Thr-Lys-Pro-Asp-Phe-His | Gly-Thr-Lys-Pro-Asp-Phe-His | Gly-Thr-Lys-Pro-Asp-Phe-His | 415 |
| Gly-Thr-Lys-Pro-Asp-Tyr-His | Gly-Thr-Lys-Pro-Asp-Tyr-His | Gly-Thr-Lys-Pro-Asp-Tyr-His | 416 |
| Gly-Thr-Lys-Pro-Asp-His-His | Gly-Thr-Lys-Pro-Asp-His-His | Gly-Thr-Lys-Pro-Asp-His-His | 417 |
| Gly-Thr-Lys-Pro-Asp-Pro-His | Gly-Thr-Lys-Pro-Asp-Pro-His | Gly-Thr-Lys-Pro-Asp-Pro-His | 418 |
| Gly-Thr-Lys-Pro-Asp-Lys-His | Gly-Thr-Lys-Pro-Asp-Lys-His | Gly-Thr-Lys-Pro-Asp-Lys-His | 419 |
| Gly-Thr-Lys-Pro-Trp-His | Gly-Thr-Lys-Pro-Trp-His | Gly-Thr-Lys-Pro-Trp-His | 420 |
| Gly-Thr-Lys-Pro-Trp-Arg-His | Gly-Thr-Lys-Pro-Trp-Arg-His | Gly-Thr-Lys-Pro-Trp-Arg-His | 421 |
| Gly-Thr-Lys-Pro-Trp-Phe-His | Gly-Thr-Lys-Pro-Trp-Phe-His | Gly-Thr-Lys-Pro-Trp-Phe-His | 422 |
| Gly-Thr-Lys-Pro-Trp-Tyr-His | Gly-Thr-Lys-Pro-Trp-Tyr-His | Gly-Thr-Lys-Pro-Trp-Tyr-His | 423 |
| Gly-Thr-Lys-Pro-Trp-His-His | Gly-Thr-Lys-Pro-Trp-His-His | Gly-Thr-Lys-Pro-Trp-His-His | 424 |
| Gly-Thr-Lys-Pro-Trp-Pro-His | Gly-Thr-Lys-Pro-Trp-Pro-His | Gly-Thr-Lys-Pro-Trp-Pro-His | 425 |
| Gly-Thr-Lys-Pro-Trp-Lys-His | Gly-Thr-Lys-Pro-Trp-Lys-His | Gly-Thr-Lys-Pro-Trp-Lys-His | 426 |
| Gly-Thr-Lys-Pro-Gln-His | Gly-Thr-Lys-Pro-Gln-His | Gly-Thr-Lys-Pro-Gln-His | 427 |
| Gly-Thr-Lys-Pro-Gln-Arg-His | Gly-Thr-Lys-Pro-Gln-Arg-His | Gly-Thr-Lys-Pro-Gln-Arg-His | 428 |
| Gly-Thr-Lys-Pro-Gln-Phe-His | Gly-Thr-Lys-Pro-Gln-Phe-His | Gly-Thr-Lys-Pro-Gln-Phe-His | 429 |
| Gly-Thr-Lys-Pro-Gln-Tyr-His | Gly-Thr-Lys-Pro-Gln-Tyr-His | Gly-Thr-Lys-Pro-Gln-Tyr-His | 430 |
| Gly-Thr-Lys-Pro-Gln-His-His | Gly-Thr-Lys-Pro-Gln-His-His | Gly-Thr-Lys-Pro-Gln-His-His | 431 |
| Gly-Thr-Lys-Pro-Gln-Pro-His | Gly-Thr-Lys-Pro-Gln-Pro-His | Gly-Thr-Lys-Pro-Gln-Pro-His | 432 |
| Gly-Thr-Lys-Pro-Gln-Lys-His | Gly-Thr-Lys-Pro-Gln-Lys-His | Gly-Thr-Lys-Pro-Gln-Lys-His | 433 |
| Gly-Thr-Lys-Pro-Asn-His | Gly-Thr-Lys-Pro-Asn-His | Gly-Thr-Lys-Pro-Asn-His | 434 |
| Gly-Thr-Lys-Pro-Asn-Arg-His | Gly-Thr-Lys-Pro-Asn-Arg-His | Gly-Thr-Lys-Pro-Asn-Arg-His | 435 |
| Gly-Thr-Lys-Pro-Asn-Phe-His | Gly-Thr-Lys-Pro-Asn-Phe-His | Gly-Thr-Lys-Pro-Asn-Phe-His | 436 |
| Gly-Thr-Lys-Pro-Asn-Tyr-His | Gly-Thr-Lys-Pro-Asn-Tyr-His | Gly-Thr-Lys-Pro-Asn-Tyr-His | 437 |
| Gly-Thr-Lys-Pro-Asn-His-His | Gly-Thr-Lys-Pro-Asn-His-His | Gly-Thr-Lys-Pro-Asn-His-His | 438 |
| Gly-Thr-Lys-Pro-Asn-Pro-His | Gly-Thr-Lys-Pro-Asn-Pro-His | Gly-Thr-Lys-Pro-Asn-Pro-His | 439 |
| Gly-Thr-Lys-Pro-Asn-Lys-His | Gly-Thr-Lys-Pro-Asn-Lys-His | Gly-Thr-Lys-Pro-Asn-Lys-His | 440 |
| Gly-Thr-Lys-Pro-Tyr-His | Gly-Thr-Lys-Pro-Tyr-His | Gly-Thr-Lys-Pro-Tyr-His | 441 |
| Gly-Thr-Lys-Pro-Tyr-Arg-His | Gly-Thr-Lys-Pro-Tyr-Arg-His | Gly-Thr-Lys-Pro-Tyr-Arg-His | 442 |
| Gly-Thr-Lys-Pro-Tyr-Phe-His | Gly-Thr-Lys-Pro-Tyr-Phe-His | Gly-Thr-Lys-Pro-Tyr-Phe-His | 443 |
| Gly-Thr-Lys-Pro-Tyr-Tyr-His | Gly-Thr-Lys-Pro-Tyr-Tyr-His | Gly-Thr-Lys-Pro-Tyr-Tyr-His | 444 |
| Gly-Thr-Lys-Pro-Tyr-His-His | Gly-Thr-Lys-Pro-Tyr-His-His | Gly-Thr-Lys-Pro-Tyr-His-His | 445 |
| Gly-Thr-Lys-Pro-Tyr-Pro-His | Gly-Thr-Lys-Pro-Tyr-Pro-His | Gly-Thr-Lys-Pro-Tyr-Pro-His | 446 |

TABLE 1-continued

| X-OH | X-OCH₃ | X-NH₂ | SEQ ID NO |
|---|---|---|---|
| Gly-Thr-Lys-Pro-Tyr-Lys-His | Gly-Thr-Lys-Pro-Tyr-Lys-His | Gly-Thr-Lys-Pro-Tyr-Lys-His | 447 |
| Gly-Thr-Lys-Pro-Arg-His | Gly-Thr-Lys-Pro-Arg-His | Gly-Thr-Lys-Pro-Arg-His | 448 |
| Gly-Thr-Lys-Pro-Arg-Arg-His | Gly-Thr-Lys-Pro-Arg-Arg-His | Gly-Thr-Lys-Pro-Arg-Arg-His | 449 |
| Gly-Thr-Lys-Pro-Arg-Phe-His | Gly-Thr-Lys-Pro-Arg-Phe-His | Gly-Thr-Lys-Pro-Arg-Phe-His | 450 |
| Gly-Thr-Lys-Pro-Arg-Tyr-His | Gly-Thr-Lys-Pro-Arg-Tyr-His | Gly-Thr-Lys-Pro-Arg-Tyr-His | 451 |
| Gly-Thr-Lys-Pro-Arg-His-His | Gly-Thr-Lys-Pro-Arg-His-His | Gly-Thr-Lys-Pro-Arg-His-His | 452 |
| Gly-Thr-Lys-Pro-Arg-Pro-His | Gly-Thr-Lys-Pro-Arg-Pro-His | Gly-Thr-Lys-Pro-Arg-Pro-His | 453 |
| Gly-Thr-Lys-Pro-Arg-Lys-His | Gly-Thr-Lys-Pro-Arg-Lys-His | Gly-Thr-Lys-Pro-Arg-Lys-His | 454 |
| Thr-Lys-Pro | Thr-Lys-Pro | Thr-Lys-Pro | 455 |
| Thr-Lys-Pro-Gly-Arg | Thr-Lys-Pro-Gly-Arg | Thr-Lys-Pro-Gly-Arg | 456 |
| Thr-Lys-Pro-Gly-Phe | Thr-Lys-Pro-Gly-Phe | Thr-Lys-Pro-Gly-Phe | 457 |
| Thr-Lys-Pro-Gly-Tyr | Thr-Lys-Pro-Gly-Tyr | Thr-Lys-Pro-Gly-Tyr | 458 |
| Thr-Lys-Pro-Gly-His | Thr-Lys-Pro-Gly-His | Thr-Lys-Pro-Gly-His | 459 |
| Thr-Lys-Pro-Gly-Pro | Thr-Lys-Pro-Gly-Pro | Thr-Lys-Pro-Gly-Pro | 460 |
| Thr-Lys-Pro-Gly-Lys | Thr-Lys-Pro-Gly-Lys | Thr-Lys-Pro-Gly-Lys | 461 |
| Thr-Lys-Pro-Asp-Arg | Thr-Lys-Pro-Asp-Arg | Thr-Lys-Pro-Asp-Arg | 462 |
| Thr-Lys-Pro-Asp-Phe | Thr-Lys-Pro-Asp-Phe | Thr-Lys-Pro-Asp-Phe | 463 |
| Thr-Lys-Pro-Asp-Tyr | Thr-Lys-Pro-Asp-Tyr | Thr-Lys-Pro-Asp-Tyr | 464 |
| Thr-Lys-Pro-Asp-His | Thr-Lys-Pro-Asp-His | Thr-Lys-Pro-Asp-His | 465 |
| Thr-Lys-Pro-Asp-Pro | Thr-Lys-Pro-Asp-Pro | Thr-Lys-Pro-Asp-Pro | 466 |
| Thr-Lys-Pro-Asp-Lys | Thr-Lys-Pro-Asp-Lys | Thr-Lys-Pro-Asp-Lys | 467 |
| Thr-Lys-Pro-Trp-Arg | Thr-Lys-Pro-Trp-Arg | Thr-Lys-Pro-Trp-Arg | 468 |
| Thr-Lys-Pro-Trp-Phe | Thr-Lys-Pro-Trp-Phe | Thr-Lys-Pro-Trp-Phe | 469 |
| Thr-Lys-Pro-Trp-Tyr | Thr-Lys-Pro-Trp-Tyr | Thr-Lys-Pro-Trp-Tyr | 470 |
| Thr-Lys-Pro-Trp-His | Thr-Lys-Pro-Trp-His | Thr-Lys-Pro-Trp-His | 471 |
| Thr-Lys-Pro-Trp-Pro | Thr-Lys-Pro-Trp-Pro | Thr-Lys-Pro-Trp-Pro | 472 |
| Thr-Lys-Pro-Trp-Lys | Thr-Lys-Pro-Trp-Lys | Thr-Lys-Pro-Trp-Lys | 473 |
| Thr-Lys-Pro-Gln-Arg | Thr-Lys-Pro-Gln-Arg | Thr-Lys-Pro-Gln-Arg | 474 |
| Thr-Lys-Pro-Gln-Phe | Thr-Lys-Pro-Gln-Phe | Thr-Lys-Pro-Gln-Phe | 475 |
| Thr-Lys-Pro-Gln-Tyr | Thr-Lys-Pro-Gln-Tyr | Thr-Lys-Pro-Gln-Tyr | 476 |
| Thr-Lys-Pro-Gln-His | Thr-Lys-Pro-Gln-His | Thr-Lys-Pro-Gln-His | 477 |
| Thr-Lys-Pro-Gln-Pro | Thr-Lys-Pro-Gln-Pro | Thr-Lys-Pro-Gln-Pro | 478 |
| Thr-Lys-Pro-Gln-Lys | Thr-Lys-Pro-Gln-Lys | Thr-Lys-Pro-Gln-Lys | 479 |
| Thr-Lys-Pro-Asn-Arg | Thr-Lys-Pro-Asn-Arg | Thr-Lys-Pro-Asn-Arg | 480 |
| Thr-Lys-Pro-Asn-Phe | Thr-Lys-Pro-Asn-Phe | Thr-Lys-Pro-Asn-Phe | 481 |
| Thr-Lys-Pro-Asn-Tyr | Thr-Lys-Pro-Asn-Tyr | Thr-Lys-Pro-Asn-Tyr | 482 |
| Thr-Lys-Pro-Asn-His | Thr-Lys-Pro-Asn-His | Thr-Lys-Pro-Asn-His | 483 |
| Thr-Lys-Pro-Asn-Pro | Thr-Lys-Pro-Asn-Pro | Thr-Lys-Pro-Asn-Pro | 484 |

TABLE 1-continued

| X-OH | X-OCH₃ | X-NH₂ | SEQ ID NO |
|---|---|---|---|
| Thr-Lys-Pro-Asn-Lys | Thr-Lys-Pro-Asn-Lys | Thr-Lys-Pro-Asn-Lys | 485 |
| Thr-Lys-Pro-Tyr-Arg | Thr-Lys-Pro-Tyr-Arg | Thr-Lys-Pro-Tyr-Arg | 486 |
| Thr-Lys-Pro-Tyr-Phe | Thr-Lys-Pro-Tyr-Phe | Thr-Lys-Pro-Tyr-Phe | 487 |
| Thr-Lys-Pro-Tyr-Tyr | Thr-Lys-Pro-Tyr-Tyr | Thr-Lys-Pro-Tyr-Tyr | 488 |
| Thr-Lys-Pro-Tyr-His | Thr-Lys-Pro-Tyr-His | Thr-Lys-Pro-Tyr-His | 489 |
| Thr-Lys-Pro-Tyr-Pro | Thr-Lys-Pro-Tyr-Pro | Thr-Lys-Pro-Tyr-Pro | 490 |
| Thr-Lys-Pro-Tyr-Lys | Thr-Lys-Pro-Tyr-Lys | Thr-Lys-Pro-Tyr-Lys | 491 |
| Thr-Lys-Pro-Arg-Arg | Thr-Lys-Pro-Arg-Arg | Thr-Lys-Pro-Arg-Arg | 492 |
| Thr-Lys-Pro-Arg-Phe | Thr-Lys-Pro-Arg-Phe | Thr-Lys-Pro-Arg-Phe | 493 |
| Thr-Lys-Pro-Arg-Tyr | Thr-Lys-Pro-Arg-Tyr | Thr-Lys-Pro-Arg-Tyr | 494 |
| Thr-Lys-Pro-Arg-His | Thr-Lys-Pro-Arg-His | Thr-Lys-Pro-Arg-His | 495 |
| Thr-Lys-Pro-Arg-Pro | Thr-Lys-Pro-Arg-Pro | Thr-Lys-Pro-Arg-Pro | 6 |
| Thr-Lys-Pro-Arg-Lys | Thr-Lys-Pro-Arg-Lys | Thr-Lys-Pro-Arg-Lys | 496 |
| Met-Thr-Lys-Pro-Arg | Met-Thr-Lys-Pro-Arg | Met-Thr-Lys-Pro-Arg | 497 |
| Met-Thr-Lys-Pro-Phe | Met-Thr-Lys-Pro-Phe | Met-Thr-Lys-Pro-Phe | 498 |
| Met-Thr-Lys-Pro-Tyr | Met-Thr-Lys-Pro-Tyr | Met-Thr-Lys-Pro-Tyr | 499 |
| Met-Thr-Lys-Pro-Gly | Met-Thr-Lys-Pro-Gly | Met-Thr-Lys-Pro-Gly | 500 |
| Met-Thr-Lys-Pro-His | Met-Thr-Lys-Pro-His | Met-Thr-Lys-Pro-His | 501 |
| Met-Thr-Lys-Pro-Lys | Met-Thr-Lys-Pro-Lys | Met-Thr-Lys-Pro-Lys | 502 |
| Met-Thr-Lys-Pro-Gly | Met-Thr-Lys-Pro-Gly | Met-Thr-Lys-Pro-Gly | 503 |
| Met-Thr-Lys-Pro-Gly-Arg | Met-Thr-Lys-Pro-Gly-Arg | Met-Thr-Lys-Pro-Gly-Arg | 504 |
| Met-Thr-Lys-Pro-Gly-Phe | Met-Thr-Lys-Pro-Gly-Phe | Met-Thr-Lys-Pro-Gly-Phe | 505 |
| Met-Thr-Lys-Pro-Gly-Tyr | Met-Thr-Lys-Pro-Gly-Tyr | Met-Thr-Lys-Pro-Gly-Tyr | 506 |
| Met-Thr-Lys-Pro-Gly-His | Met-Thr-Lys-Pro-Gly-His | Met-Thr-Lys-Pro-Gly-His | 507 |
| Met-Thr-Lys-Pro-Gly-Pro | Met-Thr-Lys-Pro-Gly-Pro | Met-Thr-Lys-Pro-Gly-Pro | 508 |
| Met-Thr-Lys-Pro-Gly-Lys | Met-Thr-Lys-Pro-Gly-Lys | Met-Thr-Lys-Pro-Gly-Lys | 509 |
| Met-Thr-Lys-Pro-Asp | Met-Thr-Lys-Pro-Asp | Met-Thr-Lys-Pro-Asp | 510 |
| Met-Thr-Lys-Pro-Asp-Arg | Met-Thr-Lys-Pro-Asp-Arg | Met-Thr-Lys-Pro-Asp-Arg | 511 |
| Met-Thr-Lys-Pro-Asp-Phe | Met-Thr-Lys-Pro-Asp-Phe | Met-Thr-Lys-Pro-Asp-Phe | 512 |
| Met-Thr-Lys-Pro-Asp-Tyr | Met-Thr-Lys-Pro-Asp-Tyr | Met-Thr-Lys-Pro-Asp-Tyr | 513 |
| Met-Thr-Lys-Pro-Asp-His | Met-Thr-Lys-Pro-Asp-His | Met-Thr-Lys-Pro-Asp-His | 514 |
| Met-Thr-Lys-Pro-Asp-Pro | Met-Thr-Lys-Pro-Asp-Pro | Met-Thr-Lys-Pro-Asp-Pro | 515 |
| Met-Thr-Lys-Pro-Asp-Lys | Met-Thr-Lys-Pro-Asp-Lys | Met-Thr-Lys-Pro-Asp-Lys | 516 |
| Met-Thr-Lys-Pro-Trp | Met-Thr-Lys-Pro-Trp | Met-Thr-Lys-Pro-Trp | 517 |
| Met-Thr-Lys-Pro-Trp-Arg | Met-Thr-Lys-Pro-Trp-Arg | Met-Thr-Lys-Pro-Trp-Arg | 518 |
| Met-Thr-Lys-Pro-Trp-Phe | Met-Thr-Lys-Pro-Trp-Phe | Met-Thr-Lys-Pro-Trp-Phe | 519 |
| Met-Thr-Lys-Pro-Trp-Tyr | Met-Thr-Lys-Pro-Trp-Tyr | Met-Thr-Lys-Pro-Trp-Tyr | 520 |
| Met-Thr-Lys-Pro-Trp-His | Met-Thr-Lys-Pro-Trp-His | Met-Thr-Lys-Pro-Trp-His | 521 |

TABLE 1-continued

| X-OH | X-OCH₃ | X-NH₂ | SEQ ID NO |
|---|---|---|---|
| Met-Thr-Lys-Pro-Trp-Pro | Met-Thr-Lys-Pro-Trp-Pro | Met-Thr-Lys-Pro-Trp-Pro | 522 |
| Met-Thr-Lys-Pro-Trp-Lys | Met-Thr-Lys-Pro-Trp-Lys | Met-Thr-Lys-Pro-Trp-Lys | 523 |
| Met-Thr-Lys-Pro-Gln | Met-Thr-Lys-Pro-Gln | Met-Thr-Lys-Pro-Gln | 524 |
| Met-Thr-Lys-Pro-Gln-Arg | Met-Thr-Lys-Pro-Gln-Arg | Met-Thr-Lys-Pro-Gln-Arg | 525 |
| Met-Thr-Lys-Pro-Gln-Phe | Met-Thr-Lys-Pro-Gln-Phe | Met-Thr-Lys-Pro-Gln-Phe | 526 |
| Met-Thr-Lys-Pro-Gln-Tyr | Met-Thr-Lys-Pro-Gln-Tyr | Met-Thr-Lys-Pro-Gln-Tyr | 527 |
| Met-Thr-Lys-Pro-Gln-His | Met-Thr-Lys-Pro-Gln-His | Met-Thr-Lys-Pro-Gln-His | 528 |
| Met-Thr-Lys-Pro-Gln-Pro | Met-Thr-Lys-Pro-Gln-Pro | Met-Thr-Lys-Pro-Gln-Pro | 529 |
| Met-Thr-Lys-Pro-Gln-Lys | Met-Thr-Lys-Pro-Gln-Lys | Met-Thr-Lys-Pro-Gln-Lys | 530 |
| Met-Thr-Lys-Pro-Asn | Met-Thr-Lys-Pro-Asn | Met-Thr-Lys-Pro-Asn | 531 |
| Met-Thr-Lys-Pro-Asn-Arg | Met-Thr-Lys-Pro-Asn-Arg | Met-Thr-Lys-Pro-Asn-Arg | 532 |
| Met-Thr-Lys-Pro-Asn-Phe | Met-Thr-Lys-Pro-Asn-Phe | Met-Thr-Lys-Pro-Asn-Phe | 533 |
| Met-Thr-Lys-Pro-Asn-Tyr | Met-Thr-Lys-Pro-Asn-Tyr | Met-Thr-Lys-Pro-Asn-Tyr | 534 |
| Met-Thr-Lys-Pro-Asn-His | Met-Thr-Lys-Pro-Asn-His | Met-Thr-Lys-Pro-Asn-His | 535 |
| Met-Thr-Lys-Pro-Asn-Pro | Met-Thr-Lys-Pro-Asn-Pro | Met-Thr-Lys-Pro-Asn-Pro | 536 |
| Met-Thr-Lys-Pro-Asn-Lys | Met-Thr-Lys-Pro-Asn-Lys | Met-Thr-Lys-Pro-Asn-Lys | 537 |
| Met-Thr-Lys-Pro-Tyr | Met-Thr-Lys-Pro-Tyr | Met-Thr-Lys-Pro-Tyr | 538 |
| Met-Thr-Lys-Pro-Tyr-Arg | Met-Thr-Lys-Pro-Tyr-Arg | Met-Thr-Lys-Pro-Tyr-Arg | 539 |
| Met-Thr-Lys-Pro-Tyr-Phe | Met-Thr-Lys-Pro-Tyr-Phe | Met-Thr-Lys-Pro-Tyr-Phe | 540 |
| Met-Thr-Lys-Pro-Tyr-Tyr | Met-Thr-Lys-Pro-Tyr-Tyr | Met-Thr-Lys-Pro-Tyr-Tyr | 541 |
| Met-Thr-Lys-Pro-Tyr-His | Met-Thr-Lys-Pro-Tyr-His | Met-Thr-Lys-Pro-Tyr-His | 542 |
| Met-Thr-Lys-Pro-Tyr-Pro | Met-Thr-Lys-Pro-Tyr-Pro | Met-Thr-Lys-Pro-Tyr-Pro | 543 |
| Met-Thr-Lys-Pro-Tyr-Lys | Met-Thr-Lys-Pro-Tyr-Lys | Met-Thr-Lys-Pro-Tyr-Lys | 544 |
| Met-Thr-Lys-Pro-Arg | Met-Thr-Lys-Pro-Arg | Met-Thr-Lys-Pro-Arg | 545 |
| Met-Thr-Lys-Pro-Arg-Arg | Met-Thr-Lys-Pro-Arg-Arg | Met-Thr-Lys-Pro-Arg-Arg | 546 |
| Met-Thr-Lys-Pro-Arg-Phe | Met-Thr-Lys-Pro-Arg-Phe | Met-Thr-Lys-Pro-Arg-Phe | 547 |
| Met-Thr-Lys-Pro-Arg-Tyr | Met-Thr-Lys-Pro-Arg-Tyr | Met-Thr-Lys-Pro-Arg-Tyr | 548 |
| Met-Thr-Lys-Pro-Arg-His | Met-Thr-Lys-Pro-Arg-His | Met-Thr-Lys-Pro-Arg-His | 549 |
| Met-Thr-Lys-Pro-Arg-Pro | Met-Thr-Lys-Pro-Arg-Pro | Met-Thr-Lys-Pro-Arg-Pro | 550 |
| Met-Thr-Lys-Pro-Arg-Lys | Met-Thr-Lys-Pro-Arg-Lys | Met-Thr-Lys-Pro-Arg-Lys | 551 |
| Met(O)-Thr-Lys-Pro-Arg | Met(O)-Thr-Lys-Pro-Arg | Met(O)-Thr-Lys-Pro-Arg | 552 |
| Met(O)-Thr-Lys-Pro-Phe | Met(O)-Thr-Lys-Pro-Phe | Met(O)-Thr-Lys-Pro-Phe | 553 |
| Met(O)-Thr-Lys-Pro-Tyr | Met(O)-Thr-Lys-Pro-Tyr | Met(O)-Thr-Lys-Pro-Tyr | 554 |
| Met(O)-Thr-Lys-Pro-Gly | Met(O)-Thr-Lys-Pro-Gly | Met(O)-Thr-Lys-Pro-Gly | 555 |
| Met(O)-Thr-Lys-Pro-His | Met(O)-Thr-Lys-Pro-His | Met(O)-Thr-Lys-Pro-His | 556 |
| Met(O)-Thr-Lys-Pro-Lys | Met(O)-Thr-Lys-Pro-Lys | Met(O)-Thr-Lys-Pro-Lys | 557 |
| Met(O)-Thr-Lys-Pro-Gly | Met(O)-Thr-Lys-Pro-Gly | Met(O)-Thr-Lys-Pro-Gly | 558 |
| Met(O)-Thr-Lys-Pro-Gly-Arg | Met(O)-Thr-Lys-Pro-Gly-Arg | Met(O)-Thr-Lys-Pro-Gly-Arg | 559 |

TABLE 1-continued

| X-OH | X-OCH₃ | X-NH₂ | SEQ ID NO |
|---|---|---|---|
| Met(O)-Thr-Lys-Pro-Gly-Phe | Met(O)-Thr-Lys-Pro-Gly-Phe | Met(O)-Thr-Lys-Pro-Gly-Phe | 560 |
| Met(O)-Thr-Lys-Pro-Gly-Tyr | Met(O)-Thr-Lys-Pro-Gly-Tyr | Met(O)-Thr-Lys-Pro-Gly-Tyr | 561 |
| Met(O)-Thr-Lys-Pro-Gly-His | Met(O)-Thr-Lys-Pro-Gly-His | Met(O)-Thr-Lys-Pro-Gly-His | 562 |
| Met(O)-Thr-Lys-Pro-Gly-Pro | Met(O)-Thr-Lys-Pro-Gly-Pro | Met(O)-Thr-Lys-Pro-Gly-Pro | 563 |
| Met(O)-Thr-Lys-Pro-Gly-Lys | Met(O)-Thr-Lys-Pro-Gly-Lys | Met(O)-Thr-Lys-Pro-Gly-Lys | 564 |
| Met(O)-Thr-Lys-Pro-Asp | Met(O)-Thr-Lys-Pro-Asp | Met(O)-Thr-Lys-Pro-Asp | 565 |
| Met(O)-Thr-Lys-Pro-Asp-Arg | Met(O)-Thr-Lys-Pro-Asp-Arg | Met(O)-Thr-Lys-Pro-Asp-Arg | 566 |
| Met(O)-Thr-Lys-Pro-Asp-Phe | Met(O)-Thr-Lys-Pro-Asp-Phe | Met(O)-Thr-Lys-Pro-Asp-Phe | 567 |
| Met(O)-Thr-Lys-Pro-Asp-Tyr | Met(O)-Thr-Lys-Pro-Asp-Tyr | Met(O)-Thr-Lys-Pro-Asp-Tyr | 568 |
| Met(O)-Thr-Lys-Pro-Asp-His | Met(O)-Thr-Lys-Pro-Asp-His | Met(O)-Thr-Lys-Pro-Asp-His | 569 |
| Met(O)-Thr-Lys-Pro-Asp-Pro | Met(O)-Thr-Lys-Pro-Asp-Pro | Met(O)-Thr-Lys-Pro-Asp-Pro | 570 |
| Met(O)-Thr-Lys-Pro-Asp-Lys | Met(O)-Thr-Lys-Pro-Asp-Lys | Met(O)-Thr-Lys-Pro-Asp-Lys | 571 |
| Met(O)-Thr-Lys-Pro-Trp | Met(O)-Thr-Lys-Pro-Trp | Met(O)-Thr-Lys-Pro-Trp | 572 |
| Met(O)-Thr-Lys-Pro-Trp-Arg | Met(O)-Thr-Lys-Pro-Trp-Arg | Met(O)-Thr-Lys-Pro-Trp-Arg | 573 |
| Met(O)-Thr-Lys-Pro-Trp-Phe | Met(O)-Thr-Lys-Pro-Trp-Phe | Met(O)-Thr-Lys-Pro-Trp-Phe | 574 |
| Met(O)-Thr-Lys-Pro-Trp-Tyr | Met(O)-Thr-Lys-Pro-Trp-Tyr | Met(O)-Thr-Lys-Pro-Trp-Tyr | 575 |
| Met(O)-Thr-Lys-Pro-Trp-His | Met(O)-Thr-Lys-Pro-Trp-His | Met(O)-Thr-Lys-Pro-Trp-His | 576 |
| Met(O)-Thr-Lys-Pro-Trp-Pro | Met(O)-Thr-Lys-Pro-Trp-Pro | Met(O)-Thr-Lys-Pro-Trp-Pro | 577 |
| Met(O)-Thr-Lys-Pro-Trp-Lys | Met(O)-Thr-Lys-Pro-Trp-Lys | Met(O)-Thr-Lys-Pro-Trp-Lys | 578 |
| Met(O)-Thr-Lys-Pro-Gln | Met(O)-Thr-Lys-Pro-Gln | Met(O)-Thr-Lys-Pro-Gln | 579 |
| Met(O)-Thr-Lys-Pro-Gln-Arg | Met(O)-Thr-Lys-Pro-Gln-Arg | Met(O)-Thr-Lys-Pro-Gln-Arg | 580 |
| Met(O)-Thr-Lys-Pro-Gln-Phe | Met(O)-Thr-Lys-Pro-Gln-Phe | Met(O)-Thr-Lys-Pro-Gln-Phe | 581 |
| Met(O)-Thr-Lys-Pro-Gln-Tyr | Met(O)-Thr-Lys-Pro-Gln-Tyr | Met(O)-Thr-Lys-Pro-Gln-Tyr | 582 |
| Met(O)-Thr-Lys-Pro-Gln-His | Met(O)-Thr-Lys-Pro-Gln-His | Met(O)-Thr-Lys-Pro-Gln-His | 583 |
| Met(O)-Thr-Lys-Pro-Gln-Pro | Met(O)-Thr-Lys-Pro-Gln-Pro | Met(O)-Thr-Lys-Pro-Gln-Pro | 584 |
| Met(O)-Thr-Lys-Pro-Gln-Lys | Met(O)-Thr-Lys-Pro-Gln-Lys | Met(O)-Thr-Lys-Pro-Gln-Lys | 585 |
| Met(O)-Thr-Lys-Pro-Asn | Met(O)-Thr-Lys-Pro-Asn | Met(O)-Thr-Lys-Pro-Asn | 586 |
| Met(O)-Thr-Lys-Pro-Asn-Arg | Met(O)-Thr-Lys-Pro-Asn-Arg | Met(O)-Thr-Lys-Pro-Asn-Arg | 587 |
| Met(O)-Thr-Lys-Pro-Asn-Phe | Met(O)-Thr-Lys-Pro-Asn-Phe | Met(O)-Thr-Lys-Pro-Asn-Phe | 588 |
| Met(O)-Thr-Lys-Pro-Asn-Tyr | Met(O)-Thr-Lys-Pro-Asn-Tyr | Met(O)-Thr-Lys-Pro-Asn-Tyr | 589 |
| Met(O)-Thr-Lys-Pro-Asn-His | Met(O)-Thr-Lys-Pro-Asn-His | Met(O)-Thr-Lys-Pro-Asn-His | 590 |
| Met(O)-Thr-Lys-Pro-Asn-Pro | Met(O)-Thr-Lys-Pro-Asn-Pro | Met(O)-Thr-Lys-Pro-Asn-Pro | 591 |
| Met(O)-Thr-Lys-Pro-Asn-Lys | Met(O)-Thr-Lys-Pro-Asn-Lys | Met(O)-Thr-Lys-Pro-Asn-Lys | 592 |
| Met(O)-Thr-Lys-Pro-Tyr | Met(O)-Thr-Lys-Pro-Tyr | Met(O)-Thr-Lys-Pro-Tyr | 593 |
| Met(O)-Thr-Lys-Pro-Tyr-Arg | Met(O)-Thr-Lys-Pro-Tyr-Arg | Met(O)-Thr-Lys-Pro-Tyr-Arg | 594 |
| Met(O)-Thr-Lys-Pro-Tyr-Phe | Met(O)-Thr-Lys-Pro-Tyr-Phe | Met(O)-Thr-Lys-Pro-Tyr-Phe | 595 |
| Met(O)-Thr-Lys-Pro-Tyr-Tyr | Met(O)-Thr-Lys-Pro-Tyr-Tyr | Met(O)-Thr-Lys-Pro-Tyr-Tyr | 596 |
| Met(O)-Thr-Lys-Pro-Tyr-His | Met(O)-Thr-Lys-Pro-Tyr-His | Met(O)-Thr-Lys-Pro-Tyr-His | 597 |

TABLE 1-continued

| X-OH | X-OCH₃ | X-NH₂ | SEQ ID NO |
|---|---|---|---|
| Met(O)-Thr-Lys-Pro-Tyr-Pro | Met(O)-Thr-Lys-Pro-Tyr-Pro | Met(O)-Thr-Lys-Pro-Tyr-Pro | 598 |
| Met(O)-Thr-Lys-Pro-Tyr-Lys | Met(O)-Thr-Lys-Pro-Tyr-Lys | Met(O)-Thr-Lys-Pro-Tyr-Lys | 599 |
| Met(O)-Thr-Lys-Pro-Arg | Met(O)-Thr-Lys-Pro-Arg | Met(O)-Thr-Lys-Pro-Arg | 600 |
| Met(O)-Thr-Lys-Pro-Arg-Arg | Met(O)-Thr-Lys-Pro-Arg-Arg | Met(O)-Thr-Lys-Pro-Arg-Arg | 601 |
| Met(O)-Thr-Lys-Pro-Arg-Phe | Met(O)-Thr-Lys-Pro-Arg-Phe | Met(O)-Thr-Lys-Pro-Arg-Phe | 602 |
| Met(O)-Thr-Lys-Pro-Arg-Tyr | Met(O)-Thr-Lys-Pro-Arg-Tyr | Met(O)-Thr-Lys-Pro-Arg-Tyr | 603 |
| Met(O)-Thr-Lys-Pro-Arg-His | Met(O)-Thr-Lys-Pro-Arg-His | Met(O)-Thr-Lys-Pro-Arg-His | 604 |
| Met(O)-Thr-Lys-Pro-Arg-Pro | Met(O)-Thr-Lys-Pro-Arg-Pro | Met(O)-Thr-Lys-Pro-Arg-Pro | 605 |
| Met(O)-Thr-Lys-Pro-Arg-Lys | Met(O)-Thr-Lys-Pro-Arg-Lys | Met(O)-Thr-Lys-Pro-Arg-Lys | 606 |
| Thr-Thr-Lys-Pro-Arg | Thr-Thr-Lys-Pro-Arg | Thr-Thr-Lys-Pro-Arg | 607 |
| Thr-Thr-Lys-Pro-Phe | Thr-Thr-Lys-Pro-Phe | Thr-Thr-Lys-Pro-Phe | 608 |
| Thr-Thr-Lys-Pro-Tyr | Thr-Thr-Lys-Pro-Tyr | Thr-Thr-Lys-Pro-Tyr | 609 |
| Thr-Thr-Lys-Pro-Gly | Thr-Thr-Lys-Pro-Gly | Thr-Thr-Lys-Pro-Gly | 610 |
| Thr-Thr-Lys-Pro-His | Thr-Thr-Lys-Pro-His | Thr-Thr-Lys-Pro-His | 611 |
| Thr-Thr-Lys-Pro-Lys | Thr-Thr-Lys-Pro-Lys | Thr-Thr-Lys-Pro-Lys | 612 |
| Thr-Thr-Lys-Pro-Gly | Thr-Thr-Lys-Pro-Gly | Thr-Thr-Lys-Pro-Gly | 613 |
| Thr-Thr-Lys-Pro-Gly-Arg | Thr-Thr-Lys-Pro-Gly-Arg | Thr-Thr-Lys-Pro-Gly-Arg | 614 |
| Thr-Thr-Lys-Pro-Gly-Phe | Thr-Thr-Lys-Pro-Gly-Phe | Thr-Thr-Lys-Pro-Gly-Phe | 615 |
| Thr-Thr-Lys-Pro-Gly-Tyr | Thr-Thr-Lys-Pro-Gly-Tyr | Thr-Thr-Lys-Pro-Gly-Tyr | 616 |
| Thr-Thr-Lys-Pro-Gly-His | Thr-Thr-Lys-Pro-Gly-His | Thr-Thr-Lys-Pro-Gly-His | 617 |
| Thr-Thr-Lys-Pro-Gly-Pro | Thr-Thr-Lys-Pro-Gly-Pro | Thr-Thr-Lys-Pro-Gly-Pro | 618 |
| Thr-Thr-Lys-Pro-Gly-Lys | Thr-Thr-Lys-Pro-Gly-Lys | Thr-Thr-Lys-Pro-Gly-Lys | 619 |
| Thr-Thr-Lys-Pro-Asp | Thr-Thr-Lys-Pro-Asp | Thr-Thr-Lys-Pro-Asp | 620 |
| Thr-Thr-Lys-Pro-Asp-Arg | Thr-Thr-Lys-Pro-Asp-Arg | Thr-Thr-Lys-Pro-Asp-Arg | 621 |
| Thr-Thr-Lys-Pro-Asp-Phe | Thr-Thr-Lys-Pro-Asp-Phe | Thr-Thr-Lys-Pro-Asp-Phe | 622 |
| Thr-Thr-Lys-Pro-Asp-Tyr | Thr-Thr-Lys-Pro-Asp-Tyr | Thr-Thr-Lys-Pro-Asp-Tyr | 623 |
| Thr-Thr-Lys-Pro-Asp-His | Thr-Thr-Lys-Pro-Asp-His | Thr-Thr-Lys-Pro-Asp-His | 624 |
| Thr-Thr-Lys-Pro-Asp-Pro | Thr-Thr-Lys-Pro-Asp-Pro | Thr-Thr-Lys-Pro-Asp-Pro | 625 |
| Thr-Thr-Lys-Pro-Asp-Lys | Thr-Thr-Lys-Pro-Asp-Lys | Thr-Thr-Lys-Pro-Asp-Lys | 626 |
| Thr-Thr-Lys-Pro-Trp | Thr-Thr-Lys-Pro-Trp | Thr-Thr-Lys-Pro-Trp | 627 |
| Thr-Thr-Lys-Pro-Trp-Arg | Thr-Thr-Lys-Pro-Trp-Arg | Thr-Thr-Lys-Pro-Trp-Arg | 628 |
| Thr-Thr-Lys-Pro-Trp-Phe | Thr-Thr-Lys-Pro-Trp-Phe | Thr-Thr-Lys-Pro-Trp-Phe | 629 |
| Thr-Thr-Lys-Pro-Trp-Tyr | Thr-Thr-Lys-Pro-Trp-Tyr | Thr-Thr-Lys-Pro-Trp-Tyr | 630 |
| Thr-Thr-Lys-Pro-Trp-His | Thr-Thr-Lys-Pro-Trp-His | Thr-Thr-Lys-Pro-Trp-His | 631 |
| Thr-Thr-Lys-Pro-Trp-Pro | Thr-Thr-Lys-Pro-Trp-Pro | Thr-Thr-Lys-Pro-Trp-Pro | 632 |
| Thr-Thr-Lys-Pro-Trp-Lys | Thr-Thr-Lys-Pro-Trp-Lys | Thr-Thr-Lys-Pro-Trp-Lys | 633 |
| Thr-Thr-Lys-Pro-Gln | Thr-Thr-Lys-Pro-Gln | Thr-Thr-Lys-Pro-Gln | 634 |
| Thr-Thr-Lys-Pro-Gln-Arg | Thr-Thr-Lys-Pro-Gln-Arg | Thr-Thr-Lys-Pro-Gln-Arg | 635 |

TABLE 1-continued

| X-OH | X-OCH₃ | X-NH₂ | SEQ ID NO |
|---|---|---|---|
| Thr-Thr-Lys-Pro-Gln-Phe | Thr-Thr-Lys-Pro-Gln-Phe | Thr-Thr-Lys-Pro-Gln-Phe | 636 |
| Thr-Thr-Lys-Pro-Gln-Tyr | Thr-Thr-Lys-Pro-Gln-Tyr | Thr-Thr-Lys-Pro-Gln-Tyr | 637 |
| Thr-Thr-Lys-Pro-Gln-His | Thr-Thr-Lys-Pro-Gln-His | Thr-Thr-Lys-Pro-Gln-His | 638 |
| Thr-Thr-Lys-Pro-Gln-Pro | Thr-Thr-Lys-Pro-Gln-Pro | Thr-Thr-Lys-Pro-Gln-Pro | 639 |
| Thr-Thr-Lys-Pro-Gln-Lys | Thr-Thr-Lys-Pro-Gln-Lys | Thr-Thr-Lys-Pro-Gln-Lys | 640 |
| Thr-Thr-Lys-Pro-Asn | Thr-Thr-Lys-Pro-Asn | Thr-Thr-Lys-Pro-Asn | 641 |
| Thr-Thr-Lys-Pro-Asn-Arg | Thr-Thr-Lys-Pro-Asn-Arg | Thr-Thr-Lys-Pro-Asn-Arg | 642 |
| Thr-Thr-Lys-Pro-Asn-Phe | Thr-Thr-Lys-Pro-Asn-Phe | Thr-Thr-Lys-Pro-Asn-Phe | 643 |
| Thr-Thr-Lys-Pro-Asn-Tyr | Thr-Thr-Lys-Pro-Asn-Tyr | Thr-Thr-Lys-Pro-Asn-Tyr | 644 |
| Thr-Thr-Lys-Pro-Asn-His | Thr-Thr-Lys-Pro-Asn-His | Thr-Thr-Lys-Pro-Asn-His | 645 |
| Thr-Thr-Lys-Pro-Asn-Pro | Thr-Thr-Lys-Pro-Asn-Pro | Thr-Thr-Lys-Pro-Asn-Pro | 646 |
| Thr-Thr-Lys-Pro-Asn-Lys | Thr-Thr-Lys-Pro-Asn-Lys | Thr-Thr-Lys-Pro-Asn-Lys | 647 |
| Thr-Thr-Lys-Pro-Tyr | Thr-Thr-Lys-Pro-Tyr | Thr-Thr-Lys-Pro-Tyr | 648 |
| Thr-Thr-Lys-Pro-Tyr-Arg | Thr-Thr-Lys-Pro-Tyr-Arg | Thr-Thr-Lys-Pro-Tyr-Arg | 649 |
| Thr-Thr-Lys-Pro-Tyr-Phe | Thr-Thr-Lys-Pro-Tyr-Phe | Thr-Thr-Lys-Pro-Tyr-Phe | 650 |
| Thr-Thr-Lys-Pro-Tyr-Tyr | Thr-Thr-Lys-Pro-Tyr-Tyr | Thr-Thr-Lys-Pro-Tyr-Tyr | 651 |
| Thr-Thr-Lys-Pro-Tyr-His | Thr-Thr-Lys-Pro-Tyr-His | Thr-Thr-Lys-Pro-Tyr-His | 652 |
| Thr-Thr-Lys-Pro-Tyr-Pro | Thr-Thr-Lys-Pro-Tyr-Pro | Thr-Thr-Lys-Pro-Tyr-Pro | 653 |
| Thr-Thr-Lys-Pro-Tyr-Lys | Thr-Thr-Lys-Pro-Tyr-Lys | Thr-Thr-Lys-Pro-Tyr-Lys | 654 |
| Thr-Thr-Lys-Pro-Arg | Thr-Thr-Lys-Pro-Arg | Thr-Thr-Lys-Pro-Arg | 655 |
| Thr-Thr-Lys-Pro-Arg-Arg | Thr-Thr-Lys-Pro-Arg-Arg | Thr-Thr-Lys-Pro-Arg-Arg | 656 |
| Thr-Thr-Lys-Pro-Arg-Phe | Thr-Thr-Lys-Pro-Arg-Phe | Thr-Thr-Lys-Pro-Arg-Phe | 657 |
| Thr-Thr-Lys-Pro-Arg-Tyr | Thr-Thr-Lys-Pro-Arg-Tyr | Thr-Thr-Lys-Pro-Arg-Tyr | 658 |
| Thr-Thr-Lys-Pro-Arg-His | Thr-Thr-Lys-Pro-Arg-His | Thr-Thr-Lys-Pro-Arg-His | 659 |
| Thr-Thr-Lys-Pro-Arg-Pro | Thr-Thr-Lys-Pro-Arg-Pro | Thr-Thr-Lys-Pro-Arg-Pro | 660 |
| Thr-Thr-Lys-Pro-Arg-Lys | Thr-Thr-Lys-Pro-Arg-Lys | Thr-Thr-Lys-Pro-Arg-Lys | 661 |
| Ala-Thr-Lys-Pro-Arg | Ala-Thr-Lys-Pro-Arg | Ala-Thr-Lys-Pro-Arg | 662 |
| Ala-Thr-Lys-Pro-Phe | Ala-Thr-Lys-Pro-Phe | Ala-Thr-Lys-Pro-Phe | 663 |
| Ala-Thr-Lys-Pro-Tyr | Ala-Thr-Lys-Pro-Tyr | Ala-Thr-Lys-Pro-Tyr | 664 |
| Ala-Thr-Lys-Pro-Gly | Ala-Thr-Lys-Pro-Gly | Ala-Thr-Lys-Pro-Gly | 665 |
| Ala-Thr-Lys-Pro-His | Ala-Thr-Lys-Pro-His | Ala-Thr-Lys-Pro-His | 666 |
| Ala-Thr-Lys-Pro-Lys | Ala-Thr-Lys-Pro-Lys | Ala-Thr-Lys-Pro-Lys | 667 |
| Ala-Thr-Lys-Pro-Gly | Ala-Thr-Lys-Pro-Gly | Ala-Thr-Lys-Pro-Gly | 668 |
| Ala-Thr-Lys-Pro-Gly-Arg | Ala-Thr-Lys-Pro-Gly-Arg | Ala-Thr-Lys-Pro-Gly-Arg | 669 |
| Ala-Thr-Lys-Pro-Gly-Phe | Ala-Thr-Lys-Pro-Gly-Phe | Ala-Thr-Lys-Pro-Gly-Phe | 670 |
| Ala-Thr-Lys-Pro-Gly-Tyr | Ala-Thr-Lys-Pro-Gly-Tyr | Ala-Thr-Lys-Pro-Gly-Tyr | 671 |
| Ala-Thr-Lys-Pro-Gly-His | Ala-Thr-Lys-Pro-Gly-His | Ala-Thr-Lys-Pro-Gly-His | 672 |
| Ala-Thr-Lys-Pro-Gly-Pro | Ala-Thr-Lys-Pro-Gly-Pro | Ala-Thr-Lys-Pro-Gly-Pro | 673 |

TABLE 1-continued

| X-OH | X-OCH₃ | X-NH₂ | SEQ ID NO |
|---|---|---|---|
| Ala-Thr-Lys-Pro-Gly-Lys | Ala-Thr-Lys-Pro-Gly-Lys | Ala-Thr-Lys-Pro-Gly-Lys | 674 |
| Ala-Thr-Lys-Pro-Asp | Ala-Thr-Lys-Pro-Asp | Ala-Thr-Lys-Pro-Asp | 675 |
| Ala-Thr-Lys-Pro-Asp-Arg | Ala-Thr-Lys-Pro-Asp-Arg | Ala-Thr-Lys-Pro-Asp-Arg | 676 |
| Ala-Thr-Lys-Pro-Asp-Phe | Ala-Thr-Lys-Pro-Asp-Phe | Ala-Thr-Lys-Pro-Asp-Phe | 677 |
| Ala-Thr-Lys-Pro-Asp-Tyr | Ala-Thr-Lys-Pro-Asp-Tyr | Ala-Thr-Lys-Pro-Asp-Tyr | 678 |
| Ala-Thr-Lys-Pro-Asp-His | Ala-Thr-Lys-Pro-Asp-His | Ala-Thr-Lys-Pro-Asp-His | 679 |
| Ala-Thr-Lys-Pro-Asp-Pro | Ala-Thr-Lys-Pro-Asp-Pro | Ala-Thr-Lys-Pro-Asp-Pro | 680 |
| Ala-Thr-Lys-Pro-Asp-Lys | Ala-Thr-Lys-Pro-Asp-Lys | Ala-Thr-Lys-Pro-Asp-Lys | 681 |
| Ala-Thr-Lys-Pro-Trp | Ala-Thr-Lys-Pro-Trp | Ala-Thr-Lys-Pro-Trp | 682 |
| Ala-Thr-Lys-Pro-Trp-Arg | Ala-Thr-Lys-Pro-Trp-Arg | Ala-Thr-Lys-Pro-Trp-Arg | 683 |
| Ala-Thr-Lys-Pro-Trp-Phe | Ala-Thr-Lys-Pro-Trp-Phe | Ala-Thr-Lys-Pro-Trp-Phe | 684 |
| Ala-Thr-Lys-Pro-Trp-Tyr | Ala-Thr-Lys-Pro-Trp-Tyr | Ala-Thr-Lys-Pro-Trp-Tyr | 685 |
| Ala-Thr-Lys-Pro-Trp-His | Ala-Thr-Lys-Pro-Trp-His | Ala-Thr-Lys-Pro-Trp-His | 686 |
| Ala-Thr-Lys-Pro-Trp-Pro | Ala-Thr-Lys-Pro-Trp-Pro | Ala-Thr-Lys-Pro-Trp-Pro | 687 |
| Ala-Thr-Lys-Pro-Trp-Lys | Ala-Thr-Lys-Pro-Trp-Lys | Ala-Thr-Lys-Pro-Trp-Lys | 688 |
| Ala-Thr-Lys-Pro-Gln | Ala-Thr-Lys-Pro-Gln | Ala-Thr-Lys-Pro-Gln | 689 |
| Ala-Thr-Lys-Pro-Gln-Arg | Ala-Thr-Lys-Pro-Gln-Arg | Ala-Thr-Lys-Pro-Gln-Arg | 690 |
| Ala-Thr-Lys-Pro-Gln-Phe | Ala-Thr-Lys-Pro-Gln-Phe | Ala-Thr-Lys-Pro-Gln-Phe | 691 |
| Ala-Thr-Lys-Pro-Gln-Tyr | Ala-Thr-Lys-Pro-Gln-Tyr | Ala-Thr-Lys-Pro-Gln-Tyr | 692 |
| Ala-Thr-Lys-Pro-Gln-His | Ala-Thr-Lys-Pro-Gln-His | Ala-Thr-Lys-Pro-Gln-His | 693 |
| Ala-Thr-Lys-Pro-Gln-Pro | Ala-Thr-Lys-Pro-Gln-Pro | Ala-Thr-Lys-Pro-Gln-Pro | 694 |
| Ala-Thr-Lys-Pro-Gln-Lys | Ala-Thr-Lys-Pro-Gln-Lys | Ala-Thr-Lys-Pro-Gln-Lys | 695 |
| Ala-Thr-Lys-Pro-Asn | Ala-Thr-Lys-Pro-Asn | Ala-Thr-Lys-Pro-Asn | 696 |
| Ala-Thr-Lys-Pro-Asn-Arg | Ala-Thr-Lys-Pro-Asn-Arg | Ala-Thr-Lys-Pro-Asn-Arg | 697 |
| Ala-Thr-Lys-Pro-Asn-Phe | Ala-Thr-Lys-Pro-Asn-Phe | Ala-Thr-Lys-Pro-Asn-Phe | 698 |
| Ala-Thr-Lys-Pro-Asn-Tyr | Ala-Thr-Lys-Pro-Asn-Tyr | Ala-Thr-Lys-Pro-Asn-Tyr | 699 |
| Ala-Thr-Lys-Pro-Asn-His | Ala-Thr-Lys-Pro-Asn-His | Ala-Thr-Lys-Pro-Asn-His | 700 |
| Ala-Thr-Lys-Pro-Asn-Pro | Ala-Thr-Lys-Pro-Asn-Pro | Ala-Thr-Lys-Pro-Asn-Pro | 701 |
| Ala-Thr-Lys-Pro-Asn-Lys | Ala-Thr-Lys-Pro-Asn-Lys | Ala-Thr-Lys-Pro-Asn-Lys | 702 |
| Ala-Thr-Lys-Pro-Tyr | Ala-Thr-Lys-Pro-Tyr | Ala-Thr-Lys-Pro-Tyr | 703 |
| Ala-Thr-Lys-Pro-Tyr-Arg | Ala-Thr-Lys-Pro-Tyr-Arg | Ala-Thr-Lys-Pro-Tyr-Arg | 704 |
| Ala-Thr-Lys-Pro-Tyr-Phe | Ala-Thr-Lys-Pro-Tyr-Phe | Ala-Thr-Lys-Pro-Tyr-Phe | 705 |
| Ala-Thr-Lys-Pro-Tyr-Tyr | Ala-Thr-Lys-Pro-Tyr-Tyr | Ala-Thr-Lys-Pro-Tyr-Tyr | 706 |
| Ala-Thr-Lys-Pro-Tyr-His | Ala-Thr-Lys-Pro-Tyr-His | Ala-Thr-Lys-Pro-Tyr-His | 707 |
| Ala-Thr-Lys-Pro-Tyr-Pro | Ala-Thr-Lys-Pro-Tyr-Pro | Ala-Thr-Lys-Pro-Tyr-Pro | 708 |
| Ala-Thr-Lys-Pro-Tyr-Lys | Ala-Thr-Lys-Pro-Tyr-Lys | Ala-Thr-Lys-Pro-Tyr-Lys | 709 |
| Ala-Thr-Lys-Pro-Arg | Ala-Thr-Lys-Pro-Arg | Ala-Thr-Lys-Pro-Arg | 710 |
| Ala-Thr-Lys-Pro-Arg-Arg | Ala-Thr-Lys-Pro-Arg-Arg | Ala-Thr-Lys-Pro-Arg-Arg | 711 |

TABLE 1-continued

| X-OH | X-OCH₃ | X-NH₂ | SEQ ID NO |
|---|---|---|---|
| Ala-Thr-Lys-Pro-Arg-Phe | Ala-Thr-Lys-Pro-Arg-Phe | Ala-Thr-Lys-Pro-Arg-Phe | 712 |
| Ala-Thr-Lys-Pro-Arg-Tyr | Ala-Thr-Lys-Pro-Arg-Tyr | Ala-Thr-Lys-Pro-Arg-Tyr | 713 |
| Ala-Thr-Lys-Pro-Arg-His | Ala-Thr-Lys-Pro-Arg-His | Ala-Thr-Lys-Pro-Arg-His | 714 |
| Ala-Thr-Lys-Pro-Arg-Pro | Ala-Thr-Lys-Pro-Arg-Pro | Ala-Thr-Lys-Pro-Arg-Pro | 715 |
| Ala-Thr-Lys-Pro-Arg-Lys | Ala-Thr-Lys-Pro-Arg-Lys | Ala-Thr-Lys-Pro-Arg-Lys | 716 |
| His-Thr-Lys-Pro-Arg | His-Thr-Lys-Pro-Arg | His-Thr-Lys-Pro-Arg | 717 |
| His-Thr-Lys-Pro-Phe | His-Thr-Lys-Pro-Phe | His-Thr-Lys-Pro-Phe | 718 |
| His-Thr-Lys-Pro-Tyr | His-Thr-Lys-Pro-Tyr | His-Thr-Lys-Pro-Tyr | 719 |
| His-Thr-Lys-Pro-Gly | His-Thr-Lys-Pro-Gly | His-Thr-Lys-Pro-Gly | 720 |
| His-Thr-Lys-Pro-His | His-Thr-Lys-Pro-His | His-Thr-Lys-Pro-His | 721 |
| His-Thr-Lys-Pro-Lys | His-Thr-Lys-Pro-Lys | His-Thr-Lys-Pro-Lys | 722 |
| His-Thr-Lys-Pro-Gly | His-Thr-Lys-Pro-Gly | His-Thr-Lys-Pro-Gly | 723 |
| His-Thr-Lys-Pro-Gly-Arg | His-Thr-Lys-Pro-Gly-Arg | His-Thr-Lys-Pro-Gly-Arg | 724 |
| His-Thr-Lys-Pro-Gly-Phe | His-Thr-Lys-Pro-Gly-Phe | His-Thr-Lys-Pro-Gly-Phe | 725 |
| His-Thr-Lys-Pro-Gly-Tyr | His-Thr-Lys-Pro-Gly-Tyr | His-Thr-Lys-Pro-Gly-Tyr | 726 |
| His-Thr-Lys-Pro-Gly-His | His-Thr-Lys-Pro-Gly-His | His-Thr-Lys-Pro-Gly-His | 727 |
| His-Thr-Lys-Pro-Gly-Pro | His-Thr-Lys-Pro-Gly-Pro | His-Thr-Lys-Pro-Gly-Pro | 728 |
| His-Thr-Lys-Pro-Gly-Lys | His-Thr-Lys-Pro-Gly-Lys | His-Thr-Lys-Pro-Gly-Lys | 729 |
| His-Thr-Lys-Pro-Asp | His-Thr-Lys-Pro-Asp | His-Thr-Lys-Pro-Asp | 730 |
| His-Thr-Lys-Pro-Asp-Arg | His-Thr-Lys-Pro-Asp-Arg | His-Thr-Lys-Pro-Asp-Arg | 731 |
| His-Thr-Lys-Pro-Asp-Phe | His-Thr-Lys-Pro-Asp-Phe | His-Thr-Lys-Pro-Asp-Phe | 732 |
| His-Thr-Lys-Pro-Asp-Tyr | His-Thr-Lys-Pro-Asp-Tyr | His-Thr-Lys-Pro-Asp-Tyr | 733 |
| His-Thr-Lys-Pro-Asp-His | His-Thr-Lys-Pro-Asp-His | His-Thr-Lys-Pro-Asp-His | 734 |
| His-Thr-Lys-Pro-Asp-Pro | His-Thr-Lys-Pro-Asp-Pro | His-Thr-Lys-Pro-Asp-Pro | 735 |
| His-Thr-Lys-Pro-Asp-Lys | His-Thr-Lys-Pro-Asp-Lys | His-Thr-Lys-Pro-Asp-Lys | 736 |
| His-Thr-Lys-Pro-Trp | His-Thr-Lys-Pro-Trp | His-Thr-Lys-Pro-Trp | 737 |
| His-Thr-Lys-Pro-Trp-Arg | His-Thr-Lys-Pro-Trp-Arg | His-Thr-Lys-Pro-Trp-Arg | 738 |
| His-Thr-Lys-Pro-Trp-Phe | His-Thr-Lys-Pro-Trp-Phe | His-Thr-Lys-Pro-Trp-Phe | 739 |
| His-Thr-Lys-Pro-Trp-Tyr | His-Thr-Lys-Pro-Trp-Tyr | His-Thr-Lys-Pro-Trp-Tyr | 740 |
| His-Thr-Lys-Pro-Trp-His | His-Thr-Lys-Pro-Trp-His | His-Thr-Lys-Pro-Trp-His | 741 |
| His-Thr-Lys-Pro-Trp-Pro | His-Thr-Lys-Pro-Trp-Pro | His-Thr-Lys-Pro-Trp-Pro | 742 |
| His-Thr-Lys-Pro-Trp-Lys | His-Thr-Lys-Pro-Trp-Lys | His-Thr-Lys-Pro-Trp-Lys | 743 |
| His-Thr-Lys-Pro-Gln | His-Thr-Lys-Pro-Gln | His-Thr-Lys-Pro-Gln | 744 |
| His-Thr-Lys-Pro-Gln-Arg | His-Thr-Lys-Pro-Gln-Arg | His-Thr-Lys-Pro-Gln-Arg | 745 |
| His-Thr-Lys-Pro-Gln-Phe | His-Thr-Lys-Pro-Gln-Phe | His-Thr-Lys-Pro-Gln-Phe | 746 |
| His-Thr-Lys-Pro-Gln-Tyr | His-Thr-Lys-Pro-Gln-Tyr | His-Thr-Lys-Pro-Gln-Tyr | 747 |
| His-Thr-Lys-Pro-Gln-His | His-Thr-Lys-Pro-Gln-His | His-Thr-Lys-Pro-Gln-His | 748 |
| His-Thr-Lys-Pro-Gln-Pro | His-Thr-Lys-Pro-Gln-Pro | His-Thr-Lys-Pro-Gln-Pro | 749 |

TABLE 1-continued

| X-OH | X-OCH₃ | X-NH₂ | SEQ ID NO |
|---|---|---|---|
| His-Thr-Lys-Pro-Gln-Lys | His-Thr-Lys-Pro-Gln-Lys | His-Thr-Lys-Pro-Gln-Lys | 750 |
| His-Thr-Lys-Pro-Asn | His-Thr-Lys-Pro-Asn | His-Thr-Lys-Pro-Asn | 751 |
| His-Thr-Lys-Pro-Asn-Arg | His-Thr-Lys-Pro-Asn-Arg | His-Thr-Lys-Pro-Asn-Arg | 752 |
| His-Thr-Lys-Pro-Asn-Phe | His-Thr-Lys-Pro-Asn-Phe | His-Thr-Lys-Pro-Asn-Phe | 753 |
| His-Thr-Lys-Pro-Asn-Tyr | His-Thr-Lys-Pro-Asn-Tyr | His-Thr-Lys-Pro-Asn-Tyr | 754 |
| His-Thr-Lys-Pro-Asn-His | His-Thr-Lys-Pro-Asn-His | His-Thr-Lys-Pro-Asn-His | 755 |
| His-Thr-Lys-Pro-Asn-Pro | His-Thr-Lys-Pro-Asn-Pro | His-Thr-Lys-Pro-Asn-Pro | 756 |
| His-Thr-Lys-Pro-Asn-Lys | His-Thr-Lys-Pro-Asn-Lys | His-Thr-Lys-Pro-Asn-Lys | 757 |
| His-Thr-Lys-Pro-Tyr | His-Thr-Lys-Pro-Tyr | His-Thr-Lys-Pro-Tyr | 758 |
| His-Thr-Lys-Pro-Tyr-Arg | His-Thr-Lys-Pro-Tyr-Arg | His-Thr-Lys-Pro-Tyr-Arg | 759 |
| His-Thr-Lys-Pro-Tyr-Phe | His-Thr-Lys-Pro-Tyr-Phe | His-Thr-Lys-Pro-Tyr-Phe | 760 |
| His-Thr-Lys-Pro-Tyr-Tyr | His-Thr-Lys-Pro-Tyr-Tyr | His-Thr-Lys-Pro-Tyr-Tyr | 761 |
| His-Thr-Lys-Pro-Tyr-His | His-Thr-Lys-Pro-Tyr-His | His-Thr-Lys-Pro-Tyr-His | 762 |
| His-Thr-Lys-Pro-Tyr-Pro | His-Thr-Lys-Pro-Tyr-Pro | His-Thr-Lys-Pro-Tyr-Pro | 763 |
| His-Thr-Lys-Pro-Tyr-Lys | His-Thr-Lys-Pro-Tyr-Lys | His-Thr-Lys-Pro-Tyr-Lys | 764 |
| His-Thr-Lys-Pro-Arg | His-Thr-Lys-Pro-Arg | His-Thr-Lys-Pro-Arg | 765 |
| His-Thr-Lys-Pro-Arg-Arg | His-Thr-Lys-Pro-Arg-Arg | His-Thr-Lys-Pro-Arg-Arg | 766 |
| His-Thr-Lys-Pro-Arg-Phe | His-Thr-Lys-Pro-Arg-Phe | His-Thr-Lys-Pro-Arg-Phe | 767 |
| His-Thr-Lys-Pro-Arg-Tyr | His-Thr-Lys-Pro-Arg-Tyr | His-Thr-Lys-Pro-Arg-Tyr | 768 |
| His-Thr-Lys-Pro-Arg-His | His-Thr-Lys-Pro-Arg-His | His-Thr-Lys-Pro-Arg-His | 769 |
| His-Thr-Lys-Pro-Arg-Pro | His-Thr-Lys-Pro-Arg-Pro | His-Thr-Lys-Pro-Arg-Pro | 770 |
| His-Thr-Lys-Pro-Arg-Lys | His-Thr-Lys-Pro-Arg-Lys | His-Thr-Lys-Pro-Arg-Lys | 771 |
| Lys-Thr-Lys-Pro-Arg | Lys-Thr-Lys-Pro-Arg | Lys-Thr-Lys-Pro-Arg | 772 |
| Lys-Thr-Lys-Pro-Phe | Lys-Thr-Lys-Pro-Phe | Lys-Thr-Lys-Pro-Phe | 773 |
| Lys-Thr-Lys-Pro-Tyr | Lys-Thr-Lys-Pro-Tyr | Lys-Thr-Lys-Pro-Tyr | 774 |
| Lys-Thr-Lys-Pro-Gly | Lys-Thr-Lys-Pro-Gly | Lys-Thr-Lys-Pro-Gly | 775 |
| Lys-Thr-Lys-Pro-His | Lys-Thr-Lys-Pro-His | Lys-Thr-Lys-Pro-His | 776 |
| Lys-Thr-Lys-Pro-Lys | Lys-Thr-Lys-Pro-Lys | Lys-Thr-Lys-Pro-Lys | 777 |
| Lys-Thr-Lys-Pro-Gly | Lys-Thr-Lys-Pro-Gly | Lys-Thr-Lys-Pro-Gly | 778 |
| Lys-Thr-Lys-Pro-Gly-Arg | Lys-Thr-Lys-Pro-Gly-Arg | Lys-Thr-Lys-Pro-Gly-Arg | 779 |
| Lys-Thr-Lys-Pro-Gly-Phe | Lys-Thr-Lys-Pro-Gly-Phe | Lys-Thr-Lys-Pro-Gly-Phe | 780 |
| Lys-Thr-Lys-Pro-Gly-Tyr | Lys-Thr-Lys-Pro-Gly-Tyr | Lys-Thr-Lys-Pro-Gly-Tyr | 781 |
| Lys-Thr-Lys-Pro-Gly-His | Lys-Thr-Lys-Pro-Gly-His | Lys-Thr-Lys-Pro-Gly-His | 782 |
| Lys-Thr-Lys-Pro-Gly-Pro | Lys-Thr-Lys-Pro-Gly-Pro | Lys-Thr-Lys-Pro-Gly-Pro | 783 |
| Lys-Thr-Lys-Pro-Gly-Lys | Lys-Thr-Lys-Pro-Gly-Lys | Lys-Thr-Lys-Pro-Gly-Lys | 784 |
| Lys-Thr-Lys-Pro-Asp | Lys-Thr-Lys-Pro-Asp | Lys-Thr-Lys-Pro-Asp | 785 |
| Lys-Thr-Lys-Pro-Asp-Arg | Lys-Thr-Lys-Pro-Asp-Arg | Lys-Thr-Lys-Pro-Asp-Arg | 786 |
| Lys-Thr-Lys-Pro-Asp-Phe | Lys-Thr-Lys-Pro-Asp-Phe | Lys-Thr-Lys-Pro-Asp-Phe | 787 |

TABLE 1-continued

| X-OH | X-OCH₃ | X-NH₂ | SEQ ID NO |
|---|---|---|---|
| Lys-Thr-Lys-Pro-Asp-Tyr | Lys-Thr-Lys-Pro-Asp-Tyr | Lys-Thr-Lys-Pro-Asp-Tyr | 788 |
| Lys-Thr-Lys-Pro-Asp-His | Lys-Thr-Lys-Pro-Asp-His | Lys-Thr-Lys-Pro-Asp-His | 789 |
| Lys-Thr-Lys-Pro-Asp-Pro | Lys-Thr-Lys-Pro-Asp-Pro | Lys-Thr-Lys-Pro-Asp-Pro | 790 |
| Lys-Thr-Lys-Pro-Asp-Lys | Lys-Thr-Lys-Pro-Asp-Lys | Lys-Thr-Lys-Pro-Asp-Lys | 791 |
| Lys-Thr-Lys-Pro-Trp | Lys-Thr-Lys-Pro-Trp | Lys-Thr-Lys-Pro-Trp | 792 |
| Lys-Thr-Lys-Pro-Trp-Arg | Lys-Thr-Lys-Pro-Trp-Arg | Lys-Thr-Lys-Pro-Trp-Arg | 793 |
| Lys-Thr-Lys-Pro-Trp-Phe | Lys-Thr-Lys-Pro-Trp-Phe | Lys-Thr-Lys-Pro-Trp-Phe | 794 |
| Lys-Thr-Lys-Pro-Trp-Tyr | Lys-Thr-Lys-Pro-Trp-Tyr | Lys-Thr-Lys-Pro-Trp-Tyr | 795 |
| Lys-Thr-Lys-Pro-Trp-His | Lys-Thr-Lys-Pro-Trp-His | Lys-Thr-Lys-Pro-Trp-His | 796 |
| Lys-Thr-Lys-Pro-Trp-Pro | Lys-Thr-Lys-Pro-Trp-Pro | Lys-Thr-Lys-Pro-Trp-Pro | 797 |
| Lys-Thr-Lys-Pro-Trp-Lys | Lys-Thr-Lys-Pro-Trp-Lys | Lys-Thr-Lys-Pro-Trp-Lys | 798 |
| Lys-Thr-Lys-Pro-Gln | Lys-Thr-Lys-Pro-Gln | Lys-Thr-Lys-Pro-Gln | 799 |
| Lys-Thr-Lys-Pro-Gln-Arg | Lys-Thr-Lys-Pro-Gln-Arg | Lys-Thr-Lys-Pro-Gln-Arg | 800 |
| Lys-Thr-Lys-Pro-Gln-Phe | Lys-Thr-Lys-Pro-Gln-Phe | Lys-Thr-Lys-Pro-Gln-Phe | 801 |
| Lys-Thr-Lys-Pro-Gln-Tyr | Lys-Thr-Lys-Pro-Gln-Tyr | Lys-Thr-Lys-Pro-Gln-Tyr | 802 |
| Lys-Thr-Lys-Pro-Gln-His | Lys-Thr-Lys-Pro-Gln-His | Lys-Thr-Lys-Pro-Gln-His | 803 |
| Lys-Thr-Lys-Pro-Gln-Pro | Lys-Thr-Lys-Pro-Gln-Pro | Lys-Thr-Lys-Pro-Gln-Pro | 804 |
| Lys-Thr-Lys-Pro-Gln-Lys | Lys-Thr-Lys-Pro-Gln-Lys | Lys-Thr-Lys-Pro-Gln-Lys | 805 |
| Lys-Thr-Lys-Pro-Asn | Lys-Thr-Lys-Pro-Asn | Lys-Thr-Lys-Pro-Asn | 806 |
| Lys-Thr-Lys-Pro-Asn-Arg | Lys-Thr-Lys-Pro-Asn-Arg | Lys-Thr-Lys-Pro-Asn-Arg | 807 |
| Lys-Thr-Lys-Pro-Asn-Phe | Lys-Thr-Lys-Pro-Asn-Phe | Lys-Thr-Lys-Pro-Asn-Phe | 808 |
| Lys-Thr-Lys-Pro-Asn-Tyr | Lys-Thr-Lys-Pro-Asn-Tyr | Lys-Thr-Lys-Pro-Asn-Tyr | 809 |
| Lys-Thr-Lys-Pro-Asn-His | Lys-Thr-Lys-Pro-Asn-His | Lys-Thr-Lys-Pro-Asn-His | 810 |
| Lys-Thr-Lys-Pro-Asn-Pro | Lys-Thr-Lys-Pro-Asn-Pro | Lys-Thr-Lys-Pro-Asn-Pro | 811 |
| Lys-Thr-Lys-Pro-Asn-Lys | Lys-Thr-Lys-Pro-Asn-Lys | Lys-Thr-Lys-Pro-Asn-Lys | 812 |
| Lys-Thr-Lys-Pro-Tyr | Lys-Thr-Lys-Pro-Tyr | Lys-Thr-Lys-Pro-Tyr | 813 |
| Lys-Thr-Lys-Pro-Tyr-Arg | Lys-Thr-Lys-Pro-Tyr-Arg | Lys-Thr-Lys-Pro-Tyr-Arg | 814 |
| Lys-Thr-Lys-Pro-Tyr-Phe | Lys-Thr-Lys-Pro-Tyr-Phe | Lys-Thr-Lys-Pro-Tyr-Phe | 815 |
| Lys-Thr-Lys-Pro-Tyr-Tyr | Lys-Thr-Lys-Pro-Tyr-Tyr | Lys-Thr-Lys-Pro-Tyr-Tyr | 816 |
| Lys-Thr-Lys-Pro-Tyr-His | Lys-Thr-Lys-Pro-Tyr-His | Lys-Thr-Lys-Pro-Tyr-His | 817 |
| Lys-Thr-Lys-Pro-Tyr-Pro | Lys-Thr-Lys-Pro-Tyr-Pro | Lys-Thr-Lys-Pro-Tyr-Pro | 818 |
| Lys-Thr-Lys-Pro-Tyr-Lys | Lys-Thr-Lys-Pro-Tyr-Lys | Lys-Thr-Lys-Pro-Tyr-Lys | 819 |
| Lys-Thr-Lys-Pro-Arg | Lys-Thr-Lys-Pro-Arg | Lys-Thr-Lys-Pro-Arg | 820 |
| Lys-Thr-Lys-Pro-Arg-Arg | Lys-Thr-Lys-Pro-Arg-Arg | Lys-Thr-Lys-Pro-Arg-Arg | 821 |
| Lys-Thr-Lys-Pro-Arg-Phe | Lys-Thr-Lys-Pro-Arg-Phe | Lys-Thr-Lys-Pro-Arg-Phe | 822 |
| Lys-Thr-Lys-Pro-Arg-Tyr | Lys-Thr-Lys-Pro-Arg-Tyr | Lys-Thr-Lys-Pro-Arg-Tyr | 823 |
| Lys-Thr-Lys-Pro-Arg-His | Lys-Thr-Lys-Pro-Arg-His | Lys-Thr-Lys-Pro-Arg-His | 824 |
| Lys-Thr-Lys-Pro-Arg-Pro | Lys-Thr-Lys-Pro-Arg-Pro | Lys-Thr-Lys-Pro-Arg-Pro | 825 |

TABLE 1-continued

| X-OH | X-OCH₃ | X-NH₂ | SEQ ID NO |
|---|---|---|---|
| Lys-Thr-Lys-Pro-Arg-Lys | Lys-Thr-Lys-Pro-Arg-Lys | Lys-Thr-Lys-Pro-Arg-Lys | 826 |
| Gly-Thr-Lys-Pro-Arg | Gly-Thr-Lys-Pro-Arg | Gly-Thr-Lys-Pro-Arg | 827 |
| Gly-Thr-Lys-Pro-Phe | Gly-Thr-Lys-Pro-Phe | Gly-Thr-Lys-Pro-Phe | 828 |
| Gly-Thr-Lys-Pro-Tyr | Gly-Thr-Lys-Pro-Tyr | Gly-Thr-Lys-Pro-Tyr | 829 |
| Gly-Thr-Lys-Pro-Gly | Gly-Thr-Lys-Pro-Gly | Gly-Thr-Lys-Pro-Gly | 830 |
| Gly-Thr-Lys-Pro-His | Gly-Thr-Lys-Pro-His | Gly-Thr-Lys-Pro-His | 831 |
| Gly-Thr-Lys-Pro-Lys | Gly-Thr-Lys-Pro-Lys | Gly-Thr-Lys-Pro-Lys | 832 |
| Gly-Thr-Lys-Pro-Gly | Gly-Thr-Lys-Pro-Gly | Gly-Thr-Lys-Pro-Gly | 833 |
| Gly-Thr-Lys-Pro-Gly-Arg | Gly-Thr-Lys-Pro-Gly-Arg | Gly-Thr-Lys-Pro-Gly-Arg | 834 |
| Gly-Thr-Lys-Pro-Gly-Phe | Gly-Thr-Lys-Pro-Gly-Phe | Gly-Thr-Lys-Pro-Gly-Phe | 835 |
| Gly-Thr-Lys-Pro-Gly-Tyr | Gly-Thr-Lys-Pro-Gly-Tyr | Gly-Thr-Lys-Pro-Gly-Tyr | 836 |
| Gly-Thr-Lys-Pro-Gly-His | Gly-Thr-Lys-Pro-Gly-His | Gly-Thr-Lys-Pro-Gly-His | 837 |
| Gly-Thr-Lys-Pro-Gly-Pro | Gly-Thr-Lys-Pro-Gly-Pro | Gly-Thr-Lys-Pro-Gly-Pro | 838 |
| Gly-Thr-Lys-Pro-Gly-Lys | Gly-Thr-Lys-Pro-Gly-Lys | Gly-Thr-Lys-Pro-Gly-Lys | 839 |
| Gly-Thr-Lys-Pro-Asp | Gly-Thr-Lys-Pro-Asp | Gly-Thr-Lys-Pro-Asp | 840 |
| Gly-Thr-Lys-Pro-Asp-Arg | Gly-Thr-Lys-Pro-Asp-Arg | Gly-Thr-Lys-Pro-Asp-Arg | 841 |
| Gly-Thr-Lys-Pro-Asp-Phe | Gly-Thr-Lys-Pro-Asp-Phe | Gly-Thr-Lys-Pro-Asp-Phe | 842 |
| Gly-Thr-Lys-Pro-Asp-Tyr | Gly-Thr-Lys-Pro-Asp-Tyr | Gly-Thr-Lys-Pro-Asp-Tyr | 843 |
| Gly-Thr-Lys-Pro-Asp-His | Gly-Thr-Lys-Pro-Asp-His | Gly-Thr-Lys-Pro-Asp-His | 844 |
| Gly-Thr-Lys-Pro-Asp-Pro | Gly-Thr-Lys-Pro-Asp-Pro | Gly-Thr-Lys-Pro-Asp-Pro | 845 |
| Gly-Thr-Lys-Pro-Asp-Lys | Gly-Thr-Lys-Pro-Asp-Lys | Gly-Thr-Lys-Pro-Asp-Lys | 846 |
| Gly-Thr-Lys-Pro-Trp | Gly-Thr-Lys-Pro-Trp | Gly-Thr-Lys-Pro-Trp | 847 |
| Gly-Thr-Lys-Pro-Trp-Arg | Gly-Thr-Lys-Pro-Trp-Arg | Gly-Thr-Lys-Pro-Trp-Arg | 848 |
| Gly-Thr-Lys-Pro-Trp-Phe | Gly-Thr-Lys-Pro-Trp-Phe | Gly-Thr-Lys-Pro-Trp-Phe | 849 |
| Gly-Thr-Lys-Pro-Trp-Tyr | Gly-Thr-Lys-Pro-Trp-Tyr | Gly-Thr-Lys-Pro-Trp-Tyr | 850 |
| Gly-Thr-Lys-Pro-Trp-His | Gly-Thr-Lys-Pro-Trp-His | Gly-Thr-Lys-Pro-Trp-His | 851 |
| Gly-Thr-Lys-Pro-Trp-Pro | Gly-Thr-Lys-Pro-Trp-Pro | Gly-Thr-Lys-Pro-Trp-Pro | 852 |
| Gly-Thr-Lys-Pro-Trp-Lys | Gly-Thr-Lys-Pro-Trp-Lys | Gly-Thr-Lys-Pro-Trp-Lys | 853 |
| Gly-Thr-Lys-Pro-Gln | Gly-Thr-Lys-Pro-Gln | Gly-Thr-Lys-Pro-Gln | 854 |
| Gly-Thr-Lys-Pro-Gln-Arg | Gly-Thr-Lys-Pro-Gln-Arg | Gly-Thr-Lys-Pro-Gln-Arg | 855 |
| Gly-Thr-Lys-Pro-Gln-Phe | Gly-Thr-Lys-Pro-Gln-Phe | Gly-Thr-Lys-Pro-Gln-Phe | 856 |
| Gly-Thr-Lys-Pro-Gln-Tyr | Gly-Thr-Lys-Pro-Gln-Tyr | Gly-Thr-Lys-Pro-Gln-Tyr | 857 |
| Gly-Thr-Lys-Pro-Gln-His | Gly-Thr-Lys-Pro-Gln-His | Gly-Thr-Lys-Pro-Gln-His | 858 |
| Gly-Thr-Lys-Pro-Gln-Pro | Gly-Thr-Lys-Pro-Gln-Pro | Gly-Thr-Lys-Pro-Gln-Pro | 859 |
| Gly-Thr-Lys-Pro-Gln-Lys | Gly-Thr-Lys-Pro-Gln-Lys | Gly-Thr-Lys-Pro-Gln-Lys | 860 |
| Gly-Thr-Lys-Pro-Asn | Gly-Thr-Lys-Pro-Asn | Gly-Thr-Lys-Pro-Asn | 861 |
| Gly-Thr-Lys-Pro-Asn-Arg | Gly-Thr-Lys-Pro-Asn-Arg | Gly-Thr-Lys-Pro-Asn-Arg | 862 |
| Gly-Thr-Lys-Pro-Asn-Phe | Gly-Thr-Lys-Pro-Asn-Phe | Gly-Thr-Lys-Pro-Asn-Phe | 863 |

TABLE 1-continued

| X-OH | X-OCH₃ | X-NH₂ | SEQ ID NO |
|---|---|---|---|
| Gly-Thr-Lys-Pro-Asn-Tyr | Gly-Thr-Lys-Pro-Asn-Tyr | Gly-Thr-Lys-Pro-Asn-Tyr | 864 |
| Gly-Thr-Lys-Pro-Asn-His | Gly-Thr-Lys-Pro-Asn-His | Gly-Thr-Lys-Pro-Asn-His | 865 |
| Gly-Thr-Lys-Pro-Asn-Pro | Gly-Thr-Lys-Pro-Asn-Pro | Gly-Thr-Lys-Pro-Asn-Pro | 866 |
| Gly-Thr-Lys-Pro-Asn-Lys | Gly-Thr-Lys-Pro-Asn-Lys | Gly-Thr-Lys-Pro-Asn-Lys | 867 |
| Gly-Thr-Lys-Pro-Tyr | Gly-Thr-Lys-Pro-Tyr | Gly-Thr-Lys-Pro-Tyr | 868 |
| Gly-Thr-Lys-Pro-Tyr-Arg | Gly-Thr-Lys-Pro-Tyr-Arg | Gly-Thr-Lys-Pro-Tyr-Arg | 869 |
| Gly-Thr-Lys-Pro-Tyr-Phe | Gly-Thr-Lys-Pro-Tyr-Phe | Gly-Thr-Lys-Pro-Tyr-Phe | 870 |
| Gly-Thr-Lys-Pro-Tyr-Tyr | Gly-Thr-Lys-Pro-Tyr-Tyr | Gly-Thr-Lys-Pro-Tyr-Tyr | 871 |
| Gly-Thr-Lys-Pro-Tyr-His | Gly-Thr-Lys-Pro-Tyr-His | Gly-Thr-Lys-Pro-Tyr-His | 872 |
| Gly-Thr-Lys-Pro-Tyr-Pro | Gly-Thr-Lys-Pro-Tyr-Pro | Gly-Thr-Lys-Pro-Tyr-Pro | 873 |
| Gly-Thr-Lys-Pro-Tyr-Lys | Gly-Thr-Lys-Pro-Tyr-Lys | Gly-Thr-Lys-Pro-Tyr-Lys | 874 |
| Gly-Thr-Lys-Pro-Arg | Gly-Thr-Lys-Pro-Arg | Gly-Thr-Lys-Pro-Arg | 875 |
| Gly-Thr-Lys-Pro-Arg-Arg | Gly-Thr-Lys-Pro-Arg-Arg | Gly-Thr-Lys-Pro-Arg-Arg | 876 |
| Gly-Thr-Lys-Pro-Arg-Phe | Gly-Thr-Lys-Pro-Arg-Phe | Gly-Thr-Lys-Pro-Arg-Phe | 877 |
| Gly-Thr-Lys-Pro-Arg-Tyr | Gly-Thr-Lys-Pro-Arg-Tyr | Gly-Thr-Lys-Pro-Arg-Tyr | 878 |
| Gly-Thr-Lys-Pro-Arg-His | Gly-Thr-Lys-Pro-Arg-His | Gly-Thr-Lys-Pro-Arg-His | 879 |
| Gly-Thr-Lys-Pro-Arg-Pro | Gly-Thr-Lys-Pro-Arg-Pro | Gly-Thr-Lys-Pro-Arg-Pro | 880 |
| Gly-Thr-Lys-Pro-Arg-Lys | Gly-Thr-Lys-Pro-Arg-Lys | Gly-Thr-Lys-Pro-Arg-Lys | 881 |
| Thr-Lys-Pro-Arg-Val | Thr-Lys-Pro-Arg-Val | Thr-Lys-Pro-Arg-Val | 882 |
| Thr-Lys-Pro-Phe-Val | Thr-Lys-Pro-Phe-Val | Thr-Lys-Pro-Phe-Val | 883 |
| Thr-Lys-Pro-Tyr-Val | Thr-Lys-Pro-Tyr-Val | Thr-Lys-Pro-Tyr-Val | 884 |
| Thr-Lys-Pro-Gly-Val | Thr-Lys-Pro-Gly-Val | Thr-Lys-Pro-Gly-Val | 885 |
| Thr-Lys-Pro-His-Val | Thr-Lys-Pro-His-Val | Thr-Lys-Pro-His-Val | 886 |
| Thr-Lys-Pro-Lys-Val | Thr-Lys-Pro-Lys-Val | Thr-Lys-Pro-Lys-Val | 887 |
| Thr-Lys-Pro-Gly-Val | Thr-Lys-Pro-Gly-Val | Thr-Lys-Pro-Gly-Val | 888 |
| Thr-Lys-Pro-Gly-Arg-Val | Thr-Lys-Pro-Gly-Arg-Val | Thr-Lys-Pro-Gly-Arg-Val | 889 |
| Thr-Lys-Pro-Gly-Phe-Val | Thr-Lys-Pro-Gly-Phe-Val | Thr-Lys-Pro-Gly-Phe-Val | 890 |
| Thr-Lys-Pro-Gly-Tyr-Val | Thr-Lys-Pro-Gly-Tyr-Val | Thr-Lys-Pro-Gly-Tyr-Val | 891 |
| Thr-Lys-Pro-Gly-His-Val | Thr-Lys-Pro-Gly-His-Val | Thr-Lys-Pro-Gly-His-Val | 892 |
| Thr-Lys-Pro-Gly-Pro-Val | Thr-Lys-Pro-Gly-Pro-Val | Thr-Lys-Pro-Gly-Pro-Val | 893 |
| Thr-Lys-Pro-Gly-Lys-Val | Thr-Lys-Pro-Gly-Lys-Val | Thr-Lys-Pro-Gly-Lys-Val | 894 |
| Thr-Lys-Pro-Asp-Val | Thr-Lys-Pro-Asp-Val | Thr-Lys-Pro-Asp-Val | 895 |
| Thr-Lys-Pro-Asp-Arg-Val | Thr-Lys-Pro-Asp-Arg-Val | Thr-Lys-Pro-Asp-Arg-Val | 896 |
| Thr-Lys-Pro-Asp-Phe-Val | Thr-Lys-Pro-Asp-Phe-Val | Thr-Lys-Pro-Asp-Phe-Val | 897 |
| Thr-Lys-Pro-Asp-Tyr-Val | Thr-Lys-Pro-Asp-Tyr-Val | Thr-Lys-Pro-Asp-Tyr-Val | 898 |
| Thr-Lys-Pro-Asp-His-Val | Thr-Lys-Pro-Asp-His-Val | Thr-Lys-Pro-Asp-His-Val | 899 |
| Thr-Lys-Pro-Asp-Pro-Val | Thr-Lys-Pro-Asp-Pro-Val | Thr-Lys-Pro-Asp-Pro-Val | 900 |
| Thr-Lys-Pro-Asp-Lys-Val | Thr-Lys-Pro-Asp-Lys-Val | Thr-Lys-Pro-Asp-Lys-Val | 901 |

TABLE 1-continued

| X-OH | X-OCH₃ | X-NH₂ | SEQ ID NO |
|---|---|---|---|
| Thr-Lys-Pro-Trp-Val | Thr-Lys-Pro-Trp-Val | Thr-Lys-Pro-Trp-Val | 902 |
| Thr-Lys-Pro-Trp-Arg-Val | Thr-Lys-Pro-Trp-Arg-Val | Thr-Lys-Pro-Trp-Arg-Val | 903 |
| Thr-Lys-Pro-Trp-Phe-Val | Thr-Lys-Pro-Trp-Phe-Val | Thr-Lys-Pro-Trp-Phe-Val | 904 |
| Thr-Lys-Pro-Trp-Tyr-Val | Thr-Lys-Pro-Trp-Tyr-Val | Thr-Lys-Pro-Trp-Tyr-Val | 905 |
| Thr-Lys-Pro-Trp-His-Val | Thr-Lys-Pro-Trp-His-Val | Thr-Lys-Pro-Trp-His-Val | 906 |
| Thr-Lys-Pro-Trp-Pro-Val | Thr-Lys-Pro-Trp-Pro-Val | Thr-Lys-Pro-Trp-Pro-Val | 907 |
| Thr-Lys-Pro-Trp-Lys-Val | Thr-Lys-Pro-Trp-Lys-Val | Thr-Lys-Pro-Trp-Lys-Val | 908 |
| Thr-Lys-Pro-Gln-Val | Thr-Lys-Pro-Gln-Val | Thr-Lys-Pro-Gln-Val | 909 |
| Thr-Lys-Pro-Gln-Arg-Val | Thr-Lys-Pro-Gln-Arg-Val | Thr-Lys-Pro-Gln-Arg-Val | 910 |
| Thr-Lys-Pro-Gln-Phe-Val | Thr-Lys-Pro-Gln-Phe-Val | Thr-Lys-Pro-Gln-Phe-Val | 911 |
| Thr-Lys-Pro-Gln-Tyr-Val | Thr-Lys-Pro-Gln-Tyr-Val | Thr-Lys-Pro-Gln-Tyr-Val | 912 |
| Thr-Lys-Pro-Gln-His-Val | Thr-Lys-Pro-Gln-His-Val | Thr-Lys-Pro-Gln-His-Val | 913 |
| Thr-Lys-Pro-Gln-Pro-Val | Thr-Lys-Pro-Gln-Pro-Val | Thr-Lys-Pro-Gln-Pro-Val | 914 |
| Thr-Lys-Pro-Gln-Lys-Val | Thr-Lys-Pro-Gln-Lys-Val | Thr-Lys-Pro-Gln-Lys-Val | 915 |
| Thr-Lys-Pro-Asn-Val | Thr-Lys-Pro-Asn-Val | Thr-Lys-Pro-Asn-Val | 916 |
| Thr-Lys-Pro-Asn-Arg-Val | Thr-Lys-Pro-Asn-Arg-Val | Thr-Lys-Pro-Asn-Arg-Val | 917 |
| Thr-Lys-Pro-Asn-Phe-Val | Thr-Lys-Pro-Asn-Phe-Val | Thr-Lys-Pro-Asn-Phe-Val | 918 |
| Thr-Lys-Pro-Asn-Tyr-Val | Thr-Lys-Pro-Asn-Tyr-Val | Thr-Lys-Pro-Asn-Tyr-Val | 919 |
| Thr-Lys-Pro-Asn-His-Val | Thr-Lys-Pro-Asn-His-Val | Thr-Lys-Pro-Asn-His-Val | 920 |
| Thr-Lys-Pro-Asn-Pro-Val | Thr-Lys-Pro-Asn-Pro-Val | Thr-Lys-Pro-Asn-Pro-Val | 921 |
| Thr-Lys-Pro-Asn-Lys-Val | Thr-Lys-Pro-Asn-Lys-Val | Thr-Lys-Pro-Asn-Lys-Val | 922 |
| Thr-Lys-Pro-Tyr-Val | Thr-Lys-Pro-Tyr-Val | Thr-Lys-Pro-Tyr-Val | 923 |
| Thr-Lys-Pro-Tyr-Arg-Val | Thr-Lys-Pro-Tyr-Arg-Val | Thr-Lys-Pro-Tyr-Arg-Val | 924 |
| Thr-Lys-Pro-Tyr-Phe-Val | Thr-Lys-Pro-Tyr-Phe-Val | Thr-Lys-Pro-Tyr-Phe-Val | 925 |
| Thr-Lys-Pro-Tyr-Tyr-Val | Thr-Lys-Pro-Tyr-Tyr-Val | Thr-Lys-Pro-Tyr-Tyr-Val | 926 |
| Thr-Lys-Pro-Tyr-His-Val | Thr-Lys-Pro-Tyr-His-Val | Thr-Lys-Pro-Tyr-His-Val | 927 |
| Thr-Lys-Pro-Tyr-Pro-Val | Thr-Lys-Pro-Tyr-Pro-Val | Thr-Lys-Pro-Tyr-Pro-Val | 928 |
| Thr-Lys-Pro-Tyr-Lys-Val | Thr-Lys-Pro-Tyr-Lys-Val | Thr-Lys-Pro-Tyr-Lys-Val | 929 |
| Thr-Lys-Pro-Arg-Val | Thr-Lys-Pro-Arg-Val | Thr-Lys-Pro-Arg-Val | 930 |
| Thr-Lys-Pro-Arg-Arg-Val | Thr-Lys-Pro-Arg-Arg-Val | Thr-Lys-Pro-Arg-Arg-Val | 931 |
| Thr-Lys-Pro-Arg-Phe-Val | Thr-Lys-Pro-Arg-Phe-Val | Thr-Lys-Pro-Arg-Phe-Val | 932 |
| Thr-Lys-Pro-Arg-Tyr-Val | Thr-Lys-Pro-Arg-Tyr-Val | Thr-Lys-Pro-Arg-Tyr-Val | 933 |
| Thr-Lys-Pro-Arg-His-Val | Thr-Lys-Pro-Arg-His-Val | Thr-Lys-Pro-Arg-His-Val | 934 |
| Thr-Lys-Pro-Arg-Pro-Val | Thr-Lys-Pro-Arg-Pro-Val | Thr-Lys-Pro-Arg-Pro-Val | 935 |
| Thr-Lys-Pro-Arg-Lys-Val | Thr-Lys-Pro-Arg-Lys-Val | Thr-Lys-Pro-Arg-Lys-Val | 936 |
| Met-Thr-Lys-Pro-Val | Met-Thr-Lys-Pro-Val | Met-Thr-Lys-Pro-Val | 937 |
| Met-Thr-Lys-Pro-Arg-Val | Met-Thr-Lys-Pro-Arg-Val | Met-Thr-Lys-Pro-Arg-Val | 938 |
| Met-Thr-Lys-Pro-Phe-Val | Met-Thr-Lys-Pro-Phe-Val | Met-Thr-Lys-Pro-Phe-Val | 939 |

TABLE 1-continued

| X-OH | X-OCH₃ | X-NH₂ | SEQ ID NO |
|---|---|---|---|
| Met-Thr-Lys-Pro-Tyr-Val | Met-Thr-Lys-Pro-Tyr-Val | Met-Thr-Lys-Pro-Tyr-Val | 940 |
| Met-Thr-Lys-Pro-His-Val | Met-Thr-Lys-Pro-His-Val | Met-Thr-Lys-Pro-His-Val | 941 |
| Met-Thr-Lys-Pro-Lys-Val | Met-Thr-Lys-Pro-Lys-Val | Met-Thr-Lys-Pro-Lys-Val | 942 |
| Met-Thr-Lys-Pro-Gly-Val | Met-Thr-Lys-Pro-Gly-Val | Met-Thr-Lys-Pro-Gly-Val | 943 |
| Met-Thr-Lys-Pro-Gly-Arg-Val | Met-Thr-Lys-Pro-Gly-Arg-Val | Met-Thr-Lys-Pro-Gly-Arg-Val | 944 |
| Met-Thr-Lys-Pro-Gly-Phe-Val | Met-Thr-Lys-Pro-Gly-Phe-Val | Met-Thr-Lys-Pro-Gly-Phe-Val | 945 |
| Met-Thr-Lys-Pro-Gly-Tyr-Val | Met-Thr-Lys-Pro-Gly-Tyr-Val | Met-Thr-Lys-Pro-Gly-Tyr-Val | 946 |
| Met-Thr-Lys-Pro-Gly-His-Val | Met-Thr-Lys-Pro-Gly-His-Val | Met-Thr-Lys-Pro-Gly-His-Val | 947 |
| Met-Thr-Lys-Pro-Gly-Pro-Val | Met-Thr-Lys-Pro-Gly-Pro-Val | Met-Thr-Lys-Pro-Gly-Pro-Val | 948 |
| Met-Thr-Lys-Pro-Gly-Lys-Val | Met-Thr-Lys-Pro-Gly-Lys-Val | Met-Thr-Lys-Pro-Gly-Lys-Val | 949 |
| Met-Thr-Lys-Pro-Asp-Val | Met-Thr-Lys-Pro-Asp-Val | Met-Thr-Lys-Pro-Asp-Val | 950 |
| Met-Thr-Lys-Pro-Asp-Arg-Val | Met-Thr-Lys-Pro-Asp-Arg-Val | Met-Thr-Lys-Pro-Asp-Arg-Val | 951 |
| Met-Thr-Lys-Pro-Asp-Phe-Val | Met-Thr-Lys-Pro-Asp-Phe-Val | Met-Thr-Lys-Pro-Asp-Phe-Val | 952 |
| Met-Thr-Lys-Pro-Asp-Tyr-Val | Met-Thr-Lys-Pro-Asp-Tyr-Val | Met-Thr-Lys-Pro-Asp-Tyr-Val | 953 |
| Met-Thr-Lys-Pro-Asp-His-Val | Met-Thr-Lys-Pro-Asp-His-Val | Met-Thr-Lys-Pro-Asp-His-Val | 954 |
| Met-Thr-Lys-Pro-Asp-Pro-Val | Met-Thr-Lys-Pro-Asp-Pro-Val | Met-Thr-Lys-Pro-Asp-Pro-Val | 955 |
| Met-Thr-Lys-Pro-Asp-Lys-Val | Met-Thr-Lys-Pro-Asp-Lys-Val | Met-Thr-Lys-Pro-Asp-Lys-Val | 956 |
| Met-Thr-Lys-Pro-Trp-Val | Met-Thr-Lys-Pro-Trp-Val | Met-Thr-Lys-Pro-Trp-Val | 957 |
| Met-Thr-Lys-Pro-Trp-Arg-Val | Met-Thr-Lys-Pro-Trp-Arg-Val | Met-Thr-Lys-Pro-Trp-Arg-Val | 958 |
| Met-Thr-Lys-Pro-Trp-Phe-Val | Met-Thr-Lys-Pro-Trp-Phe-Val | Met-Thr-Lys-Pro-Trp-Phe-Val | 959 |
| Met-Thr-Lys-Pro-Trp-Tyr-Val | Met-Thr-Lys-Pro-Trp-Tyr-Val | Met-Thr-Lys-Pro-Trp-Tyr-Val | 960 |
| Met-Thr-Lys-Pro-Trp-His-Val | Met-Thr-Lys-Pro-Trp-His-Val | Met-Thr-Lys-Pro-Trp-His-Val | 961 |
| Met-Thr-Lys-Pro-Trp-Pro-Val | Met-Thr-Lys-Pro-Trp-Pro-Val | Met-Thr-Lys-Pro-Trp-Pro-Val | 962 |
| Met-Thr-Lys-Pro-Trp-Lys-Val | Met-Thr-Lys-Pro-Trp-Lys-Val | Met-Thr-Lys-Pro-Trp-Lys-Val | 963 |
| Met-Thr-Lys-Pro-Gln-Val | Met-Thr-Lys-Pro-Gln-Val | Met-Thr-Lys-Pro-Gln-Val | 964 |
| Met-Thr-Lys-Pro-Gln-Arg-Val | Met-Thr-Lys-Pro-Gln-Arg-Val | Met-Thr-Lys-Pro-Gln-Arg-Val | 965 |
| Met-Thr-Lys-Pro-Gln-Phe-Val | Met-Thr-Lys-Pro-Gln-Phe-Val | Met-Thr-Lys-Pro-Gln-Phe-Val | 966 |
| Met-Thr-Lys-Pro-Gln-Tyr-Val | Met-Thr-Lys-Pro-Gln-Tyr-Val | Met-Thr-Lys-Pro-Gln-Tyr-Val | 967 |
| Met-Thr-Lys-Pro-Gln-His-Val | Met-Thr-Lys-Pro-Gln-His-Val | Met-Thr-Lys-Pro-Gln-His-Val | 968 |
| Met-Thr-Lys-Pro-Gln-Pro-Val | Met-Thr-Lys-Pro-Gln-Pro-Val | Met-Thr-Lys-Pro-Gln-Pro-Val | 969 |
| Met-Thr-Lys-Pro-Gln-Lys-Val | Met-Thr-Lys-Pro-Gln-Lys-Val | Met-Thr-Lys-Pro-Gln-Lys-Val | 970 |
| Met-Thr-Lys-Pro-Asn-Val | Met-Thr-Lys-Pro-Asn-Val | Met-Thr-Lys-Pro-Asn-Val | 971 |
| Met-Thr-Lys-Pro-Asn-Arg-Val | Met-Thr-Lys-Pro-Asn-Arg-Val | Met-Thr-Lys-Pro-Asn-Arg-Val | 972 |
| Met-Thr-Lys-Pro-Asn-Phe-Val | Met-Thr-Lys-Pro-Asn-Phe-Val | Met-Thr-Lys-Pro-Asn-Phe-Val | 973 |
| Met-Thr-Lys-Pro-Asn-Tyr-Val | Met-Thr-Lys-Pro-Asn-Tyr-Val | Met-Thr-Lys-Pro-Asn-Tyr-Val | 974 |
| Met-Thr-Lys-Pro-Asn-His-Val | Met-Thr-Lys-Pro-Asn-His-Val | Met-Thr-Lys-Pro-Asn-His-Val | 975 |
| Met-Thr-Lys-Pro-Asn-Pro-Val | Met-Thr-Lys-Pro-Asn-Pro-Val | Met-Thr-Lys-Pro-Asn-Pro-Val | 976 |
| Met-Thr-Lys-Pro-Asn-Lys-Val | Met-Thr-Lys-Pro-Asn-Lys-Val | Met-Thr-Lys-Pro-Asn-Lys-Val | 977 |

TABLE 1-continued

| X-OH | X-OCH₃ | X-NH₂ | SEQ ID NO |
|---|---|---|---|
| Met-Thr-Lys-Pro-Tyr-Val | Met-Thr-Lys-Pro-Tyr-Val | Met-Thr-Lys-Pro-Tyr-Val | 978 |
| Met-Thr-Lys-Pro-Tyr-Arg-Val | Met-Thr-Lys-Pro-Tyr-Arg-Val | Met-Thr-Lys-Pro-Tyr-Arg-Val | 979 |
| Met-Thr-Lys-Pro-Tyr-Phe-Val | Met-Thr-Lys-Pro-Tyr-Phe-Val | Met-Thr-Lys-Pro-Tyr-Phe-Val | 980 |
| Met-Thr-Lys-Pro-Tyr-Tyr-Val | Met-Thr-Lys-Pro-Tyr-Tyr-Val | Met-Thr-Lys-Pro-Tyr-Tyr-Val | 981 |
| Met-Thr-Lys-Pro-Tyr-His-Val | Met-Thr-Lys-Pro-Tyr-His-Val | Met-Thr-Lys-Pro-Tyr-His-Val | 982 |
| Met-Thr-Lys-Pro-Tyr-Pro-Val | Met-Thr-Lys-Pro-Tyr-Pro-Val | Met-Thr-Lys-Pro-Tyr-Pro-Val | 983 |
| Met-Thr-Lys-Pro-Tyr-Lys-Val | Met-Thr-Lys-Pro-Tyr-Lys-Val | Met-Thr-Lys-Pro-Tyr-Lys-Val | 984 |
| Met-Thr-Lys-Pro-Arg-Val | Met-Thr-Lys-Pro-Arg-Val | Met-Thr-Lys-Pro-Arg-Val | 985 |
| Met-Thr-Lys-Pro-Arg-Arg-Val | Met-Thr-Lys-Pro-Arg-Arg-Val | Met-Thr-Lys-Pro-Arg-Arg-Val | 986 |
| Met-Thr-Lys-Pro-Arg-Phe-Val | Met-Thr-Lys-Pro-Arg-Phe-Val | Met-Thr-Lys-Pro-Arg-Phe-Val | 987 |
| Met-Thr-Lys-Pro-Arg-Tyr-Val | Met-Thr-Lys-Pro-Arg-Tyr-Val | Met-Thr-Lys-Pro-Arg-Tyr-Val | 988 |
| Met-Thr-Lys-Pro-Arg-His-Val | Met-Thr-Lys-Pro-Arg-His-Val | Met-Thr-Lys-Pro-Arg-His-Val | 989 |
| Met-Thr-Lys-Pro-Arg-Pro-Val | Met-Thr-Lys-Pro-Arg-Pro-Val | Met-Thr-Lys-Pro-Arg-Pro-Val | 990 |
| Met-Thr-Lys-Pro-Arg-Lys-Val | Met-Thr-Lys-Pro-Arg-Lys-Val | Met-Thr-Lys-Pro-Arg-Lys-Val | 991 |
| Met(O)-Thr-Lys-Pro-Val | Met(O)-Thr-Lys-Pro-Val | Met(O)-Thr-Lys-Pro-Val | 992 |
| Met(O)-Thr-Lys-Pro-Arg-Val | Met(O)-Thr-Lys-Pro-Arg-Val | Met(O)-Thr-Lys-Pro-Arg-Val | 993 |
| Met(O)-Thr-Lys-Pro-Phe-Val | Met(O)-Thr-Lys-Pro-Phe-Val | Met(O)-Thr-Lys-Pro-Phe-Val | 994 |
| Met(O)-Thr-Lys-Pro-Tyr-Val | Met(O)-Thr-Lys-Pro-Tyr-Val | Met(O)-Thr-Lys-Pro-Tyr-Val | 995 |
| Met(O)-Thr-Lys-Pro-Gly-Val | Met(O)-Thr-Lys-Pro-Gly-Val | Met(O)-Thr-Lys-Pro-Gly-Val | 996 |
| Met(O)-Thr-Lys-Pro-His-Val | Met(O)-Thr-Lys-Pro-His-Val | Met(O)-Thr-Lys-Pro-His-Val | 997 |
| Met(O)-Thr-Lys-Pro-Lys-Val | Met(O)-Thr-Lys-Pro-Lys-Val | Met(O)-Thr-Lys-Pro-Lys-Val | 998 |
| Met(O)-Thr-Lys-Pro-Gly-Val | Met(O)-Thr-Lys-Pro-Gly-Val | Met(O)-Thr-Lys-Pro-Gly-Val | 999 |
| Met(O)-Thr-Lys-Pro-Gly-Arg-Val | Met(O)-Thr-Lys-Pro-Gly-Arg-Val | Met(O)-Thr-Lys-Pro-Gly-Arg-Val | 1000 |
| Met(O)-Thr-Lys-Pro-Gly-Phe-Val | Met(O)-Thr-Lys-Pro-Gly-Phe-Val | Met(O)-Thr-Lys-Pro-Gly-Phe-Val | 1001 |
| Met(O)-Thr-Lys-Pro-Gly-Tyr-Val | Met(O)-Thr-Lys-Pro-Gly-Tyr-Val | Met(O)-Thr-Lys-Pro-Gly-Tyr-Val | 1002 |
| Met(O)-Thr-Lys-Pro-Gly-His-Val | Met(O)-Thr-Lys-Pro-Gly-His-Val | Met(O)-Thr-Lys-Pro-Gly-His-Val | 1003 |
| Met(O)-Thr-Lys-Pro-Gly-Pro-Val | Met(O)-Thr-Lys-Pro-Gly-Pro-Val | Met(O)-Thr-Lys-Pro-Gly-Pro-Val | 1004 |
| Met(O)-Thr-Lys-Pro-Gly-Lys-Val | Met(O)-Thr-Lys-Pro-Gly-Lys-Val | Met(O)-Thr-Lys-Pro-Gly-Lys-Val | 1005 |
| Met(O)-Thr-Lys-Pro-Asp-Val | Met(O)-Thr-Lys-Pro-Asp-Val | Met(O)-Thr-Lys-Pro-Asp-Val | 1006 |
| Met(O)-Thr-Lys-Pro-Asp-Arg-Val | Met(O)-Thr-Lys-Pro-Asp-Arg-Val | Met(O)-Thr-Lys-Pro-Asp-Arg-Val | 1007 |
| Met(O)-Thr-Lys-Pro-Asp-Phe-Val | Met(O)-Thr-Lys-Pro-Asp-Phe-Val | Met(O)-Thr-Lys-Pro-Asp-Phe-Val | 1008 |
| Met(O)-Thr-Lys-Pro-Asp-Tyr-Val | Met(O)-Thr-Lys-Pro-Asp-Tyr-Val | Met(O)-Thr-Lys-Pro-Asp-Tyr-Val | 1009 |
| Met(O)-Thr-Lys-Pro-Asp-His-Val | Met(O)-Thr-Lys-Pro-Asp-His-Val | Met(O)-Thr-Lys-Pro-Asp-His-Val | 1010 |

TABLE 1-continued

| X-OH | X-OCH₃ | X-NH₂ | SEQ ID NO |
|---|---|---|---|
| Met(O)-Thr-Lys-Pro-Asp-Pro-Val | Met(O)-Thr-Lys-Pro-Asp-Pro-Val | Met(O)-Thr-Lys-Pro-Asp-Pro-Val | 1011 |
| Met(O)-Thr-Lys-Pro-Asp-Lys-Val | Met(O)-Thr-Lys-Pro-Asp-Lys-Val | Met(O)-Thr-Lys-Pro-Asp-Lys-Val | 1012 |
| Met(O)-Thr-Lys-Pro-Trp-Val | Met(O)-Thr-Lys-Pro-Trp-Val | Met(O)-Thr-Lys-Pro-Trp-Val | 1013 |
| Met(O)-Thr-Lys-Pro-Trp-Arg-Val | Met(O)-Thr-Lys-Pro-Trp-Arg-Val | Met(O)-Thr-Lys-Pro-Trp-Arg-Val | 1014 |
| Met(O)-Thr-Lys-Pro-Trp-Phe-Val | Met(O)-Thr-Lys-Pro-Trp-Phe-Val | Met(O)-Thr-Lys-Pro-Trp-Phe-Val | 1015 |
| Met(O)-Thr-Lys-Pro-Trp-Tyr-Val | Met(O)-Thr-Lys-Pro-Trp-Tyr-Val | Met(O)-Thr-Lys-Pro-Trp-Tyr-Val | 1016 |
| Met(O)-Thr-Lys-Pro-Trp-His-Val | Met(O)-Thr-Lys-Pro-Trp-His-Val | Met(O)-Thr-Lys-Pro-Trp-His-Val | 1017 |
| Met(O)-Thr-Lys-Pro-Trp-Pro-Val | Met(O)-Thr-Lys-Pro-Trp-Pro-Val | Met(O)-Thr-Lys-Pro-Trp-Pro-Val | 1018 |
| Met(O)-Thr-Lys-Pro-Trp-Lys-Val | Met(O)-Thr-Lys-Pro-Trp-Lys-Val | Met(O)-Thr-Lys-Pro-Trp-Lys-Val | 1019 |
| Met(O)-Thr-Lys-Pro-Gln-Val | Met(O)-Thr-Lys-Pro-Gln-Val | Met(O)-Thr-Lys-Pro-Gln-Val | 1020 |
| Met(O)-Thr-Lys-Pro-Gln-Arg-Val | Met(O)-Thr-Lys-Pro-Gln-Arg-Val | Met(O)-Thr-Lys-Pro-Gln-Arg-Val | 1021 |
| Met(O)-Thr-Lys-Pro-Gln-Phe-Val | Met(O)-Thr-Lys-Pro-Gln-Phe-Val | Met(O)-Thr-Lys-Pro-Gln-Phe-Val | 1022 |
| Met(O)-Thr-Lys-Pro-Gln-Tyr-Val | Met(O)-Thr-Lys-Pro-Gln-Tyr-Val | Met(O)-Thr-Lys-Pro-Gln-Tyr-Val | 1023 |
| Met(O)-Thr-Lys-Pro-Gln-His-Val | Met(O)-Thr-Lys-Pro-Gln-His-Val | Met(O)-Thr-Lys-Pro-Gln-His-Val | 1024 |
| Met(O)-Thr-Lys-Pro-Gln-Pro-Val | Met(O)-Thr-Lys-Pro-Gln-Pro-Val | Met(O)-Thr-Lys-Pro-Gln-Pro-Val | 1025 |
| Met(O)-Thr-Lys-Pro-Gln-Lys-Val | Met(O)-Thr-Lys-Pro-Gln-Lys-Val | Met(O)-Thr-Lys-Pro-Gln-Lys-Val | 1026 |
| Met(O)-Thr-Lys-Pro-Asn-Val | Met(O)-Thr-Lys-Pro-Asn-Val | Met(O)-Thr-Lys-Pro-Asn-Val | 1027 |
| Met(O)-Thr-Lys-Pro-Asn-Arg-Val | Met(O)-Thr-Lys-Pro-Asn-Arg-Val | Met(O)-Thr-Lys-Pro-Asn-Arg-Val | 1028 |
| Met(O)-Thr-Lys-Pro-Asn-Phe-Val | Met(O)-Thr-Lys-Pro-Asn-Phe-Val | Met(O)-Thr-Lys-Pro-Asn-Phe-Val | 1029 |
| Met(O)-Thr-Lys-Pro-Asn-Tyr-Val | Met(O)-Thr-Lys-Pro-Asn-Tyr-Val | Met(O)-Thr-Lys-Pro-Asn-Tyr-Val | 1030 |
| Met(O)-Thr-Lys-Pro-Asn-His-Val | Met(O)-Thr-Lys-Pro-Asn-His-Val | Met(O)-Thr-Lys-Pro-Asn-His-Val | 1031 |
| Met(O)-Thr-Lys-Pro-Asn-Pro-Val | Met(O)-Thr-Lys-Pro-Asn-Pro-Val | Met(O)-Thr-Lys-Pro-Asn-Pro-Val | 1032 |
| Met(O)-Thr-Lys-Pro-Asn-Lys-Val | Met(O)-Thr-Lys-Pro-Asn-Lys-Val | Met(O)-Thr-Lys-Pro-Asn-Lys-Val | 1033 |
| Met(O)-Thr-Lys-Pro-Tyr-Val | Met(O)-Thr-Lys-Pro-Tyr-Val | Met(O)-Thr-Lys-Pro-Tyr-Val | 1034 |
| Met(O)-Thr-Lys-Pro-Tyr-Arg-Val | Met(O)-Thr-Lys-Pro-Tyr-Arg-Val | Met(O)-Thr-Lys-Pro-Tyr-Arg-Val | 1035 |
| Met(O)-Thr-Lys-Pro-Tyr-Phe-Val | Met(O)-Thr-Lys-Pro-Tyr-Phe-Val | Met(O)-Thr-Lys-Pro-Tyr-Phe-Val | 1036 |

TABLE 1-continued

| X-OH | X-OCH₃ | X-NH₂ | SEQ ID NO |
|---|---|---|---|
| Met(O)-Thr-Lys-Pro-Tyr-Tyr-Val | Met(O)-Thr-Lys-Pro-Tyr-Tyr-Val | Met(O)-Thr-Lys-Pro-Tyr-Tyr-Val | 1037 |
| Met(O)-Thr-Lys-Pro-Tyr-His-Val | Met(O)-Thr-Lys-Pro-Tyr-His-Val | Met(O)-Thr-Lys-Pro-Tyr-His-Val | 1038 |
| Met(O)-Thr-Lys-Pro-Tyr-Pro-Val | Met(O)-Thr-Lys-Pro-Tyr-Pro-Val | Met(O)-Thr-Lys-Pro-Tyr-Pro-Val | 1039 |
| Met(O)-Thr-Lys-Pro-Tyr-Lys-Val | Met(O)-Thr-Lys-Pro-Tyr-Lys-Val | Met(O)-Thr-Lys-Pro-Tyr-Lys-Val | 1040 |
| Met(O)-Thr-Lys-Pro-Arg-Val | Met(O)-Thr-Lys-Pro-Arg-Val | Met(O)-Thr-Lys-Pro-Arg-Val | 1041 |
| Met(O)-Thr-Lys-Pro-Arg-Arg-Val | Met(O)-Thr-Lys-Pro-Arg-Arg-Val | Met(O)-Thr-Lys-Pro-Arg-Arg-Val | 1042 |
| Met(O)-Thr-Lys-Pro-Arg-Phe-Val | Met(O)-Thr-Lys-Pro-Arg-Phe-Val | Met(O)-Thr-Lys-Pro-Arg-Phe-Val | 1043 |
| Met(O)-Thr-Lys-Pro-Arg-Tyr-Val | Met(O)-Thr-Lys-Pro-Arg-Tyr-Val | Met(O)-Thr-Lys-Pro-Arg-Tyr-Val | 1044 |
| Met(O)-Thr-Lys-Pro-Arg-His-Val | Met(O)-Thr-Lys-Pro-Arg-His-Val | Met(O)-Thr-Lys-Pro-Arg-His-Val | 1045 |
| Met(O)-Thr-Lys-Pro-Arg-Pro-Val | Met(O)-Thr-Lys-Pro-Arg-Pro-Val | Met(O)-Thr-Lys-Pro-Arg-Pro-Val | 1046 |
| Met(O)-Thr-Lys-Pro-Arg-Lys-Val | Met(O)-Thr-Lys-Pro-Arg-Lys-Val | Met(O)-Thr-Lys-Pro-Arg-Lys-Val | 1047 |
| Thr-Thr-Lys-Pro-Val | Thr-Thr-Lys-Pro-Val | Thr-Thr-Lys-Pro-Val | 1048 |
| Thr-Thr-Lys-Pro-Arg-Val | Thr-Thr-Lys-Pro-Arg-Val | Thr-Thr-Lys-Pro-Arg-Val | 1049 |
| Thr-Thr-Lys-Pro-Phe-Val | Thr-Thr-Lys-Pro-Phe-Val | Thr-Thr-Lys-Pro-Phe-Val | 1050 |
| Thr-Thr-Lys-Pro-Tyr-Val | Thr-Thr-Lys-Pro-Tyr-Val | Thr-Thr-Lys-Pro-Tyr-Val | 1051 |
| Thr-Thr-Lys-Pro-Gly-Val | Thr-Thr-Lys-Pro-Gly-Val | Thr-Thr-Lys-Pro-Gly-Val | 1052 |
| Thr-Thr-Lys-Pro-His-Val | Thr-Thr-Lys-Pro-His-Val | Thr-Thr-Lys-Pro-His-Val | 1053 |
| Thr-Thr-Lys-Pro-Lys-Val | Thr-Thr-Lys-Pro-Lys-Val | Thr-Thr-Lys-Pro-Lys-Val | 1054 |
| Thr-Thr-Lys-Pro-Gly-Val | Thr-Thr-Lys-Pro-Gly-Val | Thr-Thr-Lys-Pro-Gly-Val | 1055 |
| Thr-Thr-Lys-Pro-Gly-Arg-Val | Thr-Thr-Lys-Pro-Gly-Arg-Val | Thr-Thr-Lys-Pro-Gly-Arg-Val | 1056 |
| Thr-Thr-Lys-Pro-Gly-Phe-Val | Thr-Thr-Lys-Pro-Gly-Phe-Val | Thr-Thr-Lys-Pro-Gly-Phe-Val | 1057 |
| Thr-Thr-Lys-Pro-Gly-Tyr-Val | Thr-Thr-Lys-Pro-Gly-Tyr-Val | Thr-Thr-Lys-Pro-Gly-Tyr-Val | 1058 |
| Thr-Thr-Lys-Pro-Gly-His-Val | Thr-Thr-Lys-Pro-Gly-His-Val | Thr-Thr-Lys-Pro-Gly-His-Val | 1059 |
| Thr-Thr-Lys-Pro-Gly-Pro-Val | Thr-Thr-Lys-Pro-Gly-Pro-Val | Thr-Thr-Lys-Pro-Gly-Pro-Val | 1060 |
| Thr-Thr-Lys-Pro-Gly-Lys-Val | Thr-Thr-Lys-Pro-Gly-Lys-Val | Thr-Thr-Lys-Pro-Gly-Lys-Val | 1061 |
| Thr-Thr-Lys-Pro-Asp-Val | Thr-Thr-Lys-Pro-Asp-Val | Thr-Thr-Lys-Pro-Asp-Val | 1062 |
| Thr-Thr-Lys-Pro-Asp-Arg-Val | Thr-Thr-Lys-Pro-Asp-Arg-Val | Thr-Thr-Lys-Pro-Asp-Arg-Val | 1063 |
| Thr-Thr-Lys-Pro-Asp-Phe-Val | Thr-Thr-Lys-Pro-Asp-Phe-Val | Thr-Thr-Lys-Pro-Asp-Phe-Val | 1064 |
| Thr-Thr-Lys-Pro-Asp-Tyr-Val | Thr-Thr-Lys-Pro-Asp-Tyr-Val | Thr-Thr-Lys-Pro-Asp-Tyr-Val | 1065 |
| Thr-Thr-Lys-Pro-Asp-His-Val | Thr-Thr-Lys-Pro-Asp-His-Val | Thr-Thr-Lys-Pro-Asp-His-Val | 1066 |
| Thr-Thr-Lys-Pro-Asp-Pro-Val | Thr-Thr-Lys-Pro-Asp-Pro-Val | Thr-Thr-Lys-Pro-Asp-Pro-Val | 1067 |
| Thr-Thr-Lys-Pro-Asp-Lys-Val | Thr-Thr-Lys-Pro-Asp-Lys-Val | Thr-Thr-Lys-Pro-Asp-Lys-Val | 1068 |
| Thr-Thr-Lys-Pro-Trp-Val | Thr-Thr-Lys-Pro-Trp-Val | Thr-Thr-Lys-Pro-Trp-Val | 1069 |

TABLE 1-continued

| X-OH | X-OCH₃ | X-NH₂ | SEQ ID NO |
|---|---|---|---|
| Thr-Thr-Lys-Pro-Trp-Arg-Val | Thr-Thr-Lys-Pro-Trp-Arg-Val | Thr-Thr-Lys-Pro-Trp-Arg-Val | 1070 |
| Thr-Thr-Lys-Pro-Trp-Phe-Val | Thr-Thr-Lys-Pro-Trp-Phe-Val | Thr-Thr-Lys-Pro-Trp-Phe-Val | 1071 |
| Thr-Thr-Lys-Pro-Trp-Tyr-Val | Thr-Thr-Lys-Pro-Trp-Tyr-Val | Thr-Thr-Lys-Pro-Trp-Tyr-Val | 1072 |
| Thr-Thr-Lys-Pro-Trp-His-Val | Thr-Thr-Lys-Pro-Trp-His-Val | Thr-Thr-Lys-Pro-Trp-His-Val | 1073 |
| Thr-Thr-Lys-Pro-Trp-Pro-Val | Thr-Thr-Lys-Pro-Trp-Pro-Val | Thr-Thr-Lys-Pro-Trp-Pro-Val | 1074 |
| Thr-Thr-Lys-Pro-Trp-Lys-Val | Thr-Thr-Lys-Pro-Trp-Lys-Val | Thr-Thr-Lys-Pro-Trp-Lys-Val | 1075 |
| Thr-Thr-Lys-Pro-Gln-Val | Thr-Thr-Lys-Pro-Gln-Val | Thr-Thr-Lys-Pro-Gln-Val | 1076 |
| Thr-Thr-Lys-Pro-Gln-Arg-Val | Thr-Thr-Lys-Pro-Gln-Arg-Val | Thr-Thr-Lys-Pro-Gln-Arg-Val | 1077 |
| Thr-Thr-Lys-Pro-Gln-Phe-Val | Thr-Thr-Lys-Pro-Gln-Phe-Val | Thr-Thr-Lys-Pro-Gln-Phe-Val | 1078 |
| Thr-Thr-Lys-Pro-Gln-Tyr-Val | Thr-Thr-Lys-Pro-Gln-Tyr-Val | Thr-Thr-Lys-Pro-Gln-Tyr-Val | 1079 |
| Thr-Thr-Lys-Pro-Gln-His-Val | Thr-Thr-Lys-Pro-Gln-His-Val | Thr-Thr-Lys-Pro-Gln-His-Val | 1080 |
| Thr-Thr-Lys-Pro-Gln-Pro-Val | Thr-Thr-Lys-Pro-Gln-Pro-Val | Thr-Thr-Lys-Pro-Gln-Pro-Val | 1081 |
| Thr-Thr-Lys-Pro-Gln-Lys-Val | Thr-Thr-Lys-Pro-Gln-Lys-Val | Thr-Thr-Lys-Pro-Gln-Lys-Val | 1082 |
| Thr-Thr-Lys-Pro-Asn-Val | Thr-Thr-Lys-Pro-Asn-Val | Thr-Thr-Lys-Pro-Asn-Val | 1083 |
| Thr-Thr-Lys-Pro-Asn-Arg-Val | Thr-Thr-Lys-Pro-Asn-Arg-Val | Thr-Thr-Lys-Pro-Asn-Arg-Val | 1084 |
| Thr-Thr-Lys-Pro-Asn-Phe-Val | Thr-Thr-Lys-Pro-Asn-Phe-Val | Thr-Thr-Lys-Pro-Asn-Phe-Val | 1085 |
| Thr-Thr-Lys-Pro-Asn-Tyr-Val | Thr-Thr-Lys-Pro-Asn-Tyr-Val | Thr-Thr-Lys-Pro-Asn-Tyr-Val | 1086 |
| Thr-Thr-Lys-Pro-Asn-His-Val | Thr-Thr-Lys-Pro-Asn-His-Val | Thr-Thr-Lys-Pro-Asn-His-Val | 1087 |
| Thr-Thr-Lys-Pro-Asn-Pro-Val | Thr-Thr-Lys-Pro-Asn-Pro-Val | Thr-Thr-Lys-Pro-Asn-Pro-Val | 1088 |
| Thr-Thr-Lys-Pro-Asn-Lys-Val | Thr-Thr-Lys-Pro-Asn-Lys-Val | Thr-Thr-Lys-Pro-Asn-Lys-Val | 1089 |
| Thr-Thr-Lys-Pro-Tyr-Val | Thr-Thr-Lys-Pro-Tyr-Val | Thr-Thr-Lys-Pro-Tyr-Val | 1090 |
| Thr-Thr-Lys-Pro-Tyr-Arg-Val | Thr-Thr-Lys-Pro-Tyr-Arg-Val | Thr-Thr-Lys-Pro-Tyr-Arg-Val | 1091 |
| Thr-Thr-Lys-Pro-Tyr-Phe-Val | Thr-Thr-Lys-Pro-Tyr-Phe-Val | Thr-Thr-Lys-Pro-Tyr-Phe-Val | 1092 |
| Thr-Thr-Lys-Pro-Tyr-Tyr-Val | Thr-Thr-Lys-Pro-Tyr-Tyr-Val | Thr-Thr-Lys-Pro-Tyr-Tyr-Val | 1093 |
| Thr-Thr-Lys-Pro-Tyr-His-Val | Thr-Thr-Lys-Pro-Tyr-His-Val | Thr-Thr-Lys-Pro-Tyr-His-Val | 1094 |
| Thr-Thr-Lys-Pro-Tyr-Pro-Val | Thr-Thr-Lys-Pro-Tyr-Pro-Val | Thr-Thr-Lys-Pro-Tyr-Pro-Val | 1095 |
| Thr-Thr-Lys-Pro-Tyr-Lys-Val | Thr-Thr-Lys-Pro-Tyr-Lys-Val | Thr-Thr-Lys-Pro-Tyr-Lys-Val | 1096 |
| Thr-Thr-Lys-Pro-Arg-Val | Thr-Thr-Lys-Pro-Arg-Val | Thr-Thr-Lys-Pro-Arg-Val | 1097 |
| Thr-Thr-Lys-Pro-Arg-Arg-Val | Thr-Thr-Lys-Pro-Arg-Arg-Val | Thr-Thr-Lys-Pro-Arg-Arg-Val | 1098 |
| Thr-Thr-Lys-Pro-Arg-Phe-Val | Thr-Thr-Lys-Pro-Arg-Phe-Val | Thr-Thr-Lys-Pro-Arg-Phe-Val | 1099 |
| Thr-Thr-Lys-Pro-Arg-Tyr-Val | Thr-Thr-Lys-Pro-Arg-Tyr-Val | Thr-Thr-Lys-Pro-Arg-Tyr-Val | 1100 |
| Thr-Thr-Lys-Pro-Arg-His-Val | Thr-Thr-Lys-Pro-Arg-His-Val | Thr-Thr-Lys-Pro-Arg-His-Val | 1101 |
| Thr-Thr-Lys-Pro-Arg-Pro-Val | Thr-Thr-Lys-Pro-Arg-Pro-Val | Thr-Thr-Lys-Pro-Arg-Pro-Val | 1102 |
| Thr-Thr-Lys-Pro-Arg-Lys-Val | Thr-Thr-Lys-Pro-Arg-Lys-Val | Thr-Thr-Lys-Pro-Arg-Lys-Val | 1103 |
| Ala-Thr-Lys-Pro-Val | Ala-Thr-Lys-Pro-Val | Ala-Thr-Lys-Pro-Val | 1104 |
| Ala-Thr-Lys-Pro-Arg-Val | Ala-Thr-Lys-Pro-Arg-Val | Ala-Thr-Lys-Pro-Arg-Val | 1105 |
| Ala-Thr-Lys-Pro-Phe-Val | Ala-Thr-Lys-Pro-Phe-Val | Ala-Thr-Lys-Pro-Phe-Val | 1106 |
| Ala-Thr-Lys-Pro-Tyr-Val | Ala-Thr-Lys-Pro-Tyr-Val | Ala-Thr-Lys-Pro-Tyr-Val | 1107 |

TABLE 1-continued

| X-OH | X-OCH₃ | X-NH₂ | SEQ ID NO |
|---|---|---|---|
| Ala-Thr-Lys-Pro-Gly-Val | Ala-Thr-Lys-Pro-Gly-Val | Ala-Thr-Lys-Pro-Gly-Val | 1108 |
| Ala-Thr-Lys-Pro-His-Val | Ala-Thr-Lys-Pro-His-Val | Ala-Thr-Lys-Pro-His-Val | 1109 |
| Ala-Thr-Lys-Pro-Lys-Val | Ala-Thr-Lys-Pro-Lys-Val | Ala-Thr-Lys-Pro-Lys-Val | 1110 |
| Ala-Thr-Lys-Pro-Gly-Val | Ala-Thr-Lys-Pro-Gly-Val | Ala-Thr-Lys-Pro-Gly-Val | 1111 |
| Ala-Thr-Lys-Pro-Gly-Arg-Val | Ala-Thr-Lys-Pro-Gly-Arg-Val | Ala-Thr-Lys-Pro-Gly-Arg-Val | 1112 |
| Ala-Thr-Lys-Pro-Gly-Phe-Val | Ala-Thr-Lys-Pro-Gly-Phe-Val | Ala-Thr-Lys-Pro-Gly-Phe-Val | 1113 |
| Ala-Thr-Lys-Pro-Gly-Tyr-Val | Ala-Thr-Lys-Pro-Gly-Tyr-Val | Ala-Thr-Lys-Pro-Gly-Tyr-Val | 1114 |
| Ala-Thr-Lys-Pro-Gly-His-Val | Ala-Thr-Lys-Pro-Gly-His-Val | Ala-Thr-Lys-Pro-Gly-His-Val | 1115 |
| Ala-Thr-Lys-Pro-Gly-Pro-Val | Ala-Thr-Lys-Pro-Gly-Pro-Val | Ala-Thr-Lys-Pro-Gly-Pro-Val | 1116 |
| Ala-Thr-Lys-Pro-Gly-Lys-Val | Ala-Thr-Lys-Pro-Gly-Lys-Val | Ala-Thr-Lys-Pro-Gly-Lys-Val | 1117 |
| Ala-Thr-Lys-Pro-Asp-Val | Ala-Thr-Lys-Pro-Asp-Val | Ala-Thr-Lys-Pro-Asp-Val | 1118 |
| Ala-Thr-Lys-Pro-Asp-Arg-Val | Ala-Thr-Lys-Pro-Asp-Arg-Val | Ala-Thr-Lys-Pro-Asp-Arg-Val | 1119 |
| Ala-Thr-Lys-Pro-Asp-Phe-Val | Ala-Thr-Lys-Pro-Asp-Phe-Val | Ala-Thr-Lys-Pro-Asp-Phe-Val | 1120 |
| Ala-Thr-Lys-Pro-Asp-Tyr-Val | Ala-Thr-Lys-Pro-Asp-Tyr-Val | Ala-Thr-Lys-Pro-Asp-Tyr-Val | 1121 |
| Ala-Thr-Lys-Pro-Asp-His-Val | Ala-Thr-Lys-Pro-Asp-His-Val | Ala-Thr-Lys-Pro-Asp-His-Val | 1122 |
| Ala-Thr-Lys-Pro-Asp-Pro-Val | Ala-Thr-Lys-Pro-Asp-Pro-Val | Ala-Thr-Lys-Pro-Asp-Pro-Val | 1123 |
| Ala-Thr-Lys-Pro-Asp-Lys-Val | Ala-Thr-Lys-Pro-Asp-Lys-Val | Ala-Thr-Lys-Pro-Asp-Lys-Val | 1124 |
| Ala-Thr-Lys-Pro-Trp-Val | Ala-Thr-Lys-Pro-Trp-Val | Ala-Thr-Lys-Pro-Trp-Val | 1125 |
| Ala-Thr-Lys-Pro-Trp-Arg-Val | Ala-Thr-Lys-Pro-Trp-Arg-Val | Ala-Thr-Lys-Pro-Trp-Arg-Val | 1126 |
| Ala-Thr-Lys-Pro-Trp-Phe-Val | Ala-Thr-Lys-Pro-Trp-Phe-Val | Ala-Thr-Lys-Pro-Trp-Phe-Val | 1127 |
| Ala-Thr-Lys-Pro-Trp-Tyr-Val | Ala-Thr-Lys-Pro-Trp-Tyr-Val | Ala-Thr-Lys-Pro-Trp-Tyr-Val | 1128 |
| Ala-Thr-Lys-Pro-Trp-His-Val | Ala-Thr-Lys-Pro-Trp-His-Val | Ala-Thr-Lys-Pro-Trp-His-Val | 1129 |
| Ala-Thr-Lys-Pro-Trp-Pro-Val | Ala-Thr-Lys-Pro-Trp-Pro-Val | Ala-Thr-Lys-Pro-Trp-Pro-Val | 1130 |
| Ala-Thr-Lys-Pro-Trp-Lys-Val | Ala-Thr-Lys-Pro-Trp-Lys-Val | Ala-Thr-Lys-Pro-Trp-Lys-Val | 1131 |
| Ala-Thr-Lys-Pro-Gln-Val | Ala-Thr-Lys-Pro-Gln-Val | Ala-Thr-Lys-Pro-Gln-Val | 1132 |
| Ala-Thr-Lys-Pro-Gln-Arg-Val | Ala-Thr-Lys-Pro-Gln-Arg-Val | Ala-Thr-Lys-Pro-Gln-Arg-Val | 1133 |
| Ala-Thr-Lys-Pro-Gln-Phe-Val | Ala-Thr-Lys-Pro-Gln-Phe-Val | Ala-Thr-Lys-Pro-Gln-Phe-Val | 1134 |
| Ala-Thr-Lys-Pro-Gln-Tyr-Val | Ala-Thr-Lys-Pro-Gln-Tyr-Val | Ala-Thr-Lys-Pro-Gln-Tyr-Val | 1135 |
| Ala-Thr-Lys-Pro-Gln-His-Val | Ala-Thr-Lys-Pro-Gln-His-Val | Ala-Thr-Lys-Pro-Gln-His-Val | 1136 |
| Ala-Thr-Lys-Pro-Gln-Pro-Val | Ala-Thr-Lys-Pro-Gln-Pro-Val | Ala-Thr-Lys-Pro-Gln-Pro-Val | 1137 |
| Ala-Thr-Lys-Pro-Gln-Lys-Val | Ala-Thr-Lys-Pro-Gln-Lys-Val | Ala-Thr-Lys-Pro-Gln-Lys-Val | 1138 |
| Ala-Thr-Lys-Pro-Asn-Val | Ala-Thr-Lys-Pro-Asn-Val | Ala-Thr-Lys-Pro-Asn-Val | 1139 |
| Ala-Thr-Lys-Pro-Asn-Arg-Val | Ala-Thr-Lys-Pro-Asn-Arg-Val | Ala-Thr-Lys-Pro-Asn-Arg-Val | 1140 |
| Ala-Thr-Lys-Pro-Asn-Phe-Val | Ala-Thr-Lys-Pro-Asn-Phe-Val | Ala-Thr-Lys-Pro-Asn-Phe-Val | 1141 |
| Ala-Thr-Lys-Pro-Asn-Tyr-Val | Ala-Thr-Lys-Pro-Asn-Tyr-Val | Ala-Thr-Lys-Pro-Asn-Tyr-Val | 1142 |
| Ala-Thr-Lys-Pro-Asn-His-Val | Ala-Thr-Lys-Pro-Asn-His-Val | Ala-Thr-Lys-Pro-Asn-His-Val | 1143 |
| Ala-Thr-Lys-Pro-Asn-Pro-Val | Ala-Thr-Lys-Pro-Asn-Pro-Val | Ala-Thr-Lys-Pro-Asn-Pro-Val | 1144 |
| Ala-Thr-Lys-Pro-Asn-Lys-Val | Ala-Thr-Lys-Pro-Asn-Lys-Val | Ala-Thr-Lys-Pro-Asn-Lys-Val | 1145 |

TABLE 1-continued

| X-OH | X-OCH₃ | X-NH₂ | SEQ ID NO |
|---|---|---|---|
| Ala-Thr-Lys-Pro-Tyr-Val | Ala-Thr-Lys-Pro-Tyr-Val | Ala-Thr-Lys-Pro-Tyr-Val | 1146 |
| Ala-Thr-Lys-Pro-Tyr-Arg-Val | Ala-Thr-Lys-Pro-Tyr-Arg-Val | Ala-Thr-Lys-Pro-Tyr-Arg-Val | 1147 |
| Ala-Thr-Lys-Pro-Tyr-Phe-Val | Ala-Thr-Lys-Pro-Tyr-Phe-Val | Ala-Thr-Lys-Pro-Tyr-Phe-Val | 1148 |
| Ala-Thr-Lys-Pro-Tyr-Tyr-Val | Ala-Thr-Lys-Pro-Tyr-Tyr-Val | Ala-Thr-Lys-Pro-Tyr-Tyr-Val | 1149 |
| Ala-Thr-Lys-Pro-Tyr-His-Val | Ala-Thr-Lys-Pro-Tyr-His-Val | Ala-Thr-Lys-Pro-Tyr-His-Val | 1150 |
| Ala-Thr-Lys-Pro-Tyr-Pro-Val | Ala-Thr-Lys-Pro-Tyr-Pro-Val | Ala-Thr-Lys-Pro-Tyr-Pro-Val | 1151 |
| Ala-Thr-Lys-Pro-Tyr-Lys-Val | Ala-Thr-Lys-Pro-Tyr-Lys-Val | Ala-Thr-Lys-Pro-Tyr-Lys-Val | 1152 |
| Ala-Thr-Lys-Pro-Arg-Val | Ala-Thr-Lys-Pro-Arg-Val | Ala-Thr-Lys-Pro-Arg-Val | 1153 |
| Ala-Thr-Lys-Pro-Arg-Arg-Val | Ala-Thr-Lys-Pro-Arg-Arg-Val | Ala-Thr-Lys-Pro-Arg-Arg-Val | 1154 |
| Ala-Thr-Lys-Pro-Arg-Phe-Val | Ala-Thr-Lys-Pro-Arg-Phe-Val | Ala-Thr-Lys-Pro-Arg-Phe-Val | 1155 |
| Ala-Thr-Lys-Pro-Arg-Tyr-Val | Ala-Thr-Lys-Pro-Arg-Tyr-Val | Ala-Thr-Lys-Pro-Arg-Tyr-Val | 1156 |
| Ala-Thr-Lys-Pro-Arg-His-Val | Ala-Thr-Lys-Pro-Arg-His-Val | Ala-Thr-Lys-Pro-Arg-His-Val | 1157 |
| Ala-Thr-Lys-Pro-Arg-Pro-Val | Ala-Thr-Lys-Pro-Arg-Pro-Val | Ala-Thr-Lys-Pro-Arg-Pro-Val | 1158 |
| Ala-Thr-Lys-Pro-Arg-Lys-Val | Ala-Thr-Lys-Pro-Arg-Lys-Val | Ala-Thr-Lys-Pro-Arg-Lys-Val | 1159 |
| His-Thr-Lys-Pro-Val | His-Thr-Lys-Pro-Val | His-Thr-Lys-Pro-Val | 1160 |
| His-Thr-Lys-Pro-Arg-Val | His-Thr-Lys-Pro-Arg-Val | His-Thr-Lys-Pro-Arg-Val | 1161 |
| His-Thr-Lys-Pro-Phe-Val | His-Thr-Lys-Pro-Phe-Val | His-Thr-Lys-Pro-Phe-Val | 1162 |
| His-Thr-Lys-Pro-Tyr-Val | His-Thr-Lys-Pro-Tyr-Val | His-Thr-Lys-Pro-Tyr-Val | 1163 |
| His-Thr-Lys-Pro-Gly-Val | His-Thr-Lys-Pro-Gly-Val | His-Thr-Lys-Pro-Gly-Val | 1164 |
| His-Thr-Lys-Pro-His-Val | His-Thr-Lys-Pro-His-Val | His-Thr-Lys-Pro-His-Val | 1165 |
| His-Thr-Lys-Pro-Lys-Val | His-Thr-Lys-Pro-Lys-Val | His-Thr-Lys-Pro-Lys-Val | 1166 |
| His-Thr-Lys-Pro-Gly-Val | His-Thr-Lys-Pro-Gly-Val | His-Thr-Lys-Pro-Gly-Val | 1167 |
| His-Thr-Lys-Pro-Gly-Arg-Val | His-Thr-Lys-Pro-Gly-Arg-Val | His-Thr-Lys-Pro-Gly-Arg-Val | 1168 |
| His-Thr-Lys-Pro-Gly-Phe-Val | His-Thr-Lys-Pro-Gly-Phe-Val | His-Thr-Lys-Pro-Gly-Phe-Val | 1169 |
| His-Thr-Lys-Pro-Gly-Tyr-Val | His-Thr-Lys-Pro-Gly-Tyr-Val | His-Thr-Lys-Pro-Gly-Tyr-Val | 1170 |
| His-Thr-Lys-Pro-Gly-His-Val | His-Thr-Lys-Pro-Gly-His-Val | His-Thr-Lys-Pro-Gly-His-Val | 1171 |
| His-Thr-Lys-Pro-Gly-Pro-Val | His-Thr-Lys-Pro-Gly-Pro-Val | His-Thr-Lys-Pro-Gly-Pro-Val | 1172 |
| His-Thr-Lys-Pro-Gly-Lys-Val | His-Thr-Lys-Pro-Gly-Lys-Val | His-Thr-Lys-Pro-Gly-Lys-Val | 1173 |
| His-Thr-Lys-Pro-Asp-Val | His-Thr-Lys-Pro-Asp-Val | His-Thr-Lys-Pro-Asp-Val | 1174 |
| His-Thr-Lys-Pro-Asp-Arg-Val | His-Thr-Lys-Pro-Asp-Arg-Val | His-Thr-Lys-Pro-Asp-Arg-Val | 1175 |
| His-Thr-Lys-Pro-Asp-Phe-Val | His-Thr-Lys-Pro-Asp-Phe-Val | His-Thr-Lys-Pro-Asp-Phe-Val | 1176 |
| His-Thr-Lys-Pro-Asp-Tyr-Val | His-Thr-Lys-Pro-Asp-Tyr-Val | His-Thr-Lys-Pro-Asp-Tyr-Val | 1177 |
| His-Thr-Lys-Pro-Asp-His-Val | His-Thr-Lys-Pro-Asp-His-Val | His-Thr-Lys-Pro-Asp-His-Val | 1178 |
| His-Thr-Lys-Pro-Asp-Pro-Val | His-Thr-Lys-Pro-Asp-Pro-Val | His-Thr-Lys-Pro-Asp-Pro-Val | 1179 |
| His-Thr-Lys-Pro-Asp-Lys-Val | His-Thr-Lys-Pro-Asp-Lys-Val | His-Thr-Lys-Pro-Asp-Lys-Val | 1180 |
| His-Thr-Lys-Pro-Trp-Val | His-Thr-Lys-Pro-Trp-Val | His-Thr-Lys-Pro-Trp-Val | 1181 |
| His-Thr-Lys-Pro-Trp-Arg-Val | His-Thr-Lys-Pro-Trp-Arg-Val | His-Thr-Lys-Pro-Trp-Arg-Val | 1182 |
| His-Thr-Lys-Pro-Trp-Phe-Val | His-Thr-Lys-Pro-Trp-Phe-Val | His-Thr-Lys-Pro-Trp-Phe-Val | 1183 |

TABLE 1-continued

| X-OH | X-OCH₃ | X-NH₂ | SEQ ID NO |
|---|---|---|---|
| His-Thr-Lys-Pro-Trp-Tyr-Val | His-Thr-Lys-Pro-Trp-Tyr-Val | His-Thr-Lys-Pro-Trp-Tyr-Val | 1184 |
| His-Thr-Lys-Pro-Trp-His-Val | His-Thr-Lys-Pro-Trp-His-Val | His-Thr-Lys-Pro-Trp-His-Val | 1185 |
| His-Thr-Lys-Pro-Trp-Pro-Val | His-Thr-Lys-Pro-Trp-Pro-Val | His-Thr-Lys-Pro-Trp-Pro-Val | 1186 |
| His-Thr-Lys-Pro-Trp-Lys-Val | His-Thr-Lys-Pro-Trp-Lys-Val | His-Thr-Lys-Pro-Trp-Lys-Val | 1187 |
| His-Thr-Lys-Pro-Gln-Val | His-Thr-Lys-Pro-Gln-Val | His-Thr-Lys-Pro-Gln-Val | 1188 |
| His-Thr-Lys-Pro-Gln-Arg-Val | His-Thr-Lys-Pro-Gln-Arg-Val | His-Thr-Lys-Pro-Gln-Arg-Val | 1189 |
| His-Thr-Lys-Pro-Gln-Phe-Val | His-Thr-Lys-Pro-Gln-Phe-Val | His-Thr-Lys-Pro-Gln-Phe-Val | 1190 |
| His-Thr-Lys-Pro-Gln-Tyr-Val | His-Thr-Lys-Pro-Gln-Tyr-Val | His-Thr-Lys-Pro-Gln-Tyr-Val | 1191 |
| His-Thr-Lys-Pro-Gln-His-Val | His-Thr-Lys-Pro-Gln-His-Val | His-Thr-Lys-Pro-Gln-His-Val | 1192 |
| His-Thr-Lys-Pro-Gln-Pro-Val | His-Thr-Lys-Pro-Gln-Pro-Val | His-Thr-Lys-Pro-Gln-Pro-Val | 1193 |
| His-Thr-Lys-Pro-Gln-Lys-Val | His-Thr-Lys-Pro-Gln-Lys-Val | His-Thr-Lys-Pro-Gln-Lys-Val | 1194 |
| His-Thr-Lys-Pro-Asn-Val | His-Thr-Lys-Pro-Asn-Val | His-Thr-Lys-Pro-Asn-Val | 1195 |
| His-Thr-Lys-Pro-Asn-Arg-Val | His-Thr-Lys-Pro-Asn-Arg-Val | His-Thr-Lys-Pro-Asn-Arg-Val | 1196 |
| His-Thr-Lys-Pro-Asn-Phe-Val | His-Thr-Lys-Pro-Asn-Phe-Val | His-Thr-Lys-Pro-Asn-Phe-Val | 1197 |
| His-Thr-Lys-Pro-Asn-Tyr-Val | His-Thr-Lys-Pro-Asn-Tyr-Val | His-Thr-Lys-Pro-Asn-Tyr-Val | 1198 |
| His-Thr-Lys-Pro-Asn-His-Val | His-Thr-Lys-Pro-Asn-His-Val | His-Thr-Lys-Pro-Asn-His-Val | 1199 |
| His-Thr-Lys-Pro-Asn-Pro-Val | His-Thr-Lys-Pro-Asn-Pro-Val | His-Thr-Lys-Pro-Asn-Pro-Val | 1200 |
| His-Thr-Lys-Pro-Asn-Lys-Val | His-Thr-Lys-Pro-Asn-Lys-Val | His-Thr-Lys-Pro-Asn-Lys-Val | 1201 |
| His-Thr-Lys-Pro-Tyr-Val | His-Thr-Lys-Pro-Tyr-Val | His-Thr-Lys-Pro-Tyr-Val | 1202 |
| His-Thr-Lys-Pro-Tyr-Arg-Val | His-Thr-Lys-Pro-Tyr-Arg-Val | His-Thr-Lys-Pro-Tyr-Arg-Val | 1203 |
| His-Thr-Lys-Pro-Tyr-Phe-Val | His-Thr-Lys-Pro-Tyr-Phe-Val | His-Thr-Lys-Pro-Tyr-Phe-Val | 1204 |
| His-Thr-Lys-Pro-Tyr-Tyr-Val | His-Thr-Lys-Pro-Tyr-Tyr-Val | His-Thr-Lys-Pro-Tyr-Tyr-Val | 1205 |
| His-Thr-Lys-Pro-Tyr-His-Val | His-Thr-Lys-Pro-Tyr-His-Val | His-Thr-Lys-Pro-Tyr-His-Val | 1206 |
| His-Thr-Lys-Pro-Tyr-Pro-Val | His-Thr-Lys-Pro-Tyr-Pro-Val | His-Thr-Lys-Pro-Tyr-Pro-Val | 1207 |
| His-Thr-Lys-Pro-Tyr-Lys-Val | His-Thr-Lys-Pro-Tyr-Lys-Val | His-Thr-Lys-Pro-Tyr-Lys-Val | 1208 |
| His-Thr-Lys-Pro-Arg-Val | His-Thr-Lys-Pro-Arg-Val | His-Thr-Lys-Pro-Arg-Val | 1209 |
| His-Thr-Lys-Pro-Arg-Arg-Val | His-Thr-Lys-Pro-Arg-Arg-Val | His-Thr-Lys-Pro-Arg-Arg-Val | 1210 |
| His-Thr-Lys-Pro-Arg-Phe-Val | His-Thr-Lys-Pro-Arg-Phe-Val | His-Thr-Lys-Pro-Arg-Phe-Val | 1211 |
| His-Thr-Lys-Pro-Arg-Tyr-Val | His-Thr-Lys-Pro-Arg-Tyr-Val | His-Thr-Lys-Pro-Arg-Tyr-Val | 1212 |
| His-Thr-Lys-Pro-Arg-His-Val | His-Thr-Lys-Pro-Arg-His-Val | His-Thr-Lys-Pro-Arg-His-Val | 1213 |
| His-Thr-Lys-Pro-Arg-Pro-Val | His-Thr-Lys-Pro-Arg-Pro-Val | His-Thr-Lys-Pro-Arg-Pro-Val | 1214 |
| His-Thr-Lys-Pro-Arg-Lys-Val | His-Thr-Lys-Pro-Arg-Lys-Val | His-Thr-Lys-Pro-Arg-Lys-Val | 1215 |
| Lys-Thr-Lys-Pro-Val | Lys-Thr-Lys-Pro-Val | Lys-Thr-Lys-Pro-Val | 1216 |
| Lys-Thr-Lys-Pro-Arg-Val | Lys-Thr-Lys-Pro-Arg-Val | Lys-Thr-Lys-Pro-Arg-Val | 1217 |
| Lys-Thr-Lys-Pro-Phe-Val | Lys-Thr-Lys-Pro-Phe-Val | Lys-Thr-Lys-Pro-Phe-Val | 1218 |
| Lys-Thr-Lys-Pro-Tyr-Val | Lys-Thr-Lys-Pro-Tyr-Val | Lys-Thr-Lys-Pro-Tyr-Val | 1219 |
| Lys-Thr-Lys-Pro-Gly-Val | Lys-Thr-Lys-Pro-Gly-Val | Lys-Thr-Lys-Pro-Gly-Val | 1220 |
| Lys-Thr-Lys-Pro-His-Val | Lys-Thr-Lys-Pro-His-Val | Lys-Thr-Lys-Pro-His-Val | 1221 |

TABLE 1-continued

| X-OH | X-OCH₃ | X-NH₂ | SEQ ID NO |
|---|---|---|---|
| Lys-Thr-Lys-Pro-Lys-Val | Lys-Thr-Lys-Pro-Lys-Val | Lys-Thr-Lys-Pro-Lys-Val | 1222 |
| Lys-Thr-Lys-Pro-Gly-Val | Lys-Thr-Lys-Pro-Gly-Val | Lys-Thr-Lys-Pro-Gly-Val | 1223 |
| Lys-Thr-Lys-Pro-Gly-Arg-Val | Lys-Thr-Lys-Pro-Gly-Arg-Val | Lys-Thr-Lys-Pro-Gly-Arg-Val | 1224 |
| Lys-Thr-Lys-Pro-Gly-Phe-Val | Lys-Thr-Lys-Pro-Gly-Phe-Val | Lys-Thr-Lys-Pro-Gly-Phe-Val | 1225 |
| Lys-Thr-Lys-Pro-Gly-Tyr-Val | Lys-Thr-Lys-Pro-Gly-Tyr-Val | Lys-Thr-Lys-Pro-Gly-Tyr-Val | 1226 |
| Lys-Thr-Lys-Pro-Gly-His-Val | Lys-Thr-Lys-Pro-Gly-His-Val | Lys-Thr-Lys-Pro-Gly-His-Val | 1227 |
| Lys-Thr-Lys-Pro-Gly-Pro-Val | Lys-Thr-Lys-Pro-Gly-Pro-Val | Lys-Thr-Lys-Pro-Gly-Pro-Val | 1228 |
| Lys-Thr-Lys-Pro-Gly-Lys-Val | Lys-Thr-Lys-Pro-Gly-Lys-Val | Lys-Thr-Lys-Pro-Gly-Lys-Val | 1229 |
| Lys-Thr-Lys-Pro-Asp-Val | Lys-Thr-Lys-Pro-Asp-Val | Lys-Thr-Lys-Pro-Asp-Val | 1230 |
| Lys-Thr-Lys-Pro-Asp-Arg-Val | Lys-Thr-Lys-Pro-Asp-Arg-Val | Lys-Thr-Lys-Pro-Asp-Arg-Val | 1231 |
| Lys-Thr-Lys-Pro-Asp-Phe-Val | Lys-Thr-Lys-Pro-Asp-Phe-Val | Lys-Thr-Lys-Pro-Asp-Phe-Val | 1232 |
| Lys-Thr-Lys-Pro-Asp-Tyr-Val | Lys-Thr-Lys-Pro-Asp-Tyr-Val | Lys-Thr-Lys-Pro-Asp-Tyr-Val | 1233 |
| Lys-Thr-Lys-Pro-Asp-His-Val | Lys-Thr-Lys-Pro-Asp-His-Val | Lys-Thr-Lys-Pro-Asp-His-Val | 1234 |
| Lys-Thr-Lys-Pro-Asp-Pro-Val | Lys-Thr-Lys-Pro-Asp-Pro-Val | Lys-Thr-Lys-Pro-Asp-Pro-Val | 1235 |
| Lys-Thr-Lys-Pro-Asp-Lys-Val | Lys-Thr-Lys-Pro-Asp-Lys-Val | Lys-Thr-Lys-Pro-Asp-Lys-Val | 1236 |
| Lys-Thr-Lys-Pro-Trp-Val | Lys-Thr-Lys-Pro-Trp-Val | Lys-Thr-Lys-Pro-Trp-Val | 1237 |
| Lys-Thr-Lys-Pro-Trp-Arg-Val | Lys-Thr-Lys-Pro-Trp-Arg-Val | Lys-Thr-Lys-Pro-Trp-Arg-Val | 1238 |
| Lys-Thr-Lys-Pro-Trp-Phe-Val | Lys-Thr-Lys-Pro-Trp-Phe-Val | Lys-Thr-Lys-Pro-Trp-Phe-Val | 1239 |
| Lys-Thr-Lys-Pro-Trp-Tyr-Val | Lys-Thr-Lys-Pro-Trp-Tyr-Val | Lys-Thr-Lys-Pro-Trp-Tyr-Val | 1240 |
| Lys-Thr-Lys-Pro-Trp-His-Val | Lys-Thr-Lys-Pro-Trp-His-Val | Lys-Thr-Lys-Pro-Trp-His-Val | 1241 |
| Lys-Thr-Lys-Pro-Trp-Pro-Val | Lys-Thr-Lys-Pro-Trp-Pro-Val | Lys-Thr-Lys-Pro-Trp-Pro-Val | 1242 |
| Lys-Thr-Lys-Pro-Trp-Lys-Val | Lys-Thr-Lys-Pro-Trp-Lys-Val | Lys-Thr-Lys-Pro-Trp-Lys-Val | 1243 |
| Lys-Thr-Lys-Pro-Gln-Val | Lys-Thr-Lys-Pro-Gln-Val | Lys-Thr-Lys-Pro-Gln-Val | 1244 |
| Lys-Thr-Lys-Pro-Gln-Arg-Val | Lys-Thr-Lys-Pro-Gln-Arg-Val | Lys-Thr-Lys-Pro-Gln-Arg-Val | 1245 |
| Lys-Thr-Lys-Pro-Gln-Phe-Val | Lys-Thr-Lys-Pro-Gln-Phe-Val | Lys-Thr-Lys-Pro-Gln-Phe-Val | 1246 |
| Lys-Thr-Lys-Pro-Gln-Tyr-Val | Lys-Thr-Lys-Pro-Gln-Tyr-Val | Lys-Thr-Lys-Pro-Gln-Tyr-Val | 1247 |
| Lys-Thr-Lys-Pro-Gln-His-Val | Lys-Thr-Lys-Pro-Gln-His-Val | Lys-Thr-Lys-Pro-Gln-His-Val | 1248 |
| Lys-Thr-Lys-Pro-Gln-Pro-Val | Lys-Thr-Lys-Pro-Gln-Pro-Val | Lys-Thr-Lys-Pro-Gln-Pro-Val | 1249 |
| Lys-Thr-Lys-Pro-Gln-Lys-Val | Lys-Thr-Lys-Pro-Gln-Lys-Val | Lys-Thr-Lys-Pro-Gln-Lys-Val | 1250 |
| Lys-Thr-Lys-Pro-Asn-Val | Lys-Thr-Lys-Pro-Asn-Val | Lys-Thr-Lys-Pro-Asn-Val | 1251 |
| Lys-Thr-Lys-Pro-Asn-Arg-Val | Lys-Thr-Lys-Pro-Asn-Arg-Val | Lys-Thr-Lys-Pro-Asn-Arg-Val | 1252 |
| Lys-Thr-Lys-Pro-Asn-Phe-Val | Lys-Thr-Lys-Pro-Asn-Phe-Val | Lys-Thr-Lys-Pro-Asn-Phe-Val | 1253 |
| Lys-Thr-Lys-Pro-Asn-Tyr-Val | Lys-Thr-Lys-Pro-Asn-Tyr-Val | Lys-Thr-Lys-Pro-Asn-Tyr-Val | 1254 |
| Lys-Thr-Lys-Pro-Asn-His-Val | Lys-Thr-Lys-Pro-Asn-His-Val | Lys-Thr-Lys-Pro-Asn-His-Val | 1255 |
| Lys-Thr-Lys-Pro-Asn-Pro-Val | Lys-Thr-Lys-Pro-Asn-Pro-Val | Lys-Thr-Lys-Pro-Asn-Pro-Val | 1256 |
| Lys-Thr-Lys-Pro-Asn-Lys-Val | Lys-Thr-Lys-Pro-Asn-Lys-Val | Lys-Thr-Lys-Pro-Asn-Lys-Val | 1257 |
| Lys-Thr-Lys-Pro-Tyr-Val | Lys-Thr-Lys-Pro-Tyr-Val | Lys-Thr-Lys-Pro-Tyr-Val | 1258 |
| Lys-Thr-Lys-Pro-Tyr-Arg-Val | Lys-Thr-Lys-Pro-Tyr-Arg-Val | Lys-Thr-Lys-Pro-Tyr-Arg-Val | 1259 |

TABLE 1-continued

| X-OH | X-OCH₃ | X-NH₂ | SEQ ID NO |
|---|---|---|---|
| Lys-Thr-Lys-Pro-Tyr-Phe-Val | Lys-Thr-Lys-Pro-Tyr-Phe-Val | Lys-Thr-Lys-Pro-Tyr-Phe-Val | 1260 |
| Lys-Thr-Lys-Pro-Tyr-Tyr-Val | Lys-Thr-Lys-Pro-Tyr-Tyr-Val | Lys-Thr-Lys-Pro-Tyr-Tyr-Val | 1261 |
| Lys-Thr-Lys-Pro-Tyr-His-Val | Lys-Thr-Lys-Pro-Tyr-His-Val | Lys-Thr-Lys-Pro-Tyr-His-Val | 1262 |
| Lys-Thr-Lys-Pro-Tyr-Pro-Val | Lys-Thr-Lys-Pro-Tyr-Pro-Val | Lys-Thr-Lys-Pro-Tyr-Pro-Val | 1263 |
| Lys-Thr-Lys-Pro-Tyr-Lys-Val | Lys-Thr-Lys-Pro-Tyr-Lys-Val | Lys-Thr-Lys-Pro-Tyr-Lys-Val | 1264 |
| Lys-Thr-Lys-Pro-Arg-Val | Lys-Thr-Lys-Pro-Arg-Val | Lys-Thr-Lys-Pro-Arg-Val | 1265 |
| Lys-Thr-Lys-Pro-Arg-Arg-Val | Lys-Thr-Lys-Pro-Arg-Arg-Val | Lys-Thr-Lys-Pro-Arg-Arg-Val | 1266 |
| Lys-Thr-Lys-Pro-Arg-Phe-Val | Lys-Thr-Lys-Pro-Arg-Phe-Val | Lys-Thr-Lys-Pro-Arg-Phe-Val | 1267 |
| Lys-Thr-Lys-Pro-Arg-Tyr-Val | Lys-Thr-Lys-Pro-Arg-Tyr-Val | Lys-Thr-Lys-Pro-Arg-Tyr-Val | 1268 |
| Lys-Thr-Lys-Pro-Arg-His-Val | Lys-Thr-Lys-Pro-Arg-His-Val | Lys-Thr-Lys-Pro-Arg-His-Val | 1269 |
| Lys-Thr-Lys-Pro-Arg-Pro-Val | Lys-Thr-Lys-Pro-Arg-Pro-Val | Lys-Thr-Lys-Pro-Arg-Pro-Val | 1270 |
| Lys-Thr-Lys-Pro-Arg-Lys-Val | Lys-Thr-Lys-Pro-Arg-Lys-Val | Lys-Thr-Lys-Pro-Arg-Lys-Val | 1271 |
| Gly-Thr-Lys-Pro-Val | Gly-Thr-Lys-Pro-Val | Gly-Thr-Lys-Pro-Val | 1272 |
| Gly-Thr-Lys-Pro-Arg-Val | Gly-Thr-Lys-Pro-Arg-Val | Gly-Thr-Lys-Pro-Arg-Val | 1273 |
| Gly-Thr-Lys-Pro-Phe-Val | Gly-Thr-Lys-Pro-Phe-Val | Gly-Thr-Lys-Pro-Phe-Val | 1274 |
| Gly-Thr-Lys-Pro-Tyr-Val | Gly-Thr-Lys-Pro-Tyr-Val | Gly-Thr-Lys-Pro-Tyr-Val | 1275 |
| Gly-Thr-Lys-Pro-Gly-Val | Gly-Thr-Lys-Pro-Gly-Val | Gly-Thr-Lys-Pro-Gly-Val | 1276 |
| Gly-Thr-Lys-Pro-His-Val | Gly-Thr-Lys-Pro-His-Val | Gly-Thr-Lys-Pro-His-Val | 1277 |
| Gly-Thr-Lys-Pro-Lys-Val | Gly-Thr-Lys-Pro-Lys-Val | Gly-Thr-Lys-Pro-Lys-Val | 1278 |
| Gly-Thr-Lys-Pro-Gly-Val | Gly-Thr-Lys-Pro-Gly-Val | Gly-Thr-Lys-Pro-Gly-Val | 1279 |
| Gly-Thr-Lys-Pro-Gly-Arg-Val | Gly-Thr-Lys-Pro-Gly-Arg-Val | Gly-Thr-Lys-Pro-Gly-Arg-Val | 1280 |
| Gly-Thr-Lys-Pro-Gly-Phe-Val | Gly-Thr-Lys-Pro-Gly-Phe-Val | Gly-Thr-Lys-Pro-Gly-Phe-Val | 1281 |
| Gly-Thr-Lys-Pro-Gly-Tyr-Val | Gly-Thr-Lys-Pro-Gly-Tyr-Val | Gly-Thr-Lys-Pro-Gly-Tyr-Val | 1282 |
| Gly-Thr-Lys-Pro-Gly-His-Val | Gly-Thr-Lys-Pro-Gly-His-Val | Gly-Thr-Lys-Pro-Gly-His-Val | 1283 |
| Gly-Thr-Lys-Pro-Gly-Pro-Val | Gly-Thr-Lys-Pro-Gly-Pro-Val | Gly-Thr-Lys-Pro-Gly-Pro-Val | 1284 |
| Gly-Thr-Lys-Pro-Gly-Lys-Val | Gly-Thr-Lys-Pro-Gly-Lys-Val | Gly-Thr-Lys-Pro-Gly-Lys-Val | 1285 |
| Gly-Thr-Lys-Pro-Asp-Val | Gly-Thr-Lys-Pro-Asp-Val | Gly-Thr-Lys-Pro-Asp-Val | 1286 |
| Gly-Thr-Lys-Pro-Asp-Arg-Val | Gly-Thr-Lys-Pro-Asp-Arg-Val | Gly-Thr-Lys-Pro-Asp-Arg-Val | 1287 |
| Gly-Thr-Lys-Pro-Asp-Phe-Val | Gly-Thr-Lys-Pro-Asp-Phe-Val | Gly-Thr-Lys-Pro-Asp-Phe-Val | 1288 |
| Gly-Thr-Lys-Pro-Asp-Tyr-Val | Gly-Thr-Lys-Pro-Asp-Tyr-Val | Gly-Thr-Lys-Pro-Asp-Tyr-Val | 1289 |
| Gly-Thr-Lys-Pro-Asp-His-Val | Gly-Thr-Lys-Pro-Asp-His-Val | Gly-Thr-Lys-Pro-Asp-His-Val | 1290 |
| Gly-Thr-Lys-Pro-Asp-Pro-Val | Gly-Thr-Lys-Pro-Asp-Pro-Val | Gly-Thr-Lys-Pro-Asp-Pro-Val | 1291 |
| Gly-Thr-Lys-Pro-Asp-Lys-Val | Gly-Thr-Lys-Pro-Asp-Lys-Val | Gly-Thr-Lys-Pro-Asp-Lys-Val | 1292 |
| Gly-Thr-Lys-Pro-Trp-Val | Gly-Thr-Lys-Pro-Trp-Val | Gly-Thr-Lys-Pro-Trp-Val | 1293 |
| Gly-Thr-Lys-Pro-Trp-Arg-Val | Gly-Thr-Lys-Pro-Trp-Arg-Val | Gly-Thr-Lys-Pro-Trp-Arg-Val | 1294 |
| Gly-Thr-Lys-Pro-Trp-Phe-Val | Gly-Thr-Lys-Pro-Trp-Phe-Val | Gly-Thr-Lys-Pro-Trp-Phe-Val | 1295 |
| Gly-Thr-Lys-Pro-Trp-Tyr-Val | Gly-Thr-Lys-Pro-Trp-Tyr-Val | Gly-Thr-Lys-Pro-Trp-Tyr-Val | 1296 |
| Gly-Thr-Lys-Pro-Trp-His-Val | Gly-Thr-Lys-Pro-Trp-His-Val | Gly-Thr-Lys-Pro-Trp-His-Val | 1297 |

TABLE 1-continued

| X—OH | X—OCH₃ | X—NH₂ | SEQ ID NO |
|---|---|---|---|
| Gly-Thr-Lys-Pro-Trp-Pro-Val | Gly-Thr-Lys-Pro-Trp-Pro-Val | Gly-Thr-Lys-Pro-Trp-Pro-Val | 1298 |
| Gly-Thr-Lys-Pro-Trp-Lys-Val | Gly-Thr-Lys-Pro-Trp-Lys-Val | Gly-Thr-Lys-Pro-Trp-Lys-Val | 1299 |
| Gly-Thr-Lys-Pro-Gln-Val | Gly-Thr-Lys-Pro-Gln-Val | Gly-Thr-Lys-Pro-Gln-Val | 1300 |
| Gly-Thr-Lys-Pro-Gln-Arg-Val | Gly-Thr-Lys-Pro-Gln-Arg-Val | Gly-Thr-Lys-Pro-Gln-Arg-Val | 1301 |
| Gly-Thr-Lys-Pro-Gln-Phe-Val | Gly-Thr-Lys-Pro-Gln-Phe-Val | Gly-Thr-Lys-Pro-Gln-Phe-Val | 1302 |
| Gly-Thr-Lys-Pro-Gln-Tyr-Val | Gly-Thr-Lys-Pro-Gln-Tyr-Val | Gly-Thr-Lys-Pro-Gln-Tyr-Val | 1303 |
| Gly-Thr-Lys-Pro-Gln-His-Val | Gly-Thr-Lys-Pro-Gln-His-Val | Gly-Thr-Lys-Pro-Gln-His-Val | 1304 |
| Gly-Thr-Lys-Pro-Gln-Pro-Val | Gly-Thr-Lys-Pro-Gln-Pro-Val | Gly-Thr-Lys-Pro-Gln-Pro-Val | 1305 |
| Gly-Thr-Lys-Pro-Gln-Lys-Val | Gly-Thr-Lys-Pro-Gln-Lys-Val | Gly-Thr-Lys-Pro-Gln-Lys-Val | 1306 |
| Gly-Thr-Lys-Pro-Asn-Val | Gly-Thr-Lys-Pro-Asn-Val | Gly-Thr-Lys-Pro-Asn-Val | 1307 |
| Gly-Thr-Lys-Pro-Asn-Arg-Val | Gly-Thr-Lys-Pro-Asn-Arg-Val | Gly-Thr-Lys-Pro-Asn-Arg-Val | 1308 |
| Gly-Thr-Lys-Pro-Asn-Phe-Val | Gly-Thr-Lys-Pro-Asn-Phe-Val | Gly-Thr-Lys-Pro-Asn-Phe-Val | 1309 |
| Gly-Thr-Lys-Pro-Asn-Tyr-Val | Gly-Thr-Lys-Pro-Asn-Tyr-Val | Gly-Thr-Lys-Pro-Asn-Tyr-Val | 1310 |
| Gly-Thr-Lys-Pro-Asn-His-Val | Gly-Thr-Lys-Pro-Asn-His-Val | Gly-Thr-Lys-Pro-Asn-His-Val | 1311 |
| Gly-Thr-Lys-Pro-Asn-Pro-Val | Gly-Thr-Lys-Pro-Asn-Pro-Val | Gly-Thr-Lys-Pro-Asn-Pro-Val | 1312 |
| Gly-Thr-Lys-Pro-Asn-Lys-Val | Gly-Thr-Lys-Pro-Asn-Lys-Val | Gly-Thr-Lys-Pro-Asn-Lys-Val | 1313 |
| Gly-Thr-Lys-Pro-Tyr-Val | Gly-Thr-Lys-Pro-Tyr-Val | Gly-Thr-Lys-Pro-Tyr-Val | 1314 |
| Gly-Thr-Lys-Pro-Tyr-Arg-Val | Gly-Thr-Lys-Pro-Tyr-Arg-Val | Gly-Thr-Lys-Pro-Tyr-Arg-Val | 1315 |
| Gly-Thr-Lys-Pro-Tyr-Phe-Val | Gly-Thr-Lys-Pro-Tyr-Phe-Val | Gly-Thr-Lys-Pro-Tyr-Phe-Val | 1316 |
| Gly-Thr-Lys-Pro-Tyr-Tyr-Val | Gly-Thr-Lys-Pro-Tyr-Tyr-Val | Gly-Thr-Lys-Pro-Tyr-Tyr-Val | 1317 |
| Gly-Thr-Lys-Pro-Tyr-His-Val | Gly-Thr-Lys-Pro-Tyr-His-Val | Gly-Thr-Lys-Pro-Tyr-His-Val | 1318 |
| Gly-Thr-Lys-Pro-Tyr-Pro-Val | Gly-Thr-Lys-Pro-Tyr-Pro-Val | Gly-Thr-Lys-Pro-Tyr-Pro-Val | 1319 |
| Gly-Thr-Lys-Pro-Tyr-Lys-Val | Gly-Thr-Lys-Pro-Tyr-Lys-Val | Gly-Thr-Lys-Pro-Tyr-Lys-Val | 1320 |
| Gly-Thr-Lys-Pro-Arg-Val | Gly-Thr-Lys-Pro-Arg-Val | Gly-Thr-Lys-Pro-Arg-Val | 1321 |
| Gly-Thr-Lys-Pro-Arg-Arg-Val | Gly-Thr-Lys-Pro-Arg-Arg-Val | Gly-Thr-Lys-Pro-Arg-Arg-Val | 1322 |
| Gly-Thr-Lys-Pro-Arg-Phe-Val | Gly-Thr-Lys-Pro-Arg-Phe-Val | Gly-Thr-Lys-Pro-Arg-Phe-Val | 1323 |
| Gly-Thr-Lys-Pro-Arg-Tyr-Val | Gly-Thr-Lys-Pro-Arg-Tyr-Val | Gly-Thr-Lys-Pro-Arg-Tyr-Val | 1324 |
| Gly-Thr-Lys-Pro-Arg-His-Val | Gly-Thr-Lys-Pro-Arg-His-Val | Gly-Thr-Lys-Pro-Arg-His-Val | 1325 |
| Gly-Thr-Lys-Pro-Arg-Pro-Val | Gly-Thr-Lys-Pro-Arg-Pro-Val | Gly-Thr-Lys-Pro-Arg-Pro-Val | 1326 |
| Gly-Thr-Lys-Pro-Arg-Lys-Val | Gly-Thr-Lys-Pro-Arg-Lys-Val | Gly-Thr-Lys-Pro-Arg-Lys-Val | 1327 |
| Met-Thr-Lys-Pro-Gly | Met-Thr-Lys-Pro-Gly | Met-Thr-Lys-Pro-Gly | 1328 |
| Met(O)-Thr-Lys-Pro-Gly | Met(O)-Thr-Lys-Pro-Gly | Met(O)-Thr-Lys-Pro-Gly | 1329 |
| Thr-Thr-Lys-Pro-Gly | Thr-Thr-Lys-Pro-Gly | Thr-Thr-Lys-Pro-Gly | 1330 |
| Ala-Thr-Lys-Pro-Gly | Ala-Thr-Lys-Pro-Gly | Ala-Thr-Lys-Pro-Gly | 1331 |
| His-Thr-Lys-Pro-Gly | His-Thr-Lys-Pro-Gly | His-Thr-Lys-Pro-Gly | 1332 |
| Lys-Thr-Lys-Pro-Gly | Lys-Thr-Lys-Pro-Gly | Lys-Thr-Lys-Pro-Gly | 1333 |
| Gly-Thr-Lys-Pro-Gly | Gly-Thr-Lys-Pro-Gly | Gly-Thr-Lys-Pro-Gly | 1334 |
| Thr-Lys-Pro-Arg-Tyr | Thr-Lys-Pro-Arg-Tyr | Thr-Lys-Pro-Arg-Tyr | 1335 |

TABLE 1-continued

| X-OH | X-OCH₃ | X-NH₂ | SEQ ID NO |
|---|---|---|---|
| Thr-Lys-Pro-Phe-Tyr | Thr-Lys-Pro-Phe-Tyr | Thr-Lys-Pro-Phe-Tyr | 1336 |
| Thr-Lys-Pro-Tyr-Tyr | Thr-Lys-Pro-Tyr-Tyr | Thr-Lys-Pro-Tyr-Tyr | 1337 |
| Thr-Lys-Pro-Gly-Tyr | Thr-Lys-Pro-Gly-Tyr | Thr-Lys-Pro-Gly-Tyr | 1338 |
| Thr-Lys-Pro-His-Tyr | Thr-Lys-Pro-His-Tyr | Thr-Lys-Pro-His-Tyr | 1339 |
| Thr-Lys-Pro-Lys-Tyr | Thr-Lys-Pro-Lys-Tyr | Thr-Lys-Pro-Lys-Tyr | 1340 |
| Thr-Lys-Pro-Gly-Tyr | Thr-Lys-Pro-Gly-Tyr | Thr-Lys-Pro-Gly-Tyr | 1341 |
| Thr-Lys-Pro-Gly-Arg-Tyr | Thr-Lys-Pro-Gly-Arg-Tyr | Thr-Lys-Pro-Gly-Arg-Tyr | 1342 |
| Thr-Lys-Pro-Gly-Phe-Tyr | Thr-Lys-Pro-Gly-Phe-Tyr | Thr-Lys-Pro-Gly-Phe-Tyr | 1343 |
| Thr-Lys-Pro-Gly-Tyr-Tyr | Thr-Lys-Pro-Gly-Tyr-Tyr | Thr-Lys-Pro-Gly-Tyr-Tyr | 1344 |
| Thr-Lys-Pro-Gly-His-Tyr | Thr-Lys-Pro-Gly-His-Tyr | Thr-Lys-Pro-Gly-His-Tyr | 1345 |
| Thr-Lys-Pro-Gly-Pro-Tyr | Thr-Lys-Pro-Gly-Pro-Tyr | Thr-Lys-Pro-Gly-Pro-Tyr | 1346 |
| Thr-Lys-Pro-Gly-Lys-Tyr | Thr-Lys-Pro-Gly-Lys-Tyr | Thr-Lys-Pro-Gly-Lys-Tyr | 1347 |
| Thr-Lys-Pro-Asp-Tyr | Thr-Lys-Pro-Asp-Tyr | Thr-Lys-Pro-Asp-Tyr | 1348 |
| Thr-Lys-Pro-Asp-Arg-Tyr | Thr-Lys-Pro-Asp-Arg-Tyr | Thr-Lys-Pro-Asp-Arg-Tyr | 1349 |
| Thr-Lys-Pro-Asp-Phe-Tyr | Thr-Lys-Pro-Asp-Phe-Tyr | Thr-Lys-Pro-Asp-Phe-Tyr | 1350 |
| Thr-Lys-Pro-Asp-Tyr-Tyr | Thr-Lys-Pro-Asp-Tyr-Tyr | Thr-Lys-Pro-Asp-Tyr-Tyr | 1351 |
| Thr-Lys-Pro-Asp-His-Tyr | Thr-Lys-Pro-Asp-His-Tyr | Thr-Lys-Pro-Asp-His-Tyr | 1352 |
| Thr-Lys-Pro-Asp-Pro-Tyr | Thr-Lys-Pro-Asp-Pro-Tyr | Thr-Lys-Pro-Asp-Pro-Tyr | 1353 |
| Thr-Lys-Pro-Asp-Lys-Tyr | Thr-Lys-Pro-Asp-Lys-Tyr | Thr-Lys-Pro-Asp-Lys-Tyr | 1354 |
| Thr-Lys-Pro-Trp-Tyr | Thr-Lys-Pro-Trp-Tyr | Thr-Lys-Pro-Trp-Tyr | 1355 |
| Thr-Lys-Pro-Trp-Arg-Tyr | Thr-Lys-Pro-Trp-Arg-Tyr | Thr-Lys-Pro-Trp-Arg-Tyr | 1356 |
| Thr-Lys-Pro-Trp-Phe-Tyr | Thr-Lys-Pro-Trp-Phe-Tyr | Thr-Lys-Pro-Trp-Phe-Tyr | 1357 |
| Thr-Lys-Pro-Trp-Tyr-Tyr | Thr-Lys-Pro-Trp-Tyr-Tyr | Thr-Lys-Pro-Trp-Tyr-Tyr | 1358 |
| Thr-Lys-Pro-Trp-His-Tyr | Thr-Lys-Pro-Trp-His-Tyr | Thr-Lys-Pro-Trp-His-Tyr | 1359 |
| Thr-Lys-Pro-Trp-Pro-Tyr | Thr-Lys-Pro-Trp-Pro-Tyr | Thr-Lys-Pro-Trp-Pro-Tyr | 1360 |
| Thr-Lys-Pro-Trp-Lys-Tyr | Thr-Lys-Pro-Trp-Lys-Tyr | Thr-Lys-Pro-Trp-Lys-Tyr | 1361 |
| Thr-Lys-Pro-Gln-Tyr | Thr-Lys-Pro-Gln-Tyr | Thr-Lys-Pro-Gln-Tyr | 1362 |
| Thr-Lys-Pro-Gln-Arg-Tyr | Thr-Lys-Pro-Gln-Arg-Tyr | Thr-Lys-Pro-Gln-Arg-Tyr | 1363 |
| Thr-Lys-Pro-Gln-Phe-Tyr | Thr-Lys-Pro-Gln-Phe-Tyr | Thr-Lys-Pro-Gln-Phe-Tyr | 1364 |
| Thr-Lys-Pro-Gln-Tyr-Tyr | Thr-Lys-Pro-Gln-Tyr-Tyr | Thr-Lys-Pro-Gln-Tyr-Tyr | 1365 |
| Thr-Lys-Pro-Gln-His-Tyr | Thr-Lys-Pro-Gln-His-Tyr | Thr-Lys-Pro-Gln-His-Tyr | 1366 |
| Thr-Lys-Pro-Gln-Pro-Tyr | Thr-Lys-Pro-Gln-Pro-Tyr | Thr-Lys-Pro-Gln-Pro-Tyr | 1367 |
| Thr-Lys-Pro-Gln-Lys-Tyr | Thr-Lys-Pro-Gln-Lys-Tyr | Thr-Lys-Pro-Gln-Lys-Tyr | 1368 |
| Thr-Lys-Pro-Asn-Tyr | Thr-Lys-Pro-Asn-Tyr | Thr-Lys-Pro-Asn-Tyr | 1369 |
| Thr-Lys-Pro-Asn-Arg-Tyr | Thr-Lys-Pro-Asn-Arg-Tyr | Thr-Lys-Pro-Asn-Arg-Tyr | 1370 |
| Thr-Lys-Pro-Asn-Phe-Tyr | Thr-Lys-Pro-Asn-Phe-Tyr | Thr-Lys-Pro-Asn-Phe-Tyr | 1371 |
| Thr-Lys-Pro-Asn-Tyr-Tyr | Thr-Lys-Pro-Asn-Tyr-Tyr | Thr-Lys-Pro-Asn-Tyr-Tyr | 1372 |
| Thr-Lys-Pro-Asn-His-Tyr | Thr-Lys-Pro-Asn-His-Tyr | Thr-Lys-Pro-Asn-His-Tyr | 1373 |

TABLE 1-continued

| X-OH | X-OCH₃ | X-NH₂ | SEQ ID NO |
|---|---|---|---|
| Thr-Lys-Pro-Asn-Pro-Tyr | Thr-Lys-Pro-Asn-Pro-Tyr | Thr-Lys-Pro-Asn-Pro-Tyr | 1374 |
| Thr-Lys-Pro-Asn-Lys-Tyr | Thr-Lys-Pro-Asn-Lys-Tyr | Thr-Lys-Pro-Asn-Lys-Tyr | 1375 |
| Thr-Lys-Pro-Tyr-Tyr | Thr-Lys-Pro-Tyr-Tyr | Thr-Lys-Pro-Tyr-Tyr | 1376 |
| Thr-Lys-Pro-Tyr-Arg-Tyr | Thr-Lys-Pro-Tyr-Arg-Tyr | Thr-Lys-Pro-Tyr-Arg-Tyr | 1377 |
| Thr-Lys-Pro-Tyr-Phe-Tyr | Thr-Lys-Pro-Tyr-Phe-Tyr | Thr-Lys-Pro-Tyr-Phe-Tyr | 1378 |
| Thr-Lys-Pro-Tyr-Tyr-Tyr | Thr-Lys-Pro-Tyr-Tyr-Tyr | Thr-Lys-Pro-Tyr-Tyr-Tyr | 1379 |
| Thr-Lys-Pro-Tyr-His-Tyr | Thr-Lys-Pro-Tyr-His-Tyr | Thr-Lys-Pro-Tyr-His-Tyr | 1380 |
| Thr-Lys-Pro-Tyr-Pro-Tyr | Thr-Lys-Pro-Tyr-Pro-Tyr | Thr-Lys-Pro-Tyr-Pro-Tyr | 1381 |
| Thr-Lys-Pro-Tyr-Lys-Tyr | Thr-Lys-Pro-Tyr-Lys-Tyr | Thr-Lys-Pro-Tyr-Lys-Tyr | 1382 |
| Thr-Lys-Pro-Arg-Tyr | Thr-Lys-Pro-Arg-Tyr | Thr-Lys-Pro-Arg-Tyr | 1383 |
| Thr-Lys-Pro-Arg-Arg-Tyr | Thr-Lys-Pro-Arg-Arg-Tyr | Thr-Lys-Pro-Arg-Arg-Tyr | 1384 |
| Thr-Lys-Pro-Arg-Phe-Tyr | Thr-Lys-Pro-Arg-Phe-Tyr | Thr-Lys-Pro-Arg-Phe-Tyr | 1385 |
| Thr-Lys-Pro-Arg-Tyr-Tyr | Thr-Lys-Pro-Arg-Tyr-Tyr | Thr-Lys-Pro-Arg-Tyr-Tyr | 1386 |
| Thr-Lys-Pro-Arg-His-Tyr | Thr-Lys-Pro-Arg-His-Tyr | Thr-Lys-Pro-Arg-His-Tyr | 1387 |
| Thr-Lys-Pro-Arg-Pro-Tyr | Thr-Lys-Pro-Arg-Pro-Tyr | Thr-Lys-Pro-Arg-Pro-Tyr | 1388 |
| Thr-Lys-Pro-Arg-Lys-Tyr | Thr-Lys-Pro-Arg-Lys-Tyr | Thr-Lys-Pro-Arg-Lys-Tyr | 1389 |
| Met-Thr-Lys-Pro-Tyr | Met-Thr-Lys-Pro-Tyr | Met-Thr-Lys-Pro-Tyr | 1390 |
| Met-Thr-Lys-Pro-Arg-Tyr | Met-Thr-Lys-Pro-Arg-Tyr | Met-Thr-Lys-Pro-Arg-Tyr | 1391 |
| Met-Thr-Lys-Pro-Phe-Tyr | Met-Thr-Lys-Pro-Phe-Tyr | Met-Thr-Lys-Pro-Phe-Tyr | 1392 |
| Met-Thr-Lys-Pro-Tyr-Tyr | Met-Thr-Lys-Pro-Tyr-Tyr | Met-Thr-Lys-Pro-Tyr-Tyr | 1393 |
| Met-Thr-Lys-Pro-Gly-Tyr | Met-Thr-Lys-Pro-Gly-Tyr | Met-Thr-Lys-Pro-Gly-Tyr | 1394 |
| Met-Thr-Lys-Pro-His-Tyr | Met-Thr-Lys-Pro-His-Tyr | Met-Thr-Lys-Pro-His-Tyr | 1395 |
| Met-Thr-Lys-Pro-Lys-Tyr | Met-Thr-Lys-Pro-Lys-Tyr | Met-Thr-Lys-Pro-Lys-Tyr | 1396 |
| Met-Thr-Lys-Pro-Gly-Tyr | Met-Thr-Lys-Pro-Gly-Tyr | Met-Thr-Lys-Pro-Gly-Tyr | 1397 |
| Met-Thr-Lys-Pro-Gly-Arg-Tyr | Met-Thr-Lys-Pro-Gly-Arg-Tyr | Met-Thr-Lys-Pro-Gly-Arg-Tyr | 1398 |
| Met-Thr-Lys-Pro-Gly-Phe-Tyr | Met-Thr-Lys-Pro-Gly-Phe-Tyr | Met-Thr-Lys-Pro-Gly-Phe-Tyr | 1399 |
| Met-Thr-Lys-Pro-Gly-Tyr-Tyr | Met-Thr-Lys-Pro-Gly-Tyr-Tyr | Met-Thr-Lys-Pro-Gly-Tyr-Tyr | 1400 |
| Met-Thr-Lys-Pro-Gly-His-Tyr | Met-Thr-Lys-Pro-Gly-His-Tyr | Met-Thr-Lys-Pro-Gly-His-Tyr | 1401 |
| Met-Thr-Lys-Pro-Gly-Pro-Tyr | Met-Thr-Lys-Pro-Gly-Pro-Tyr | Met-Thr-Lys-Pro-Gly-Pro-Tyr | 1402 |
| Met-Thr-Lys-Pro-Gly-Lys-Tyr | Met-Thr-Lys-Pro-Gly-Lys-Tyr | Met-Thr-Lys-Pro-Gly-Lys-Tyr | 1403 |
| Met-Thr-Lys-Pro-Asp-Tyr | Met-Thr-Lys-Pro-Asp-Tyr | Met-Thr-Lys-Pro-Asp-Tyr | 1404 |
| Met-Thr-Lys-Pro-Asp-Arg-Tyr | Met-Thr-Lys-Pro-Asp-Arg-Tyr | Met-Thr-Lys-Pro-Asp-Arg-Tyr | 1405 |
| Met-Thr-Lys-Pro-Asp-Phe-Tyr | Met-Thr-Lys-Pro-Asp-Phe-Tyr | Met-Thr-Lys-Pro-Asp-Phe-Tyr | 1406 |
| Met-Thr-Lys-Pro-Asp-Tyr-Tyr | Met-Thr-Lys-Pro-Asp-Tyr-Tyr | Met-Thr-Lys-Pro-Asp-Tyr-Tyr | 1407 |
| Met-Thr-Lys-Pro-Asp-His-Tyr | Met-Thr-Lys-Pro-Asp-His-Tyr | Met-Thr-Lys-Pro-Asp-His-Tyr | 1408 |
| Met-Thr-Lys-Pro-Asp-Pro-Tyr | Met-Thr-Lys-Pro-Asp-Pro-Tyr | Met-Thr-Lys-Pro-Asp-Pro-Tyr | 1409 |
| Met-Thr-Lys-Pro-Asp-Lys-Tyr | Met-Thr-Lys-Pro-Asp-Lys-Tyr | Met-Thr-Lys-Pro-Asp-Lys-Tyr | 1410 |
| Met-Thr-Lys-Pro-Trp-Tyr | Met-Thr-Lys-Pro-Trp-Tyr | Met-Thr-Lys-Pro-Trp-Tyr | 1411 |

TABLE 1-continued

| X-OH | X-OCH₃ | X-NH₂ | SEQ ID NO |
|---|---|---|---|
| Met-Thr-Lys-Pro-Trp-Arg-Tyr | Met-Thr-Lys-Pro-Trp-Arg-Tyr | Met-Thr-Lys-Pro-Trp-Arg-Tyr | 1412 |
| Met-Thr-Lys-Pro-Trp-Phe-Tyr | Met-Thr-Lys-Pro-Trp-Phe-Tyr | Met-Thr-Lys-Pro-Trp-Phe-Tyr | 1413 |
| Met-Thr-Lys-Pro-Trp-Tyr-Tyr | Met-Thr-Lys-Pro-Trp-Tyr-Tyr | Met-Thr-Lys-Pro-Trp-Tyr-Tyr | 1414 |
| Met-Thr-Lys-Pro-Trp-His-Tyr | Met-Thr-Lys-Pro-Trp-His-Tyr | Met-Thr-Lys-Pro-Trp-His-Tyr | 1415 |
| Met-Thr-Lys-Pro-Trp-Pro-Tyr | Met-Thr-Lys-Pro-Trp-Pro-Tyr | Met-Thr-Lys-Pro-Trp-Pro-Tyr | 1416 |
| Met-Thr-Lys-Pro-Trp-Lys-Tyr | Met-Thr-Lys-Pro-Trp-Lys-Tyr | Met-Thr-Lys-Pro-Trp-Lys-Tyr | 1417 |
| Met-Thr-Lys-Pro-Gln-Tyr | Met-Thr-Lys-Pro-Gln-Tyr | Met-Thr-Lys-Pro-Gln-Tyr | 1418 |
| Met-Thr-Lys-Pro-Gln-Arg-Tyr | Met-Thr-Lys-Pro-Gln-Arg-Tyr | Met-Thr-Lys-Pro-Gln-Arg-Tyr | 1419 |
| Met-Thr-Lys-Pro-Gln-Phe-Tyr | Met-Thr-Lys-Pro-Gln-Phe-Tyr | Met-Thr-Lys-Pro-Gln-Phe-Tyr | 1420 |
| Met-Thr-Lys-Pro-Gln-Tyr-Tyr | Met-Thr-Lys-Pro-Gln-Tyr-Tyr | Met-Thr-Lys-Pro-Gln-Tyr-Tyr | 1421 |
| Met-Thr-Lys-Pro-Gln-His-Tyr | Met-Thr-Lys-Pro-Gln-His-Tyr | Met-Thr-Lys-Pro-Gln-His-Tyr | 1422 |
| Met-Thr-Lys-Pro-Gln-Pro-Tyr | Met-Thr-Lys-Pro-Gln-Pro-Tyr | Met-Thr-Lys-Pro-Gln-Pro-Tyr | 1423 |
| Met-Thr-Lys-Pro-Gln-Lys-Tyr | Met-Thr-Lys-Pro-Gln-Lys-Tyr | Met-Thr-Lys-Pro-Gln-Lys-Tyr | 1424 |
| Met-Thr-Lys-Pro-Asn-Tyr | Met-Thr-Lys-Pro-Asn-Tyr | Met-Thr-Lys-Pro-Asn-Tyr | 1425 |
| Met-Thr-Lys-Pro-Asn-Arg-Tyr | Met-Thr-Lys-Pro-Asn-Arg-Tyr | Met-Thr-Lys-Pro-Asn-Arg-Tyr | 1426 |
| Met-Thr-Lys-Pro-Asn-Phe-Tyr | Met-Thr-Lys-Pro-Asn-Phe-Tyr | Met-Thr-Lys-Pro-Asn-Phe-Tyr | 1427 |
| Met-Thr-Lys-Pro-Asn-Tyr-Tyr | Met-Thr-Lys-Pro-Asn-Tyr-Tyr | Met-Thr-Lys-Pro-Asn-Tyr-Tyr | 1428 |
| Met-Thr-Lys-Pro-Asn-His-Tyr | Met-Thr-Lys-Pro-Asn-His-Tyr | Met-Thr-Lys-Pro-Asn-His-Tyr | 1429 |
| Met-Thr-Lys-Pro-Asn-Pro-Tyr | Met-Thr-Lys-Pro-Asn-Pro-Tyr | Met-Thr-Lys-Pro-Asn-Pro-Tyr | 1430 |
| Met-Thr-Lys-Pro-Asn-Lys-Tyr | Met-Thr-Lys-Pro-Asn-Lys-Tyr | Met-Thr-Lys-Pro-Asn-Lys-Tyr | 1431 |
| Met-Thr-Lys-Pro-Tyr-Tyr | Met-Thr-Lys-Pro-Tyr-Tyr | Met-Thr-Lys-Pro-Tyr-Tyr | 1432 |
| Met-Thr-Lys-Pro-Tyr-Arg-Tyr | Met-Thr-Lys-Pro-Tyr-Arg-Tyr | Met-Thr-Lys-Pro-Tyr-Arg-Tyr | 1433 |
| Met-Thr-Lys-Pro-Tyr-Phe-Tyr | Met-Thr-Lys-Pro-Tyr-Phe-Tyr | Met-Thr-Lys-Pro-Tyr-Phe-Tyr | 1434 |
| Met-Thr-Lys-Pro-Tyr-Tyr-Tyr | Met-Thr-Lys-Pro-Tyr-Tyr-Tyr | Met-Thr-Lys-Pro-Tyr-Tyr-Tyr | 1435 |
| Met-Thr-Lys-Pro-Tyr-His-Tyr | Met-Thr-Lys-Pro-Tyr-His-Tyr | Met-Thr-Lys-Pro-Tyr-His-Tyr | 1436 |
| Met-Thr-Lys-Pro-Tyr-Pro-Tyr | Met-Thr-Lys-Pro-Tyr-Pro-Tyr | Met-Thr-Lys-Pro-Tyr-Pro-Tyr | 1437 |
| Met-Thr-Lys-Pro-Tyr-Lys-Tyr | Met-Thr-Lys-Pro-Tyr-Lys-Tyr | Met-Thr-Lys-Pro-Tyr-Lys-Tyr | 1438 |
| Met-Thr-Lys-Pro-Arg-Tyr | Met-Thr-Lys-Pro-Arg-Tyr | Met-Thr-Lys-Pro-Arg-Tyr | 1439 |
| Met-Thr-Lys-Pro-Arg-Arg-Tyr | Met-Thr-Lys-Pro-Arg-Arg-Tyr | Met-Thr-Lys-Pro-Arg-Arg-Tyr | 1440 |
| Met-Thr-Lys-Pro-Arg-Phe-Tyr | Met-Thr-Lys-Pro-Arg-Phe-Tyr | Met-Thr-Lys-Pro-Arg-Phe-Tyr | 1441 |
| Met-Thr-Lys-Pro-Arg-Tyr-Tyr | Met-Thr-Lys-Pro-Arg-Tyr-Tyr | Met-Thr-Lys-Pro-Arg-Tyr-Tyr | 1442 |
| Met-Thr-Lys-Pro-Arg-His-Tyr | Met-Thr-Lys-Pro-Arg-His-Tyr | Met-Thr-Lys-Pro-Arg-His-Tyr | 1443 |
| Met-Thr-Lys-Pro-Arg-Pro-Tyr | Met-Thr-Lys-Pro-Arg-Pro-Tyr | Met-Thr-Lys-Pro-Arg-Pro-Tyr | 1444 |
| Met-Thr-Lys-Pro-Arg-Lys-Tyr | Met-Thr-Lys-Pro-Arg-Lys-Tyr | Met-Thr-Lys-Pro-Arg-Lys-Tyr | 1445 |
| Met(O)-Thr-Lys-Pro-Tyr | Met(O)-Thr-Lys-Pro-Tyr | Met(O)-Thr-Lys-Pro-Tyr | 1446 |
| Met(O)-Thr-Lys-Pro-Arg-Tyr | Met(O)-Thr-Lys-Pro-Arg-Tyr | Met(O)-Thr-Lys-Pro-Arg-Tyr | 1447 |
| Met(O)-Thr-Lys-Pro-Phe-Tyr | Met(O)-Thr-Lys-Pro-Phe-Tyr | Met(O)-Thr-Lys-Pro-Phe-Tyr | 1448 |
| Met(O)-Thr-Lys-Pro-Tyr-Tyr | Met(O)-Thr-Lys-Pro-Tyr-Tyr | Met(O)-Thr-Lys-Pro-Tyr-Tyr | 1449 |

TABLE 1-continued

| X-OH | X-OCH$_3$ | X-NH$_2$ | SEQ ID NO |
|---|---|---|---|
| Met(O)-Thr-Lys-Pro-Gly-Tyr | Met(O)-Thr-Lys-Pro-Gly-Tyr | Met(O)-Thr-Lys-Pro-Gly-Tyr | 1450 |
| Met(O)-Thr-Lys-Pro-His-Tyr | Met(O)-Thr-Lys-Pro-His-Tyr | Met(O)-Thr-Lys-Pro-His-Tyr | 1451 |
| Met(O)-Thr-Lys-Pro-Lys-Tyr | Met(O)-Thr-Lys-Pro-Lys-Tyr | Met(O)-Thr-Lys-Pro-Lys-Tyr | 1452 |
| Met(O)-Thr-Lys-Pro-Gly-Tyr | Met(O)-Thr-Lys-Pro-Gly-Tyr | Met(O)-Thr-Lys-Pro-Gly-Tyr | 1453 |
| Met(O)-Thr-Lys-Pro-Gly-Arg-Tyr | Met(O)-Thr-Lys-Pro-Gly-Arg-Tyr | Met(O)-Thr-Lys-Pro-Gly-Arg-Tyr | 1454 |
| Met(O)-Thr-Lys-Pro-Gly-Phe-Tyr | Met(O)-Thr-Lys-Pro-Gly-Phe-Tyr | Met(O)-Thr-Lys-Pro-Gly-Phe-Tyr | 1455 |
| Met(O)-Thr-Lys-Pro-Gly-Tyr-Tyr | Met(O)-Thr-Lys-Pro-Gly-Tyr-Tyr | Met(O)-Thr-Lys-Pro-Gly-Tyr-Tyr | 1456 |
| Met(O)-Thr-Lys-Pro-Gly-His-Tyr | Met(O)-Thr-Lys-Pro-Gly-His-Tyr | Met(O)-Thr-Lys-Pro-Gly-His-Tyr | 1457 |
| Met(O)-Thr-Lys-Pro-Gly-Pro-Tyr | Met(O)-Thr-Lys-Pro-Gly-Pro-Tyr | Met(O)-Thr-Lys-Pro-Gly-Pro-Tyr | 1458 |
| Met(O)-Thr-Lys-Pro-Gly-Lys-Tyr | Met(O)-Thr-Lys-Pro-Gly-Lys-Tyr | Met(O)-Thr-Lys-Pro-Gly-Lys-Tyr | 1459 |
| Met(O)-Thr-Lys-Pro-Asp-Tyr | Met(O)-Thr-Lys-Pro-Asp-Tyr | Met(O)-Thr-Lys-Pro-Asp-Tyr | 1460 |
| Met(O)-Thr-Lys-Pro-Asp-Arg-Tyr | Met(O)-Thr-Lys-Pro-Asp-Arg-Tyr | Met(O)-Thr-Lys-Pro-Asp-Arg-Tyr | 1461 |
| Met(O)-Thr-Lys-Pro-Asp-Phe-Tyr | Met(O)-Thr-Lys-Pro-Asp-Phe-Tyr | Met(O)-Thr-Lys-Pro-Asp-Phe-Tyr | 1462 |
| Met(O)-Thr-Lys-Pro-Asp-Tyr-Tyr | Met(O)-Thr-Lys-Pro-Asp-Tyr-Tyr | Met(O)-Thr-Lys-Pro-Asp-Tyr-Tyr | 1463 |
| Met(O)-Thr-Lys-Pro-Asp-His-Tyr | Met(O)-Thr-Lys-Pro-Asp-His-Tyr | Met(O)-Thr-Lys-Pro-Asp-His-Tyr | 1464 |
| Met(O)-Thr-Lys-Pro-Asp-Pro-Tyr | Met(O)-Thr-Lys-Pro-Asp-Pro-Tyr | Met(O)-Thr-Lys-Pro-Asp-Pro-Tyr | 1465 |
| Met(O)-Thr-Lys-Pro-Asp-Lys-Tyr | Met(O)-Thr-Lys-Pro-Asp-Lys-Tyr | Met(O)-Thr-Lys-Pro-Asp-Lys-Tyr | 1466 |
| Met(O)-Thr-Lys-Pro-Trp-Tyr | Met(O)-Thr-Lys-Pro-Trp-Tyr | Met(O)-Thr-Lys-Pro-Trp-Tyr | 1467 |
| Met(O)-Thr-Lys-Pro-Trp-Arg-Tyr | Met(O)-Thr-Lys-Pro-Trp-Arg-Tyr | Met(O)-Thr-Lys-Pro-Trp-Arg-Tyr | 1468 |
| Met(O)-Thr-Lys-Pro-Trp-Phe-Tyr | Met(O)-Thr-Lys-Pro-Trp-Phe-Tyr | Met(O)-Thr-Lys-Pro-Trp-Phe-Tyr | 1469 |
| Met(O)-Thr-Lys-Pro-Trp-Tyr-Tyr | Met(O)-Thr-Lys-Pro-Trp-Tyr-Tyr | Met(O)-Thr-Lys-Pro-Trp-Tyr-Tyr | 1470 |
| Met(O)-Thr-Lys-Pro-Trp-His-Tyr | Met(O)-Thr-Lys-Pro-Trp-His-Tyr | Met(O)-Thr-Lys-Pro-Trp-His-Tyr | 1471 |
| Met(O)-Thr-Lys-Pro-Trp-Pro-Tyr | Met(O)-Thr-Lys-Pro-Trp-Pro-Tyr | Met(O)-Thr-Lys-Pro-Trp-Pro-Tyr | 1472 |
| Met(O)-Thr-Lys-Pro-Trp-Lys-Tyr | Met(O)-Thr-Lys-Pro-Trp-Lys-Tyr | Met(O)-Thr-Lys-Pro-Trp-Lys-Tyr | 1473 |
| Met(O)-Thr-Lys-Pro-Gln-Tyr | Met(O)-Thr-Lys-Pro-Gln-Tyr | Met(O)-Thr-Lys-Pro-Gln-Tyr | 1474 |
| Met(O)-Thr-Lys-Pro-Gln-Arg-Tyr | Met(O)-Thr-Lys-Pro-Gln-Arg-Tyr | Met(O)-Thr-Lys-Pro-Gln-Arg-Tyr | 1475 |
| Met(O)-Thr-Lys-Pro-Gln-Phe-Tyr | Met(O)-Thr-Lys-Pro-Gln-Phe-Tyr | Met(O)-Thr-Lys-Pro-Gln-Phe-Tyr | 1476 |
| Met(O)-Thr-Lys-Pro-Gln-Tyr- | Met(O)-Thr-Lys-Pro-Gln-Tyr- | Met(O)-Thr-Lys-Pro-Gln-Tyr- | 1477 |

TABLE 1-continued

| X-OH | X-OCH₃ | X-NH₂ | SEQ ID NO |
|---|---|---|---|
| Tyr | Tyr | Tyr | |
| Met(O)-Thr-Lys-Pro-Gln-His-Tyr | Met(O)-Thr-Lys-Pro-Gln-His-Tyr | Met(O)-Thr-Lys-Pro-Gln-His-Tyr | 1478 |
| Met(O)-Thr-Lys-Pro-Gln-Pro-Tyr | Met(O)-Thr-Lys-Pro-Gln-Pro-Tyr | Met(O)-Thr-Lys-Pro-Gln-Pro-Tyr | 1479 |
| Met(O)-Thr-Lys-Pro-Gln-Lys-Tyr | Met(O)-Thr-Lys-Pro-Gln-Lys-Tyr | Met(O)-Thr-Lys-Pro-Gln-Lys-Tyr | 1480 |
| Met(O)-Thr-Lys-Pro-Asn-Tyr | Met(O)-Thr-Lys-Pro-Asn-Tyr | Met(O)-Thr-Lys-Pro-Asn-Tyr | 1481 |
| Met(O)-Thr-Lys-Pro-Asn-Arg-Tyr | Met(O)-Thr-Lys-Pro-Asn-Arg-Tyr | Met(O)-Thr-Lys-Pro-Asn-Arg-Tyr | 1482 |
| Met(O)-Thr-Lys-Pro-Asn-Phe-Tyr | Met(O)-Thr-Lys-Pro-Asn-Phe-Tyr | Met(O)-Thr-Lys-Pro-Asn-Phe-Tyr | 1483 |
| Met(O)-Thr-Lys-Pro-Asn-Tyr-Tyr | Met(O)-Thr-Lys-Pro-Asn-Tyr-Tyr | Met(O)-Thr-Lys-Pro-Asn-Tyr-Tyr | 1484 |
| Met(O)-Thr-Lys-Pro-Asn-His-Tyr | Met(O)-Thr-Lys-Pro-Asn-His-Tyr | Met(O)-Thr-Lys-Pro-Asn-His-Tyr | 1485 |
| Met(O)-Thr-Lys-Pro-Asn-Pro-Tyr | Met(O)-Thr-Lys-Pro-Asn-Pro-Tyr | Met(O)-Thr-Lys-Pro-Asn-Pro-Tyr | 1486 |
| Met(O)-Thr-Lys-Pro-Asn-Lys-Tyr | Met(O)-Thr-Lys-Pro-Asn-Lys-Tyr | Met(O)-Thr-Lys-Pro-Asn-Lys-Tyr | 1487 |
| Met(O)-Thr-Lys-Pro-Tyr-Tyr | Met(O)-Thr-Lys-Pro-Tyr-Tyr | Met(O)-Thr-Lys-Pro-Tyr-Tyr | 1488 |
| Met(O)-Thr-Lys-Pro-Tyr-Arg-Tyr | Met(O)-Thr-Lys-Pro-Tyr-Arg-Tyr | Met(O)-Thr-Lys-Pro-Tyr-Arg-Tyr | 1489 |
| Met(O)-Thr-Lys-Pro-Tyr-Phe-Tyr | Met(O)-Thr-Lys-Pro-Tyr-Phe-Tyr | Met(O)-Thr-Lys-Pro-Tyr-Phe-Tyr | 1490 |
| Met(O)-Thr-Lys-Pro-Tyr-Tyr-Tyr | Met(O)-Thr-Lys-Pro-Tyr-Tyr-Tyr | Met(O)-Thr-Lys-Pro-Tyr-Tyr-Tyr | 1491 |
| Met(O)-Thr-Lys-Pro-Tyr-His-Tyr | Met(O)-Thr-Lys-Pro-Tyr-His-Tyr | Met(O)-Thr-Lys-Pro-Tyr-His-Tyr | 1492 |
| Met(O)-Thr-Lys-Pro-Tyr-Pro-Tyr | Met(O)-Thr-Lys-Pro-Tyr-Pro-Tyr | Met(O)-Thr-Lys-Pro-Tyr-Pro-Tyr | 1493 |
| Met(O)-Thr-Lys-Pro-Tyr-Lys-Tyr | Met(O)-Thr-Lys-Pro-Tyr-Lys-Tyr | Met(O)-Thr-Lys-Pro-Tyr-Lys-Tyr | 1494 |
| Met(O)-Thr-Lys-Pro-Arg-Tyr | Met(O)-Thr-Lys-Pro-Arg-Tyr | Met(O)-Thr-Lys-Pro-Arg-Tyr | 1495 |
| Met(O)-Thr-Lys-Pro-Arg-Arg-Tyr | Met(O)-Thr-Lys-Pro-Arg-Arg-Tyr | Met(O)-Thr-Lys-Pro-Arg-Arg-Tyr | 1496 |
| Met(O)-Thr-Lys-Pro-Arg-Phe-Tyr | Met(O)-Thr-Lys-Pro-Arg-Phe-Tyr | Met(O)-Thr-Lys-Pro-Arg-Phe-Tyr | 1497 |
| Met(O)-Thr-Lys-Pro-Arg-Tyr-Tyr | Met(O)-Thr-Lys-Pro-Arg-Tyr-Tyr | Met(O)-Thr-Lys-Pro-Arg-Tyr-Tyr | 1498 |
| Met(O)-Thr-Lys-Pro-Arg-His-Tyr | Met(O)-Thr-Lys-Pro-Arg-His-Tyr | Met(O)-Thr-Lys-Pro-Arg-His-Tyr | 1499 |
| Met(O)-Thr-Lys-Pro-Arg-Pro-Tyr | Met(O)-Thr-Lys-Pro-Arg-Pro-Tyr | Met(O)-Thr-Lys-Pro-Arg-Pro-Tyr | 1500 |
| Met(O)-Thr-Lys-Pro-Arg-Lys-Tyr | Met(O)-Thr-Lys-Pro-Arg-Lys-Tyr | Met(O)-Thr-Lys-Pro-Arg-Lys-Tyr | 1501 |
| Thr-Thr-Lys-Pro-Tyr | Thr-Thr-Lys-Pro-Tyr | Thr-Thr-Lys-Pro-Tyr | 1502 |
| Thr-Thr-Lys-Pro-Arg-Tyr | Thr-Thr-Lys-Pro-Arg-Tyr | Thr-Thr-Lys-Pro-Arg-Tyr | 1503 |
| Thr-Thr-Lys-Pro-Phe-Tyr | Thr-Thr-Lys-Pro-Phe-Tyr | Thr-Thr-Lys-Pro-Phe-Tyr | 1504 |

TABLE 1-continued

| X-OH | X-OCH₃ | X-NH₂ | SEQ ID NO |
|---|---|---|---|
| Thr-Thr-Lys-Pro-Tyr-Tyr | Thr-Thr-Lys-Pro-Tyr-Tyr | Thr-Thr-Lys-Pro-Tyr-Tyr | 1505 |
| Thr-Thr-Lys-Pro-Gly-Tyr | Thr-Thr-Lys-Pro-Gly-Tyr | Thr-Thr-Lys-Pro-Gly-Tyr | 1506 |
| Thr-Thr-Lys-Pro-His-Tyr | Thr-Thr-Lys-Pro-His-Tyr | Thr-Thr-Lys-Pro-His-Tyr | 1507 |
| Thr-Thr-Lys-Pro-Lys-Tyr | Thr-Thr-Lys-Pro-Lys-Tyr | Thr-Thr-Lys-Pro-Lys-Tyr | 1508 |
| Thr-Thr-Lys-Pro-Gly-Tyr | Thr-Thr-Lys-Pro-Gly-Tyr | Thr-Thr-Lys-Pro-Gly-Tyr | 1509 |
| Thr-Thr-Lys-Pro-Gly-Arg-Tyr | Thr-Thr-Lys-Pro-Gly-Arg-Tyr | Thr-Thr-Lys-Pro-Gly-Arg-Tyr | 1510 |
| Thr-Thr-Lys-Pro-Gly-Phe-Tyr | Thr-Thr-Lys-Pro-Gly-Phe-Tyr | Thr-Thr-Lys-Pro-Gly-Phe-Tyr | 1511 |
| Thr-Thr-Lys-Pro-Gly-Tyr-Tyr | Thr-Thr-Lys-Pro-Gly-Tyr-Tyr | Thr-Thr-Lys-Pro-Gly-Tyr-Tyr | 1512 |
| Thr-Thr-Lys-Pro-Gly-His-Tyr | Thr-Thr-Lys-Pro-Gly-His-Tyr | Thr-Thr-Lys-Pro-Gly-His-Tyr | 1513 |
| Thr-Thr-Lys-Pro-Gly-Pro-Tyr | Thr-Thr-Lys-Pro-Gly-Pro-Tyr | Thr-Thr-Lys-Pro-Gly-Pro-Tyr | 1514 |
| Thr-Thr-Lys-Pro-Gly-Lys-Tyr | Thr-Thr-Lys-Pro-Gly-Lys-Tyr | Thr-Thr-Lys-Pro-Gly-Lys-Tyr | 1515 |
| Thr-Thr-Lys-Pro-Asp-Tyr | Thr-Thr-Lys-Pro-Asp-Tyr | Thr-Thr-Lys-Pro-Asp-Tyr | 1516 |
| Thr-Thr-Lys-Pro-Asp-Arg-Tyr | Thr-Thr-Lys-Pro-Asp-Arg-Tyr | Thr-Thr-Lys-Pro-Asp-Arg-Tyr | 1517 |
| Thr-Thr-Lys-Pro-Asp-Phe-Tyr | Thr-Thr-Lys-Pro-Asp-Phe-Tyr | Thr-Thr-Lys-Pro-Asp-Phe-Tyr | 1518 |
| Thr-Thr-Lys-Pro-Asp-Tyr-Tyr | Thr-Thr-Lys-Pro-Asp-Tyr-Tyr | Thr-Thr-Lys-Pro-Asp-Tyr-Tyr | 1519 |
| Thr-Thr-Lys-Pro-Asp-His-Tyr | Thr-Thr-Lys-Pro-Asp-His-Tyr | Thr-Thr-Lys-Pro-Asp-His-Tyr | 1520 |
| Thr-Thr-Lys-Pro-Asp-Pro-Tyr | Thr-Thr-Lys-Pro-Asp-Pro-Tyr | Thr-Thr-Lys-Pro-Asp-Pro-Tyr | 1521 |
| Thr-Thr-Lys-Pro-Asp-Lys-Tyr | Thr-Thr-Lys-Pro-Asp-Lys-Tyr | Thr-Thr-Lys-Pro-Asp-Lys-Tyr | 1522 |
| Thr-Thr-Lys-Pro-Trp-Tyr | Thr-Thr-Lys-Pro-Trp-Tyr | Thr-Thr-Lys-Pro-Trp-Tyr | 1523 |
| Thr-Thr-Lys-Pro-Trp-Arg-Tyr | Thr-Thr-Lys-Pro-Trp-Arg-Tyr | Thr-Thr-Lys-Pro-Trp-Arg-Tyr | 1524 |
| Thr-Thr-Lys-Pro-Trp-Phe-Tyr | Thr-Thr-Lys-Pro-Trp-Phe-Tyr | Thr-Thr-Lys-Pro-Trp-Phe-Tyr | 1525 |
| Thr-Thr-Lys-Pro-Trp-Tyr-Tyr | Thr-Thr-Lys-Pro-Trp-Tyr-Tyr | Thr-Thr-Lys-Pro-Trp-Tyr-Tyr | 1526 |
| Thr-Thr-Lys-Pro-Trp-His-Tyr | Thr-Thr-Lys-Pro-Trp-His-Tyr | Thr-Thr-Lys-Pro-Trp-His-Tyr | 1527 |
| Thr-Thr-Lys-Pro-Trp-Pro-Tyr | Thr-Thr-Lys-Pro-Trp-Pro-Tyr | Thr-Thr-Lys-Pro-Trp-Pro-Tyr | 1528 |
| Thr-Thr-Lys-Pro-Trp-Lys-Tyr | Thr-Thr-Lys-Pro-Trp-Lys-Tyr | Thr-Thr-Lys-Pro-Trp-Lys-Tyr | 1529 |
| Thr-Thr-Lys-Pro-Gln-Tyr | Thr-Thr-Lys-Pro-Gln-Tyr | Thr-Thr-Lys-Pro-Gln-Tyr | 1530 |
| Thr-Thr-Lys-Pro-Gln-Arg-Tyr | Thr-Thr-Lys-Pro-Gln-Arg-Tyr | Thr-Thr-Lys-Pro-Gln-Arg-Tyr | 1531 |
| Thr-Thr-Lys-Pro-Gln-Phe-Tyr | Thr-Thr-Lys-Pro-Gln-Phe-Tyr | Thr-Thr-Lys-Pro-Gln-Phe-Tyr | 1532 |
| Thr-Thr-Lys-Pro-Gln-Tyr-Tyr | Thr-Thr-Lys-Pro-Gln-Tyr-Tyr | Thr-Thr-Lys-Pro-Gln-Tyr-Tyr | 1533 |
| Thr-Thr-Lys-Pro-Gln-His-Tyr | Thr-Thr-Lys-Pro-Gln-His-Tyr | Thr-Thr-Lys-Pro-Gln-His-Tyr | 1534 |
| Thr-Thr-Lys-Pro-Gln-Pro-Tyr | Thr-Thr-Lys-Pro-Gln-Pro-Tyr | Thr-Thr-Lys-Pro-Gln-Pro-Tyr | 1535 |
| Thr-Thr-Lys-Pro-Gln-Lys-Tyr | Thr-Thr-Lys-Pro-Gln-Lys-Tyr | Thr-Thr-Lys-Pro-Gln-Lys-Tyr | 1536 |
| Thr-Thr-Lys-Pro-Asn-Tyr | Thr-Thr-Lys-Pro-Asn-Tyr | Thr-Thr-Lys-Pro-Asn-Tyr | 1537 |
| Thr-Thr-Lys-Pro-Asn-Arg-Tyr | Thr-Thr-Lys-Pro-Asn-Arg-Tyr | Thr-Thr-Lys-Pro-Asn-Arg-Tyr | 1538 |
| Thr-Thr-Lys-Pro-Asn-Phe-Tyr | Thr-Thr-Lys-Pro-Asn-Phe-Tyr | Thr-Thr-Lys-Pro-Asn-Phe-Tyr | 1539 |
| Thr-Thr-Lys-Pro-Asn-Tyr-Tyr | Thr-Thr-Lys-Pro-Asn-Tyr-Tyr | Thr-Thr-Lys-Pro-Asn-Tyr-Tyr | 1540 |
| Thr-Thr-Lys-Pro-Asn-His-Tyr | Thr-Thr-Lys-Pro-Asn-His-Tyr | Thr-Thr-Lys-Pro-Asn-His-Tyr | 1541 |
| Thr-Thr-Lys-Pro-Asn-Pro-Tyr | Thr-Thr-Lys-Pro-Asn-Pro-Tyr | Thr-Thr-Lys-Pro-Asn-Pro-Tyr | 1542 |

TABLE 1-continued

| X-OH | X-OCH₃ | X-NH₂ | SEQ ID NO |
|---|---|---|---|
| Thr-Thr-Lys-Pro-Asn-Lys-Tyr | Thr-Thr-Lys-Pro-Asn-Lys-Tyr | Thr-Thr-Lys-Pro-Asn-Lys-Tyr | 1543 |
| Thr-Thr-Lys-Pro-Tyr-Tyr | Thr-Thr-Lys-Pro-Tyr-Tyr | Thr-Thr-Lys-Pro-Tyr-Tyr | 1544 |
| Thr-Thr-Lys-Pro-Tyr-Arg-Tyr | Thr-Thr-Lys-Pro-Tyr-Arg-Tyr | Thr-Thr-Lys-Pro-Tyr-Arg-Tyr | 1545 |
| Thr-Thr-Lys-Pro-Tyr-Phe-Tyr | Thr-Thr-Lys-Pro-Tyr-Phe-Tyr | Thr-Thr-Lys-Pro-Tyr-Phe-Tyr | 1546 |
| Thr-Thr-Lys-Pro-Tyr-Tyr-Tyr | Thr-Thr-Lys-Pro-Tyr-Tyr-Tyr | Thr-Thr-Lys-Pro-Tyr-Tyr-Tyr | 1547 |
| Thr-Thr-Lys-Pro-Tyr-His-Tyr | Thr-Thr-Lys-Pro-Tyr-His-Tyr | Thr-Thr-Lys-Pro-Tyr-His-Tyr | 1548 |
| Thr-Thr-Lys-Pro-Tyr-Pro-Tyr | Thr-Thr-Lys-Pro-Tyr-Pro-Tyr | Thr-Thr-Lys-Pro-Tyr-Pro-Tyr | 1549 |
| Thr-Thr-Lys-Pro-Tyr-Lys-Tyr | Thr-Thr-Lys-Pro-Tyr-Lys-Tyr | Thr-Thr-Lys-Pro-Tyr-Lys-Tyr | 1550 |
| Thr-Thr-Lys-Pro-Arg-Tyr | Thr-Thr-Lys-Pro-Arg-Tyr | Thr-Thr-Lys-Pro-Arg-Tyr | 1551 |
| Thr-Thr-Lys-Pro-Arg-Arg-Tyr | Thr-Thr-Lys-Pro-Arg-Arg-Tyr | Thr-Thr-Lys-Pro-Arg-Arg-Tyr | 1552 |
| Thr-Thr-Lys-Pro-Arg-Phe-Tyr | Thr-Thr-Lys-Pro-Arg-Phe-Tyr | Thr-Thr-Lys-Pro-Arg-Phe-Tyr | 1553 |
| Thr-Thr-Lys-Pro-Arg-Tyr-Tyr | Thr-Thr-Lys-Pro-Arg-Tyr-Tyr | Thr-Thr-Lys-Pro-Arg-Tyr-Tyr | 1554 |
| Thr-Thr-Lys-Pro-Arg-His-Tyr | Thr-Thr-Lys-Pro-Arg-His-Tyr | Thr-Thr-Lys-Pro-Arg-His-Tyr | 1555 |
| Thr-Thr-Lys-Pro-Arg-Pro-Tyr | Thr-Thr-Lys-Pro-Arg-Pro-Tyr | Thr-Thr-Lys-Pro-Arg-Pro-Tyr | 1556 |
| Thr-Thr-Lys-Pro-Arg-Lys-Tyr | Thr-Thr-Lys-Pro-Arg-Lys-Tyr | Thr-Thr-Lys-Pro-Arg-Lys-Tyr | 1557 |
| Ala-Thr-Lys-Pro-Tyr | Ala-Thr-Lys-Pro-Tyr | Ala-Thr-Lys-Pro-Tyr | 1558 |
| Ala-Thr-Lys-Pro-Arg-Tyr | Ala-Thr-Lys-Pro-Arg-Tyr | Ala-Thr-Lys-Pro-Arg-Tyr | 1559 |
| Ala-Thr-Lys-Pro-Phe-Tyr | Ala-Thr-Lys-Pro-Phe-Tyr | Ala-Thr-Lys-Pro-Phe-Tyr | 1560 |
| Ala-Thr-Lys-Pro-Tyr-Tyr | Ala-Thr-Lys-Pro-Tyr-Tyr | Ala-Thr-Lys-Pro-Tyr-Tyr | 1561 |
| Ala-Thr-Lys-Pro-Gly-Tyr | Ala-Thr-Lys-Pro-Gly-Tyr | Ala-Thr-Lys-Pro-Gly-Tyr | 1562 |
| Ala-Thr-Lys-Pro-His-Tyr | Ala-Thr-Lys-Pro-His-Tyr | Ala-Thr-Lys-Pro-His-Tyr | 1563 |
| Ala-Thr-Lys-Pro-Lys-Tyr | Ala-Thr-Lys-Pro-Lys-Tyr | Ala-Thr-Lys-Pro-Lys-Tyr | 1564 |
| Ala-Thr-Lys-Pro-Gly-Tyr | Ala-Thr-Lys-Pro-Gly-Tyr | Ala-Thr-Lys-Pro-Gly-Tyr | 1565 |
| Ala-Thr-Lys-Pro-Gly-Arg-Tyr | Ala-Thr-Lys-Pro-Gly-Arg-Tyr | Ala-Thr-Lys-Pro-Gly-Arg-Tyr | 1566 |
| Ala-Thr-Lys-Pro-Gly-Phe-Tyr | Ala-Thr-Lys-Pro-Gly-Phe-Tyr | Ala-Thr-Lys-Pro-Gly-Phe-Tyr | 1567 |
| Ala-Thr-Lys-Pro-Gly-Tyr-Tyr | Ala-Thr-Lys-Pro-Gly-Tyr-Tyr | Ala-Thr-Lys-Pro-Gly-Tyr-Tyr | 1568 |
| Ala-Thr-Lys-Pro-Gly-His-Tyr | Ala-Thr-Lys-Pro-Gly-His-Tyr | Ala-Thr-Lys-Pro-Gly-His-Tyr | 1569 |
| Ala-Thr-Lys-Pro-Gly-Pro-Tyr | Ala-Thr-Lys-Pro-Gly-Pro-Tyr | Ala-Thr-Lys-Pro-Gly-Pro-Tyr | 1570 |
| Ala-Thr-Lys-Pro-Gly-Lys-Tyr | Ala-Thr-Lys-Pro-Gly-Lys-Tyr | Ala-Thr-Lys-Pro-Gly-Lys-Tyr | 1571 |
| Ala-Thr-Lys-Pro-Asp-Tyr | Ala-Thr-Lys-Pro-Asp-Tyr | Ala-Thr-Lys-Pro-Asp-Tyr | 1572 |
| Ala-Thr-Lys-Pro-Asp-Arg-Tyr | Ala-Thr-Lys-Pro-Asp-Arg-Tyr | Ala-Thr-Lys-Pro-Asp-Arg-Tyr | 1573 |
| Ala-Thr-Lys-Pro-Asp-Phe-Tyr | Ala-Thr-Lys-Pro-Asp-Phe-Tyr | Ala-Thr-Lys-Pro-Asp-Phe-Tyr | 1574 |
| Ala-Thr-Lys-Pro-Asp-Tyr-Tyr | Ala-Thr-Lys-Pro-Asp-Tyr-Tyr | Ala-Thr-Lys-Pro-Asp-Tyr-Tyr | 1575 |
| Ala-Thr-Lys-Pro-Asp-His-Tyr | Ala-Thr-Lys-Pro-Asp-His-Tyr | Ala-Thr-Lys-Pro-Asp-His-Tyr | 1576 |
| Ala-Thr-Lys-Pro-Asp-Pro-Tyr | Ala-Thr-Lys-Pro-Asp-Pro-Tyr | Ala-Thr-Lys-Pro-Asp-Pro-Tyr | 1577 |
| Ala-Thr-Lys-Pro-Asp-Lys-Tyr | Ala-Thr-Lys-Pro-Asp-Lys-Tyr | Ala-Thr-Lys-Pro-Asp-Lys-Tyr | 1578 |
| Ala-Thr-Lys-Pro-Trp-Tyr | Ala-Thr-Lys-Pro-Trp-Tyr | Ala-Thr-Lys-Pro-Trp-Tyr | 1579 |
| Ala-Thr-Lys-Pro-Trp-Arg-Tyr | Ala-Thr-Lys-Pro-Trp-Arg-Tyr | Ala-Thr-Lys-Pro-Trp-Arg-Tyr | 1580 |

TABLE 1-continued

| X-OH | X-OCH₃ | X-NH₂ | SEQ ID NO |
|---|---|---|---|
| Ala-Thr-Lys-Pro-Trp-Phe-Tyr | Ala-Thr-Lys-Pro-Trp-Phe-Tyr | Ala-Thr-Lys-Pro-Trp-Phe-Tyr | 1581 |
| Ala-Thr-Lys-Pro-Trp-Tyr-Tyr | Ala-Thr-Lys-Pro-Trp-Tyr-Tyr | Ala-Thr-Lys-Pro-Trp-Tyr-Tyr | 1582 |
| Ala-Thr-Lys-Pro-Trp-His-Tyr | Ala-Thr-Lys-Pro-Trp-His-Tyr | Ala-Thr-Lys-Pro-Trp-His-Tyr | 1583 |
| Ala-Thr-Lys-Pro-Trp-Pro-Tyr | Ala-Thr-Lys-Pro-Trp-Pro-Tyr | Ala-Thr-Lys-Pro-Trp-Pro-Tyr | 1584 |
| Ala-Thr-Lys-Pro-Trp-Lys-Tyr | Ala-Thr-Lys-Pro-Trp-Lys-Tyr | Ala-Thr-Lys-Pro-Trp-Lys-Tyr | 1585 |
| Ala-Thr-Lys-Pro-Gln-Tyr | Ala-Thr-Lys-Pro-Gln-Tyr | Ala-Thr-Lys-Pro-Gln-Tyr | 1586 |
| Ala-Thr-Lys-Pro-Gln-Arg-Tyr | Ala-Thr-Lys-Pro-Gln-Arg-Tyr | Ala-Thr-Lys-Pro-Gln-Arg-Tyr | 1587 |
| Ala-Thr-Lys-Pro-Gln-Phe-Tyr | Ala-Thr-Lys-Pro-Gln-Phe-Tyr | Ala-Thr-Lys-Pro-Gln-Phe-Tyr | 1588 |
| Ala-Thr-Lys-Pro-Gln-Tyr-Tyr | Ala-Thr-Lys-Pro-Gln-Tyr-Tyr | Ala-Thr-Lys-Pro-Gln-Tyr-Tyr | 1589 |
| Ala-Thr-Lys-Pro-Gln-His-Tyr | Ala-Thr-Lys-Pro-Gln-His-Tyr | Ala-Thr-Lys-Pro-Gln-His-Tyr | 1590 |
| Ala-Thr-Lys-Pro-Gln-Pro-Tyr | Ala-Thr-Lys-Pro-Gln-Pro-Tyr | Ala-Thr-Lys-Pro-Gln-Pro-Tyr | 1591 |
| Ala-Thr-Lys-Pro-Gln-Lys-Tyr | Ala-Thr-Lys-Pro-Gln-Lys-Tyr | Ala-Thr-Lys-Pro-Gln-Lys-Tyr | 1592 |
| Ala-Thr-Lys-Pro-Asn-Tyr | Ala-Thr-Lys-Pro-Asn-Tyr | Ala-Thr-Lys-Pro-Asn-Tyr | 1593 |
| Ala-Thr-Lys-Pro-Asn-Arg-Tyr | Ala-Thr-Lys-Pro-Asn-Arg-Tyr | Ala-Thr-Lys-Pro-Asn-Arg-Tyr | 1594 |
| Ala-Thr-Lys-Pro-Asn-Phe-Tyr | Ala-Thr-Lys-Pro-Asn-Phe-Tyr | Ala-Thr-Lys-Pro-Asn-Phe-Tyr | 1595 |
| Ala-Thr-Lys-Pro-Asn-Tyr-Tyr | Ala-Thr-Lys-Pro-Asn-Tyr-Tyr | Ala-Thr-Lys-Pro-Asn-Tyr-Tyr | 1596 |
| Ala-Thr-Lys-Pro-Asn-His-Tyr | Ala-Thr-Lys-Pro-Asn-His-Tyr | Ala-Thr-Lys-Pro-Asn-His-Tyr | 1597 |
| Ala-Thr-Lys-Pro-Asn-Pro-Tyr | Ala-Thr-Lys-Pro-Asn-Pro-Tyr | Ala-Thr-Lys-Pro-Asn-Pro-Tyr | 1598 |
| Ala-Thr-Lys-Pro-Asn-Lys-Tyr | Ala-Thr-Lys-Pro-Asn-Lys-Tyr | Ala-Thr-Lys-Pro-Asn-Lys-Tyr | 1599 |
| Ala-Thr-Lys-Pro-Tyr-Tyr | Ala-Thr-Lys-Pro-Tyr-Tyr | Ala-Thr-Lys-Pro-Tyr-Tyr | 1600 |
| Ala-Thr-Lys-Pro-Tyr-Arg-Tyr | Ala-Thr-Lys-Pro-Tyr-Arg-Tyr | Ala-Thr-Lys-Pro-Tyr-Arg-Tyr | 1601 |
| Ala-Thr-Lys-Pro-Tyr-Phe-Tyr | Ala-Thr-Lys-Pro-Tyr-Phe-Tyr | Ala-Thr-Lys-Pro-Tyr-Phe-Tyr | 1602 |
| Ala-Thr-Lys-Pro-Tyr-Tyr-Tyr | Ala-Thr-Lys-Pro-Tyr-Tyr-Tyr | Ala-Thr-Lys-Pro-Tyr-Tyr-Tyr | 1603 |
| Ala-Thr-Lys-Pro-Tyr-His-Tyr | Ala-Thr-Lys-Pro-Tyr-His-Tyr | Ala-Thr-Lys-Pro-Tyr-His-Tyr | 1604 |
| Ala-Thr-Lys-Pro-Tyr-Pro-Tyr | Ala-Thr-Lys-Pro-Tyr-Pro-Tyr | Ala-Thr-Lys-Pro-Tyr-Pro-Tyr | 1605 |
| Ala-Thr-Lys-Pro-Tyr-Lys-Tyr | Ala-Thr-Lys-Pro-Tyr-Lys-Tyr | Ala-Thr-Lys-Pro-Tyr-Lys-Tyr | 1606 |
| Ala-Thr-Lys-Pro-Arg-Tyr | Ala-Thr-Lys-Pro-Arg-Tyr | Ala-Thr-Lys-Pro-Arg-Tyr | 1607 |
| Ala-Thr-Lys-Pro-Arg-Arg-Tyr | Ala-Thr-Lys-Pro-Arg-Arg-Tyr | Ala-Thr-Lys-Pro-Arg-Arg-Tyr | 1608 |
| Ala-Thr-Lys-Pro-Arg-Phe-Tyr | Ala-Thr-Lys-Pro-Arg-Phe-Tyr | Ala-Thr-Lys-Pro-Arg-Phe-Tyr | 1609 |
| Ala-Thr-Lys-Pro-Arg-Tyr-Tyr | Ala-Thr-Lys-Pro-Arg-Tyr-Tyr | Ala-Thr-Lys-Pro-Arg-Tyr-Tyr | 1610 |
| Ala-Thr-Lys-Pro-Arg-His-Tyr | Ala-Thr-Lys-Pro-Arg-His-Tyr | Ala-Thr-Lys-Pro-Arg-His-Tyr | 1611 |
| Ala-Thr-Lys-Pro-Arg-Pro-Tyr | Ala-Thr-Lys-Pro-Arg-Pro-Tyr | Ala-Thr-Lys-Pro-Arg-Pro-Tyr | 1612 |
| Ala-Thr-Lys-Pro-Arg-Lys-Tyr | Ala-Thr-Lys-Pro-Arg-Lys-Tyr | Ala-Thr-Lys-Pro-Arg-Lys-Tyr | 1613 |
| His-Thr-Lys-Pro-Tyr | His-Thr-Lys-Pro-Tyr | His-Thr-Lys-Pro-Tyr | 1614 |
| His-Thr-Lys-Pro-Arg-Tyr | His-Thr-Lys-Pro-Arg-Tyr | His-Thr-Lys-Pro-Arg-Tyr | 1615 |
| His-Thr-Lys-Pro-Phe-Tyr | His-Thr-Lys-Pro-Phe-Tyr | His-Thr-Lys-Pro-Phe-Tyr | 1616 |
| His-Thr-Lys-Pro-Tyr-Tyr | His-Thr-Lys-Pro-Tyr-Tyr | His-Thr-Lys-Pro-Tyr-Tyr | 1617 |
| His-Thr-Lys-Pro-Gly-Tyr | His-Thr-Lys-Pro-Gly-Tyr | His-Thr-Lys-Pro-Gly-Tyr | 1618 |

TABLE 1-continued

| X-OH | X-OCH₃ | X-NH₂ | SEQ ID NO |
|---|---|---|---|
| His-Thr-Lys-Pro-His-Tyr | His-Thr-Lys-Pro-His-Tyr | His-Thr-Lys-Pro-His-Tyr | 1619 |
| His-Thr-Lys-Pro-Lys-Tyr | His-Thr-Lys-Pro-Lys-Tyr | His-Thr-Lys-Pro-Lys-Tyr | 1620 |
| His-Thr-Lys-Pro-Gly-Tyr | His-Thr-Lys-Pro-Gly-Tyr | His-Thr-Lys-Pro-Gly-Tyr | 1621 |
| His-Thr-Lys-Pro-Gly-Arg-Tyr | His-Thr-Lys-Pro-Gly-Arg-Tyr | His-Thr-Lys-Pro-Gly-Arg-Tyr | 1622 |
| His-Thr-Lys-Pro-Gly-Phe-Tyr | His-Thr-Lys-Pro-Gly-Phe-Tyr | His-Thr-Lys-Pro-Gly-Phe-Tyr | 1623 |
| His-Thr-Lys-Pro-Gly-Tyr-Tyr | His-Thr-Lys-Pro-Gly-Tyr-Tyr | His-Thr-Lys-Pro-Gly-Tyr-Tyr | 1624 |
| His-Thr-Lys-Pro-Gly-His-Tyr | His-Thr-Lys-Pro-Gly-His-Tyr | His-Thr-Lys-Pro-Gly-His-Tyr | 1625 |
| His-Thr-Lys-Pro-Gly-Pro-Tyr | His-Thr-Lys-Pro-Gly-Pro-Tyr | His-Thr-Lys-Pro-Gly-Pro-Tyr | 1626 |
| His-Thr-Lys-Pro-Gly-Lys-Tyr | His-Thr-Lys-Pro-Gly-Lys-Tyr | His-Thr-Lys-Pro-Gly-Lys-Tyr | 1627 |
| His-Thr-Lys-Pro-Asp-Tyr | His-Thr-Lys-Pro-Asp-Tyr | His-Thr-Lys-Pro-Asp-Tyr | 1628 |
| His-Thr-Lys-Pro-Asp-Arg-Tyr | His-Thr-Lys-Pro-Asp-Arg-Tyr | His-Thr-Lys-Pro-Asp-Arg-Tyr | 1629 |
| His-Thr-Lys-Pro-Asp-Phe-Tyr | His-Thr-Lys-Pro-Asp-Phe-Tyr | His-Thr-Lys-Pro-Asp-Phe-Tyr | 1630 |
| His-Thr-Lys-Pro-Asp-Tyr-Tyr | His-Thr-Lys-Pro-Asp-Tyr-Tyr | His-Thr-Lys-Pro-Asp-Tyr-Tyr | 1631 |
| His-Thr-Lys-Pro-Asp-His-Tyr | His-Thr-Lys-Pro-Asp-His-Tyr | His-Thr-Lys-Pro-Asp-His-Tyr | 1632 |
| His-Thr-Lys-Pro-Asp-Pro-Tyr | His-Thr-Lys-Pro-Asp-Pro-Tyr | His-Thr-Lys-Pro-Asp-Pro-Tyr | 1633 |
| His-Thr-Lys-Pro-Asp-Lys-Tyr | His-Thr-Lys-Pro-Asp-Lys-Tyr | His-Thr-Lys-Pro-Asp-Lys-Tyr | 1634 |
| His-Thr-Lys-Pro-Trp-Tyr | His-Thr-Lys-Pro-Trp-Tyr | His-Thr-Lys-Pro-Trp-Tyr | 1635 |
| His-Thr-Lys-Pro-Trp-Arg-Tyr | His-Thr-Lys-Pro-Trp-Arg-Tyr | His-Thr-Lys-Pro-Trp-Arg-Tyr | 1636 |
| His-Thr-Lys-Pro-Trp-Phe-Tyr | His-Thr-Lys-Pro-Trp-Phe-Tyr | His-Thr-Lys-Pro-Trp-Phe-Tyr | 1637 |
| His-Thr-Lys-Pro-Trp-Tyr-Tyr | His-Thr-Lys-Pro-Trp-Tyr-Tyr | His-Thr-Lys-Pro-Trp-Tyr-Tyr | 1638 |
| His-Thr-Lys-Pro-Trp-His-Tyr | His-Thr-Lys-Pro-Trp-His-Tyr | His-Thr-Lys-Pro-Trp-His-Tyr | 1639 |
| His-Thr-Lys-Pro-Trp-Pro-Tyr | His-Thr-Lys-Pro-Trp-Pro-Tyr | His-Thr-Lys-Pro-Trp-Pro-Tyr | 1640 |
| His-Thr-Lys-Pro-Trp-Lys-Tyr | His-Thr-Lys-Pro-Trp-Lys-Tyr | His-Thr-Lys-Pro-Trp-Lys-Tyr | 1641 |
| His-Thr-Lys-Pro-Gln-Tyr | His-Thr-Lys-Pro-Gln-Tyr | His-Thr-Lys-Pro-Gln-Tyr | 1642 |
| His-Thr-Lys-Pro-Gln-Arg-Tyr | His-Thr-Lys-Pro-Gln-Arg-Tyr | His-Thr-Lys-Pro-Gln-Arg-Tyr | 1643 |
| His-Thr-Lys-Pro-Gln-Phe-Tyr | His-Thr-Lys-Pro-Gln-Phe-Tyr | His-Thr-Lys-Pro-Gln-Phe-Tyr | 1644 |
| His-Thr-Lys-Pro-Gln-Tyr-Tyr | His-Thr-Lys-Pro-Gln-Tyr-Tyr | His-Thr-Lys-Pro-Gln-Tyr-Tyr | 1645 |
| His-Thr-Lys-Pro-Gln-His-Tyr | His-Thr-Lys-Pro-Gln-His-Tyr | His-Thr-Lys-Pro-Gln-His-Tyr | 1646 |
| His-Thr-Lys-Pro-Gln-Pro-Tyr | His-Thr-Lys-Pro-Gln-Pro-Tyr | His-Thr-Lys-Pro-Gln-Pro-Tyr | 1647 |
| His-Thr-Lys-Pro-Gln-Lys-Tyr | His-Thr-Lys-Pro-Gln-Lys-Tyr | His-Thr-Lys-Pro-Gln-Lys-Tyr | 1648 |
| His-Thr-Lys-Pro-Asn-Tyr | His-Thr-Lys-Pro-Asn-Tyr | His-Thr-Lys-Pro-Asn-Tyr | 1649 |
| His-Thr-Lys-Pro-Asn-Arg-Tyr | His-Thr-Lys-Pro-Asn-Arg-Tyr | His-Thr-Lys-Pro-Asn-Arg-Tyr | 1650 |
| His-Thr-Lys-Pro-Asn-Phe-Tyr | His-Thr-Lys-Pro-Asn-Phe-Tyr | His-Thr-Lys-Pro-Asn-Phe-Tyr | 1651 |
| His-Thr-Lys-Pro-Asn-Tyr-Tyr | His-Thr-Lys-Pro-Asn-Tyr-Tyr | His-Thr-Lys-Pro-Asn-Tyr-Tyr | 1652 |
| His-Thr-Lys-Pro-Asn-His-Tyr | His-Thr-Lys-Pro-Asn-His-Tyr | His-Thr-Lys-Pro-Asn-His-Tyr | 1653 |
| His-Thr-Lys-Pro-Asn-Pro-Tyr | His-Thr-Lys-Pro-Asn-Pro-Tyr | His-Thr-Lys-Pro-Asn-Pro-Tyr | 1654 |
| His-Thr-Lys-Pro-Asn-Lys-Tyr | His-Thr-Lys-Pro-Asn-Lys-Tyr | His-Thr-Lys-Pro-Asn-Lys-Tyr | 1655 |
| His-Thr-Lys-Pro-Tyr-Tyr | His-Thr-Lys-Pro-Tyr-Tyr | His-Thr-Lys-Pro-Tyr-Tyr | 1656 |

TABLE 1-continued

| X-OH | X-OCH₃ | X-NH₂ | SEQ ID NO |
|---|---|---|---|
| His-Thr-Lys-Pro-Tyr-Arg-Tyr | His-Thr-Lys-Pro-Tyr-Arg-Tyr | His-Thr-Lys-Pro-Tyr-Arg-Tyr | 1657 |
| His-Thr-Lys-Pro-Tyr-Phe-Tyr | His-Thr-Lys-Pro-Tyr-Phe-Tyr | His-Thr-Lys-Pro-Tyr-Phe-Tyr | 1658 |
| His-Thr-Lys-Pro-Tyr-Tyr-Tyr | His-Thr-Lys-Pro-Tyr-Tyr-Tyr | His-Thr-Lys-Pro-Tyr-Tyr-Tyr | 1659 |
| His-Thr-Lys-Pro-Tyr-His-Tyr | His-Thr-Lys-Pro-Tyr-His-Tyr | His-Thr-Lys-Pro-Tyr-His-Tyr | 1660 |
| His-Thr-Lys-Pro-Tyr-Pro-Tyr | His-Thr-Lys-Pro-Tyr-Pro-Tyr | His-Thr-Lys-Pro-Tyr-Pro-Tyr | 1661 |
| His-Thr-Lys-Pro-Tyr-Lys-Tyr | His-Thr-Lys-Pro-Tyr-Lys-Tyr | His-Thr-Lys-Pro-Tyr-Lys-Tyr | 1662 |
| His-Thr-Lys-Pro-Arg-Tyr | His-Thr-Lys-Pro-Arg-Tyr | His-Thr-Lys-Pro-Arg-Tyr | 1663 |
| His-Thr-Lys-Pro-Arg-Arg-Tyr | His-Thr-Lys-Pro-Arg-Arg-Tyr | His-Thr-Lys-Pro-Arg-Arg-Tyr | 1664 |
| His-Thr-Lys-Pro-Arg-Phe-Tyr | His-Thr-Lys-Pro-Arg-Phe-Tyr | His-Thr-Lys-Pro-Arg-Phe-Tyr | 1665 |
| His-Thr-Lys-Pro-Arg-Tyr-Tyr | His-Thr-Lys-Pro-Arg-Tyr-Tyr | His-Thr-Lys-Pro-Arg-Tyr-Tyr | 1666 |
| His-Thr-Lys-Pro-Arg-His-Tyr | His-Thr-Lys-Pro-Arg-His-Tyr | His-Thr-Lys-Pro-Arg-His-Tyr | 1667 |
| His-Thr-Lys-Pro-Arg-Pro-Tyr | His-Thr-Lys-Pro-Arg-Pro-Tyr | His-Thr-Lys-Pro-Arg-Pro-Tyr | 1668 |
| His-Thr-Lys-Pro-Arg-Lys-Tyr | His-Thr-Lys-Pro-Arg-Lys-Tyr | His-Thr-Lys-Pro-Arg-Lys-Tyr | 1669 |
| Lys-Thr-Lys-Pro-Tyr | Lys-Thr-Lys-Pro-Tyr | Lys-Thr-Lys-Pro-Tyr | 1670 |
| Lys-Thr-Lys-Pro-Arg-Tyr | Lys-Thr-Lys-Pro-Arg-Tyr | Lys-Thr-Lys-Pro-Arg-Tyr | 1671 |
| Lys-Thr-Lys-Pro-Phe-Tyr | Lys-Thr-Lys-Pro-Phe-Tyr | Lys-Thr-Lys-Pro-Phe-Tyr | 1672 |
| Lys-Thr-Lys-Pro-Tyr-Tyr | Lys-Thr-Lys-Pro-Tyr-Tyr | Lys-Thr-Lys-Pro-Tyr-Tyr | 1673 |
| Lys-Thr-Lys-Pro-Gly-Tyr | Lys-Thr-Lys-Pro-Gly-Tyr | Lys-Thr-Lys-Pro-Gly-Tyr | 1674 |
| Lys-Thr-Lys-Pro-His-Tyr | Lys-Thr-Lys-Pro-His-Tyr | Lys-Thr-Lys-Pro-His-Tyr | 1675 |
| Lys-Thr-Lys-Pro-Lys-Tyr | Lys-Thr-Lys-Pro-Lys-Tyr | Lys-Thr-Lys-Pro-Lys-Tyr | 1676 |
| Lys-Thr-Lys-Pro-Gly-Tyr | Lys-Thr-Lys-Pro-Gly-Tyr | Lys-Thr-Lys-Pro-Gly-Tyr | 1677 |
| Lys-Thr-Lys-Pro-Gly-Arg-Tyr | Lys-Thr-Lys-Pro-Gly-Arg-Tyr | Lys-Thr-Lys-Pro-Gly-Arg-Tyr | 1678 |
| Lys-Thr-Lys-Pro-Gly-Phe-Tyr | Lys-Thr-Lys-Pro-Gly-Phe-Tyr | Lys-Thr-Lys-Pro-Gly-Phe-Tyr | 1679 |
| Lys-Thr-Lys-Pro-Gly-Tyr-Tyr | Lys-Thr-Lys-Pro-Gly-Tyr-Tyr | Lys-Thr-Lys-Pro-Gly-Tyr-Tyr | 1680 |
| Lys-Thr-Lys-Pro-Gly-His-Tyr | Lys-Thr-Lys-Pro-Gly-His-Tyr | Lys-Thr-Lys-Pro-Gly-His-Tyr | 1681 |
| Lys-Thr-Lys-Pro-Gly-Pro-Tyr | Lys-Thr-Lys-Pro-Gly-Pro-Tyr | Lys-Thr-Lys-Pro-Gly-Pro-Tyr | 1682 |
| Lys-Thr-Lys-Pro-Gly-Lys-Tyr | Lys-Thr-Lys-Pro-Gly-Lys-Tyr | Lys-Thr-Lys-Pro-Gly-Lys-Tyr | 1683 |
| Lys-Thr-Lys-Pro-Asp-Tyr | Lys-Thr-Lys-Pro-Asp-Tyr | Lys-Thr-Lys-Pro-Asp-Tyr | 1684 |
| Lys-Thr-Lys-Pro-Asp-Arg-Tyr | Lys-Thr-Lys-Pro-Asp-Arg-Tyr | Lys-Thr-Lys-Pro-Asp-Arg-Tyr | 1685 |
| Lys-Thr-Lys-Pro-Asp-Phe-Tyr | Lys-Thr-Lys-Pro-Asp-Phe-Tyr | Lys-Thr-Lys-Pro-Asp-Phe-Tyr | 1686 |
| Lys-Thr-Lys-Pro-Asp-Tyr-Tyr | Lys-Thr-Lys-Pro-Asp-Tyr-Tyr | Lys-Thr-Lys-Pro-Asp-Tyr-Tyr | 1687 |
| Lys-Thr-Lys-Pro-Asp-His-Tyr | Lys-Thr-Lys-Pro-Asp-His-Tyr | Lys-Thr-Lys-Pro-Asp-His-Tyr | 1688 |
| Lys-Thr-Lys-Pro-Asp-Pro-Tyr | Lys-Thr-Lys-Pro-Asp-Pro-Tyr | Lys-Thr-Lys-Pro-Asp-Pro-Tyr | 1689 |
| Lys-Thr-Lys-Pro-Asp-Lys-Tyr | Lys-Thr-Lys-Pro-Asp-Lys-Tyr | Lys-Thr-Lys-Pro-Asp-Lys-Tyr | 1690 |
| Lys-Thr-Lys-Pro-Trp-Tyr | Lys-Thr-Lys-Pro-Trp-Tyr | Lys-Thr-Lys-Pro-Trp-Tyr | 1691 |
| Lys-Thr-Lys-Pro-Trp-Arg-Tyr | Lys-Thr-Lys-Pro-Trp-Arg-Tyr | Lys-Thr-Lys-Pro-Trp-Arg-Tyr | 1692 |
| Lys-Thr-Lys-Pro-Trp-Phe-Tyr | Lys-Thr-Lys-Pro-Trp-Phe-Tyr | Lys-Thr-Lys-Pro-Trp-Phe-Tyr | 1693 |
| Lys-Thr-Lys-Pro-Trp-Tyr-Tyr | Lys-Thr-Lys-Pro-Trp-Tyr-Tyr | Lys-Thr-Lys-Pro-Trp-Tyr-Tyr | 1694 |

TABLE 1-continued

| X-OH | X-OCH₃ | X-NH₂ | SEQ ID NO |
|---|---|---|---|
| Lys-Thr-Lys-Pro-Trp-His-Tyr | Lys-Thr-Lys-Pro-Trp-His-Tyr | Lys-Thr-Lys-Pro-Trp-His-Tyr | 1695 |
| Lys-Thr-Lys-Pro-Trp-Pro-Tyr | Lys-Thr-Lys-Pro-Trp-Pro-Tyr | Lys-Thr-Lys-Pro-Trp-Pro-Tyr | 1696 |
| Lys-Thr-Lys-Pro-Trp-Lys-Tyr | Lys-Thr-Lys-Pro-Trp-Lys-Tyr | Lys-Thr-Lys-Pro-Trp-Lys-Tyr | 1697 |
| Lys-Thr-Lys-Pro-Gln-Tyr | Lys-Thr-Lys-Pro-Gln-Tyr | Lys-Thr-Lys-Pro-Gln-Tyr | 1698 |
| Lys-Thr-Lys-Pro-Gln-Arg-Tyr | Lys-Thr-Lys-Pro-Gln-Arg-Tyr | Lys-Thr-Lys-Pro-Gln-Arg-Tyr | 1699 |
| Lys-Thr-Lys-Pro-Gln-Phe-Tyr | Lys-Thr-Lys-Pro-Gln-Phe-Tyr | Lys-Thr-Lys-Pro-Gln-Phe-Tyr | 1700 |
| Lys-Thr-Lys-Pro-Gln-Tyr-Tyr | Lys-Thr-Lys-Pro-Gln-Tyr-Tyr | Lys-Thr-Lys-Pro-Gln-Tyr-Tyr | 1701 |
| Lys-Thr-Lys-Pro-Gln-His-Tyr | Lys-Thr-Lys-Pro-Gln-His-Tyr | Lys-Thr-Lys-Pro-Gln-His-Tyr | 1702 |
| Lys-Thr-Lys-Pro-Gln-Pro-Tyr | Lys-Thr-Lys-Pro-Gln-Pro-Tyr | Lys-Thr-Lys-Pro-Gln-Pro-Tyr | 1703 |
| Lys-Thr-Lys-Pro-Gln-Lys-Tyr | Lys-Thr-Lys-Pro-Gln-Lys-Tyr | Lys-Thr-Lys-Pro-Gln-Lys-Tyr | 1704 |
| Lys-Thr-Lys-Pro-Asn-Tyr | Lys-Thr-Lys-Pro-Asn-Tyr | Lys-Thr-Lys-Pro-Asn-Tyr | 1705 |
| Lys-Thr-Lys-Pro-Asn-Arg-Tyr | Lys-Thr-Lys-Pro-Asn-Arg-Tyr | Lys-Thr-Lys-Pro-Asn-Arg-Tyr | 1706 |
| Lys-Thr-Lys-Pro-Asn-Phe-Tyr | Lys-Thr-Lys-Pro-Asn-Phe-Tyr | Lys-Thr-Lys-Pro-Asn-Phe-Tyr | 1707 |
| Lys-Thr-Lys-Pro-Asn-Tyr-Tyr | Lys-Thr-Lys-Pro-Asn-Tyr-Tyr | Lys-Thr-Lys-Pro-Asn-Tyr-Tyr | 1708 |
| Lys-Thr-Lys-Pro-Asn-His-Tyr | Lys-Thr-Lys-Pro-Asn-His-Tyr | Lys-Thr-Lys-Pro-Asn-His-Tyr | 1709 |
| Lys-Thr-Lys-Pro-Asn-Pro-Tyr | Lys-Thr-Lys-Pro-Asn-Pro-Tyr | Lys-Thr-Lys-Pro-Asn-Pro-Tyr | 1710 |
| Lys-Thr-Lys-Pro-Asn-Lys-Tyr | Lys-Thr-Lys-Pro-Asn-Lys-Tyr | Lys-Thr-Lys-Pro-Asn-Lys-Tyr | 1711 |
| Lys-Thr-Lys-Pro-Tyr-Tyr | Lys-Thr-Lys-Pro-Tyr-Tyr | Lys-Thr-Lys-Pro-Tyr-Tyr | 1712 |
| Lys-Thr-Lys-Pro-Tyr-Arg-Tyr | Lys-Thr-Lys-Pro-Tyr-Arg-Tyr | Lys-Thr-Lys-Pro-Tyr-Arg-Tyr | 1713 |
| Lys-Thr-Lys-Pro-Tyr-Phe-Tyr | Lys-Thr-Lys-Pro-Tyr-Phe-Tyr | Lys-Thr-Lys-Pro-Tyr-Phe-Tyr | 1714 |
| Lys-Thr-Lys-Pro-Tyr-Tyr-Tyr | Lys-Thr-Lys-Pro-Tyr-Tyr-Tyr | Lys-Thr-Lys-Pro-Tyr-Tyr-Tyr | 1715 |
| Lys-Thr-Lys-Pro-Tyr-His-Tyr | Lys-Thr-Lys-Pro-Tyr-His-Tyr | Lys-Thr-Lys-Pro-Tyr-His-Tyr | 1716 |
| Lys-Thr-Lys-Pro-Tyr-Pro-Tyr | Lys-Thr-Lys-Pro-Tyr-Pro-Tyr | Lys-Thr-Lys-Pro-Tyr-Pro-Tyr | 1717 |
| Lys-Thr-Lys-Pro-Tyr-Lys-Tyr | Lys-Thr-Lys-Pro-Tyr-Lys-Tyr | Lys-Thr-Lys-Pro-Tyr-Lys-Tyr | 1718 |
| Lys-Thr-Lys-Pro-Arg-Tyr | Lys-Thr-Lys-Pro-Arg-Tyr | Lys-Thr-Lys-Pro-Arg-Tyr | 1719 |
| Lys-Thr-Lys-Pro-Arg-Arg-Tyr | Lys-Thr-Lys-Pro-Arg-Arg-Tyr | Lys-Thr-Lys-Pro-Arg-Arg-Tyr | 1720 |
| Lys-Thr-Lys-Pro-Arg-Phe-Tyr | Lys-Thr-Lys-Pro-Arg-Phe-Tyr | Lys-Thr-Lys-Pro-Arg-Phe-Tyr | 1721 |
| Lys-Thr-Lys-Pro-Arg-Tyr-Tyr | Lys-Thr-Lys-Pro-Arg-Tyr-Tyr | Lys-Thr-Lys-Pro-Arg-Tyr-Tyr | 1722 |
| Lys-Thr-Lys-Pro-Arg-His-Tyr | Lys-Thr-Lys-Pro-Arg-His-Tyr | Lys-Thr-Lys-Pro-Arg-His-Tyr | 1723 |
| Lys-Thr-Lys-Pro-Arg-Pro-Tyr | Lys-Thr-Lys-Pro-Arg-Pro-Tyr | Lys-Thr-Lys-Pro-Arg-Pro-Tyr | 1724 |
| Lys-Thr-Lys-Pro-Arg-Lys-Tyr | Lys-Thr-Lys-Pro-Arg-Lys-Tyr | Lys-Thr-Lys-Pro-Arg-Lys-Tyr | 1725 |
| Gly-Thr-Lys-Pro-Tyr | Gly-Thr-Lys-Pro-Tyr | Gly-Thr-Lys-Pro-Tyr | 1726 |
| Gly-Thr-Lys-Pro-Arg-Tyr | Gly-Thr-Lys-Pro-Arg-Tyr | Gly-Thr-Lys-Pro-Arg-Tyr | 1727 |
| Gly-Thr-Lys-Pro-Phe-Tyr | Gly-Thr-Lys-Pro-Phe-Tyr | Gly-Thr-Lys-Pro-Phe-Tyr | 1728 |
| Gly-Thr-Lys-Pro-Tyr-Tyr | Gly-Thr-Lys-Pro-Tyr-Tyr | Gly-Thr-Lys-Pro-Tyr-Tyr | 1729 |
| Gly-Thr-Lys-Pro-Gly-Tyr | Gly-Thr-Lys-Pro-Gly-Tyr | Gly-Thr-Lys-Pro-Gly-Tyr | 1730 |
| Gly-Thr-Lys-Pro-His-Tyr | Gly-Thr-Lys-Pro-His-Tyr | Gly-Thr-Lys-Pro-His-Tyr | 1731 |
| Gly-Thr-Lys-Pro-Lys-Tyr | Gly-Thr-Lys-Pro-Lys-Tyr | Gly-Thr-Lys-Pro-Lys-Tyr | 1732 |

TABLE 1-continued

| X-OH | X-OCH₃ | X-NH₂ | SEQ ID NO |
|---|---|---|---|
| Gly-Thr-Lys-Pro-Gly-Tyr | Gly-Thr-Lys-Pro-Gly-Tyr | Gly-Thr-Lys-Pro-Gly-Tyr | 1733 |
| Gly-Thr-Lys-Pro-Gly-Arg-Tyr | Gly-Thr-Lys-Pro-Gly-Arg-Tyr | Gly-Thr-Lys-Pro-Gly-Arg-Tyr | 1734 |
| Gly-Thr-Lys-Pro-Gly-Phe-Tyr | Gly-Thr-Lys-Pro-Gly-Phe-Tyr | Gly-Thr-Lys-Pro-Gly-Phe-Tyr | 1735 |
| Gly-Thr-Lys-Pro-Gly-Tyr-Tyr | Gly-Thr-Lys-Pro-Gly-Tyr-Tyr | Gly-Thr-Lys-Pro-Gly-Tyr-Tyr | 1736 |
| Gly-Thr-Lys-Pro-Gly-His-Tyr | Gly-Thr-Lys-Pro-Gly-His-Tyr | Gly-Thr-Lys-Pro-Gly-His-Tyr | 1737 |
| Gly-Thr-Lys-Pro-Gly-Pro-Tyr | Gly-Thr-Lys-Pro-Gly-Pro-Tyr | Gly-Thr-Lys-Pro-Gly-Pro-Tyr | 1738 |
| Gly-Thr-Lys-Pro-Gly-Lys-Tyr | Gly-Thr-Lys-Pro-Gly-Lys-Tyr | Gly-Thr-Lys-Pro-Gly-Lys-Tyr | 1739 |
| Gly-Thr-Lys-Pro-Asp-Tyr | Gly-Thr-Lys-Pro-Asp-Tyr | Gly-Thr-Lys-Pro-Asp-Tyr | 1740 |
| Gly-Thr-Lys-Pro-Asp-Arg-Tyr | Gly-Thr-Lys-Pro-Asp-Arg-Tyr | Gly-Thr-Lys-Pro-Asp-Arg-Tyr | 1741 |
| Gly-Thr-Lys-Pro-Asp-Phe-Tyr | Gly-Thr-Lys-Pro-Asp-Phe-Tyr | Gly-Thr-Lys-Pro-Asp-Phe-Tyr | 1742 |
| Gly-Thr-Lys-Pro-Asp-Tyr-Tyr | Gly-Thr-Lys-Pro-Asp-Tyr-Tyr | Gly-Thr-Lys-Pro-Asp-Tyr-Tyr | 1743 |
| Gly-Thr-Lys-Pro-Asp-His-Tyr | Gly-Thr-Lys-Pro-Asp-His-Tyr | Gly-Thr-Lys-Pro-Asp-His-Tyr | 1744 |
| Gly-Thr-Lys-Pro-Asp-Pro-Tyr | Gly-Thr-Lys-Pro-Asp-Pro-Tyr | Gly-Thr-Lys-Pro-Asp-Pro-Tyr | 1745 |
| Gly-Thr-Lys-Pro-Asp-Lys-Tyr | Gly-Thr-Lys-Pro-Asp-Lys-Tyr | Gly-Thr-Lys-Pro-Asp-Lys-Tyr | 1746 |
| Gly-Thr-Lys-Pro-Trp-Tyr | Gly-Thr-Lys-Pro-Trp-Tyr | Gly-Thr-Lys-Pro-Trp-Tyr | 1747 |
| Gly-Thr-Lys-Pro-Trp-Arg-Tyr | Gly-Thr-Lys-Pro-Trp-Arg-Tyr | Gly-Thr-Lys-Pro-Trp-Arg-Tyr | 1748 |
| Gly-Thr-Lys-Pro-Trp-Phe-Tyr | Gly-Thr-Lys-Pro-Trp-Phe-Tyr | Gly-Thr-Lys-Pro-Trp-Phe-Tyr | 1749 |
| Gly-Thr-Lys-Pro-Trp-Tyr-Tyr | Gly-Thr-Lys-Pro-Trp-Tyr-Tyr | Gly-Thr-Lys-Pro-Trp-Tyr-Tyr | 1750 |
| Gly-Thr-Lys-Pro-Trp-His-Tyr | Gly-Thr-Lys-Pro-Trp-His-Tyr | Gly-Thr-Lys-Pro-Trp-His-Tyr | 1751 |
| Gly-Thr-Lys-Pro-Trp-Pro-Tyr | Gly-Thr-Lys-Pro-Trp-Pro-Tyr | Gly-Thr-Lys-Pro-Trp-Pro-Tyr | 1752 |
| Gly-Thr-Lys-Pro-Trp-Lys-Tyr | Gly-Thr-Lys-Pro-Trp-Lys-Tyr | Gly-Thr-Lys-Pro-Trp-Lys-Tyr | 1753 |
| Gly-Thr-Lys-Pro-Gln-Tyr | Gly-Thr-Lys-Pro-Gln-Tyr | Gly-Thr-Lys-Pro-Gln-Tyr | 1754 |
| Gly-Thr-Lys-Pro-Gln-Arg-Tyr | Gly-Thr-Lys-Pro-Gln-Arg-Tyr | Gly-Thr-Lys-Pro-Gln-Arg-Tyr | 1755 |
| Gly-Thr-Lys-Pro-Gln-Phe-Tyr | Gly-Thr-Lys-Pro-Gln-Phe-Tyr | Gly-Thr-Lys-Pro-Gln-Phe-Tyr | 1756 |
| Gly-Thr-Lys-Pro-Gln-Tyr-Tyr | Gly-Thr-Lys-Pro-Gln-Tyr-Tyr | Gly-Thr-Lys-Pro-Gln-Tyr-Tyr | 1757 |
| Gly-Thr-Lys-Pro-Gln-His-Tyr | Gly-Thr-Lys-Pro-Gln-His-Tyr | Gly-Thr-Lys-Pro-Gln-His-Tyr | 1758 |
| Gly-Thr-Lys-Pro-Gln-Pro-Tyr | Gly-Thr-Lys-Pro-Gln-Pro-Tyr | Gly-Thr-Lys-Pro-Gln-Pro-Tyr | 1759 |
| Gly-Thr-Lys-Pro-Gln-Lys-Tyr | Gly-Thr-Lys-Pro-Gln-Lys-Tyr | Gly-Thr-Lys-Pro-Gln-Lys-Tyr | 1760 |
| Gly-Thr-Lys-Pro-Asn-Tyr | Gly-Thr-Lys-Pro-Asn-Tyr | Gly-Thr-Lys-Pro-Asn-Tyr | 1761 |
| Gly-Thr-Lys-Pro-Asn-Arg-Tyr | Gly-Thr-Lys-Pro-Asn-Arg-Tyr | Gly-Thr-Lys-Pro-Asn-Arg-Tyr | 1762 |
| Gly-Thr-Lys-Pro-Asn-Phe-Tyr | Gly-Thr-Lys-Pro-Asn-Phe-Tyr | Gly-Thr-Lys-Pro-Asn-Phe-Tyr | 1763 |
| Gly-Thr-Lys-Pro-Asn-Tyr-Tyr | Gly-Thr-Lys-Pro-Asn-Tyr-Tyr | Gly-Thr-Lys-Pro-Asn-Tyr-Tyr | 1764 |
| Gly-Thr-Lys-Pro-Asn-His-Tyr | Gly-Thr-Lys-Pro-Asn-His-Tyr | Gly-Thr-Lys-Pro-Asn-His-Tyr | 1765 |
| Gly-Thr-Lys-Pro-Asn-Pro-Tyr | Gly-Thr-Lys-Pro-Asn-Pro-Tyr | Gly-Thr-Lys-Pro-Asn-Pro-Tyr | 1766 |
| Gly-Thr-Lys-Pro-Asn-Lys-Tyr | Gly-Thr-Lys-Pro-Asn-Lys-Tyr | Gly-Thr-Lys-Pro-Asn-Lys-Tyr | 1767 |
| Gly-Thr-Lys-Pro-Tyr-Tyr | Gly-Thr-Lys-Pro-Tyr-Tyr | Gly-Thr-Lys-Pro-Tyr-Tyr | 1768 |
| Gly-Thr-Lys-Pro-Tyr-Arg-Tyr | Gly-Thr-Lys-Pro-Tyr-Arg-Tyr | Gly-Thr-Lys-Pro-Tyr-Arg-Tyr | 1769 |
| Gly-Thr-Lys-Pro-Tyr-Phe-Tyr | Gly-Thr-Lys-Pro-Tyr-Phe-Tyr | Gly-Thr-Lys-Pro-Tyr-Phe-Tyr | 1770 |

TABLE 1-continued

| X-OH | X-OCH₃ | X-NH₂ | SEQ ID NO |
|---|---|---|---|
| Gly-Thr-Lys-Pro-Tyr-Tyr-Tyr | Gly-Thr-Lys-Pro-Tyr-Tyr-Tyr | Gly-Thr-Lys-Pro-Tyr-Tyr-Tyr | 1771 |
| Gly-Thr-Lys-Pro-Tyr-His-Tyr | Gly-Thr-Lys-Pro-Tyr-His-Tyr | Gly-Thr-Lys-Pro-Tyr-His-Tyr | 1772 |
| Gly-Thr-Lys-Pro-Tyr-Pro-Tyr | Gly-Thr-Lys-Pro-Tyr-Pro-Tyr | Gly-Thr-Lys-Pro-Tyr-Pro-Tyr | 1773 |
| Gly-Thr-Lys-Pro-Tyr-Lys-Tyr | Gly-Thr-Lys-Pro-Tyr-Lys-Tyr | Gly-Thr-Lys-Pro-Tyr-Lys-Tyr | 1774 |
| Gly-Thr-Lys-Pro-Arg-Tyr | Gly-Thr-Lys-Pro-Arg-Tyr | Gly-Thr-Lys-Pro-Arg-Tyr | 1775 |
| Gly-Thr-Lys-Pro-Arg-Arg-Tyr | Gly-Thr-Lys-Pro-Arg-Arg-Tyr | Gly-Thr-Lys-Pro-Arg-Arg-Tyr | 1776 |
| Gly-Thr-Lys-Pro-Arg-Phe-Tyr | Gly-Thr-Lys-Pro-Arg-Phe-Tyr | Gly-Thr-Lys-Pro-Arg-Phe-Tyr | 1777 |
| Gly-Thr-Lys-Pro-Arg-Tyr-Tyr | Gly-Thr-Lys-Pro-Arg-Tyr-Tyr | Gly-Thr-Lys-Pro-Arg-Tyr-Tyr | 1778 |
| Gly-Thr-Lys-Pro-Arg-His-Tyr | Gly-Thr-Lys-Pro-Arg-His-Tyr | Gly-Thr-Lys-Pro-Arg-His-Tyr | 1779 |
| Gly-Thr-Lys-Pro-Arg-Pro-Tyr | Gly-Thr-Lys-Pro-Arg-Pro-Tyr | Gly-Thr-Lys-Pro-Arg-Pro-Tyr | 1780 |
| Gly-Thr-Lys-Pro-Arg-Lys-Tyr | Gly-Thr-Lys-Pro-Arg-Lys-Tyr | Gly-Thr-Lys-Pro-Arg-Lys-Tyr | 1781 |
| Thr-Lys-Pro-Arg-Trp | Thr-Lys-Pro-Arg-Trp | Thr-Lys-Pro-Arg-Trp | 1782 |
| Thr-Lys-Pro-Phe-Trp | Thr-Lys-Pro-Phe-Trp | Thr-Lys-Pro-Phe-Trp | 1783 |
| Thr-Lys-Pro-Tyr-Trp | Thr-Lys-Pro-Tyr-Trp | Thr-Lys-Pro-Tyr-Trp | 1784 |
| Thr-Lys-Pro-Gly-Trp | Thr-Lys-Pro-Gly-Trp | Thr-Lys-Pro-Gly-Trp | 1785 |
| Thr-Lys-Pro-His-Trp | Thr-Lys-Pro-His-Trp | Thr-Lys-Pro-His-Trp | 1786 |
| Thr-Lys-Pro-Lys-Trp | Thr-Lys-Pro-Lys-Trp | Thr-Lys-Pro-Lys-Trp | 1787 |
| Thr-Lys-Pro-Gly-Trp | Thr-Lys-Pro-Gly-Trp | Thr-Lys-Pro-Gly-Trp | 1788 |
| Thr-Lys-Pro-Gly-Arg-Trp | Thr-Lys-Pro-Gly-Arg-Trp | Thr-Lys-Pro-Gly-Arg-Trp | 1789 |
| Thr-Lys-Pro-Gly-Phe-Trp | Thr-Lys-Pro-Gly-Phe-Trp | Thr-Lys-Pro-Gly-Phe-Trp | 1790 |
| Thr-Lys-Pro-Gly-Tyr-Trp | Thr-Lys-Pro-Gly-Tyr-Trp | Thr-Lys-Pro-Gly-Tyr-Trp | 1791 |
| Thr-Lys-Pro-Gly-His-Trp | Thr-Lys-Pro-Gly-His-Trp | Thr-Lys-Pro-Gly-His-Trp | 1792 |
| Thr-Lys-Pro-Gly-Pro-Trp | Thr-Lys-Pro-Gly-Pro-Trp | Thr-Lys-Pro-Gly-Pro-Trp | 1793 |
| Thr-Lys-Pro-Gly-Lys-Trp | Thr-Lys-Pro-Gly-Lys-Trp | Thr-Lys-Pro-Gly-Lys-Trp | 1794 |
| Thr-Lys-Pro-Asp-Trp | Thr-Lys-Pro-Asp-Trp | Thr-Lys-Pro-Asp-Trp | 1795 |
| Thr-Lys-Pro-Asp-Arg-Trp | Thr-Lys-Pro-Asp-Arg-Trp | Thr-Lys-Pro-Asp-Arg-Trp | 1796 |
| Thr-Lys-Pro-Asp-Phe-Trp | Thr-Lys-Pro-Asp-Phe-Trp | Thr-Lys-Pro-Asp-Phe-Trp | 1797 |
| Thr-Lys-Pro-Asp-Tyr-Trp | Thr-Lys-Pro-Asp-Tyr-Trp | Thr-Lys-Pro-Asp-Tyr-Trp | 1798 |
| Thr-Lys-Pro-Asp-His-Trp | Thr-Lys-Pro-Asp-His-Trp | Thr-Lys-Pro-Asp-His-Trp | 1799 |
| Thr-Lys-Pro-Asp-Pro-Trp | Thr-Lys-Pro-Asp-Pro-Trp | Thr-Lys-Pro-Asp-Pro-Trp | 1800 |
| Thr-Lys-Pro-Asp-Lys-Trp | Thr-Lys-Pro-Asp-Lys-Trp | Thr-Lys-Pro-Asp-Lys-Trp | 1801 |
| Thr-Lys-Pro-Trp-Trp | Thr-Lys-Pro-Trp-Trp | Thr-Lys-Pro-Trp-Trp | 1802 |
| Thr-Lys-Pro-Trp-Arg-Trp | Thr-Lys-Pro-Trp-Arg-Trp | Thr-Lys-Pro-Trp-Arg-Trp | 1803 |
| Thr-Lys-Pro-Trp-Phe-Trp | Thr-Lys-Pro-Trp-Phe-Trp | Thr-Lys-Pro-Trp-Phe-Trp | 1804 |
| Thr-Lys-Pro-Trp-Tyr-Trp | Thr-Lys-Pro-Trp-Tyr-Trp | Thr-Lys-Pro-Trp-Tyr-Trp | 1805 |
| Thr-Lys-Pro-Trp-His-Trp | Thr-Lys-Pro-Trp-His-Trp | Thr-Lys-Pro-Trp-His-Trp | 1806 |
| Thr-Lys-Pro-Trp-Pro-Trp | Thr-Lys-Pro-Trp-Pro-Trp | Thr-Lys-Pro-Trp-Pro-Trp | 1807 |
| Thr-Lys-Pro-Trp-Lys-Trp | Thr-Lys-Pro-Trp-Lys-Trp | Thr-Lys-Pro-Trp-Lys-Trp | 1808 |

TABLE 1-continued

| X-OH | X-OCH₃ | X-NH₂ | SEQ ID NO |
|---|---|---|---|
| Thr-Lys-Pro-Gln-Trp | Thr-Lys-Pro-Gln-Trp | Thr-Lys-Pro-Gln-Trp | 1809 |
| Thr-Lys-Pro-Gln-Arg-Trp | Thr-Lys-Pro-Gln-Arg-Trp | Thr-Lys-Pro-Gln-Arg-Trp | 1810 |
| Thr-Lys-Pro-Gln-Phe-Trp | Thr-Lys-Pro-Gln-Phe-Trp | Thr-Lys-Pro-Gln-Phe-Trp | 1811 |
| Thr-Lys-Pro-Gln-Tyr-Trp | Thr-Lys-Pro-Gln-Tyr-Trp | Thr-Lys-Pro-Gln-Tyr-Trp | 1812 |
| Thr-Lys-Pro-Gln-His-Trp | Thr-Lys-Pro-Gln-His-Trp | Thr-Lys-Pro-Gln-His-Trp | 1813 |
| Thr-Lys-Pro-Gln-Pro-Trp | Thr-Lys-Pro-Gln-Pro-Trp | Thr-Lys-Pro-Gln-Pro-Trp | 1814 |
| Thr-Lys-Pro-Gln-Lys-Trp | Thr-Lys-Pro-Gln-Lys-Trp | Thr-Lys-Pro-Gln-Lys-Trp | 1815 |
| Thr-Lys-Pro-Asn-Trp | Thr-Lys-Pro-Asn-Trp | Thr-Lys-Pro-Asn-Trp | 1816 |
| Thr-Lys-Pro-Asn-Arg-Trp | Thr-Lys-Pro-Asn-Arg-Trp | Thr-Lys-Pro-Asn-Arg-Trp | 1817 |
| Thr-Lys-Pro-Asn-Phe-Trp | Thr-Lys-Pro-Asn-Phe-Trp | Thr-Lys-Pro-Asn-Phe-Trp | 1818 |
| Thr-Lys-Pro-Asn-Tyr-Trp | Thr-Lys-Pro-Asn-Tyr-Trp | Thr-Lys-Pro-Asn-Tyr-Trp | 1819 |
| Thr-Lys-Pro-Asn-His-Trp | Thr-Lys-Pro-Asn-His-Trp | Thr-Lys-Pro-Asn-His-Trp | 1820 |
| Thr-Lys-Pro-Asn-Pro-Trp | Thr-Lys-Pro-Asn-Pro-Trp | Thr-Lys-Pro-Asn-Pro-Trp | 1821 |
| Thr-Lys-Pro-Asn-Lys-Trp | Thr-Lys-Pro-Asn-Lys-Trp | Thr-Lys-Pro-Asn-Lys-Trp | 1822 |
| Thr-Lys-Pro-Tyr-Trp | Thr-Lys-Pro-Tyr-Trp | Thr-Lys-Pro-Tyr-Trp | 1823 |
| Thr-Lys-Pro-Tyr-Arg-Trp | Thr-Lys-Pro-Tyr-Arg-Trp | Thr-Lys-Pro-Tyr-Arg-Trp | 1824 |
| Thr-Lys-Pro-Tyr-Phe-Trp | Thr-Lys-Pro-Tyr-Phe-Trp | Thr-Lys-Pro-Tyr-Phe-Trp | 1825 |
| Thr-Lys-Pro-Tyr-Tyr-Trp | Thr-Lys-Pro-Tyr-Tyr-Trp | Thr-Lys-Pro-Tyr-Tyr-Trp | 1826 |
| Thr-Lys-Pro-Tyr-His-Trp | Thr-Lys-Pro-Tyr-His-Trp | Thr-Lys-Pro-Tyr-His-Trp | 1827 |
| Thr-Lys-Pro-Tyr-Pro-Trp | Thr-Lys-Pro-Tyr-Pro-Trp | Thr-Lys-Pro-Tyr-Pro-Trp | 1828 |
| Thr-Lys-Pro-Tyr-Lys-Trp | Thr-Lys-Pro-Tyr-Lys-Trp | Thr-Lys-Pro-Tyr-Lys-Trp | 1829 |
| Thr-Lys-Pro-Arg-Trp | Thr-Lys-Pro-Arg-Trp | Thr-Lys-Pro-Arg-Trp | 1830 |
| Thr-Lys-Pro-Arg-Arg-Trp | Thr-Lys-Pro-Arg-Arg-Trp | Thr-Lys-Pro-Arg-Arg-Trp | 1831 |
| Thr-Lys-Pro-Arg-Phe-Trp | Thr-Lys-Pro-Arg-Phe-Trp | Thr-Lys-Pro-Arg-Phe-Trp | 1832 |
| Thr-Lys-Pro-Arg-Tyr-Trp | Thr-Lys-Pro-Arg-Tyr-Trp | Thr-Lys-Pro-Arg-Tyr-Trp | 1833 |
| Thr-Lys-Pro-Arg-His-Trp | Thr-Lys-Pro-Arg-His-Trp | Thr-Lys-Pro-Arg-His-Trp | 1834 |
| Thr-Lys-Pro-Arg-Pro-Trp | Thr-Lys-Pro-Arg-Pro-Trp | Thr-Lys-Pro-Arg-Pro-Trp | 1835 |
| Thr-Lys-Pro-Arg-Lys-Trp | Thr-Lys-Pro-Arg-Lys-Trp | Thr-Lys-Pro-Arg-Lys-Trp | 1836 |
| Met-Thr-Lys-Pro-Trp | Met-Thr-Lys-Pro-Trp | Met-Thr-Lys-Pro-Trp | 1837 |
| Met-Thr-Lys-Pro-Arg-Trp | Met-Thr-Lys-Pro-Arg-Trp | Met-Thr-Lys-Pro-Arg-Trp | 1838 |
| Met-Thr-Lys-Pro-Phe-Trp | Met-Thr-Lys-Pro-Phe-Trp | Met-Thr-Lys-Pro-Phe-Trp | 1839 |
| Met-Thr-Lys-Pro-Tyr-Trp | Met-Thr-Lys-Pro-Tyr-Trp | Met-Thr-Lys-Pro-Tyr-Trp | 1840 |
| Met-Thr-Lys-Pro-Gly-Trp | Met-Thr-Lys-Pro-Gly-Trp | Met-Thr-Lys-Pro-Gly-Trp | 1841 |
| Met-Thr-Lys-Pro-His-Trp | Met-Thr-Lys-Pro-His-Trp | Met-Thr-Lys-Pro-His-Trp | 1842 |
| Met-Thr-Lys-Pro-Lys-Trp | Met-Thr-Lys-Pro-Lys-Trp | Met-Thr-Lys-Pro-Lys-Trp | 1843 |
| Met-Thr-Lys-Pro-Gly-Trp | Met-Thr-Lys-Pro-Gly-Trp | Met-Thr-Lys-Pro-Gly-Trp | 1844 |
| Met-Thr-Lys-Pro-Gly-Arg-Trp | Met-Thr-Lys-Pro-Gly-Arg-Trp | Met-Thr-Lys-Pro-Gly-Arg-Trp | 1845 |
| Met-Thr-Lys-Pro-Gly-Phe-Trp | Met-Thr-Lys-Pro-Gly-Phe-Trp | Met-Thr-Lys-Pro-Gly-Phe-Trp | 1846 |

TABLE 1-continued

| X-OH | X-OCH₃ | X-NH₂ | SEQ ID NO |
|---|---|---|---|
| Met-Thr-Lys-Pro-Gly-Tyr-Trp | Met-Thr-Lys-Pro-Gly-Tyr-Trp | Met-Thr-Lys-Pro-Gly-Tyr-Trp | 1847 |
| Met-Thr-Lys-Pro-Gly-His-Trp | Met-Thr-Lys-Pro-Gly-His-Trp | Met-Thr-Lys-Pro-Gly-His-Trp | 1848 |
| Met-Thr-Lys-Pro-Gly-Pro-Trp | Met-Thr-Lys-Pro-Gly-Pro-Trp | Met-Thr-Lys-Pro-Gly-Pro-Trp | 1849 |
| Met-Thr-Lys-Pro-Gly-Lys-Trp | Met-Thr-Lys-Pro-Gly-Lys-Trp | Met-Thr-Lys-Pro-Gly-Lys-Trp | 1850 |
| Met-Thr-Lys-Pro-Asp-Trp | Met-Thr-Lys-Pro-Asp-Trp | Met-Thr-Lys-Pro-Asp-Trp | 1851 |
| Met-Thr-Lys-Pro-Asp-Arg-Trp | Met-Thr-Lys-Pro-Asp-Arg-Trp | Met-Thr-Lys-Pro-Asp-Arg-Trp | 1852 |
| Met-Thr-Lys-Pro-Asp-Phe-Trp | Met-Thr-Lys-Pro-Asp-Phe-Trp | Met-Thr-Lys-Pro-Asp-Phe-Trp | 1853 |
| Met-Thr-Lys-Pro-Asp-Tyr-Trp | Met-Thr-Lys-Pro-Asp-Tyr-Trp | Met-Thr-Lys-Pro-Asp-Tyr-Trp | 1854 |
| Met-Thr-Lys-Pro-Asp-His-Trp | Met-Thr-Lys-Pro-Asp-His-Trp | Met-Thr-Lys-Pro-Asp-His-Trp | 1855 |
| Met-Thr-Lys-Pro-Asp-Pro-Trp | Met-Thr-Lys-Pro-Asp-Pro-Trp | Met-Thr-Lys-Pro-Asp-Pro-Trp | 1856 |
| Met-Thr-Lys-Pro-Asp-Lys-Trp | Met-Thr-Lys-Pro-Asp-Lys-Trp | Met-Thr-Lys-Pro-Asp-Lys-Trp | 1857 |
| Met-Thr-Lys-Pro-Trp-Trp | Met-Thr-Lys-Pro-Trp-Trp | Met-Thr-Lys-Pro-Trp-Trp | 1858 |
| Met-Thr-Lys-Pro-Trp-Arg-Trp | Met-Thr-Lys-Pro-Trp-Arg-Trp | Met-Thr-Lys-Pro-Trp-Arg-Trp | 1859 |
| Met-Thr-Lys-Pro-Trp-Phe-Trp | Met-Thr-Lys-Pro-Trp-Phe-Trp | Met-Thr-Lys-Pro-Trp-Phe-Trp | 1860 |
| Met-Thr-Lys-Pro-Trp-Tyr-Trp | Met-Thr-Lys-Pro-Trp-Tyr-Trp | Met-Thr-Lys-Pro-Trp-Tyr-Trp | 1861 |
| Met-Thr-Lys-Pro-Trp-His-Trp | Met-Thr-Lys-Pro-Trp-His-Trp | Met-Thr-Lys-Pro-Trp-His-Trp | 1862 |
| Met-Thr-Lys-Pro-Trp-Pro-Trp | Met-Thr-Lys-Pro-Trp-Pro-Trp | Met-Thr-Lys-Pro-Trp-Pro-Trp | 1863 |
| Met-Thr-Lys-Pro-Trp-Lys-Trp | Met-Thr-Lys-Pro-Trp-Lys-Trp | Met-Thr-Lys-Pro-Trp-Lys-Trp | 1864 |
| Met-Thr-Lys-Pro-Gln-Trp | Met-Thr-Lys-Pro-Gln-Trp | Met-Thr-Lys-Pro-Gln-Trp | 1865 |
| Met-Thr-Lys-Pro-Gln-Arg-Trp | Met-Thr-Lys-Pro-Gln-Arg-Trp | Met-Thr-Lys-Pro-Gln-Arg-Trp | 1866 |
| Met-Thr-Lys-Pro-Gln-Phe-Trp | Met-Thr-Lys-Pro-Gln-Phe-Trp | Met-Thr-Lys-Pro-Gln-Phe-Trp | 1867 |
| Met-Thr-Lys-Pro-Gln-Tyr-Trp | Met-Thr-Lys-Pro-Gln-Tyr-Trp | Met-Thr-Lys-Pro-Gln-Tyr-Trp | 1868 |
| Met-Thr-Lys-Pro-Gln-His-Trp | Met-Thr-Lys-Pro-Gln-His-Trp | Met-Thr-Lys-Pro-Gln-His-Trp | 1869 |
| Met-Thr-Lys-Pro-Gln-Pro-Trp | Met-Thr-Lys-Pro-Gln-Pro-Trp | Met-Thr-Lys-Pro-Gln-Pro-Trp | 1870 |
| Met-Thr-Lys-Pro-Gln-Lys-Trp | Met-Thr-Lys-Pro-Gln-Lys-Trp | Met-Thr-Lys-Pro-Gln-Lys-Trp | 1871 |
| Met-Thr-Lys-Pro-Asn-Trp | Met-Thr-Lys-Pro-Asn-Trp | Met-Thr-Lys-Pro-Asn-Trp | 1872 |
| Met-Thr-Lys-Pro-Asn-Arg-Trp | Met-Thr-Lys-Pro-Asn-Arg-Trp | Met-Thr-Lys-Pro-Asn-Arg-Trp | 1873 |
| Met-Thr-Lys-Pro-Asn-Phe-Trp | Met-Thr-Lys-Pro-Asn-Phe-Trp | Met-Thr-Lys-Pro-Asn-Phe-Trp | 1874 |
| Met-Thr-Lys-Pro-Asn-Tyr-Trp | Met-Thr-Lys-Pro-Asn-Tyr-Trp | Met-Thr-Lys-Pro-Asn-Tyr-Trp | 1875 |
| Met-Thr-Lys-Pro-Asn-His-Trp | Met-Thr-Lys-Pro-Asn-His-Trp | Met-Thr-Lys-Pro-Asn-His-Trp | 1876 |
| Met-Thr-Lys-Pro-Asn-Pro-Trp | Met-Thr-Lys-Pro-Asn-Pro-Trp | Met-Thr-Lys-Pro-Asn-Pro-Trp | 1877 |
| Met-Thr-Lys-Pro-Asn-Lys-Trp | Met-Thr-Lys-Pro-Asn-Lys-Trp | Met-Thr-Lys-Pro-Asn-Lys-Trp | 1878 |
| Met-Thr-Lys-Pro-Tyr-Trp | Met-Thr-Lys-Pro-Tyr-Trp | Met-Thr-Lys-Pro-Tyr-Trp | 1879 |
| Met-Thr-Lys-Pro-Tyr-Arg-Trp | Met-Thr-Lys-Pro-Tyr-Arg-Trp | Met-Thr-Lys-Pro-Tyr-Arg-Trp | 1880 |
| Met-Thr-Lys-Pro-Tyr-Phe-Trp | Met-Thr-Lys-Pro-Tyr-Phe-Trp | Met-Thr-Lys-Pro-Tyr-Phe-Trp | 1881 |
| Met-Thr-Lys-Pro-Tyr-Tyr-Trp | Met-Thr-Lys-Pro-Tyr-Tyr-Trp | Met-Thr-Lys-Pro-Tyr-Tyr-Trp | 1882 |
| Met-Thr-Lys-Pro-Tyr-His-Trp | Met-Thr-Lys-Pro-Tyr-His-Trp | Met-Thr-Lys-Pro-Tyr-His-Trp | 1883 |
| Met-Thr-Lys-Pro-Tyr-Pro-Trp | Met-Thr-Lys-Pro-Tyr-Pro-Trp | Met-Thr-Lys-Pro-Tyr-Pro-Trp | 1884 |

TABLE 1-continued

| X-OH | X-OCH₃ | X-NH₂ | SEQ ID NO |
|---|---|---|---|
| Met-Thr-Lys-Pro-Tyr-Lys-Trp | Met-Thr-Lys-Pro-Tyr-Lys-Trp | Met-Thr-Lys-Pro-Tyr-Lys-Trp | 1885 |
| Met-Thr-Lys-Pro-Arg-Trp | Met-Thr-Lys-Pro-Arg-Trp | Met-Thr-Lys-Pro-Arg-Trp | 1886 |
| Met-Thr-Lys-Pro-Arg-Arg-Trp | Met-Thr-Lys-Pro-Arg-Arg-Trp | Met-Thr-Lys-Pro-Arg-Arg-Trp | 1887 |
| Met-Thr-Lys-Pro-Arg-Phe-Trp | Met-Thr-Lys-Pro-Arg-Phe-Trp | Met-Thr-Lys-Pro-Arg-Phe-Trp | 1888 |
| Met-Thr-Lys-Pro-Arg-Tyr-Trp | Met-Thr-Lys-Pro-Arg-Tyr-Trp | Met-Thr-Lys-Pro-Arg-Tyr-Trp | 1889 |
| Met-Thr-Lys-Pro-Arg-His-Trp | Met-Thr-Lys-Pro-Arg-His-Trp | Met-Thr-Lys-Pro-Arg-His-Trp | 1890 |
| Met-Thr-Lys-Pro-Arg-Pro-Trp | Met-Thr-Lys-Pro-Arg-Pro-Trp | Met-Thr-Lys-Pro-Arg-Pro-Trp | 1891 |
| Met-Thr-Lys-Pro-Arg-Lys-Trp | Met-Thr-Lys-Pro-Arg-Lys-Trp | Met-Thr-Lys-Pro-Arg-Lys-Trp | 1892 |
| Met(O)-Thr-Lys-Pro-Trp | Met(O)-Thr-Lys-Pro-Trp | Met(O)-Thr-Lys-Pro-Trp | 1893 |
| Met(O)-Thr-Lys-Pro-Arg-Trp | Met(O)-Thr-Lys-Pro-Arg-Trp | Met(O)-Thr-Lys-Pro-Arg-Trp | 1894 |
| Met(O)-Thr-Lys-Pro-Phe-Trp | Met(O)-Thr-Lys-Pro-Phe-Trp | Met(O)-Thr-Lys-Pro-Phe-Trp | 1895 |
| Met(O)-Thr-Lys-Pro-Tyr-Trp | Met(O)-Thr-Lys-Pro-Tyr-Trp | Met(O)-Thr-Lys-Pro-Tyr-Trp | 1896 |
| Met(O)-Thr-Lys-Pro-Gly-Trp | Met(O)-Thr-Lys-Pro-Gly-Trp | Met(O)-Thr-Lys-Pro-Gly-Trp | 1897 |
| Met(O)-Thr-Lys-Pro-His-Trp | Met(O)-Thr-Lys-Pro-His-Trp | Met(O)-Thr-Lys-Pro-His-Trp | 1898 |
| Met(O)-Thr-Lys-Pro-Lys-Trp | Met(O)-Thr-Lys-Pro-Lys-Trp | Met(O)-Thr-Lys-Pro-Lys-Trp | 1899 |
| Met(O)-Thr-Lys-Pro-Gly-Trp | Met(O)-Thr-Lys-Pro-Gly-Trp | Met(O)-Thr-Lys-Pro-Gly-Trp | 1900 |
| Met(O)-Thr-Lys-Pro-Gly-Arg-Trp | Met(O)-Thr-Lys-Pro-Gly-Arg-Trp | Met(O)-Thr-Lys-Pro-Gly-Arg-Trp | 1901 |
| Met(O)-Thr-Lys-Pro-Gly-Phe-Trp | Met(O)-Thr-Lys-Pro-Gly-Phe-Trp | Met(O)-Thr-Lys-Pro-Gly-Phe-Trp | 1902 |
| Met(O)-Thr-Lys-Pro-Gly-Tyr-Trp | Met(O)-Thr-Lys-Pro-Gly-Tyr-Trp | Met(O)-Thr-Lys-Pro-Gly-Tyr-Trp | 1903 |
| Met(O)-Thr-Lys-Pro-Gly-His-Trp | Met(O)-Thr-Lys-Pro-Gly-His-Trp | Met(O)-Thr-Lys-Pro-Gly-His-Trp | 1904 |
| Met(O)-Thr-Lys-Pro-Gly-Pro-Trp | Met(O)-Thr-Lys-Pro-Gly-Pro-Trp | Met(O)-Thr-Lys-Pro-Gly-Pro-Trp | 1905 |
| Met(O)-Thr-Lys-Pro-Gly-Lys-Trp | Met(O)-Thr-Lys-Pro-Gly-Lys-Trp | Met(O)-Thr-Lys-Pro-Gly-Lys-Trp | 1906 |
| Met(O)-Thr-Lys-Pro-Asp-Trp | Met(O)-Thr-Lys-Pro-Asp-Trp | Met(O)-Thr-Lys-Pro-Asp-Trp | 1907 |
| Met(O)-Thr-Lys-Pro-Asp-Arg-Trp | Met(O)-Thr-Lys-Pro-Asp-Arg-Trp | Met(O)-Thr-Lys-Pro-Asp-Arg-Trp | 1908 |
| Met(O)-Thr-Lys-Pro-Asp-Phe-Trp | Met(O)-Thr-Lys-Pro-Asp-Phe-Trp | Met(O)-Thr-Lys-Pro-Asp-Phe-Trp | 1909 |
| Met(O)-Thr-Lys-Pro-Asp-Tyr-Trp | Met(O)-Thr-Lys-Pro-Asp-Tyr-Trp | Met(O)-Thr-Lys-Pro-Asp-Tyr-Trp | 1910 |
| Met(O)-Thr-Lys-Pro-Asp-His-Trp | Met(O)-Thr-Lys-Pro-Asp-His-Trp | Met(O)-Thr-Lys-Pro-Asp-His-Trp | 1911 |
| Met(O)-Thr-Lys-Pro-Asp-Pro-Trp | Met(O)-Thr-Lys-Pro-Asp-Pro-Trp | Met(O)-Thr-Lys-Pro-Asp-Pro-Trp | 1912 |
| Met(O)-Thr-Lys-Pro-Asp-Lys-Trp | Met(O)-Thr-Lys-Pro-Asp-Lys-Trp | Met(O)-Thr-Lys-Pro-Asp-Lys-Trp | 1913 |
| Met(O)-Thr-Lys-Pro-Trp-Trp | Met(O)-Thr-Lys-Pro-Trp-Trp | Met(O)-Thr-Lys-Pro-Trp-Trp | 1914 |
| Met(O)-Thr-Lys-Pro-Trp-Arg-Trp | Met(O)-Thr-Lys-Pro-Trp-Arg-Trp | Met(O)-Thr-Lys-Pro-Trp-Arg-Trp | 1915 |

TABLE 1-continued

| X-OH | X-OCH₃ | X-NH₂ | SEQ ID NO |
|---|---|---|---|
| Met(O)-Thr-Lys-Pro-Trp-Phe-Trp | Met(O)-Thr-Lys-Pro-Trp-Phe-Trp | Met(O)-Thr-Lys-Pro-Trp-Phe-Trp | 1916 |
| Met(O)-Thr-Lys-Pro-Trp-Tyr-Trp | Met(O)-Thr-Lys-Pro-Trp-Tyr-Trp | Met(O)-Thr-Lys-Pro-Trp-Tyr-Trp | 1917 |
| Met(O)-Thr-Lys-Pro-Trp-His-Trp | Met(O)-Thr-Lys-Pro-Trp-His-Trp | Met(O)-Thr-Lys-Pro-Trp-His-Trp | 1918 |
| Met(O)-Thr-Lys-Pro-Trp-Pro-Trp | Met(O)-Thr-Lys-Pro-Trp-Pro-Trp | Met(O)-Thr-Lys-Pro-Trp-Pro-Trp | 1919 |
| Met(O)-Thr-Lys-Pro-Trp-Lys-Trp | Met(O)-Thr-Lys-Pro-Trp-Lys-Trp | Met(O)-Thr-Lys-Pro-Trp-Lys-Trp | 1920 |
| Met(O)-Thr-Lys-Pro-Gln-Trp | Met(O)-Thr-Lys-Pro-Gln-Trp | Met(O)-Thr-Lys-Pro-Gln-Trp | 1921 |
| Met(O)-Thr-Lys-Pro-Gln-Arg-Trp | Met(O)-Thr-Lys-Pro-Gln-Arg-Trp | Met(O)-Thr-Lys-Pro-Gln-Arg-Trp | 1922 |
| Met(O)-Thr-Lys-Pro-Gln-Phe-Trp | Met(O)-Thr-Lys-Pro-Gln-Phe-Trp | Met(O)-Thr-Lys-Pro-Gln-Phe-Trp | 1923 |
| Met(O)-Thr-Lys-Pro-Gln-Tyr-Trp | Met(O)-Thr-Lys-Pro-Gln-Tyr-Trp | Met(O)-Thr-Lys-Pro-Gln-Tyr-Trp | 1924 |
| Met(O)-Thr-Lys-Pro-Gln-His-Trp | Met(O)-Thr-Lys-Pro-Gln-His-Trp | Met(O)-Thr-Lys-Pro-Gln-His-Trp | 1925 |
| Met(O)-Thr-Lys-Pro-Gln-Pro-Trp | Met(O)-Thr-Lys-Pro-Gln-Pro-Trp | Met(O)-Thr-Lys-Pro-Gln-Pro-Trp | 1926 |
| Met(O)-Thr-Lys-Pro-Gln-Lys-Trp | Met(O)-Thr-Lys-Pro-Gln-Lys-Trp | Met(O)-Thr-Lys-Pro-Gln-Lys-Trp | 1927 |
| Met(O)-Thr-Lys-Pro-Asn-Trp | Met(O)-Thr-Lys-Pro-Asn-Trp | Met(O)-Thr-Lys-Pro-Asn-Trp | 1928 |
| Met(O)-Thr-Lys-Pro-Asn-Arg-Trp | Met(O)-Thr-Lys-Pro-Asn-Arg-Trp | Met(O)-Thr-Lys-Pro-Asn-Arg-Trp | 1929 |
| Met(O)-Thr-Lys-Pro-Asn-Phe-Trp | Met(O)-Thr-Lys-Pro-Asn-Phe-Trp | Met(O)-Thr-Lys-Pro-Asn-Phe-Trp | 1930 |
| Met(O)-Thr-Lys-Pro-Asn-Tyr-Trp | Met(O)-Thr-Lys-Pro-Asn-Tyr-Trp | Met(O)-Thr-Lys-Pro-Asn-Tyr-Trp | 1931 |
| Met(O)-Thr-Lys-Pro-Asn-His-Trp | Met(O)-Thr-Lys-Pro-Asn-His-Trp | Met(O)-Thr-Lys-Pro-Asn-His-Trp | 1932 |
| Met(O)-Thr-Lys-Pro-Asn-Pro-Trp | Met(O)-Thr-Lys-Pro-Asn-Pro-Trp | Met(O)-Thr-Lys-Pro-Asn-Pro-Trp | 1933 |
| Met(O)-Thr-Lys-Pro-Asn-Lys-Trp | Met(O)-Thr-Lys-Pro-Asn-Lys-Trp | Met(O)-Thr-Lys-Pro-Asn-Lys-Trp | 1934 |
| Met(O)-Thr-Lys-Pro-Tyr-Trp | Met(O)-Thr-Lys-Pro-Tyr-Trp | Met(O)-Thr-Lys-Pro-Tyr-Trp | 1935 |
| Met(O)-Thr-Lys-Pro-Tyr-Arg-Trp | Met(O)-Thr-Lys-Pro-Tyr-Arg-Trp | Met(O)-Thr-Lys-Pro-Tyr-Arg-Trp | 1936 |
| Met(O)-Thr-Lys-Pro-Tyr-Phe-Trp | Met(O)-Thr-Lys-Pro-Tyr-Phe-Trp | Met(O)-Thr-Lys-Pro-Tyr-Phe-Trp | 1937 |
| Met(O)-Thr-Lys-Pro-Tyr-Tyr-Trp | Met(O)-Thr-Lys-Pro-Tyr-Tyr-Trp | Met(O)-Thr-Lys-Pro-Tyr-Tyr-Trp | 1938 |
| Met(O)-Thr-Lys-Pro-Tyr-His-Trp | Met(O)-Thr-Lys-Pro-Tyr-His-Trp | Met(O)-Thr-Lys-Pro-Tyr-His-Trp | 1939 |
| Met(O)-Thr-Lys-Pro-Tyr-Pro-Trp | Met(O)-Thr-Lys-Pro-Tyr-Pro-Trp | Met(O)-Thr-Lys-Pro-Tyr-Pro-Trp | 1940 |
| Met(O)-Thr-Lys-Pro-Tyr-Lys-Trp | Met(O)-Thr-Lys-Pro-Tyr-Lys-Trp | Met(O)-Thr-Lys-Pro-Tyr-Lys-Trp | 1941 |
| Met(O)-Thr-Lys-Pro-Arg-Trp | Met(O)-Thr-Lys-Pro-Arg-Trp | Met(O)-Thr-Lys-Pro-Arg-Trp | 1942 |

TABLE 1-continued

| X-OH | X-OCH₃ | X-NH₂ | SEQ ID NO |
|---|---|---|---|
| Met(O)-Thr-Lys-Pro-Arg-Arg-Trp | Met(O)-Thr-Lys-Pro-Arg-Arg-Trp | Met(O)-Thr-Lys-Pro-Arg-Arg-Trp | 1943 |
| Met(O)-Thr-Lys-Pro-Arg-Phe-Trp | Met(O)-Thr-Lys-Pro-Arg-Phe-Trp | Met(O)-Thr-Lys-Pro-Arg-Phe-Trp | 1944 |
| Met(O)-Thr-Lys-Pro-Arg-Tyr-Trp | Met(O)-Thr-Lys-Pro-Arg-Tyr-Trp | Met(O)-Thr-Lys-Pro-Arg-Tyr-Trp | 1945 |
| Met(O)-Thr-Lys-Pro-Arg-His-Trp | Met(O)-Thr-Lys-Pro-Arg-His-Trp | Met(O)-Thr-Lys-Pro-Arg-His-Trp | 1946 |
| Met(O)-Thr-Lys-Pro-Arg-Pro-Trp | Met(O)-Thr-Lys-Pro-Arg-Pro-Trp | Met(O)-Thr-Lys-Pro-Arg-Pro-Trp | 1947 |
| Met(O)-Thr-Lys-Pro-Arg-Lys-Trp | Met(O)-Thr-Lys-Pro-Arg-Lys-Trp | Met(O)-Thr-Lys-Pro-Arg-Lys-Trp | 1948 |
| Thr-Thr-Lys-Pro-Trp | Thr-Thr-Lys-Pro-Trp | Thr-Thr-Lys-Pro-Trp | 1949 |
| Thr-Thr-Lys-Pro-Arg-Trp | Thr-Thr-Lys-Pro-Arg-Trp | Thr-Thr-Lys-Pro-Arg-Trp | 1950 |
| Thr-Thr-Lys-Pro-Phe-Trp | Thr-Thr-Lys-Pro-Phe-Trp | Thr-Thr-Lys-Pro-Phe-Trp | 1951 |
| Thr-Thr-Lys-Pro-Tyr-Trp | Thr-Thr-Lys-Pro-Tyr-Trp | Thr-Thr-Lys-Pro-Tyr-Trp | 1952 |
| Thr-Thr-Lys-Pro-Gly-Trp | Thr-Thr-Lys-Pro-Gly-Trp | Thr-Thr-Lys-Pro-Gly-Trp | 1953 |
| Thr-Thr-Lys-Pro-His-Trp | Thr-Thr-Lys-Pro-His-Trp | Thr-Thr-Lys-Pro-His-Trp | 1954 |
| Thr-Thr-Lys-Pro-Lys-Trp | Thr-Thr-Lys-Pro-Lys-Trp | Thr-Thr-Lys-Pro-Lys-Trp | 1955 |
| Thr-Thr-Lys-Pro-Gly-Trp | Thr-Thr-Lys-Pro-Gly-Trp | Thr-Thr-Lys-Pro-Gly-Trp | 1956 |
| Thr-Thr-Lys-Pro-Gly-Arg-Trp | Thr-Thr-Lys-Pro-Gly-Arg-Trp | Thr-Thr-Lys-Pro-Gly-Arg-Trp | 1957 |
| Thr-Thr-Lys-Pro-Gly-Phe-Trp | Thr-Thr-Lys-Pro-Gly-Phe-Trp | Thr-Thr-Lys-Pro-Gly-Phe-Trp | 1958 |
| Thr-Thr-Lys-Pro-Gly-Tyr-Trp | Thr-Thr-Lys-Pro-Gly-Tyr-Trp | Thr-Thr-Lys-Pro-Gly-Tyr-Trp | 1959 |
| Thr-Thr-Lys-Pro-Gly-His-Trp | Thr-Thr-Lys-Pro-Gly-His-Trp | Thr-Thr-Lys-Pro-Gly-His-Trp | 1960 |
| Thr-Thr-Lys-Pro-Gly-Pro-Trp | Thr-Thr-Lys-Pro-Gly-Pro-Trp | Thr-Thr-Lys-Pro-Gly-Pro-Trp | 1961 |
| Thr-Thr-Lys-Pro-Gly-Lys-Trp | Thr-Thr-Lys-Pro-Gly-Lys-Trp | Thr-Thr-Lys-Pro-Gly-Lys-Trp | 1962 |
| Thr-Thr-Lys-Pro-Asp-Trp | Thr-Thr-Lys-Pro-Asp-Trp | Thr-Thr-Lys-Pro-Asp-Trp | 1963 |
| Thr-Thr-Lys-Pro-Asp-Arg-Trp | Thr-Thr-Lys-Pro-Asp-Arg-Trp | Thr-Thr-Lys-Pro-Asp-Arg-Trp | 1964 |
| Thr-Thr-Lys-Pro-Asp-Phe-Trp | Thr-Thr-Lys-Pro-Asp-Phe-Trp | Thr-Thr-Lys-Pro-Asp-Phe-Trp | 1965 |
| Thr-Thr-Lys-Pro-Asp-Tyr-Trp | Thr-Thr-Lys-Pro-Asp-Tyr-Trp | Thr-Thr-Lys-Pro-Asp-Tyr-Trp | 1966 |
| Thr-Thr-Lys-Pro-Asp-His-Trp | Thr-Thr-Lys-Pro-Asp-His-Trp | Thr-Thr-Lys-Pro-Asp-His-Trp | 1967 |
| Thr-Thr-Lys-Pro-Asp-Pro-Trp | Thr-Thr-Lys-Pro-Asp-Pro-Trp | Thr-Thr-Lys-Pro-Asp-Pro-Trp | 1968 |
| Thr-Thr-Lys-Pro-Asp-Lys-Trp | Thr-Thr-Lys-Pro-Asp-Lys-Trp | Thr-Thr-Lys-Pro-Asp-Lys-Trp | 1969 |
| Thr-Thr-Lys-Pro-Trp-Trp | Thr-Thr-Lys-Pro-Trp-Trp | Thr-Thr-Lys-Pro-Trp-Trp | 1970 |
| Thr-Thr-Lys-Pro-Trp-Arg-Trp | Thr-Thr-Lys-Pro-Trp-Arg-Trp | Thr-Thr-Lys-Pro-Trp-Arg-Trp | 1971 |
| Thr-Thr-Lys-Pro-Trp-Phe-Trp | Thr-Thr-Lys-Pro-Trp-Phe-Trp | Thr-Thr-Lys-Pro-Trp-Phe-Trp | 1972 |
| Thr-Thr-Lys-Pro-Trp-Tyr-Trp | Thr-Thr-Lys-Pro-Trp-Tyr-Trp | Thr-Thr-Lys-Pro-Trp-Tyr-Trp | 1973 |
| Thr-Thr-Lys-Pro-Trp-His-Trp | Thr-Thr-Lys-Pro-Trp-His-Trp | Thr-Thr-Lys-Pro-Trp-His-Trp | 1974 |
| Thr-Thr-Lys-Pro-Trp-Pro-Trp | Thr-Thr-Lys-Pro-Trp-Pro-Trp | Thr-Thr-Lys-Pro-Trp-Pro-Trp | 1975 |
| Thr-Thr-Lys-Pro-Trp-Lys-Trp | Thr-Thr-Lys-Pro-Trp-Lys-Trp | Thr-Thr-Lys-Pro-Trp-Lys-Trp | 1976 |
| Thr-Thr-Lys-Pro-Gln-Trp | Thr-Thr-Lys-Pro-Gln-Trp | Thr-Thr-Lys-Pro-Gln-Trp | 1977 |

TABLE 1-continued

| X-OH | X-OCH₃ | X-NH₂ | SEQ ID NO |
|---|---|---|---|
| Thr-Thr-Lys-Pro-Gln-Arg-Trp | Thr-Thr-Lys-Pro-Gln-Arg-Trp | Thr-Thr-Lys-Pro-Gln-Arg-Trp | 1978 |
| Thr-Thr-Lys-Pro-Gln-Phe-Trp | Thr-Thr-Lys-Pro-Gln-Phe-Trp | Thr-Thr-Lys-Pro-Gln-Phe-Trp | 1979 |
| Thr-Thr-Lys-Pro-Gln-Tyr-Trp | Thr-Thr-Lys-Pro-Gln-Tyr-Trp | Thr-Thr-Lys-Pro-Gln-Tyr-Trp | 1980 |
| Thr-Thr-Lys-Pro-Gln-His-Trp | Thr-Thr-Lys-Pro-Gln-His-Trp | Thr-Thr-Lys-Pro-Gln-His-Trp | 1981 |
| Thr-Thr-Lys-Pro-Gln-Pro-Trp | Thr-Thr-Lys-Pro-Gln-Pro-Trp | Thr-Thr-Lys-Pro-Gln-Pro-Trp | 1982 |
| Thr-Thr-Lys-Pro-Gln-Lys-Trp | Thr-Thr-Lys-Pro-Gln-Lys-Trp | Thr-Thr-Lys-Pro-Gln-Lys-Trp | 1983 |
| Thr-Thr-Lys-Pro-Asn-Trp | Thr-Thr-Lys-Pro-Asn-Trp | Thr-Thr-Lys-Pro-Asn-Trp | 1984 |
| Thr-Thr-Lys-Pro-Asn-Arg-Trp | Thr-Thr-Lys-Pro-Asn-Arg-Trp | Thr-Thr-Lys-Pro-Asn-Arg-Trp | 1985 |
| Thr-Thr-Lys-Pro-Asn-Phe-Trp | Thr-Thr-Lys-Pro-Asn-Phe-Trp | Thr-Thr-Lys-Pro-Asn-Phe-Trp | 1986 |
| Thr-Thr-Lys-Pro-Asn-Tyr-Trp | Thr-Thr-Lys-Pro-Asn-Tyr-Trp | Thr-Thr-Lys-Pro-Asn-Tyr-Trp | 1987 |
| Thr-Thr-Lys-Pro-Asn-His-Trp | Thr-Thr-Lys-Pro-Asn-His-Trp | Thr-Thr-Lys-Pro-Asn-His-Trp | 1988 |
| Thr-Thr-Lys-Pro-Asn-Pro-Trp | Thr-Thr-Lys-Pro-Asn-Pro-Trp | Thr-Thr-Lys-Pro-Asn-Pro-Trp | 1989 |
| Thr-Thr-Lys-Pro-Asn-Lys-Trp | Thr-Thr-Lys-Pro-Asn-Lys-Trp | Thr-Thr-Lys-Pro-Asn-Lys-Trp | 1990 |
| Thr-Thr-Lys-Pro-Tyr-Trp | Thr-Thr-Lys-Pro-Tyr-Trp | Thr-Thr-Lys-Pro-Tyr-Trp | 1991 |
| Thr-Thr-Lys-Pro-Tyr-Arg-Trp | Thr-Thr-Lys-Pro-Tyr-Arg-Trp | Thr-Thr-Lys-Pro-Tyr-Arg-Trp | 1992 |
| Thr-Thr-Lys-Pro-Tyr-Phe-Trp | Thr-Thr-Lys-Pro-Tyr-Phe-Trp | Thr-Thr-Lys-Pro-Tyr-Phe-Trp | 1993 |
| Thr-Thr-Lys-Pro-Tyr-Tyr-Trp | Thr-Thr-Lys-Pro-Tyr-Tyr-Trp | Thr-Thr-Lys-Pro-Tyr-Tyr-Trp | 1994 |
| Thr-Thr-Lys-Pro-Tyr-His-Trp | Thr-Thr-Lys-Pro-Tyr-His-Trp | Thr-Thr-Lys-Pro-Tyr-His-Trp | 1995 |
| Thr-Thr-Lys-Pro-Tyr-Pro-Trp | Thr-Thr-Lys-Pro-Tyr-Pro-Trp | Thr-Thr-Lys-Pro-Tyr-Pro-Trp | 1996 |
| Thr-Thr-Lys-Pro-Tyr-Lys-Trp | Thr-Thr-Lys-Pro-Tyr-Lys-Trp | Thr-Thr-Lys-Pro-Tyr-Lys-Trp | 1997 |
| Thr-Thr-Lys-Pro-Arg-Trp | Thr-Thr-Lys-Pro-Arg-Trp | Thr-Thr-Lys-Pro-Arg-Trp | 1998 |
| Thr-Thr-Lys-Pro-Arg-Arg-Trp | Thr-Thr-Lys-Pro-Arg-Arg-Trp | Thr-Thr-Lys-Pro-Arg-Arg-Trp | 1999 |
| Thr-Thr-Lys-Pro-Arg-Phe-Trp | Thr-Thr-Lys-Pro-Arg-Phe-Trp | Thr-Thr-Lys-Pro-Arg-Phe-Trp | 2000 |
| Thr-Thr-Lys-Pro-Arg-Tyr-Trp | Thr-Thr-Lys-Pro-Arg-Tyr-Trp | Thr-Thr-Lys-Pro-Arg-Tyr-Trp | 2001 |
| Thr-Thr-Lys-Pro-Arg-His-Trp | Thr-Thr-Lys-Pro-Arg-His-Trp | Thr-Thr-Lys-Pro-Arg-His-Trp | 2002 |
| Thr-Thr-Lys-Pro-Arg-Pro-Trp | Thr-Thr-Lys-Pro-Arg-Pro-Trp | Thr-Thr-Lys-Pro-Arg-Pro-Trp | 2003 |
| Thr-Thr-Lys-Pro-Arg-Lys-Trp | Thr-Thr-Lys-Pro-Arg-Lys-Trp | Thr-Thr-Lys-Pro-Arg-Lys-Trp | 2004 |
| Ala-Thr-Lys-Pro-Trp | Ala-Thr-Lys-Pro-Trp | Ala-Thr-Lys-Pro-Trp | 2005 |
| Ala-Thr-Lys-Pro-Arg-Trp | Ala-Thr-Lys-Pro-Arg-Trp | Ala-Thr-Lys-Pro-Arg-Trp | 2006 |
| Ala-Thr-Lys-Pro-Phe-Trp | Ala-Thr-Lys-Pro-Phe-Trp | Ala-Thr-Lys-Pro-Phe-Trp | 2007 |
| Ala-Thr-Lys-Pro-Tyr-Trp | Ala-Thr-Lys-Pro-Tyr-Trp | Ala-Thr-Lys-Pro-Tyr-Trp | 2008 |
| Ala-Thr-Lys-Pro-Gly-Trp | Ala-Thr-Lys-Pro-Gly-Trp | Ala-Thr-Lys-Pro-Gly-Trp | 2009 |
| Ala-Thr-Lys-Pro-His-Trp | Ala-Thr-Lys-Pro-His-Trp | Ala-Thr-Lys-Pro-His-Trp | 2010 |
| Ala-Thr-Lys-Pro-Lys-Trp | Ala-Thr-Lys-Pro-Lys-Trp | Ala-Thr-Lys-Pro-Lys-Trp | 2011 |
| Ala-Thr-Lys-Pro-Gly-Trp | Ala-Thr-Lys-Pro-Gly-Trp | Ala-Thr-Lys-Pro-Gly-Trp | 2012 |
| Ala-Thr-Lys-Pro-Gly-Arg-Trp | Ala-Thr-Lys-Pro-Gly-Arg-Trp | Ala-Thr-Lys-Pro-Gly-Arg-Trp | 2013 |
| Ala-Thr-Lys-Pro-Gly-Phe-Trp | Ala-Thr-Lys-Pro-Gly-Phe-Trp | Ala-Thr-Lys-Pro-Gly-Phe-Trp | 2014 |
| Ala-Thr-Lys-Pro-Gly-Tyr-Trp | Ala-Thr-Lys-Pro-Gly-Tyr-Trp | Ala-Thr-Lys-Pro-Gly-Tyr-Trp | 2015 |

TABLE 1-continued

| X-OH | X-OCH₃ | X-NH₂ | SEQ ID NO |
|---|---|---|---|
| Ala-Thr-Lys-Pro-Gly-His-Trp | Ala-Thr-Lys-Pro-Gly-His-Trp | Ala-Thr-Lys-Pro-Gly-His-Trp | 2016 |
| Ala-Thr-Lys-Pro-Gly-Pro-Trp | Ala-Thr-Lys-Pro-Gly-Pro-Trp | Ala-Thr-Lys-Pro-Gly-Pro-Trp | 2017 |
| Ala-Thr-Lys-Pro-Gly-Lys-Trp | Ala-Thr-Lys-Pro-Gly-Lys-Trp | Ala-Thr-Lys-Pro-Gly-Lys-Trp | 2018 |
| Ala-Thr-Lys-Pro-Asp-Trp | Ala-Thr-Lys-Pro-Asp-Trp | Ala-Thr-Lys-Pro-Asp-Trp | 2019 |
| Ala-Thr-Lys-Pro-Asp-Arg-Trp | Ala-Thr-Lys-Pro-Asp-Arg-Trp | Ala-Thr-Lys-Pro-Asp-Arg-Trp | 2020 |
| Ala-Thr-Lys-Pro-Asp-Phe-Trp | Ala-Thr-Lys-Pro-Asp-Phe-Trp | Ala-Thr-Lys-Pro-Asp-Phe-Trp | 2021 |
| Ala-Thr-Lys-Pro-Asp-Tyr-Trp | Ala-Thr-Lys-Pro-Asp-Tyr-Trp | Ala-Thr-Lys-Pro-Asp-Tyr-Trp | 2022 |
| Ala-Thr-Lys-Pro-Asp-His-Trp | Ala-Thr-Lys-Pro-Asp-His-Trp | Ala-Thr-Lys-Pro-Asp-His-Trp | 2023 |
| Ala-Thr-Lys-Pro-Asp-Pro-Trp | Ala-Thr-Lys-Pro-Asp-Pro-Trp | Ala-Thr-Lys-Pro-Asp-Pro-Trp | 2024 |
| Ala-Thr-Lys-Pro-Asp-Lys-Trp | Ala-Thr-Lys-Pro-Asp-Lys-Trp | Ala-Thr-Lys-Pro-Asp-Lys-Trp | 2025 |
| Ala-Thr-Lys-Pro-Trp-Trp | Ala-Thr-Lys-Pro-Trp-Trp | Ala-Thr-Lys-Pro-Trp-Trp | 2026 |
| Ala-Thr-Lys-Pro-Trp-Arg-Trp | Ala-Thr-Lys-Pro-Trp-Arg-Trp | Ala-Thr-Lys-Pro-Trp-Arg-Trp | 2027 |
| Ala-Thr-Lys-Pro-Trp-Phe-Trp | Ala-Thr-Lys-Pro-Trp-Phe-Trp | Ala-Thr-Lys-Pro-Trp-Phe-Trp | 2028 |
| Ala-Thr-Lys-Pro-Trp-Tyr-Trp | Ala-Thr-Lys-Pro-Trp-Tyr-Trp | Ala-Thr-Lys-Pro-Trp-Tyr-Trp | 2029 |
| Ala-Thr-Lys-Pro-Trp-His-Trp | Ala-Thr-Lys-Pro-Trp-His-Trp | Ala-Thr-Lys-Pro-Trp-His-Trp | 2030 |
| Ala-Thr-Lys-Pro-Trp-Pro-Trp | Ala-Thr-Lys-Pro-Trp-Pro-Trp | Ala-Thr-Lys-Pro-Trp-Pro-Trp | 2031 |
| Ala-Thr-Lys-Pro-Trp-Lys-Trp | Ala-Thr-Lys-Pro-Trp-Lys-Trp | Ala-Thr-Lys-Pro-Trp-Lys-Trp | 2032 |
| Ala-Thr-Lys-Pro-Gln-Trp | Ala-Thr-Lys-Pro-Gln-Trp | Ala-Thr-Lys-Pro-Gln-Trp | 2033 |
| Ala-Thr-Lys-Pro-Gln-Arg-Trp | Ala-Thr-Lys-Pro-Gln-Arg-Trp | Ala-Thr-Lys-Pro-Gln-Arg-Trp | 2034 |
| Ala-Thr-Lys-Pro-Gln-Phe-Trp | Ala-Thr-Lys-Pro-Gln-Phe-Trp | Ala-Thr-Lys-Pro-Gln-Phe-Trp | 2035 |
| Ala-Thr-Lys-Pro-Gln-Tyr-Trp | Ala-Thr-Lys-Pro-Gln-Tyr-Trp | Ala-Thr-Lys-Pro-Gln-Tyr-Trp | 2036 |
| Ala-Thr-Lys-Pro-Gln-His-Trp | Ala-Thr-Lys-Pro-Gln-His-Trp | Ala-Thr-Lys-Pro-Gln-His-Trp | 2037 |
| Ala-Thr-Lys-Pro-Gln-Pro-Trp | Ala-Thr-Lys-Pro-Gln-Pro-Trp | Ala-Thr-Lys-Pro-Gln-Pro-Trp | 2038 |
| Ala-Thr-Lys-Pro-Gln-Lys-Trp | Ala-Thr-Lys-Pro-Gln-Lys-Trp | Ala-Thr-Lys-Pro-Gln-Lys-Trp | 2039 |
| Ala-Thr-Lys-Pro-Asn-Trp | Ala-Thr-Lys-Pro-Asn-Trp | Ala-Thr-Lys-Pro-Asn-Trp | 2040 |
| Ala-Thr-Lys-Pro-Asn-Arg-Trp | Ala-Thr-Lys-Pro-Asn-Arg-Trp | Ala-Thr-Lys-Pro-Asn-Arg-Trp | 2041 |
| Ala-Thr-Lys-Pro-Asn-Phe-Trp | Ala-Thr-Lys-Pro-Asn-Phe-Trp | Ala-Thr-Lys-Pro-Asn-Phe-Trp | 2042 |
| Ala-Thr-Lys-Pro-Asn-Tyr-Trp | Ala-Thr-Lys-Pro-Asn-Tyr-Trp | Ala-Thr-Lys-Pro-Asn-Tyr-Trp | 2043 |
| Ala-Thr-Lys-Pro-Asn-His-Trp | Ala-Thr-Lys-Pro-Asn-His-Trp | Ala-Thr-Lys-Pro-Asn-His-Trp | 2044 |
| Ala-Thr-Lys-Pro-Asn-Pro-Trp | Ala-Thr-Lys-Pro-Asn-Pro-Trp | Ala-Thr-Lys-Pro-Asn-Pro-Trp | 2045 |
| Ala-Thr-Lys-Pro-Asn-Lys-Trp | Ala-Thr-Lys-Pro-Asn-Lys-Trp | Ala-Thr-Lys-Pro-Asn-Lys-Trp | 2046 |
| Ala-Thr-Lys-Pro-Tyr-Trp | Ala-Thr-Lys-Pro-Tyr-Trp | Ala-Thr-Lys-Pro-Tyr-Trp | 2047 |
| Ala-Thr-Lys-Pro-Tyr-Arg-Trp | Ala-Thr-Lys-Pro-Tyr-Arg-Trp | Ala-Thr-Lys-Pro-Tyr-Arg-Trp | 2048 |
| Ala-Thr-Lys-Pro-Tyr-Phe-Trp | Ala-Thr-Lys-Pro-Tyr-Phe-Trp | Ala-Thr-Lys-Pro-Tyr-Phe-Trp | 2049 |
| Ala-Thr-Lys-Pro-Tyr-Tyr-Trp | Ala-Thr-Lys-Pro-Tyr-Tyr-Trp | Ala-Thr-Lys-Pro-Tyr-Tyr-Trp | 2050 |
| Ala-Thr-Lys-Pro-Tyr-His-Trp | Ala-Thr-Lys-Pro-Tyr-His-Trp | Ala-Thr-Lys-Pro-Tyr-His-Trp | 2051 |
| Ala-Thr-Lys-Pro-Tyr-Pro-Trp | Ala-Thr-Lys-Pro-Tyr-Pro-Trp | Ala-Thr-Lys-Pro-Tyr-Pro-Trp | 2052 |
| Ala-Thr-Lys-Pro-Tyr-Lys-Trp | Ala-Thr-Lys-Pro-Tyr-Lys-Trp | Ala-Thr-Lys-Pro-Tyr-Lys-Trp | 2053 |

TABLE 1-continued

| X-OH | X-OCH₃ | X-NH₂ | SEQ ID NO |
|---|---|---|---|
| Ala-Thr-Lys-Pro-Arg-Trp | Ala-Thr-Lys-Pro-Arg-Trp | Ala-Thr-Lys-Pro-Arg-Trp | 2054 |
| Ala-Thr-Lys-Pro-Arg-Arg-Trp | Ala-Thr-Lys-Pro-Arg-Arg-Trp | Ala-Thr-Lys-Pro-Arg-Arg-Trp | 2055 |
| Ala-Thr-Lys-Pro-Arg-Phe-Trp | Ala-Thr-Lys-Pro-Arg-Phe-Trp | Ala-Thr-Lys-Pro-Arg-Phe-Trp | 2056 |
| Ala-Thr-Lys-Pro-Arg-Tyr-Trp | Ala-Thr-Lys-Pro-Arg-Tyr-Trp | Ala-Thr-Lys-Pro-Arg-Tyr-Trp | 2057 |
| Ala-Thr-Lys-Pro-Arg-His-Trp | Ala-Thr-Lys-Pro-Arg-His-Trp | Ala-Thr-Lys-Pro-Arg-His-Trp | 2058 |
| Ala-Thr-Lys-Pro-Arg-Pro-Trp | Ala-Thr-Lys-Pro-Arg-Pro-Trp | Ala-Thr-Lys-Pro-Arg-Pro-Trp | 2059 |
| Ala-Thr-Lys-Pro-Arg-Lys-Trp | Ala-Thr-Lys-Pro-Arg-Lys-Trp | Ala-Thr-Lys-Pro-Arg-Lys-Trp | 2060 |
| His-Thr-Lys-Pro-Trp | His-Thr-Lys-Pro-Trp | His-Thr-Lys-Pro-Trp | 2061 |
| His-Thr-Lys-Pro-Arg-Trp | His-Thr-Lys-Pro-Arg-Trp | His-Thr-Lys-Pro-Arg-Trp | 2062 |
| His-Thr-Lys-Pro-Phe-Trp | His-Thr-Lys-Pro-Phe-Trp | His-Thr-Lys-Pro-Phe-Trp | 2063 |
| His-Thr-Lys-Pro-Tyr-Trp | His-Thr-Lys-Pro-Tyr-Trp | His-Thr-Lys-Pro-Tyr-Trp | 2064 |
| His-Thr-Lys-Pro-Gly-Trp | His-Thr-Lys-Pro-Gly-Trp | His-Thr-Lys-Pro-Gly-Trp | 2065 |
| His-Thr-Lys-Pro-His-Trp | His-Thr-Lys-Pro-His-Trp | His-Thr-Lys-Pro-His-Trp | 2066 |
| His-Thr-Lys-Pro-Lys-Trp | His-Thr-Lys-Pro-Lys-Trp | His-Thr-Lys-Pro-Lys-Trp | 2067 |
| His-Thr-Lys-Pro-Gly-Trp | His-Thr-Lys-Pro-Gly-Trp | His-Thr-Lys-Pro-Gly-Trp | 2068 |
| His-Thr-Lys-Pro-Gly-Arg-Trp | His-Thr-Lys-Pro-Gly-Arg-Trp | His-Thr-Lys-Pro-Gly-Arg-Trp | 2069 |
| His-Thr-Lys-Pro-Gly-Phe-Trp | His-Thr-Lys-Pro-Gly-Phe-Trp | His-Thr-Lys-Pro-Gly-Phe-Trp | 2070 |
| His-Thr-Lys-Pro-Gly-Tyr-Trp | His-Thr-Lys-Pro-Gly-Tyr-Trp | His-Thr-Lys-Pro-Gly-Tyr-Trp | 2071 |
| His-Thr-Lys-Pro-Gly-His-Trp | His-Thr-Lys-Pro-Gly-His-Trp | His-Thr-Lys-Pro-Gly-His-Trp | 2072 |
| His-Thr-Lys-Pro-Gly-Pro-Trp | His-Thr-Lys-Pro-Gly-Pro-Trp | His-Thr-Lys-Pro-Gly-Pro-Trp | 2073 |
| His-Thr-Lys-Pro-Gly-Lys-Trp | His-Thr-Lys-Pro-Gly-Lys-Trp | His-Thr-Lys-Pro-Gly-Lys-Trp | 2074 |
| His-Thr-Lys-Pro-Asp-Trp | His-Thr-Lys-Pro-Asp-Trp | His-Thr-Lys-Pro-Asp-Trp | 2075 |
| His-Thr-Lys-Pro-Asp-Arg-Trp | His-Thr-Lys-Pro-Asp-Arg-Trp | His-Thr-Lys-Pro-Asp-Arg-Trp | 2076 |
| His-Thr-Lys-Pro-Asp-Phe-Trp | His-Thr-Lys-Pro-Asp-Phe-Trp | His-Thr-Lys-Pro-Asp-Phe-Trp | 2077 |
| His-Thr-Lys-Pro-Asp-Tyr-Trp | His-Thr-Lys-Pro-Asp-Tyr-Trp | His-Thr-Lys-Pro-Asp-Tyr-Trp | 2078 |
| His-Thr-Lys-Pro-Asp-His-Trp | His-Thr-Lys-Pro-Asp-His-Trp | His-Thr-Lys-Pro-Asp-His-Trp | 2079 |
| His-Thr-Lys-Pro-Asp-Pro-Trp | His-Thr-Lys-Pro-Asp-Pro-Trp | His-Thr-Lys-Pro-Asp-Pro-Trp | 2080 |
| His-Thr-Lys-Pro-Asp-Lys-Trp | His-Thr-Lys-Pro-Asp-Lys-Trp | His-Thr-Lys-Pro-Asp-Lys-Trp | 2081 |
| His-Thr-Lys-Pro-Trp-Trp | His-Thr-Lys-Pro-Trp-Trp | His-Thr-Lys-Pro-Trp-Trp | 2082 |
| His-Thr-Lys-Pro-Trp-Arg-Trp | His-Thr-Lys-Pro-Trp-Arg-Trp | His-Thr-Lys-Pro-Trp-Arg-Trp | 2083 |
| His-Thr-Lys-Pro-Trp-Phe-Trp | His-Thr-Lys-Pro-Trp-Phe-Trp | His-Thr-Lys-Pro-Trp-Phe-Trp | 2084 |
| His-Thr-Lys-Pro-Trp-Tyr-Trp | His-Thr-Lys-Pro-Trp-Tyr-Trp | His-Thr-Lys-Pro-Trp-Tyr-Trp | 2085 |
| His-Thr-Lys-Pro-Trp-His-Trp | His-Thr-Lys-Pro-Trp-His-Trp | His-Thr-Lys-Pro-Trp-His-Trp | 2086 |
| His-Thr-Lys-Pro-Trp-Pro-Trp | His-Thr-Lys-Pro-Trp-Pro-Trp | His-Thr-Lys-Pro-Trp-Pro-Trp | 2087 |
| His-Thr-Lys-Pro-Trp-Lys-Trp | His-Thr-Lys-Pro-Trp-Lys-Trp | His-Thr-Lys-Pro-Trp-Lys-Trp | 2088 |
| His-Thr-Lys-Pro-Gln-Trp | His-Thr-Lys-Pro-Gln-Trp | His-Thr-Lys-Pro-Gln-Trp | 2089 |
| His-Thr-Lys-Pro-Gln-Arg-Trp | His-Thr-Lys-Pro-Gln-Arg-Trp | His-Thr-Lys-Pro-Gln-Arg-Trp | 2090 |
| His-Thr-Lys-Pro-Gln-Phe-Trp | His-Thr-Lys-Pro-Gln-Phe-Trp | His-Thr-Lys-Pro-Gln-Phe-Trp | 2091 |

TABLE 1-continued

| X-OH | X-OCH₃ | X-NH₂ | SEQ ID NO |
|---|---|---|---|
| His-Thr-Lys-Pro-Gln-Tyr-Trp | His-Thr-Lys-Pro-Gln-Tyr-Trp | His-Thr-Lys-Pro-Gln-Tyr-Trp | 2092 |
| His-Thr-Lys-Pro-Gln-His-Trp | His-Thr-Lys-Pro-Gln-His-Trp | His-Thr-Lys-Pro-Gln-His-Trp | 2093 |
| His-Thr-Lys-Pro-Gln-Pro-Trp | His-Thr-Lys-Pro-Gln-Pro-Trp | His-Thr-Lys-Pro-Gln-Pro-Trp | 2094 |
| His-Thr-Lys-Pro-Gln-Lys-Trp | His-Thr-Lys-Pro-Gln-Lys-Trp | His-Thr-Lys-Pro-Gln-Lys-Trp | 2095 |
| His-Thr-Lys-Pro-Asn-Trp | His-Thr-Lys-Pro-Asn-Trp | His-Thr-Lys-Pro-Asn-Trp | 2096 |
| His-Thr-Lys-Pro-Asn-Arg-Trp | His-Thr-Lys-Pro-Asn-Arg-Trp | His-Thr-Lys-Pro-Asn-Arg-Trp | 2097 |
| His-Thr-Lys-Pro-Asn-Phe-Trp | His-Thr-Lys-Pro-Asn-Phe-Trp | His-Thr-Lys-Pro-Asn-Phe-Trp | 2098 |
| His-Thr-Lys-Pro-Asn-Tyr-Trp | His-Thr-Lys-Pro-Asn-Tyr-Trp | His-Thr-Lys-Pro-Asn-Tyr-Trp | 2099 |
| His-Thr-Lys-Pro-Asn-His-Trp | His-Thr-Lys-Pro-Asn-His-Trp | His-Thr-Lys-Pro-Asn-His-Trp | 2100 |
| His-Thr-Lys-Pro-Asn-Pro-Trp | His-Thr-Lys-Pro-Asn-Pro-Trp | His-Thr-Lys-Pro-Asn-Pro-Trp | 2101 |
| His-Thr-Lys-Pro-Asn-Lys-Trp | His-Thr-Lys-Pro-Asn-Lys-Trp | His-Thr-Lys-Pro-Asn-Lys-Trp | 2102 |
| His-Thr-Lys-Pro-Tyr-Trp | His-Thr-Lys-Pro-Tyr-Trp | His-Thr-Lys-Pro-Tyr-Trp | 2103 |
| His-Thr-Lys-Pro-Tyr-Arg-Trp | His-Thr-Lys-Pro-Tyr-Arg-Trp | His-Thr-Lys-Pro-Tyr-Arg-Trp | 2104 |
| His-Thr-Lys-Pro-Tyr-Phe-Trp | His-Thr-Lys-Pro-Tyr-Phe-Trp | His-Thr-Lys-Pro-Tyr-Phe-Trp | 2105 |
| His-Thr-Lys-Pro-Tyr-Tyr-Trp | His-Thr-Lys-Pro-Tyr-Tyr-Trp | His-Thr-Lys-Pro-Tyr-Tyr-Trp | 2106 |
| His-Thr-Lys-Pro-Tyr-His-Trp | His-Thr-Lys-Pro-Tyr-His-Trp | His-Thr-Lys-Pro-Tyr-His-Trp | 2107 |
| His-Thr-Lys-Pro-Tyr-Pro-Trp | His-Thr-Lys-Pro-Tyr-Pro-Trp | His-Thr-Lys-Pro-Tyr-Pro-Trp | 2108 |
| His-Thr-Lys-Pro-Tyr-Lys-Trp | His-Thr-Lys-Pro-Tyr-Lys-Trp | His-Thr-Lys-Pro-Tyr-Lys-Trp | 2109 |
| His-Thr-Lys-Pro-Arg-Trp | His-Thr-Lys-Pro-Arg-Trp | His-Thr-Lys-Pro-Arg-Trp | 2110 |
| His-Thr-Lys-Pro-Arg-Arg-Trp | His-Thr-Lys-Pro-Arg-Arg-Trp | His-Thr-Lys-Pro-Arg-Arg-Trp | 2111 |
| His-Thr-Lys-Pro-Arg-Phe-Trp | His-Thr-Lys-Pro-Arg-Phe-Trp | His-Thr-Lys-Pro-Arg-Phe-Trp | 2112 |
| His-Thr-Lys-Pro-Arg-Tyr-Trp | His-Thr-Lys-Pro-Arg-Tyr-Trp | His-Thr-Lys-Pro-Arg-Tyr-Trp | 2113 |
| His-Thr-Lys-Pro-Arg-His-Trp | His-Thr-Lys-Pro-Arg-His-Trp | His-Thr-Lys-Pro-Arg-His-Trp | 2114 |
| His-Thr-Lys-Pro-Arg-Pro-Trp | His-Thr-Lys-Pro-Arg-Pro-Trp | His-Thr-Lys-Pro-Arg-Pro-Trp | 2115 |
| His-Thr-Lys-Pro-Arg-Lys-Trp | His-Thr-Lys-Pro-Arg-Lys-Trp | His-Thr-Lys-Pro-Arg-Lys-Trp | 2116 |
| Lys-Thr-Lys-Pro-Trp | Lys-Thr-Lys-Pro-Trp | Lys-Thr-Lys-Pro-Trp | 2117 |
| Lys-Thr-Lys-Pro-Arg-Trp | Lys-Thr-Lys-Pro-Arg-Trp | Lys-Thr-Lys-Pro-Arg-Trp | 2118 |
| Lys-Thr-Lys-Pro-Phe-Trp | Lys-Thr-Lys-Pro-Phe-Trp | Lys-Thr-Lys-Pro-Phe-Trp | 2119 |
| Lys-Thr-Lys-Pro-Tyr-Trp | Lys-Thr-Lys-Pro-Tyr-Trp | Lys-Thr-Lys-Pro-Tyr-Trp | 2120 |
| Lys-Thr-Lys-Pro-Gly-Trp | Lys-Thr-Lys-Pro-Gly-Trp | Lys-Thr-Lys-Pro-Gly-Trp | 2121 |
| Lys-Thr-Lys-Pro-His-Trp | Lys-Thr-Lys-Pro-His-Trp | Lys-Thr-Lys-Pro-His-Trp | 2122 |
| Lys-Thr-Lys-Pro-Lys-Trp | Lys-Thr-Lys-Pro-Lys-Trp | Lys-Thr-Lys-Pro-Lys-Trp | 2123 |
| Lys-Thr-Lys-Pro-Gly-Trp | Lys-Thr-Lys-Pro-Gly-Trp | Lys-Thr-Lys-Pro-Gly-Trp | 2124 |
| Lys-Thr-Lys-Pro-Gly-Arg-Trp | Lys-Thr-Lys-Pro-Gly-Arg-Trp | Lys-Thr-Lys-Pro-Gly-Arg-Trp | 2125 |
| Lys-Thr-Lys-Pro-Gly-Phe-Trp | Lys-Thr-Lys-Pro-Gly-Phe-Trp | Lys-Thr-Lys-Pro-Gly-Phe-Trp | 2126 |
| Lys-Thr-Lys-Pro-Gly-Tyr-Trp | Lys-Thr-Lys-Pro-Gly-Tyr-Trp | Lys-Thr-Lys-Pro-Gly-Tyr-Trp | 2127 |
| Lys-Thr-Lys-Pro-Gly-His-Trp | Lys-Thr-Lys-Pro-Gly-His-Trp | Lys-Thr-Lys-Pro-Gly-His-Trp | 2128 |
| Lys-Thr-Lys-Pro-Gly-Pro-Trp | Lys-Thr-Lys-Pro-Gly-Pro-Trp | Lys-Thr-Lys-Pro-Gly-Pro-Trp | 2129 |

TABLE 1-continued

| X-OH | X-OCH₃ | X-NH₂ | SEQ ID NO |
|---|---|---|---|
| Lys-Thr-Lys-Pro-Gly-Lys-Trp | Lys-Thr-Lys-Pro-Gly-Lys-Trp | Lys-Thr-Lys-Pro-Gly-Lys-Trp | 2130 |
| Lys-Thr-Lys-Pro-Asp-Trp | Lys-Thr-Lys-Pro-Asp-Trp | Lys-Thr-Lys-Pro-Asp-Trp | 2131 |
| Lys-Thr-Lys-Pro-Asp-Arg-Trp | Lys-Thr-Lys-Pro-Asp-Arg-Trp | Lys-Thr-Lys-Pro-Asp-Arg-Trp | 2132 |
| Lys-Thr-Lys-Pro-Asp-Phe-Trp | Lys-Thr-Lys-Pro-Asp-Phe-Trp | Lys-Thr-Lys-Pro-Asp-Phe-Trp | 2133 |
| Lys-Thr-Lys-Pro-Asp-Tyr-Trp | Lys-Thr-Lys-Pro-Asp-Tyr-Trp | Lys-Thr-Lys-Pro-Asp-Tyr-Trp | 2134 |
| Lys-Thr-Lys-Pro-Asp-His-Trp | Lys-Thr-Lys-Pro-Asp-His-Trp | Lys-Thr-Lys-Pro-Asp-His-Trp | 2135 |
| Lys-Thr-Lys-Pro-Asp-Pro-Trp | Lys-Thr-Lys-Pro-Asp-Pro-Trp | Lys-Thr-Lys-Pro-Asp-Pro-Trp | 2136 |
| Lys-Thr-Lys-Pro-Asp-Lys-Trp | Lys-Thr-Lys-Pro-Asp-Lys-Trp | Lys-Thr-Lys-Pro-Asp-Lys-Trp | 2137 |
| Lys-Thr-Lys-Pro-Trp-Trp | Lys-Thr-Lys-Pro-Trp-Trp | Lys-Thr-Lys-Pro-Trp-Trp | 2138 |
| Lys-Thr-Lys-Pro-Trp-Arg-Trp | Lys-Thr-Lys-Pro-Trp-Arg-Trp | Lys-Thr-Lys-Pro-Trp-Arg-Trp | 2139 |
| Lys-Thr-Lys-Pro-Trp-Phe-Trp | Lys-Thr-Lys-Pro-Trp-Phe-Trp | Lys-Thr-Lys-Pro-Trp-Phe-Trp | 2140 |
| Lys-Thr-Lys-Pro-Trp-Tyr-Trp | Lys-Thr-Lys-Pro-Trp-Tyr-Trp | Lys-Thr-Lys-Pro-Trp-Tyr-Trp | 2141 |
| Lys-Thr-Lys-Pro-Trp-His-Trp | Lys-Thr-Lys-Pro-Trp-His-Trp | Lys-Thr-Lys-Pro-Trp-His-Trp | 2142 |
| Lys-Thr-Lys-Pro-Trp-Pro-Trp | Lys-Thr-Lys-Pro-Trp-Pro-Trp | Lys-Thr-Lys-Pro-Trp-Pro-Trp | 2143 |
| Lys-Thr-Lys-Pro-Trp-Lys-Trp | Lys-Thr-Lys-Pro-Trp-Lys-Trp | Lys-Thr-Lys-Pro-Trp-Lys-Trp | 2144 |
| Lys-Thr-Lys-Pro-Gln-Trp | Lys-Thr-Lys-Pro-Gln-Trp | Lys-Thr-Lys-Pro-Gln-Trp | 2145 |
| Lys-Thr-Lys-Pro-Gln-Arg-Trp | Lys-Thr-Lys-Pro-Gln-Arg-Trp | Lys-Thr-Lys-Pro-Gln-Arg-Trp | 2146 |
| Lys-Thr-Lys-Pro-Gln-Phe-Trp | Lys-Thr-Lys-Pro-Gln-Phe-Trp | Lys-Thr-Lys-Pro-Gln-Phe-Trp | 2147 |
| Lys-Thr-Lys-Pro-Gln-Tyr-Trp | Lys-Thr-Lys-Pro-Gln-Tyr-Trp | Lys-Thr-Lys-Pro-Gln-Tyr-Trp | 2148 |
| Lys-Thr-Lys-Pro-Gln-His-Trp | Lys-Thr-Lys-Pro-Gln-His-Trp | Lys-Thr-Lys-Pro-Gln-His-Trp | 2149 |
| Lys-Thr-Lys-Pro-Gln-Pro-Trp | Lys-Thr-Lys-Pro-Gln-Pro-Trp | Lys-Thr-Lys-Pro-Gln-Pro-Trp | 2150 |
| Lys-Thr-Lys-Pro-Gln-Lys-Trp | Lys-Thr-Lys-Pro-Gln-Lys-Trp | Lys-Thr-Lys-Pro-Gln-Lys-Trp | 2151 |
| Lys-Thr-Lys-Pro-Asn-Trp | Lys-Thr-Lys-Pro-Asn-Trp | Lys-Thr-Lys-Pro-Asn-Trp | 2152 |
| Lys-Thr-Lys-Pro-Asn-Arg-Trp | Lys-Thr-Lys-Pro-Asn-Arg-Trp | Lys-Thr-Lys-Pro-Asn-Arg-Trp | 2153 |
| Lys-Thr-Lys-Pro-Asn-Phe-Trp | Lys-Thr-Lys-Pro-Asn-Phe-Trp | Lys-Thr-Lys-Pro-Asn-Phe-Trp | 2154 |
| Lys-Thr-Lys-Pro-Asn-Tyr-Trp | Lys-Thr-Lys-Pro-Asn-Tyr-Trp | Lys-Thr-Lys-Pro-Asn-Tyr-Trp | 2155 |
| Lys-Thr-Lys-Pro-Asn-His-Trp | Lys-Thr-Lys-Pro-Asn-His-Trp | Lys-Thr-Lys-Pro-Asn-His-Trp | 2156 |
| Lys-Thr-Lys-Pro-Asn-Pro-Trp | Lys-Thr-Lys-Pro-Asn-Pro-Trp | Lys-Thr-Lys-Pro-Asn-Pro-Trp | 2157 |
| Lys-Thr-Lys-Pro-Asn-Lys-Trp | Lys-Thr-Lys-Pro-Asn-Lys-Trp | Lys-Thr-Lys-Pro-Asn-Lys-Trp | 2158 |
| Lys-Thr-Lys-Pro-Tyr-Trp | Lys-Thr-Lys-Pro-Tyr-Trp | Lys-Thr-Lys-Pro-Tyr-Trp | 2159 |
| Lys-Thr-Lys-Pro-Tyr-Arg-Tr pLys-Thr-Lys-Pro-Tyr-Arg-Trp | Lys-Thr-Lys-Pro-Tyr-Arg-Trp | 2160 |
| Lys-Thr-Lys-Pro-Tyr-Phe-Tr pLys-Thr-Lys-Pro-Tyr-Phe-Trp | Lys-Thr-Lys-Pro-Tyr-Phe-Trp | 2161 |
| Lys-Thr-Lys-Pro-Tyr-Tyr-Tr pLys-Thr-Lys-Pro-Tyr-Tyr-Trp | Lys-Thr-Lys-Pro-Tyr-Tyr-Trp | 2162 |
| Lys-Thr-Lys-Pro-Tyr-His-Tr pLys-Thr-Lys-Pro-Tyr-His-Trp | Lys-Thr-Lys-Pro-Tyr-His-Trp | 2163 |
| Lys-Thr-Lys-Pro-Tyr-Pro-Tr pLys-Thr-Lys-Pro-Tyr-Pro-Trp | Lys-Thr-Lys-Pro-Tyr-Pro-Trp | 2164 |
| Lys-Thr-Lys-Pro-Tyr-Lys-Tr pLys-Thr-Lys-Pro-Tyr-Lys-Trp | Lys-Thr-Lys-Pro-Tyr-Lys-Trp | 2165 |
| Lys-Thr-Lys-Pro-Arg-Trp | Lys-Thr-Lys-Pro-Arg-Trp | Lys-Thr-Lys-Pro-Arg-Trp | 2166 |
| Lys-Thr-Lys-Pro-Arg-Arg-Trp | Lys-Thr-Lys-Pro-Arg-Arg-Trp | Lys-Thr-Lys-Pro-Arg-Arg-Trp | 2167 |

TABLE 1-continued

| X-OH | X-OCH₃ | X-NH₂ | SEQ ID NO |
|---|---|---|---|
| Lys-Thr-Lys-Pro-Arg-Phe-Trp | Lys-Thr-Lys-Pro-Arg-Phe-Trp | Lys-Thr-Lys-Pro-Arg-Phe-Trp | 2168 |
| Lys-Thr-Lys-Pro-Arg-Tyr-Trp | Lys-Thr-Lys-Pro-Arg-Tyr-Trp | Lys-Thr-Lys-Pro-Arg-Tyr-Trp | 2169 |
| Lys-Thr-Lys-Pro-Arg-His-Trp | Lys-Thr-Lys-Pro-Arg-His-Trp | Lys-Thr-Lys-Pro-Arg-His-Trp | 2170 |
| Lys-Thr-Lys-Pro-Arg-Pro-Trp | Lys-Thr-Lys-Pro-Arg-Pro-Trp | Lys-Thr-Lys-Pro-Arg-Pro-Trp | 2171 |
| Lys-Thr-Lys-Pro-Arg-Lys-Trp | Lys-Thr-Lys-Pro-Arg-Lys-Trp | Lys-Thr-Lys-Pro-Arg-Lys-Trp | 2172 |
| Gly-Thr-Lys-Pro-Trp | Gly-Thr-Lys-Pro-Trp | Gly-Thr-Lys-Pro-Trp | 2173 |
| Gly-Thr-Lys-Pro-Arg-Trp | Gly-Thr-Lys-Pro-Arg-Trp | Gly-Thr-Lys-Pro-Arg-Trp | 2174 |
| Gly-Thr-Lys-Pro-Phe-Trp | Gly-Thr-Lys-Pro-Phe-Trp | Gly-Thr-Lys-Pro-Phe-Trp | 2175 |
| Gly-Thr-Lys-Pro-Tyr-Trp | Gly-Thr-Lys-Pro-Tyr-Trp | Gly-Thr-Lys-Pro-Tyr-Trp | 2176 |
| Gly-Thr-Lys-Pro-Gly-Trp | Gly-Thr-Lys-Pro-Gly-Trp | Gly-Thr-Lys-Pro-Gly-Trp | 2177 |
| Gly-Thr-Lys-Pro-His-Trp | Gly-Thr-Lys-Pro-His-Trp | Gly-Thr-Lys-Pro-His-Trp | 2178 |
| Gly-Thr-Lys-Pro-Lys-Trp | Gly-Thr-Lys-Pro-Lys-Trp | Gly-Thr-Lys-Pro-Lys-Trp | 2179 |
| Gly-Thr-Lys-Pro-Gly-Trp | Gly-Thr-Lys-Pro-Gly-Trp | Gly-Thr-Lys-Pro-Gly-Trp | 2180 |
| Gly-Thr-Lys-Pro-Gly-Arg-Trp | Gly-Thr-Lys-Pro-Gly-Arg-Trp | Gly-Thr-Lys-Pro-Gly-Arg-Trp | 2181 |
| Gly-Thr-Lys-Pro-Gly-Phe-Trp | Gly-Thr-Lys-Pro-Gly-Phe-Trp | Gly-Thr-Lys-Pro-Gly-Phe-Trp | 2182 |
| Gly-Thr-Lys-Pro-Gly-Tyr-Trp | Gly-Thr-Lys-Pro-Gly-Tyr-Trp | Gly-Thr-Lys-Pro-Gly-Tyr-Trp | 2183 |
| Gly-Thr-Lys-Pro-Gly-His-Trp | Gly-Thr-Lys-Pro-Gly-His-Trp | Gly-Thr-Lys-Pro-Gly-His-Trp | 2184 |
| Gly-Thr-Lys-Pro-Gly-Pro-Trp | Gly-Thr-Lys-Pro-Gly-Pro-Trp | Gly-Thr-Lys-Pro-Gly-Pro-Trp | 2185 |
| Gly-Thr-Lys-Pro-Gly-Lys-Trp | Gly-Thr-Lys-Pro-Gly-Lys-Trp | Gly-Thr-Lys-Pro-Gly-Lys-Trp | 2186 |
| Gly-Thr-Lys-Pro-Asp-Trp | Gly-Thr-Lys-Pro-Asp-Trp | Gly-Thr-Lys-Pro-Asp-Trp | 2187 |
| Gly-Thr-Lys-Pro-Asp-Arg-Trp | Gly-Thr-Lys-Pro-Asp-Arg-Trp | Gly-Thr-Lys-Pro-Asp-Arg-Trp | 2188 |
| Gly-Thr-Lys-Pro-Asp-Phe-Trp | Gly-Thr-Lys-Pro-Asp-Phe-Trp | Gly-Thr-Lys-Pro-Asp-Phe-Trp | 2189 |
| Gly-Thr-Lys-Pro-Asp-Tyr-Trp | Gly-Thr-Lys-Pro-Asp-Tyr-Trp | Gly-Thr-Lys-Pro-Asp-Tyr-Trp | 2190 |
| Gly-Thr-Lys-Pro-Asp-His-Trp | Gly-Thr-Lys-Pro-Asp-His-Trp | Gly-Thr-Lys-Pro-Asp-His-Trp | 2191 |
| Gly-Thr-Lys-Pro-Asp-Pro-Trp | Gly-Thr-Lys-Pro-Asp-Pro-Trp | Gly-Thr-Lys-Pro-Asp-Pro-Trp | 2192 |
| Gly-Thr-Lys-Pro-Asp-Lys-Trp | Gly-Thr-Lys-Pro-Asp-Lys-Trp | Gly-Thr-Lys-Pro-Asp-Lys-Trp | 2193 |
| Gly-Thr-Lys-Pro-Trp-Trp | Gly-Thr-Lys-Pro-Trp-Trp | Gly-Thr-Lys-Pro-Trp-Trp | 2194 |
| Gly-Thr-Lys-Pro-Trp-Arg-Trp | Gly-Thr-Lys-Pro-Trp-Arg-Trp | Gly-Thr-Lys-Pro-Trp-Arg-Trp | 2195 |
| Gly-Thr-Lys-Pro-Trp-Phe-Trp | Gly-Thr-Lys-Pro-Trp-Phe-Trp | Gly-Thr-Lys-Pro-Trp-Phe-Trp | 2196 |
| Gly-Thr-Lys-Pro-Trp-Tyr-Trp | Gly-Thr-Lys-Pro-Trp-Tyr-Trp | Gly-Thr-Lys-Pro-Trp-Tyr-Trp | 2197 |
| Gly-Thr-Lys-Pro-Trp-His-Trp | Gly-Thr-Lys-Pro-Trp-His-Trp | Gly-Thr-Lys-Pro-Trp-His-Trp | 2198 |
| Gly-Thr-Lys-Pro-Trp-Pro-Trp | Gly-Thr-Lys-Pro-Trp-Pro-Trp | Gly-Thr-Lys-Pro-Trp-Pro-Trp | 2199 |
| Gly-Thr-Lys-Pro-Trp-Lys-Trp | Gly-Thr-Lys-Pro-Trp-Lys-Trp | Gly-Thr-Lys-Pro-Trp-Lys-Trp | 2200 |
| Gly-Thr-Lys-Pro-Gln-Trp | Gly-Thr-Lys-Pro-Gln-Trp | Gly-Thr-Lys-Pro-Gln-Trp | 2201 |
| Gly-Thr-Lys-Pro-Gln-Arg-Trp | Gly-Thr-Lys-Pro-Gln-Arg-Trp | Gly-Thr-Lys-Pro-Gln-Arg-Trp | 2202 |
| Gly-Thr-Lys-Pro-Gln-Phe-Trp | Gly-Thr-Lys-Pro-Gln-Phe-Trp | Gly-Thr-Lys-Pro-Gln-Phe-Trp | 2203 |
| Gly-Thr-Lys-Pro-Gln-Tyr-Trp | Gly-Thr-Lys-Pro-Gln-Tyr-Trp | Gly-Thr-Lys-Pro-Gln-Tyr-Trp | 2204 |
| Gly-Thr-Lys-Pro-Gln-His-Trp | Gly-Thr-Lys-Pro-Gln-His-Trp | Gly-Thr-Lys-Pro-Gln-His-Trp | 2205 |

TABLE 1-continued

| X-OH | X-OCH₃ | X-NH₂ | SEQ ID NO |
|---|---|---|---|
| Gly-Thr-Lys-Pro-Gln-Pro-Trp | Gly-Thr-Lys-Pro-Gln-Pro-Trp | Gly-Thr-Lys-Pro-Gln-Pro-Trp | 2206 |
| Gly-Thr-Lys-Pro-Gln-Lys-Trp | Gly-Thr-Lys-Pro-Gln-Lys-Trp | Gly-Thr-Lys-Pro-Gln-Lys-Trp | 2207 |
| Gly-Thr-Lys-Pro-Asn-Trp | Gly-Thr-Lys-Pro-Asn-Trp | Gly-Thr-Lys-Pro-Asn-Trp | 2208 |
| Gly-Thr-Lys-Pro-Asn-Arg-Trp | Gly-Thr-Lys-Pro-Asn-Arg-Trp | Gly-Thr-Lys-Pro-Asn-Arg-Trp | 2209 |
| Gly-Thr-Lys-Pro-Asn-Phe-Trp | Gly-Thr-Lys-Pro-Asn-Phe-Trp | Gly-Thr-Lys-Pro-Asn-Phe-Trp | 2210 |
| Gly-Thr-Lys-Pro-Asn-Tyr-Trp | Gly-Thr-Lys-Pro-Asn-Tyr-Trp | Gly-Thr-Lys-Pro-Asn-Tyr-Trp | 2211 |
| Gly-Thr-Lys-Pro-Asn-His-Trp | Gly-Thr-Lys-Pro-Asn-His-Trp | Gly-Thr-Lys-Pro-Asn-His-Trp | 2212 |
| Gly-Thr-Lys-Pro-Asn-Pro-Trp | Gly-Thr-Lys-Pro-Asn-Pro-Trp | Gly-Thr-Lys-Pro-Asn-Pro-Trp | 2213 |
| Gly-Thr-Lys-Pro-Asn-Lys-Trp | Gly-Thr-Lys-Pro-Asn-Lys-Trp | Gly-Thr-Lys-Pro-Asn-Lys-Trp | 2214 |
| Gly-Thr-Lys-Pro-Tyr-Trp | Gly-Thr-Lys-Pro-Tyr-Trp | Gly-Thr-Lys-Pro-Tyr-Trp | 2215 |
| Gly-Thr-Lys-Pro-Tyr-Arg-Trp | Gly-Thr-Lys-Pro-Tyr-Arg-Trp | Gly-Thr-Lys-Pro-Tyr-Arg-Trp | 2216 |
| Gly-Thr-Lys-Pro-Tyr-Phe-Trp | Gly-Thr-Lys-Pro-Tyr-Phe-Trp | Gly-Thr-Lys-Pro-Tyr-Phe-Trp | 2217 |
| Gly-Thr-Lys-Pro-Tyr-Tyr-Trp | Gly-Thr-Lys-Pro-Tyr-Tyr-Trp | Gly-Thr-Lys-Pro-Tyr-Tyr-Trp | 2218 |
| Gly-Thr-Lys-Pro-Tyr-His-Trp | Gly-Thr-Lys-Pro-Tyr-His-Trp | Gly-Thr-Lys-Pro-Tyr-His-Trp | 2219 |
| Gly-Thr-Lys-Pro-Tyr-Pro-Trp | Gly-Thr-Lys-Pro-Tyr-Pro-Trp | Gly-Thr-Lys-Pro-Tyr-Pro-Trp | 2220 |
| Gly-Thr-Lys-Pro-Tyr-Lys-Trp | Gly-Thr-Lys-Pro-Tyr-Lys-Trp | Gly-Thr-Lys-Pro-Tyr-Lys-Trp | 2221 |
| Gly-Thr-Lys-Pro-Arg-Trp | Gly-Thr-Lys-Pro-Arg-Trp | Gly-Thr-Lys-Pro-Arg-Trp | 2222 |
| Gly-Thr-Lys-Pro-Arg-Arg-Trp | Gly-Thr-Lys-Pro-Arg-Arg-Trp | Gly-Thr-Lys-Pro-Arg-Arg-Trp | 2223 |
| Gly-Thr-Lys-Pro-Arg-Phe-Trp | Gly-Thr-Lys-Pro-Arg-Phe-Trp | Gly-Thr-Lys-Pro-Arg-Phe-Trp | 2224 |
| Gly-Thr-Lys-Pro-Arg-Tyr-Trp | Gly-Thr-Lys-Pro-Arg-Tyr-Trp | Gly-Thr-Lys-Pro-Arg-Tyr-Trp | 2225 |
| Gly-Thr-Lys-Pro-Arg-His-Trp | Gly-Thr-Lys-Pro-Arg-His-Trp | Gly-Thr-Lys-Pro-Arg-His-Trp | 2226 |
| Gly-Thr-Lys-Pro-Arg-Pro-Trp | Gly-Thr-Lys-Pro-Arg-Pro-Trp | Gly-Thr-Lys-Pro-Arg-Pro-Trp | 2227 |
| Gly-Thr-Lys-Pro-Arg-Lys-Trp | Gly-Thr-Lys-Pro-Arg-Lys-Trp | Gly-Thr-Lys-Pro-Arg-Lys-Trp | 2228 |
| Thr-Lys-Pro-Arg-Phe | Thr-Lys-Pro-Arg-Phe | Thr-Lys-Pro-Arg-Phe | 2229 |
| Thr-Lys-Pro-Phe-Phe | Thr-Lys-Pro-Phe-Phe | Thr-Lys-Pro-Phe-Phe | 2230 |
| Thr-Lys-Pro-Tyr-Phe | Thr-Lys-Pro-Tyr-Phe | Thr-Lys-Pro-Tyr-Phe | 2231 |
| Thr-Lys-Pro-Gly-Phe | Thr-Lys-Pro-Gly-Phe | Thr-Lys-Pro-Gly-Phe | 2232 |
| Thr-Lys-Pro-His-Phe | Thr-Lys-Pro-His-Phe | Thr-Lys-Pro-His-Phe | 2233 |
| Thr-Lys-Pro-Lys-Phe | Thr-Lys-Pro-Lys-Phe | Thr-Lys-Pro-Lys-Phe | 2234 |
| Thr-Lys-Pro-Gly-Phe | Thr-Lys-Pro-Gly-Phe | Thr-Lys-Pro-Gly-Phe | 2235 |
| Thr-Lys-Pro-Gly-Arg-Phe | Thr-Lys-Pro-Gly-Arg-Phe | Thr-Lys-Pro-Gly-Arg-Phe | 2236 |
| Thr-Lys-Pro-Gly-Phe-Phe | Thr-Lys-Pro-Gly-Phe-Phe | Thr-Lys-Pro-Gly-Phe-Phe | 2237 |
| Thr-Lys-Pro-Gly-Tyr-Phe | Thr-Lys-Pro-Gly-Tyr-Phe | Thr-Lys-Pro-Gly-Tyr-Phe | 2238 |
| Thr-Lys-Pro-Gly-His-Phe | Thr-Lys-Pro-Gly-His-Phe | Thr-Lys-Pro-Gly-His-Phe | 2239 |
| Thr-Lys-Pro-Gly-Pro-Phe | Thr-Lys-Pro-Gly-Pro-Phe | Thr-Lys-Pro-Gly-Pro-Phe | 2240 |
| Thr-Lys-Pro-Gly-Lys-Phe | Thr-Lys-Pro-Gly-Lys-Phe | Thr-Lys-Pro-Gly-Lys-Phe | 2241 |
| Thr-Lys-Pro-Asp-Phe | Thr-Lys-Pro-Asp-Phe | Thr-Lys-Pro-Asp-Phe | 2242 |
| Thr-Lys-Pro-Asp-Arg-Phe | Thr-Lys-Pro-Asp-Arg-Phe | Thr-Lys-Pro-Asp-Arg-Phe | 2243 |

TABLE 1-continued

| X-OH | X-OCH₃ | X-NH₂ | SEQ ID NO |
|---|---|---|---|
| Thr-Lys-Pro-Asp-Phe-Phe | Thr-Lys-Pro-Asp-Phe-Phe | Thr-Lys-Pro-Asp-Phe-Phe | 2244 |
| Thr-Lys-Pro-Asp-Tyr-Phe | Thr-Lys-Pro-Asp-Tyr-Phe | Thr-Lys-Pro-Asp-Tyr-Phe | 2245 |
| Thr-Lys-Pro-Asp-His-Phe | Thr-Lys-Pro-Asp-His-Phe | Thr-Lys-Pro-Asp-His-Phe | 2246 |
| Thr-Lys-Pro-Asp-Pro-Phe | Thr-Lys-Pro-Asp-Pro-Phe | Thr-Lys-Pro-Asp-Pro-Phe | 2247 |
| Thr-Lys-Pro-Asp-Lys-Phe | Thr-Lys-Pro-Asp-Lys-Phe | Thr-Lys-Pro-Asp-Lys-Phe | 2248 |
| Thr-Lys-Pro-Trp-Phe | Thr-Lys-Pro-Trp-Phe | Thr-Lys-Pro-Trp-Phe | 2249 |
| Thr-Lys-Pro-Trp-Arg-Phe | Thr-Lys-Pro-Trp-Arg-Phe | Thr-Lys-Pro-Trp-Arg-Phe | 2250 |
| Thr-Lys-Pro-Trp-Phe-Phe | Thr-Lys-Pro-Trp-Phe-Phe | Thr-Lys-Pro-Trp-Phe-Phe | 2251 |
| Thr-Lys-Pro-Trp-Tyr-Phe | Thr-Lys-Pro-Trp-Tyr-Phe | Thr-Lys-Pro-Trp-Tyr-Phe | 2252 |
| Thr-Lys-Pro-Trp-His-Phe | Thr-Lys-Pro-Trp-His-Phe | Thr-Lys-Pro-Trp-His-Phe | 2253 |
| Thr-Lys-Pro-Trp-Pro-Phe | Thr-Lys-Pro-Trp-Pro-Phe | Thr-Lys-Pro-Trp-Pro-Phe | 2254 |
| Thr-Lys-Pro-Trp-Lys-Phe | Thr-Lys-Pro-Trp-Lys-Phe | Thr-Lys-Pro-Trp-Lys-Phe | 2255 |
| Thr-Lys-Pro-Gln-Phe | Thr-Lys-Pro-Gln-Phe | Thr-Lys-Pro-Gln-Phe | 2256 |
| Thr-Lys-Pro-Gln-Arg-Phe | Thr-Lys-Pro-Gln-Arg-Phe | Thr-Lys-Pro-Gln-Arg-Phe | 2257 |
| Thr-Lys-Pro-Gln-Phe-Phe | Thr-Lys-Pro-Gln-Phe-Phe | Thr-Lys-Pro-Gln-Phe-Phe | 2258 |
| Thr-Lys-Pro-Gln-Tyr-Phe | Thr-Lys-Pro-Gln-Tyr-Phe | Thr-Lys-Pro-Gln-Tyr-Phe | 2259 |
| Thr-Lys-Pro-Gln-His-Phe | Thr-Lys-Pro-Gln-His-Phe | Thr-Lys-Pro-Gln-His-Phe | 2260 |
| Thr-Lys-Pro-Gln-Pro-Phe | Thr-Lys-Pro-Gln-Pro-Phe | Thr-Lys-Pro-Gln-Pro-Phe | 2261 |
| Thr-Lys-Pro-Gln-Lys-Phe | Thr-Lys-Pro-Gln-Lys-Phe | Thr-Lys-Pro-Gln-Lys-Phe | 2262 |
| Thr-Lys-Pro-Asn-Phe | Thr-Lys-Pro-Asn-Phe | Thr-Lys-Pro-Asn-Phe | 2263 |
| Thr-Lys-Pro-Asn-Arg-Phe | Thr-Lys-Pro-Asn-Arg-Phe | Thr-Lys-Pro-Asn-Arg-Phe | 2264 |
| Thr-Lys-Pro-Asn-Phe-Phe | Thr-Lys-Pro-Asn-Phe-Phe | Thr-Lys-Pro-Asn-Phe-Phe | 2265 |
| Thr-Lys-Pro-Asn-Tyr-Phe | Thr-Lys-Pro-Asn-Tyr-Phe | Thr-Lys-Pro-Asn-Tyr-Phe | 2266 |
| Thr-Lys-Pro-Asn-His-Phe | Thr-Lys-Pro-Asn-His-Phe | Thr-Lys-Pro-Asn-His-Phe | 2267 |
| Thr-Lys-Pro-Asn-Pro-Phe | Thr-Lys-Pro-Asn-Pro-Phe | Thr-Lys-Pro-Asn-Pro-Phe | 2268 |
| Thr-Lys-Pro-Asn-Lys-Phe | Thr-Lys-Pro-Asn-Lys-Phe | Thr-Lys-Pro-Asn-Lys-Phe | 2269 |
| Thr-Lys-Pro-Tyr-Phe | Thr-Lys-Pro-Tyr-Phe | Thr-Lys-Pro-Tyr-Phe | 2270 |
| Thr-Lys-Pro-Tyr-Arg-Phe | Thr-Lys-Pro-Tyr-Arg-Phe | Thr-Lys-Pro-Tyr-Arg-Phe | 2271 |
| Thr-Lys-Pro-Tyr-Phe-Phe | Thr-Lys-Pro-Tyr-Phe-Phe | Thr-Lys-Pro-Tyr-Phe-Phe | 2272 |
| Thr-Lys-Pro-Tyr-Tyr-Phe | Thr-Lys-Pro-Tyr-Tyr-Phe | Thr-Lys-Pro-Tyr-Tyr-Phe | 2273 |
| Thr-Lys-Pro-Tyr-His-Phe | Thr-Lys-Pro-Tyr-His-Phe | Thr-Lys-Pro-Tyr-His-Phe | 2274 |
| Thr-Lys-Pro-Tyr-Pro-Phe | Thr-Lys-Pro-Tyr-Pro-Phe | Thr-Lys-Pro-Tyr-Pro-Phe | 2275 |
| Thr-Lys-Pro-Tyr-Lys-Phe | Thr-Lys-Pro-Tyr-Lys-Phe | Thr-Lys-Pro-Tyr-Lys-Phe | 2276 |
| Thr-Lys-Pro-Arg-Phe | Thr-Lys-Pro-Arg-Phe | Thr-Lys-Pro-Arg-Phe | 2277 |
| Thr-Lys-Pro-Arg-Arg-Phe | Thr-Lys-Pro-Arg-Arg-Phe | Thr-Lys-Pro-Arg-Arg-Phe | 2278 |
| Thr-Lys-Pro-Arg-Phe-Phe | Thr-Lys-Pro-Arg-Phe-Phe | Thr-Lys-Pro-Arg-Phe-Phe | 2279 |
| Thr-Lys-Pro-Arg-Tyr-Phe | Thr-Lys-Pro-Arg-Tyr-Phe | Thr-Lys-Pro-Arg-Tyr-Phe | 2280 |
| Thr-Lys-Pro-Arg-His-Phe | Thr-Lys-Pro-Arg-His-Phe | Thr-Lys-Pro-Arg-His-Phe | 2281 |

TABLE 1-continued

| X-OH | X-OCH₃ | X-NH₂ | SEQ ID NO |
|---|---|---|---|
| Thr-Lys-Pro-Arg-Pro-Phe | Thr-Lys-Pro-Arg-Pro-Phe | Thr-Lys-Pro-Arg-Pro-Phe | 7 |
| Thr-Lys-Pro-Arg-Lys-Phe | Thr-Lys-Pro-Arg-Lys-Phe | Thr-Lys-Pro-Arg-Lys-Phe | 2282 |
| Met-Thr-Lys-Pro-Phe | Met-Thr-Lys-Pro-Phe | Met-Thr-Lys-Pro-Phe | 2283 |
| Met-Thr-Lys-Pro-Arg-Phe | Met-Thr-Lys-Pro-Arg-Phe | Met-Thr-Lys-Pro-Arg-Phe | 2284 |
| Met-Thr-Lys-Pro-Phe-Phe | Met-Thr-Lys-Pro-Phe-Phe | Met-Thr-Lys-Pro-Phe-Phe | 2285 |
| Met-Thr-Lys-Pro-Tyr-Phe | Met-Thr-Lys-Pro-Tyr-Phe | Met-Thr-Lys-Pro-Tyr-Phe | 2286 |
| Met-Thr-Lys-Pro-Gly-Phe | Met-Thr-Lys-Pro-Gly-Phe | Met-Thr-Lys-Pro-Gly-Phe | 2287 |
| Met-Thr-Lys-Pro-His-Phe | Met-Thr-Lys-Pro-His-Phe | Met-Thr-Lys-Pro-His-Phe | 2288 |
| Met-Thr-Lys-Pro-Lys-Phe | Met-Thr-Lys-Pro-Lys-Phe | Met-Thr-Lys-Pro-Lys-Phe | 2289 |
| Met-Thr-Lys-Pro-Gly-Phe | Met-Thr-Lys-Pro-Gly-Phe | Met-Thr-Lys-Pro-Gly-Phe | 2290 |
| Met-Thr-Lys-Pro-Gly-Arg-Phe | Met-Thr-Lys-Pro-Gly-Arg-Phe | Met-Thr-Lys-Pro-Gly-Arg-Phe | 2291 |
| Met-Thr-Lys-Pro-Gly-Phe-Phe | Met-Thr-Lys-Pro-Gly-Phe-Phe | Met-Thr-Lys-Pro-Gly-Phe-Phe | 2292 |
| Met-Thr-Lys-Pro-Gly-Tyr-Phe | Met-Thr-Lys-Pro-Gly-Tyr-Phe | Met-Thr-Lys-Pro-Gly-Tyr-Phe | 2293 |
| Met-Thr-Lys-Pro-Gly-His-Phe | Met-Thr-Lys-Pro-Gly-His-Phe | Met-Thr-Lys-Pro-Gly-His-Phe | 2294 |
| Met-Thr-Lys-Pro-Gly-Pro-Phe | Met-Thr-Lys-Pro-Gly-Pro-Phe | Met-Thr-Lys-Pro-Gly-Pro-Phe | 2295 |
| Met-Thr-Lys-Pro-Gly-Lys-Phe | Met-Thr-Lys-Pro-Gly-Lys-Phe | Met-Thr-Lys-Pro-Gly-Lys-Phe | 2296 |
| Met-Thr-Lys-Pro-Asp-Phe | Met-Thr-Lys-Pro-Asp-Phe | Met-Thr-Lys-Pro-Asp-Phe | 2297 |
| Met-Thr-Lys-Pro-Asp-Arg-Phe | Met-Thr-Lys-Pro-Asp-Arg-Phe | Met-Thr-Lys-Pro-Asp-Arg-Phe | 2298 |
| Met-Thr-Lys-Pro-Asp-Phe-Phe | Met-Thr-Lys-Pro-Asp-Phe-Phe | Met-Thr-Lys-Pro-Asp-Phe-Phe | 2299 |
| Met-Thr-Lys-Pro-Asp-Tyr-Phe | Met-Thr-Lys-Pro-Asp-Tyr-Phe | Met-Thr-Lys-Pro-Asp-Tyr-Phe | 2300 |
| Met-Thr-Lys-Pro-Asp-His-Phe | Met-Thr-Lys-Pro-Asp-His-Phe | Met-Thr-Lys-Pro-Asp-His-Phe | 2301 |
| Met-Thr-Lys-Pro-Asp-Pro-Phe | Met-Thr-Lys-Pro-Asp-Pro-Phe | Met-Thr-Lys-Pro-Asp-Pro-Phe | 2302 |
| Met-Thr-Lys-Pro-Asp-Lys-Phe | Met-Thr-Lys-Pro-Asp-Lys-Phe | Met-Thr-Lys-Pro-Asp-Lys-Phe | 2303 |
| Met-Thr-Lys-Pro-Trp-Phe | Met-Thr-Lys-Pro-Trp-Phe | Met-Thr-Lys-Pro-Trp-Phe | 2304 |
| Met-Thr-Lys-Pro-Trp-Arg-Phe | Met-Thr-Lys-Pro-Trp-Arg-Phe | Met-Thr-Lys-Pro-Trp-Arg-Phe | 2305 |
| Met-Thr-Lys-Pro-Trp-Phe-Phe | Met-Thr-Lys-Pro-Trp-Phe-Phe | Met-Thr-Lys-Pro-Trp-Phe-Phe | 2306 |
| Met-Thr-Lys-Pro-Trp-Tyr-Phe | Met-Thr-Lys-Pro-Trp-Tyr-Phe | Met-Thr-Lys-Pro-Trp-Tyr-Phe | 2307 |
| Met-Thr-Lys-Pro-Trp-His-Phe | Met-Thr-Lys-Pro-Trp-His-Phe | Met-Thr-Lys-Pro-Trp-His-Phe | 2308 |
| Met-Thr-Lys-Pro-Trp-Pro-Phe | Met-Thr-Lys-Pro-Trp-Pro-Phe | Met-Thr-Lys-Pro-Trp-Pro-Phe | 2309 |
| Met-Thr-Lys-Pro-Trp-Lys-Phe | Met-Thr-Lys-Pro-Trp-Lys-Phe | Met-Thr-Lys-Pro-Trp-Lys-Phe | 2310 |
| Met-Thr-Lys-Pro-Gln-Phe | Met-Thr-Lys-Pro-Gln-Phe | Met-Thr-Lys-Pro-Gln-Phe | 2311 |
| Met-Thr-Lys-Pro-Gln-Arg-Phe | Met-Thr-Lys-Pro-Gln-Arg-Phe | Met-Thr-Lys-Pro-Gln-Arg-Phe | 2312 |
| Met-Thr-Lys-Pro-Gln-Phe-Phe | Met-Thr-Lys-Pro-Gln-Phe-Phe | Met-Thr-Lys-Pro-Gln-Phe-Phe | 2313 |
| Met-Thr-Lys-Pro-Gln-Tyr-Phe | Met-Thr-Lys-Pro-Gln-Tyr-Phe | Met-Thr-Lys-Pro-Gln-Tyr-Phe | 2314 |
| Met-Thr-Lys-Pro-Gln-His-Phe | Met-Thr-Lys-Pro-Gln-His-Phe | Met-Thr-Lys-Pro-Gln-His-Phe | 2315 |
| Met-Thr-Lys-Pro-Gln-Pro-Phe | Met-Thr-Lys-Pro-Gln-Pro-Phe | Met-Thr-Lys-Pro-Gln-Pro-Phe | 2316 |
| Met-Thr-Lys-Pro-Gln-Lys-Phe | Met-Thr-Lys-Pro-Gln-Lys-Phe | Met-Thr-Lys-Pro-Gln-Lys-Phe | 2317 |
| Met-Thr-Lys-Pro-Asn-Phe | Met-Thr-Lys-Pro-Asn-Phe | Met-Thr-Lys-Pro-Asn-Phe | 2318 |

TABLE 1-continued

| X-OH | X-OCH₃ | X-NH₂ | SEQ ID NO |
|---|---|---|---|
| Met-Thr-Lys-Pro-Asn-Arg-Phe | Met-Thr-Lys-Pro-Asn-Arg-Phe | Met-Thr-Lys-Pro-Asn-Arg-Phe | 2319 |
| Met-Thr-Lys-Pro-Asn-Phe-Phe | Met-Thr-Lys-Pro-Asn-Phe-Phe | Met-Thr-Lys-Pro-Asn-Phe-Phe | 2320 |
| Met-Thr-Lys-Pro-Asn-Tyr-Phe | Met-Thr-Lys-Pro-Asn-Tyr-Phe | Met-Thr-Lys-Pro-Asn-Tyr-Phe | 2321 |
| Met-Thr-Lys-Pro-Asn-His-Phe | Met-Thr-Lys-Pro-Asn-His-Phe | Met-Thr-Lys-Pro-Asn-His-Phe | 2322 |
| Met-Thr-Lys-Pro-Asn-Pro-Phe | Met-Thr-Lys-Pro-Asn-Pro-Phe | Met-Thr-Lys-Pro-Asn-Pro-Phe | 2323 |
| Met-Thr-Lys-Pro-Asn-Lys-Phe | Met-Thr-Lys-Pro-Asn-Lys-Phe | Met-Thr-Lys-Pro-Asn-Lys-Phe | 2324 |
| Met-Thr-Lys-Pro-Tyr-Phe | Met-Thr-Lys-Pro-Tyr-Phe | Met-Thr-Lys-Pro-Tyr-Phe | 2325 |
| Met-Thr-Lys-Pro-Tyr-Arg-Phe | Met-Thr-Lys-Pro-Tyr-Arg-Phe | Met-Thr-Lys-Pro-Tyr-Arg-Phe | 2326 |
| Met-Thr-Lys-Pro-Tyr-Phe-Phe | Met-Thr-Lys-Pro-Tyr-Phe-Phe | Met-Thr-Lys-Pro-Tyr-Phe-Phe | 2327 |
| Met-Thr-Lys-Pro-Tyr-Tyr-Phe | Met-Thr-Lys-Pro-Tyr-Tyr-Phe | Met-Thr-Lys-Pro-Tyr-Tyr-Phe | 2328 |
| Met-Thr-Lys-Pro-Tyr-His-Phe | Met-Thr-Lys-Pro-Tyr-His-Phe | Met-Thr-Lys-Pro-Tyr-His-Phe | 2329 |
| Met-Thr-Lys-Pro-Tyr-Pro-Phe | Met-Thr-Lys-Pro-Tyr-Pro-Phe | Met-Thr-Lys-Pro-Tyr-Pro-Phe | 2330 |
| Met-Thr-Lys-Pro-Tyr-Lys-Phe | Met-Thr-Lys-Pro-Tyr-Lys-Phe | Met-Thr-Lys-Pro-Tyr-Lys-Phe | 2331 |
| Met-Thr-Lys-Pro-Arg-Phe | Met-Thr-Lys-Pro-Arg-Phe | Met-Thr-Lys-Pro-Arg-Phe | 2332 |
| Met-Thr-Lys-Pro-Arg-Arg-Phe | Met-Thr-Lys-Pro-Arg-Arg-Phe | Met-Thr-Lys-Pro-Arg-Arg-Phe | 2333 |
| Met-Thr-Lys-Pro-Arg-Phe-Phe | Met-Thr-Lys-Pro-Arg-Phe-Phe | Met-Thr-Lys-Pro-Arg-Phe-Phe | 2334 |
| Met-Thr-Lys-Pro-Arg-Tyr-Phe | Met-Thr-Lys-Pro-Arg-Tyr-Phe | Met-Thr-Lys-Pro-Arg-Tyr-Phe | 2335 |
| Met-Thr-Lys-Pro-Arg-His-Phe | Met-Thr-Lys-Pro-Arg-His-Phe | Met-Thr-Lys-Pro-Arg-His-Phe | 2336 |
| Met-Thr-Lys-Pro-Arg-Pro-Phe | Met-Thr-Lys-Pro-Arg-Pro-Phe | Met-Thr-Lys-Pro-Arg-Pro-Phe | 2337 |
| Met-Thr-Lys-Pro-Arg-Lys-Phe | Met-Thr-Lys-Pro-Arg-Lys-Phe | Met-Thr-Lys-Pro-Arg-Lys-Phe | 2338 |
| Met(O)-Thr-Lys-Pro-Phe | Met(O)-Thr-Lys-Pro-Phe | Met(O)-Thr-Lys-Pro-Phe | 2339 |
| Met(O)-Thr-Lys-Pro-Arg-Phe | Met(O)-Thr-Lys-Pro-Arg-Phe | Met(O)-Thr-Lys-Pro-Arg-Phe | 2340 |
| Met(O)-Thr-Lys-Pro-Phe-Phe | Met(O)-Thr-Lys-Pro-Phe-Phe | Met(O)-Thr-Lys-Pro-Phe-Phe | 2341 |
| Met(O)-Thr-Lys-Pro-Tyr-Phe | Met(O)-Thr-Lys-Pro-Tyr-Phe | Met(O)-Thr-Lys-Pro-Tyr-Phe | 2342 |
| Met(O)-Thr-Lys-Pro-Gly-Phe | Met(O)-Thr-Lys-Pro-Gly-Phe | Met(O)-Thr-Lys-Pro-Gly-Phe | 2343 |
| Met(O)-Thr-Lys-Pro-His-Phe | Met(O)-Thr-Lys-Pro-His-Phe | Met(O)-Thr-Lys-Pro-His-Phe | 2344 |
| Met(O)-Thr-Lys-Pro-Lys-Phe | Met(O)-Thr-Lys-Pro-Lys-Phe | Met(O)-Thr-Lys-Pro-Lys-Phe | 2345 |
| Met(O)-Thr-Lys-Pro-Gly-Phe | Met(O)-Thr-Lys-Pro-Gly-Phe | Met(O)-Thr-Lys-Pro-Gly-Phe | 2346 |
| Met(O)-Thr-Lys-Pro-Gly-Arg-Phe | Met(O)-Thr-Lys-Pro-Gly-Arg-Phe | Met(O)-Thr-Lys-Pro-Gly-Arg-Phe | 2347 |
| Met(O)-Thr-Lys-Pro-Gly-Phe-Phe | Met(O)-Thr-Lys-Pro-Gly-Phe-Phe | Met(O)-Thr-Lys-Pro-Gly-Phe-Phe | 2348 |
| Met(O)-Thr-Lys-Pro-Gly-Tyr-Phe | Met(O)-Thr-Lys-Pro-Gly-Tyr-Phe | Met(O)-Thr-Lys-Pro-Gly-Tyr-Phe | 2349 |
| Met(O)-Thr-Lys-Pro-Gly-His-Phe | Met(O)-Thr-Lys-Pro-Gly-His-Phe | Met(O)-Thr-Lys-Pro-Gly-His-Phe | 2350 |
| Met(O)-Thr-Lys-Pro-Gly-Pro-Phe | Met(O)-Thr-Lys-Pro-Gly-Pro-Phe | Met(O)-Thr-Lys-Pro-Gly-Pro-Phe | 2351 |
| Met(O)-Thr-Lys-Pro-Gly-Lys-Phe | Met(O)-Thr-Lys-Pro-Gly-Lys-Phe | Met(O)-Thr-Lys-Pro-Gly-Lys-Phe | 2352 |
| Met(O)-Thr-Lys-Pro-Asp-Phe | Met(O)-Thr-Lys-Pro-Asp-Phe | Met(O)-Thr-Lys-Pro-Asp-Phe | 2353 |

TABLE 1-continued

| X-OH | X-OCH₃ | X-NH₂ | SEQ ID NO |
|---|---|---|---|
| Met(O)-Thr-Lys-Pro-Asp-Arg-Phe | Met(O)-Thr-Lys-Pro-Asp-Arg-Phe | Met(O)-Thr-Lys-Pro-Asp-Arg-Phe | 2354 |
| Met(O)-Thr-Lys-Pro-Asp-Phe-Phe | Met(O)-Thr-Lys-Pro-Asp-Phe-Phe | Met(O)-Thr-Lys-Pro-Asp-Phe-Phe | 2355 |
| Met(O)-Thr-Lys-Pro-Asp-Tyr-Phe | Met(O)-Thr-Lys-Pro-Asp-Tyr-Phe | Met(O)-Thr-Lys-Pro-Asp-Tyr-Phe | 2356 |
| Met(O)-Thr-Lys-Pro-Asp-His-Phe | Met(O)-Thr-Lys-Pro-Asp-His-Phe | Met(O)-Thr-Lys-Pro-Asp-His-Phe | 2357 |
| Met(O)-Thr-Lys-Pro-Asp-Pro-Phe | Met(O)-Thr-Lys-Pro-Asp-Pro-Phe | Met(O)-Thr-Lys-Pro-Asp-Pro-Phe | 2358 |
| Met(O)-Thr-Lys-Pro-Asp-Lys-Phe | Met(O)-Thr-Lys-Pro-Asp-Lys-Phe | Met(O)-Thr-Lys-Pro-Asp-Lys-Phe | 2359 |
| Met(O)-Thr-Lys-Pro-Trp-Phe | Met(O)-Thr-Lys-Pro-Trp-Phe | Met(O)-Thr-Lys-Pro-Trp-Phe | 2360 |
| Met(O)-Thr-Lys-Pro-Trp-Arg-Phe | Met(O)-Thr-Lys-Pro-Trp-Arg-Phe | Met(O)-Thr-Lys-Pro-Trp-Arg-Phe | 2361 |
| Met(O)-Thr-Lys-Pro-Trp-Phe-Phe | Met(O)-Thr-Lys-Pro-Trp-Phe-Phe | Met(O)-Thr-Lys-Pro-Trp-Phe-Phe | 2362 |
| Met(O)-Thr-Lys-Pro-Trp-Tyr-Phe | Met(O)-Thr-Lys-Pro-Trp-Tyr-Phe | Met(O)-Thr-Lys-Pro-Trp-Tyr-Phe | 2363 |
| Met(O)-Thr-Lys-Pro-Trp-His-Phe | Met(O)-Thr-Lys-Pro-Trp-His-Phe | Met(O)-Thr-Lys-Pro-Trp-His-Phe | 2364 |
| Met(O)-Thr-Lys-Pro-Trp-Pro-Phe | Met(O)-Thr-Lys-Pro-Trp-Pro-Phe | Met(O)-Thr-Lys-Pro-Trp-Pro-Phe | 2365 |
| Met(O)-Thr-Lys-Pro-Trp-Lys-Phe | Met(O)-Thr-Lys-Pro-Trp-Lys-Phe | Met(O)-Thr-Lys-Pro-Trp-Lys-Phe | 2366 |
| Met(O)-Thr-Lys-Pro-Gln-Phe | Met(O)-Thr-Lys-Pro-Gln-Phe | Met(O)-Thr-Lys-Pro-Gln-Phe | 2367 |
| Met(O)-Thr-Lys-Pro-Gln-Arg-Phe | Met(O)-Thr-Lys-Pro-Gln-Arg-Phe | Met(O)-Thr-Lys-Pro-Gln-Arg-Phe | 2368 |
| Met(O)-Thr-Lys-Pro-Gln-Phe-Phe | Met(O)-Thr-Lys-Pro-Gln-Phe-Phe | Met(O)-Thr-Lys-Pro-Gln-Phe-Phe | 2369 |
| Met(O)-Thr-Lys-Pro-Gln-Tyr-Phe | Met(O)-Thr-Lys-Pro-Gln-Tyr-Phe | Met(O)-Thr-Lys-Pro-Gln-Tyr-Phe | 2370 |
| Met(O)-Thr-Lys-Pro-Gln-His-Phe | Met(O)-Thr-Lys-Pro-Gln-His-Phe | Met(O)-Thr-Lys-Pro-Gln-His-Phe | 2371 |
| Met(O)-Thr-Lys-Pro-Gln-Pro-Phe | Met(O)-Thr-Lys-Pro-Gln-Pro-Phe | Met(O)-Thr-Lys-Pro-Gln-Pro-Phe | 2372 |
| Met(O)-Thr-Lys-Pro-Gln-Lys-Phe | Met(O)-Thr-Lys-Pro-Gln-Lys-Phe | Met(O)-Thr-Lys-Pro-Gln-Lys-Phe | 2373 |
| Met(O)-Thr-Lys-Pro-Asn-Phe | Met(O)-Thr-Lys-Pro-Asn-Phe | Met(O)-Thr-Lys-Pro-Asn-Phe | 2374 |
| Met(O)-Thr-Lys-Pro-Asn-Arg-Phe | Met(O)-Thr-Lys-Pro-Asn-Arg-Phe | Met(O)-Thr-Lys-Pro-Asn-Arg-Phe | 2375 |
| Met(O)-Thr-Lys-Pro-Asn-Phe-Phe | Met(O)-Thr-Lys-Pro-Asn-Phe-Phe | Met(O)-Thr-Lys-Pro-Asn-Phe-Phe | 2376 |
| Met(O)-Thr-Lys-Pro-Asn-Tyr-Phe | Met(O)-Thr-Lys-Pro-Asn-Tyr-Phe | Met(O)-Thr-Lys-Pro-Asn-Tyr-Phe | 2377 |
| Met(O)-Thr-Lys-Pro-Asn-His-Phe | Met(O)-Thr-Lys-Pro-Asn-His-Phe | Met(O)-Thr-Lys-Pro-Asn-His-Phe | 2378 |
| Met(O)-Thr-Lys-Pro-Asn-Pro-Phe | Met(O)-Thr-Lys-Pro-Asn-Pro-Phe | Met(O)-Thr-Lys-Pro-Asn-Pro-Phe | 2379 |

TABLE 1-continued

| X-OH | X-OCH₃ | X-NH₂ | SEQ ID NO |
|---|---|---|---|
| Met(O)-Thr-Lys-Pro-Asn-Lys-Phe | Met(O)-Thr-Lys-Pro-Asn-Lys-Phe | Met(O)-Thr-Lys-Pro-Asn-Lys-Phe | 2380 |
| Met(O)-Thr-Lys-Pro-Tyr-Phe | Met(O)-Thr-Lys-Pro-Tyr-Phe | Met(O)-Thr-Lys-Pro-Tyr-Phe | 2381 |
| Met(O)-Thr-Lys-Pro-Tyr-Arg-Phe | Met(O)-Thr-Lys-Pro-Tyr-Arg-Phe | Met(O)-Thr-Lys-Pro-Tyr-Arg-Phe | 2382 |
| Met(O)-Thr-Lys-Pro-Tyr-Phe-Phe | Met(O)-Thr-Lys-Pro-Tyr-Phe-Phe | Met(O)-Thr-Lys-Pro-Tyr-Phe-Phe | 2383 |
| Met(O)-Thr-Lys-Pro-Tyr-Tyr-Phe | Met(O)-Thr-Lys-Pro-Tyr-Tyr-Phe | Met(O)-Thr-Lys-Pro-Tyr-Tyr-Phe | 2384 |
| Met(O)-Thr-Lys-Pro-Tyr-His-Phe | Met(O)-Thr-Lys-Pro-Tyr-His-Phe | Met(O)-Thr-Lys-Pro-Tyr-His-Phe | 2385 |
| Met(O)-Thr-Lys-Pro-Tyr-Pro-Phe | Met(O)-Thr-Lys-Pro-Tyr-Pro-Phe | Met(O)-Thr-Lys-Pro-Tyr-Pro-Phe | 2386 |
| Met(O)-Thr-Lys-Pro-Tyr-Lys-Phe | Met(O)-Thr-Lys-Pro-Tyr-Lys-Phe | Met(O)-Thr-Lys-Pro-Tyr-Lys-Phe | 2387 |
| Met(O)-Thr-Lys-Pro-Arg-Phe | Met(O)-Thr-Lys-Pro-Arg-Phe | Met(O)-Thr-Lys-Pro-Arg-Phe | 2388 |
| Met(O)-Thr-Lys-Pro-Arg-Arg-Phe | Met(O)-Thr-Lys-Pro-Arg-Arg-Phe | Met(O)-Thr-Lys-Pro-Arg-Arg-Phe | 2389 |
| Met(O)-Thr-Lys-Pro-Arg-Phe-Phe | Met(O)-Thr-Lys-Pro-Arg-Phe-Phe | Met(O)-Thr-Lys-Pro-Arg-Phe-Phe | 2390 |
| Met(O)-Thr-Lys-Pro-Arg-Tyr-Phe | Met(O)-Thr-Lys-Pro-Arg-Tyr-Phe | Met(O)-Thr-Lys-Pro-Arg-Tyr-Phe | 2391 |
| Met(O)-Thr-Lys-Pro-Arg-His-Phe | Met(O)-Thr-Lys-Pro-Arg-His-Phe | Met(O)-Thr-Lys-Pro-Arg-His-Phe | 2392 |
| Met(O)-Thr-Lys-Pro-Arg-Pro-Phe | Met(O)-Thr-Lys-Pro-Arg-Pro-Phe | Met(O)-Thr-Lys-Pro-Arg-Pro-Phe | 2393 |
| Met(O)-Thr-Lys-Pro-Arg-Lys-Phe | Met(O)-Thr-Lys-Pro-Arg-Lys-Phe | Met(O)-Thr-Lys-Pro-Arg-Lys-Phe | 2394 |
| Thr-Thr-Lys-Pro-Phe | Thr-Thr-Lys-Pro-Phe | Thr-Thr-Lys-Pro-Phe | 2395 |
| Thr-Thr-Lys-Pro-Arg-Phe | Thr-Thr-Lys-Pro-Arg-Phe | Thr-Thr-Lys-Pro-Arg-Phe | 2396 |
| Thr-Thr-Lys-Pro-Phe-Phe | Thr-Thr-Lys-Pro-Phe-Phe | Thr-Thr-Lys-Pro-Phe-Phe | 2397 |
| Thr-Thr-Lys-Pro-Tyr-Phe | Thr-Thr-Lys-Pro-Tyr-Phe | Thr-Thr-Lys-Pro-Tyr-Phe | 2398 |
| Thr-Thr-Lys-Pro-Gly-Phe | Thr-Thr-Lys-Pro-Gly-Phe | Thr-Thr-Lys-Pro-Gly-Phe | 2399 |
| Thr-Thr-Lys-Pro-His-Phe | Thr-Thr-Lys-Pro-His-Phe | Thr-Thr-Lys-Pro-His-Phe | 2400 |
| Thr-Thr-Lys-Pro-Lys-Phe | Thr-Thr-Lys-Pro-Lys-Phe | Thr-Thr-Lys-Pro-Lys-Phe | 2401 |
| Thr-Thr-Lys-Pro-Gly-Phe | Thr-Thr-Lys-Pro-Gly-Phe | Thr-Thr-Lys-Pro-Gly-Phe | 2402 |
| Thr-Thr-Lys-Pro-Gly-Arg-Phe | Thr-Thr-Lys-Pro-Gly-Arg-Phe | Thr-Thr-Lys-Pro-Gly-Arg-Phe | 2403 |
| Thr-Thr-Lys-Pro-Gly-Phe-Phe | Thr-Thr-Lys-Pro-Gly-Phe-Phe | Thr-Thr-Lys-Pro-Gly-Phe-Phe | 2404 |
| Thr-Thr-Lys-Pro-Gly-Tyr-Phe | Thr-Thr-Lys-Pro-Gly-Tyr-Phe | Thr-Thr-Lys-Pro-Gly-Tyr-Phe | 2405 |
| Thr-Thr-Lys-Pro-Gly-His-Phe | Thr-Thr-Lys-Pro-Gly-His-Phe | Thr-Thr-Lys-Pro-Gly-His-Phe | 2406 |
| Thr-Thr-Lys-Pro-Gly-Pro-Phe | Thr-Thr-Lys-Pro-Gly-Pro-Phe | Thr-Thr-Lys-Pro-Gly-Pro-Phe | 2407 |
| Thr-Thr-Lys-Pro-Gly-Lys-Phe | Thr-Thr-Lys-Pro-Gly-Lys-Phe | Thr-Thr-Lys-Pro-Gly-Lys-Phe | 2408 |
| Thr-Thr-Lys-Pro-Asp-Phe | Thr-Thr-Lys-Pro-Asp-Phe | Thr-Thr-Lys-Pro-Asp-Phe | 2409 |
| Thr-Thr-Lys-Pro-Asp-Arg-Phe | Thr-Thr-Lys-Pro-Asp-Arg-Phe | Thr-Thr-Lys-Pro-Asp-Arg-Phe | 2410 |
| Thr-Thr-Lys-Pro-Asp-Phe-Phe | Thr-Thr-Lys-Pro-Asp-Phe-Phe | Thr-Thr-Lys-Pro-Asp-Phe-Phe | 2411 |

TABLE 1-continued

| X-OH | X-OCH₃ | X-NH₂ | SEQ ID NO |
|---|---|---|---|
| Thr-Thr-Lys-Pro-Asp-Tyr-Phe | Thr-Thr-Lys-Pro-Asp-Tyr-Phe | Thr-Thr-Lys-Pro-Asp-Tyr-Phe | 2412 |
| Thr-Thr-Lys-Pro-Asp-His-Phe | Thr-Thr-Lys-Pro-Asp-His-Phe | Thr-Thr-Lys-Pro-Asp-His-Phe | 2413 |
| Thr-Thr-Lys-Pro-Asp-Pro-Phe | Thr-Thr-Lys-Pro-Asp-Pro-Phe | Thr-Thr-Lys-Pro-Asp-Pro-Phe | 2414 |
| Thr-Thr-Lys-Pro-Asp-Lys-Phe | Thr-Thr-Lys-Pro-Asp-Lys-Phe | Thr-Thr-Lys-Pro-Asp-Lys-Phe | 2415 |
| Thr-Thr-Lys-Pro-Trp-Phe | Thr-Thr-Lys-Pro-Trp-Phe | Thr-Thr-Lys-Pro-Trp-Phe | 2416 |
| Thr-Thr-Lys-Pro-Trp-Arg-Phe | Thr-Thr-Lys-Pro-Trp-Arg-Phe | Thr-Thr-Lys-Pro-Trp-Arg-Phe | 2417 |
| Thr-Thr-Lys-Pro-Trp-Phe-Phe | Thr-Thr-Lys-Pro-Trp-Phe-Phe | Thr-Thr-Lys-Pro-Trp-Phe-Phe | 2418 |
| Thr-Thr-Lys-Pro-Trp-Tyr-Phe | Thr-Thr-Lys-Pro-Trp-Tyr-Phe | Thr-Thr-Lys-Pro-Trp-Tyr-Phe | 2419 |
| Thr-Thr-Lys-Pro-Trp-His-Phe | Thr-Thr-Lys-Pro-Trp-His-Phe | Thr-Thr-Lys-Pro-Trp-His-Phe | 2420 |
| Thr-Thr-Lys-Pro-Trp-Pro-Phe | Thr-Thr-Lys-Pro-Trp-Pro-Phe | Thr-Thr-Lys-Pro-Trp-Pro-Phe | 2421 |
| Thr-Thr-Lys-Pro-Trp-Lys-Phe | Thr-Thr-Lys-Pro-Trp-Lys-Phe | Thr-Thr-Lys-Pro-Trp-Lys-Phe | 2422 |
| Thr-Thr-Lys-Pro-Gln-Phe | Thr-Thr-Lys-Pro-Gln-Phe | Thr-Thr-Lys-Pro-Gln-Phe | 2423 |
| Thr-Thr-Lys-Pro-Gln-Arg-Phe | Thr-Thr-Lys-Pro-Gln-Arg-Phe | Thr-Thr-Lys-Pro-Gln-Arg-Phe | 2424 |
| Thr-Thr-Lys-Pro-Gln-Phe-Phe | Thr-Thr-Lys-Pro-Gln-Phe-Phe | Thr-Thr-Lys-Pro-Gln-Phe-Phe | 2425 |
| Thr-Thr-Lys-Pro-Gln-Tyr-Phe | Thr-Thr-Lys-Pro-Gln-Tyr-Phe | Thr-Thr-Lys-Pro-Gln-Tyr-Phe | 2426 |
| Thr-Thr-Lys-Pro-Gln-His-Phe | Thr-Thr-Lys-Pro-Gln-His-Phe | Thr-Thr-Lys-Pro-Gln-His-Phe | 2427 |
| Thr-Thr-Lys-Pro-Gln-Pro-Phe | Thr-Thr-Lys-Pro-Gln-Pro-Phe | Thr-Thr-Lys-Pro-Gln-Pro-Phe | 2428 |
| Thr-Thr-Lys-Pro-Gln-Lys-Phe | Thr-Thr-Lys-Pro-Gln-Lys-Phe | Thr-Thr-Lys-Pro-Gln-Lys-Phe | 2429 |
| Thr-Thr-Lys-Pro-Asn-Phe | Thr-Thr-Lys-Pro-Asn-Phe | Thr-Thr-Lys-Pro-Asn-Phe | 2430 |
| Thr-Thr-Lys-Pro-Asn-Arg-Phe | Thr-Thr-Lys-Pro-Asn-Arg-Phe | Thr-Thr-Lys-Pro-Asn-Arg-Phe | 2431 |
| Thr-Thr-Lys-Pro-Asn-Phe-Phe | Thr-Thr-Lys-Pro-Asn-Phe-Phe | Thr-Thr-Lys-Pro-Asn-Phe-Phe | 2432 |
| Thr-Thr-Lys-Pro-Asn-Tyr-Phe | Thr-Thr-Lys-Pro-Asn-Tyr-Phe | Thr-Thr-Lys-Pro-Asn-Tyr-Phe | 2433 |
| Thr-Thr-Lys-Pro-Asn-His-Phe | Thr-Thr-Lys-Pro-Asn-His-Phe | Thr-Thr-Lys-Pro-Asn-His-Phe | 2434 |
| Thr-Thr-Lys-Pro-Asn-Pro-Phe | Thr-Thr-Lys-Pro-Asn-Pro-Phe | Thr-Thr-Lys-Pro-Asn-Pro-Phe | 2435 |
| Thr-Thr-Lys-Pro-Asn-Lys-Phe | Thr-Thr-Lys-Pro-Asn-Lys-Phe | Thr-Thr-Lys-Pro-Asn-Lys-Phe | 2436 |
| Thr-Thr-Lys-Pro-Tyr-Phe | Thr-Thr-Lys-Pro-Tyr-Phe | Thr-Thr-Lys-Pro-Tyr-Phe | 2437 |
| Thr-Thr-Lys-Pro-Tyr-Arg-Phe | Thr-Thr-Lys-Pro-Tyr-Arg-Phe | Thr-Thr-Lys-Pro-Tyr-Arg-Phe | 2438 |
| Thr-Thr-Lys-Pro-Tyr-Phe-Phe | Thr-Thr-Lys-Pro-Tyr-Phe-Phe | Thr-Thr-Lys-Pro-Tyr-Phe-Phe | 2439 |
| Thr-Thr-Lys-Pro-Tyr-Tyr-Phe | Thr-Thr-Lys-Pro-Tyr-Tyr-Phe | Thr-Thr-Lys-Pro-Tyr-Tyr-Phe | 2440 |
| Thr-Thr-Lys-Pro-Tyr-His-Phe | Thr-Thr-Lys-Pro-Tyr-His-Phe | Thr-Thr-Lys-Pro-Tyr-His-Phe | 2441 |
| Thr-Thr-Lys-Pro-Tyr-Pro-Phe | Thr-Thr-Lys-Pro-Tyr-Pro-Phe | Thr-Thr-Lys-Pro-Tyr-Pro-Phe | 2442 |
| Thr-Thr-Lys-Pro-Tyr-Lys-Phe | Thr-Thr-Lys-Pro-Tyr-Lys-Phe | Thr-Thr-Lys-Pro-Tyr-Lys-Phe | 2443 |
| Thr-Thr-Lys-Pro-Arg-Phe | Thr-Thr-Lys-Pro-Arg-Phe | Thr-Thr-Lys-Pro-Arg-Phe | 2444 |
| Thr-Thr-Lys-Pro-Arg-Arg-Phe | Thr-Thr-Lys-Pro-Arg-Arg-Phe | Thr-Thr-Lys-Pro-Arg-Arg-Phe | 2445 |
| Thr-Thr-Lys-Pro-Arg-Phe-Phe | Thr-Thr-Lys-Pro-Arg-Phe-Phe | Thr-Thr-Lys-Pro-Arg-Phe-Phe | 2446 |
| Thr-Thr-Lys-Pro-Arg-Tyr-Phe | Thr-Thr-Lys-Pro-Arg-Tyr-Phe | Thr-Thr-Lys-Pro-Arg-Tyr-Phe | 2447 |
| Thr-Thr-Lys-Pro-Arg-His-Phe | Thr-Thr-Lys-Pro-Arg-His-Phe | Thr-Thr-Lys-Pro-Arg-His-Phe | 2448 |
| Thr-Thr-Lys-Pro-Arg-Pro-Phe | Thr-Thr-Lys-Pro-Arg-Pro-Phe | Thr-Thr-Lys-Pro-Arg-Pro-Phe | 2449 |

TABLE 1-continued

| X-OH | X-OCH₃ | X-NH₂ | SEQ ID NO |
|---|---|---|---|
| Thr-Thr-Lys-Pro-Arg-Lys-Phe | Thr-Thr-Lys-Pro-Arg-Lys-Phe | Thr-Thr-Lys-Pro-Arg-Lys-Phe | 2450 |
| Ala-Thr-Lys-Pro-Phe | Ala-Thr-Lys-Pro-Phe | Ala-Thr-Lys-Pro-Phe | 2451 |
| Ala-Thr-Lys-Pro-Arg-Phe | Ala-Thr-Lys-Pro-Arg-Phe | Ala-Thr-Lys-Pro-Arg-Phe | 2452 |
| Ala-Thr-Lys-Pro-Phe-Phe | Ala-Thr-Lys-Pro-Phe-Phe | Ala-Thr-Lys-Pro-Phe-Phe | 2453 |
| Ala-Thr-Lys-Pro-Tyr-Phe | Ala-Thr-Lys-Pro-Tyr-Phe | Ala-Thr-Lys-Pro-Tyr-Phe | 2454 |
| Ala-Thr-Lys-Pro-Gly-Phe | Ala-Thr-Lys-Pro-Gly-Phe | Ala-Thr-Lys-Pro-Gly-Phe | 2455 |
| Ala-Thr-Lys-Pro-His-Phe | Ala-Thr-Lys-Pro-His-Phe | Ala-Thr-Lys-Pro-His-Phe | 2456 |
| Ala-Thr-Lys-Pro-Lys-Phe | Ala-Thr-Lys-Pro-Lys-Phe | Ala-Thr-Lys-Pro-Lys-Phe | 2457 |
| Ala-Thr-Lys-Pro-Gly-Phe | Ala-Thr-Lys-Pro-Gly-Phe | Ala-Thr-Lys-Pro-Gly-Phe | 2458 |
| Ala-Thr-Lys-Pro-Gly-Arg-Phe | Ala-Thr-Lys-Pro-Gly-Arg-Phe | Ala-Thr-Lys-Pro-Gly-Arg-Phe | 2459 |
| Ala-Thr-Lys-Pro-Gly-Phe-Phe | Ala-Thr-Lys-Pro-Gly-Phe-Phe | Ala-Thr-Lys-Pro-Gly-Phe-Phe | 2460 |
| Ala-Thr-Lys-Pro-Gly-Tyr-Phe | Ala-Thr-Lys-Pro-Gly-Tyr-Phe | Ala-Thr-Lys-Pro-Gly-Tyr-Phe | 2461 |
| Ala-Thr-Lys-Pro-Gly-His-Phe | Ala-Thr-Lys-Pro-Gly-His-Phe | Ala-Thr-Lys-Pro-Gly-His-Phe | 2462 |
| Ala-Thr-Lys-Pro-Gly-Pro-Phe | Ala-Thr-Lys-Pro-Gly-Pro-Phe | Ala-Thr-Lys-Pro-Gly-Pro-Phe | 2463 |
| Ala-Thr-Lys-Pro-Gly-Lys-Phe | Ala-Thr-Lys-Pro-Gly-Lys-Phe | Ala-Thr-Lys-Pro-Gly-Lys-Phe | 2464 |
| Ala-Thr-Lys-Pro-Asp-Phe | Ala-Thr-Lys-Pro-Asp-Phe | Ala-Thr-Lys-Pro-Asp-Phe | 2465 |
| Ala-Thr-Lys-Pro-Asp-Arg-Phe | Ala-Thr-Lys-Pro-Asp-Arg-Phe | Ala-Thr-Lys-Pro-Asp-Arg-Phe | 2466 |
| Ala-Thr-Lys-Pro-Asp-Phe-Phe | Ala-Thr-Lys-Pro-Asp-Phe-Phe | Ala-Thr-Lys-Pro-Asp-Phe-Phe | 2467 |
| Ala-Thr-Lys-Pro-Asp-Tyr-Phe | Ala-Thr-Lys-Pro-Asp-Tyr-Phe | Ala-Thr-Lys-Pro-Asp-Tyr-Phe | 2468 |
| Ala-Thr-Lys-Pro-Asp-His-Phe | Ala-Thr-Lys-Pro-Asp-His-Phe | Ala-Thr-Lys-Pro-Asp-His-Phe | 2469 |
| Ala-Thr-Lys-Pro-Asp-Pro-Phe | Ala-Thr-Lys-Pro-Asp-Pro-Phe | Ala-Thr-Lys-Pro-Asp-Pro-Phe | 2470 |
| Ala-Thr-Lys-Pro-Asp-Lys-Phe | Ala-Thr-Lys-Pro-Asp-Lys-Phe | Ala-Thr-Lys-Pro-Asp-Lys-Phe | 2471 |
| Ala-Thr-Lys-Pro-Trp-Phe | Ala-Thr-Lys-Pro-Trp-Phe | Ala-Thr-Lys-Pro-Trp-Phe | 2472 |
| Ala-Thr-Lys-Pro-Trp-Arg-Phe | Ala-Thr-Lys-Pro-Trp-Arg-Phe | Ala-Thr-Lys-Pro-Trp-Arg-Phe | 2473 |
| Ala-Thr-Lys-Pro-Trp-Phe-Phe | Ala-Thr-Lys-Pro-Trp-Phe-Phe | Ala-Thr-Lys-Pro-Trp-Phe-Phe | 2474 |
| Ala-Thr-Lys-Pro-Trp-Tyr-Phe | Ala-Thr-Lys-Pro-Trp-Tyr-Phe | Ala-Thr-Lys-Pro-Trp-Tyr-Phe | 2475 |
| Ala-Thr-Lys-Pro-Trp-His-Phe | Ala-Thr-Lys-Pro-Trp-His-Phe | Ala-Thr-Lys-Pro-Trp-His-Phe | 2476 |
| Ala-Thr-Lys-Pro-Trp-Pro-Phe | Ala-Thr-Lys-Pro-Trp-Pro-Phe | Ala-Thr-Lys-Pro-Trp-Pro-Phe | 2477 |
| Ala-Thr-Lys-Pro-Trp-Lys-Phe | Ala-Thr-Lys-Pro-Trp-Lys-Phe | Ala-Thr-Lys-Pro-Trp-Lys-Phe | 2478 |
| Ala-Thr-Lys-Pro-Gln-Phe | Ala-Thr-Lys-Pro-Gln-Phe | Ala-Thr-Lys-Pro-Gln-Phe | 2479 |
| Ala-Thr-Lys-Pro-Gln-Arg-Phe | Ala-Thr-Lys-Pro-Gln-Arg-Phe | Ala-Thr-Lys-Pro-Gln-Arg-Phe | 2480 |
| Ala-Thr-Lys-Pro-Gln-Phe-Phe | Ala-Thr-Lys-Pro-Gln-Phe-Phe | Ala-Thr-Lys-Pro-Gln-Phe-Phe | 2481 |
| Ala-Thr-Lys-Pro-Gln-Tyr-Phe | Ala-Thr-Lys-Pro-Gln-Tyr-Phe | Ala-Thr-Lys-Pro-Gln-Tyr-Phe | 2482 |
| Ala-Thr-Lys-Pro-Gln-His-Phe | Ala-Thr-Lys-Pro-Gln-His-Phe | Ala-Thr-Lys-Pro-Gln-His-Phe | 2483 |
| Ala-Thr-Lys-Pro-Gln-Pro-Phe | Ala-Thr-Lys-Pro-Gln-Pro-Phe | Ala-Thr-Lys-Pro-Gln-Pro-Phe | 2484 |
| Ala-Thr-Lys-Pro-Gln-Lys-Phe | Ala-Thr-Lys-Pro-Gln-Lys-Phe | Ala-Thr-Lys-Pro-Gln-Lys-Phe | 2485 |
| Ala-Thr-Lys-Pro-Asn-Phe | Ala-Thr-Lys-Pro-Asn-Phe | Ala-Thr-Lys-Pro-Asn-Phe | 2486 |
| Ala-Thr-Lys-Pro-Asn-Arg-Phe | Ala-Thr-Lys-Pro-Asn-Arg-Phe | Ala-Thr-Lys-Pro-Asn-Arg-Phe | 2487 |

TABLE 1-continued

| X-OH | X-OCH₃ | X-NH₂ | SEQ ID NO |
|---|---|---|---|
| Ala-Thr-Lys-Pro-Asn-Phe-Phe | Ala-Thr-Lys-Pro-Asn-Phe-Phe | Ala-Thr-Lys-Pro-Asn-Phe-Phe | 2488 |
| Ala-Thr-Lys-Pro-Asn-Tyr-Phe | Ala-Thr-Lys-Pro-Asn-Tyr-Phe | Ala-Thr-Lys-Pro-Asn-Tyr-Phe | 2489 |
| Ala-Thr-Lys-Pro-Asn-His-Phe | Ala-Thr-Lys-Pro-Asn-His-Phe | Ala-Thr-Lys-Pro-Asn-His-Phe | 2490 |
| Ala-Thr-Lys-Pro-Asn-Pro-Phe | Ala-Thr-Lys-Pro-Asn-Pro-Phe | Ala-Thr-Lys-Pro-Asn-Pro-Phe | 2491 |
| Ala-Thr-Lys-Pro-Asn-Lys-Phe | Ala-Thr-Lys-Pro-Asn-Lys-Phe | Ala-Thr-Lys-Pro-Asn-Lys-Phe | 2492 |
| Ala-Thr-Lys-Pro-Tyr-Phe | Ala-Thr-Lys-Pro-Tyr-Phe | Ala-Thr-Lys-Pro-Tyr-Phe | 2493 |
| Ala-Thr-Lys-Pro-Tyr-Arg-Phe | Ala-Thr-Lys-Pro-Tyr-Arg-Phe | Ala-Thr-Lys-Pro-Tyr-Arg-Phe | 2494 |
| Ala-Thr-Lys-Pro-Tyr-Phe-Phe | Ala-Thr-Lys-Pro-Tyr-Phe-Phe | Ala-Thr-Lys-Pro-Tyr-Phe-Phe | 2495 |
| Ala-Thr-Lys-Pro-Tyr-Tyr-Phe | Ala-Thr-Lys-Pro-Tyr-Tyr-Phe | Ala-Thr-Lys-Pro-Tyr-Tyr-Phe | 2496 |
| Ala-Thr-Lys-Pro-Tyr-His-Phe | Ala-Thr-Lys-Pro-Tyr-His-Phe | Ala-Thr-Lys-Pro-Tyr-His-Phe | 2497 |
| Ala-Thr-Lys-Pro-Tyr-Pro-Phe | Ala-Thr-Lys-Pro-Tyr-Pro-Phe | Ala-Thr-Lys-Pro-Tyr-Pro-Phe | 2498 |
| Ala-Thr-Lys-Pro-Tyr-Lys-Phe | Ala-Thr-Lys-Pro-Tyr-Lys-Phe | Ala-Thr-Lys-Pro-Tyr-Lys-Phe | 2499 |
| Ala-Thr-Lys-Pro-Arg-Phe | Ala-Thr-Lys-Pro-Arg-Phe | Ala-Thr-Lys-Pro-Arg-Phe | 2500 |
| Ala-Thr-Lys-Pro-Arg-Arg-Phe | Ala-Thr-Lys-Pro-Arg-Arg-Phe | Ala-Thr-Lys-Pro-Arg-Arg-Phe | 2501 |
| Ala-Thr-Lys-Pro-Arg-Phe-Phe | Ala-Thr-Lys-Pro-Arg-Phe-Phe | Ala-Thr-Lys-Pro-Arg-Phe-Phe | 2502 |
| Ala-Thr-Lys-Pro-Arg-Tyr-Phe | Ala-Thr-Lys-Pro-Arg-Tyr-Phe | Ala-Thr-Lys-Pro-Arg-Tyr-Phe | 2503 |
| Ala-Thr-Lys-Pro-Arg-His-Phe | Ala-Thr-Lys-Pro-Arg-His-Phe | Ala-Thr-Lys-Pro-Arg-His-Phe | 2504 |
| Ala-Thr-Lys-Pro-Arg-Pro-Phe | Ala-Thr-Lys-Pro-Arg-Pro-Phe | Ala-Thr-Lys-Pro-Arg-Pro-Phe | 2505 |
| Ala-Thr-Lys-Pro-Arg-Lys-Phe | Ala-Thr-Lys-Pro-Arg-Lys-Phe | Ala-Thr-Lys-Pro-Arg-Lys-Phe | 2506 |
| His-Thr-Lys-Pro-Phe | His-Thr-Lys-Pro-Phe | His-Thr-Lys-Pro-Phe | 2507 |
| His-Thr-Lys-Pro-Arg-Phe | His-Thr-Lys-Pro-Arg-Phe | His-Thr-Lys-Pro-Arg-Phe | 2508 |
| His-Thr-Lys-Pro-Phe-Phe | His-Thr-Lys-Pro-Phe-Phe | His-Thr-Lys-Pro-Phe-Phe | 2509 |
| His-Thr-Lys-Pro-Tyr-Phe | His-Thr-Lys-Pro-Tyr-Phe | His-Thr-Lys-Pro-Tyr-Phe | 2510 |
| His-Thr-Lys-Pro-Gly-Phe | His-Thr-Lys-Pro-Gly-Phe | His-Thr-Lys-Pro-Gly-Phe | 2511 |
| His-Thr-Lys-Pro-His-Phe | His-Thr-Lys-Pro-His-Phe | His-Thr-Lys-Pro-His-Phe | 2512 |
| His-Thr-Lys-Pro-Lys-Phe | His-Thr-Lys-Pro-Lys-Phe | His-Thr-Lys-Pro-Lys-Phe | 2513 |
| His-Thr-Lys-Pro-Gly-Phe | His-Thr-Lys-Pro-Gly-Phe | His-Thr-Lys-Pro-Gly-Phe | 2514 |
| His-Thr-Lys-Pro-Gly-Arg-Phe | His-Thr-Lys-Pro-Gly-Arg-Phe | His-Thr-Lys-Pro-Gly-Arg-Phe | 2515 |
| His-Thr-Lys-Pro-Gly-Phe-Phe | His-Thr-Lys-Pro-Gly-Phe-Phe | His-Thr-Lys-Pro-Gly-Phe-Phe | 2516 |
| His-Thr-Lys-Pro-Gly-Tyr-Phe | His-Thr-Lys-Pro-Gly-Tyr-Phe | His-Thr-Lys-Pro-Gly-Tyr-Phe | 2517 |
| His-Thr-Lys-Pro-Gly-His-Phe | His-Thr-Lys-Pro-Gly-His-Phe | His-Thr-Lys-Pro-Gly-His-Phe | 2518 |
| His-Thr-Lys-Pro-Gly-Pro-Phe | His-Thr-Lys-Pro-Gly-Pro-Phe | His-Thr-Lys-Pro-Gly-Pro-Phe | 2519 |
| His-Thr-Lys-Pro-Gly-Lys-Phe | His-Thr-Lys-Pro-Gly-Lys-Phe | His-Thr-Lys-Pro-Gly-Lys-Phe | 2520 |
| His-Thr-Lys-Pro-Asp-Phe | His-Thr-Lys-Pro-Asp-Phe | His-Thr-Lys-Pro-Asp-Phe | 2521 |
| His-Thr-Lys-Pro-Asp-Arg-Phe | His-Thr-Lys-Pro-Asp-Arg-Phe | His-Thr-Lys-Pro-Asp-Arg-Phe | 2522 |
| His-Thr-Lys-Pro-Asp-Phe-Phe | His-Thr-Lys-Pro-Asp-Phe-Phe | His-Thr-Lys-Pro-Asp-Phe-Phe | 2523 |
| His-Thr-Lys-Pro-Asp-Tyr-Phe | His-Thr-Lys-Pro-Asp-Tyr-Phe | His-Thr-Lys-Pro-Asp-Tyr-Phe | 2524 |
| His-Thr-Lys-Pro-Asp-His-Phe | His-Thr-Lys-Pro-Asp-His-Phe | His-Thr-Lys-Pro-Asp-His-Phe | 2525 |

TABLE 1-continued

| X-OH | X-OCH₃ | X-NH₂ | SEQ ID NO |
|---|---|---|---|
| His-Thr-Lys-Pro-Asp-Pro-Phe | His-Thr-Lys-Pro-Asp-Pro-Phe | His-Thr-Lys-Pro-Asp-Pro-Phe | 2526 |
| His-Thr-Lys-Pro-Asp-Lys-Phe | His-Thr-Lys-Pro-Asp-Lys-Phe | His-Thr-Lys-Pro-Asp-Lys-Phe | 2527 |
| His-Thr-Lys-Pro-Trp-Phe | His-Thr-Lys-Pro-Trp-Phe | His-Thr-Lys-Pro-Trp-Phe | 2528 |
| His-Thr-Lys-Pro-Trp-Arg-Ph | eHis-Thr-Lys-Pro-Trp-Arg-Phe | His-Thr-Lys-Pro-Trp-Arg-Phe | 2529 |
| His-Thr-Lys-Pro-Trp-Phe-Phe | His-Thr-Lys-Pro-Trp-Phe-Phe | His-Thr-Lys-Pro-Trp-Phe-Phe | 2530 |
| His-Thr-Lys-Pro-Trp-Tyr-Phe | His-Thr-Lys-Pro-Trp-Tyr-Phe | His-Thr-Lys-Pro-Trp-Tyr-Phe | 2531 |
| His-Thr-Lys-Pro-Trp-His-Phe | His-Thr-Lys-Pro-Trp-His-Phe | His-Thr-Lys-Pro-Trp-His-Phe | 2532 |
| His-Thr-Lys-Pro-Trp-Pro-Phe | His-Thr-Lys-Pro-Trp-Pro-Phe | His-Thr-Lys-Pro-Trp-Pro-Phe | 2533 |
| His-Thr-Lys-Pro-Trp-Lys-Phe | His-Thr-Lys-Pro-Trp-Lys-Phe | His-Thr-Lys-Pro-Trp-Lys-Phe | 2534 |
| His-Thr-Lys-Pro-Gln-Phe | His-Thr-Lys-Pro-Gln-Phe | His-Thr-Lys-Pro-Gln-Phe | 2535 |
| His-Thr-Lys-Pro-Gln-Arg-Phe | His-Thr-Lys-Pro-Gln-Arg-Phe | His-Thr-Lys-Pro-Gln-Arg-Phe | 2536 |
| His-Thr-Lys-Pro-Gln-Phe-Phe | His-Thr-Lys-Pro-Gln-Phe-Phe | His-Thr-Lys-Pro-Gln-Phe-Phe | 2537 |
| His-Thr-Lys-Pro-Gln-Tyr-Phe | His-Thr-Lys-Pro-Gln-Tyr-Phe | His-Thr-Lys-Pro-Gln-Tyr-Phe | 2538 |
| His-Thr-Lys-Pro-Gln-His-Phe | His-Thr-Lys-Pro-Gln-His-Phe | His-Thr-Lys-Pro-Gln-His-Phe | 2539 |
| His-Thr-Lys-Pro-Gln-Pro-Phe | His-Thr-Lys-Pro-Gln-Pro-Phe | His-Thr-Lys-Pro-Gln-Pro-Phe | 2540 |
| His-Thr-Lys-Pro-Gln-Lys-Phe | His-Thr-Lys-Pro-Gln-Lys-Phe | His-Thr-Lys-Pro-Gln-Lys-Phe | 2541 |
| His-Thr-Lys-Pro-Asn-Phe | His-Thr-Lys-Pro-Asn-Phe | His-Thr-Lys-Pro-Asn-Phe | 2542 |
| His-Thr-Lys-Pro-Asn-Arg-Phe | His-Thr-Lys-Pro-Asn-Arg-Phe | His-Thr-Lys-Pro-Asn-Arg-Phe | 2543 |
| His-Thr-Lys-Pro-Asn-Phe-Phe | His-Thr-Lys-Pro-Asn-Phe-Phe | His-Thr-Lys-Pro-Asn-Phe-Phe | 2544 |
| His-Thr-Lys-Pro-Asn-Tyr-Phe | His-Thr-Lys-Pro-Asn-Tyr-Phe | His-Thr-Lys-Pro-Asn-Tyr-Phe | 2545 |
| His-Thr-Lys-Pro-Asn-His-Phe | His-Thr-Lys-Pro-Asn-His-Phe | His-Thr-Lys-Pro-Asn-His-Phe | 2546 |
| His-Thr-Lys-Pro-Asn-Pro-Phe | His-Thr-Lys-Pro-Asn-Pro-Phe | His-Thr-Lys-Pro-Asn-Pro-Phe | 2547 |
| His-Thr-Lys-Pro-Asn-Lys-Phe | His-Thr-Lys-Pro-Asn-Lys-Phe | His-Thr-Lys-Pro-Asn-Lys-Phe | 2548 |
| His-Thr-Lys-Pro-Tyr-Phe | His-Thr-Lys-Pro-Tyr-Phe | His-Thr-Lys-Pro-Tyr-Phe | 2549 |
| His-Thr-Lys-Pro-Tyr-Arg-Phe | His-Thr-Lys-Pro-Tyr-Arg-Phe | His-Thr-Lys-Pro-Tyr-Arg-Phe | 2550 |
| His-Thr-Lys-Pro-Tyr-Phe-Phe | His-Thr-Lys-Pro-Tyr-Phe-Phe | His-Thr-Lys-Pro-Tyr-Phe-Phe | 2551 |
| His-Thr-Lys-Pro-Tyr-Tyr-Phe | His-Thr-Lys-Pro-Tyr-Tyr-Phe | His-Thr-Lys-Pro-Tyr-Tyr-Phe | 2552 |
| His-Thr-Lys-Pro-Tyr-His-Phe | His-Thr-Lys-Pro-Tyr-His-Phe | His-Thr-Lys-Pro-Tyr-His-Phe | 2553 |
| His-Thr-Lys-Pro-Tyr-Pro-Phe | His-Thr-Lys-Pro-Tyr-Pro-Phe | His-Thr-Lys-Pro-Tyr-Pro-Phe | 2554 |
| His-Thr-Lys-Pro-Tyr-Lys-Phe | His-Thr-Lys-Pro-Tyr-Lys-Phe | His-Thr-Lys-Pro-Tyr-Lys-Phe | 2555 |
| His-Thr-Lys-Pro-Arg-Phe | His-Thr-Lys-Pro-Arg-Phe | His-Thr-Lys-Pro-Arg-Phe | 2556 |
| His-Thr-Lys-Pro-Arg-Arg-Phe | His-Thr-Lys-Pro-Arg-Arg-Phe | His-Thr-Lys-Pro-Arg-Arg-Phe | 2557 |
| His-Thr-Lys-Pro-Arg-Phe-Phe | His-Thr-Lys-Pro-Arg-Phe-Phe | His-Thr-Lys-Pro-Arg-Phe-Phe | 2558 |
| His-Thr-Lys-Pro-Arg-Tyr-Phe | His-Thr-Lys-Pro-Arg-Tyr-Phe | His-Thr-Lys-Pro-Arg-Tyr-Phe | 2559 |
| His-Thr-Lys-Pro-Arg-His-Phe | His-Thr-Lys-Pro-Arg-His-Phe | His-Thr-Lys-Pro-Arg-His-Phe | 2560 |
| His-Thr-Lys-Pro-Arg-Pro-Phe | His-Thr-Lys-Pro-Arg-Pro-Phe | His-Thr-Lys-Pro-Arg-Pro-Phe | 2561 |
| His-Thr-Lys-Pro-Arg-Lys-Phe | His-Thr-Lys-Pro-Arg-Lys-Phe | His-Thr-Lys-Pro-Arg-Lys-Phe | 2562 |
| Lys-Thr-Lys-Pro-Phe | Lys-Thr-Lys-Pro-Phe | Lys-Thr-Lys-Pro-Phe | 2563 |

TABLE 1-continued

| X-OH | X-OCH₃ | X-NH₂ | SEQ ID NO |
|---|---|---|---|
| Lys-Thr-Lys-Pro-Arg-Phe | Lys-Thr-Lys-Pro-Arg-Phe | Lys-Thr-Lys-Pro-Arg-Phe | 2564 |
| Lys-Thr-Lys-Pro-Phe-Phe | Lys-Thr-Lys-Pro-Phe-Phe | Lys-Thr-Lys-Pro-Phe-Phe | 2565 |
| Lys-Thr-Lys-Pro-Tyr-Phe | Lys-Thr-Lys-Pro-Tyr-Phe | Lys-Thr-Lys-Pro-Tyr-Phe | 2566 |
| Lys-Thr-Lys-Pro-Gly-Phe | Lys-Thr-Lys-Pro-Gly-Phe | Lys-Thr-Lys-Pro-Gly-Phe | 2567 |
| Lys-Thr-Lys-Pro-His-Phe | Lys-Thr-Lys-Pro-His-Phe | Lys-Thr-Lys-Pro-His-Phe | 2568 |
| Lys-Thr-Lys-Pro-Lys-Phe | Lys-Thr-Lys-Pro-Lys-Phe | Lys-Thr-Lys-Pro-Lys-Phe | 2569 |
| Lys-Thr-Lys-Pro-Gly-Phe | Lys-Thr-Lys-Pro-Gly-Phe | Lys-Thr-Lys-Pro-Gly-Phe | 2570 |
| Lys-Thr-Lys-Pro-Gly-Arg-Phe | Lys-Thr-Lys-Pro-Gly-Arg-Phe | Lys-Thr-Lys-Pro-Gly-Arg-Phe | 2571 |
| Lys-Thr-Lys-Pro-Gly-Phe-Phe | Lys-Thr-Lys-Pro-Gly-Phe-Phe | Lys-Thr-Lys-Pro-Gly-Phe-Phe | 2572 |
| Lys-Thr-Lys-Pro-Gly-Tyr-Phe | Lys-Thr-Lys-Pro-Gly-Tyr-Phe | Lys-Thr-Lys-Pro-Gly-Tyr-Phe | 2573 |
| Lys-Thr-Lys-Pro-Gly-His-Phe | Lys-Thr-Lys-Pro-Gly-His-Phe | Lys-Thr-Lys-Pro-Gly-His-Phe | 2574 |
| Lys-Thr-Lys-Pro-Gly-Pro-Phe | Lys-Thr-Lys-Pro-Gly-Pro-Phe | Lys-Thr-Lys-Pro-Gly-Pro-Phe | 2575 |
| Lys-Thr-Lys-Pro-Gly-Lys-Phe | Lys-Thr-Lys-Pro-Gly-Lys-Phe | Lys-Thr-Lys-Pro-Gly-Lys-Phe | 2576 |
| Lys-Thr-Lys-Pro-Asp-Phe | Lys-Thr-Lys-Pro-Asp-Phe | Lys-Thr-Lys-Pro-Asp-Phe | 2577 |
| Lys-Thr-Lys-Pro-Asp-Arg-Phe | Lys-Thr-Lys-Pro-Asp-Arg-Phe | Lys-Thr-Lys-Pro-Asp-Arg-Phe | 2578 |
| Lys-Thr-Lys-Pro-Asp-Phe-Phe | Lys-Thr-Lys-Pro-Asp-Phe-Phe | Lys-Thr-Lys-Pro-Asp-Phe-Phe | 2579 |
| Lys-Thr-Lys-Pro-Asp-Tyr-Phe | Lys-Thr-Lys-Pro-Asp-Tyr-Phe | Lys-Thr-Lys-Pro-Asp-Tyr-Phe | 2580 |
| Lys-Thr-Lys-Pro-Asp-His-Phe | Lys-Thr-Lys-Pro-Asp-His-Phe | Lys-Thr-Lys-Pro-Asp-His-Phe | 2581 |
| Lys-Thr-Lys-Pro-Asp-Pro-Phe | Lys-Thr-Lys-Pro-Asp-Pro-Phe | Lys-Thr-Lys-Pro-Asp-Pro-Phe | 2582 |
| Lys-Thr-Lys-Pro-Asp-Lys-Phe | Lys-Thr-Lys-Pro-Asp-Lys-Phe | Lys-Thr-Lys-Pro-Asp-Lys-Phe | 2583 |
| Lys-Thr-Lys-Pro-Trp-Phe | Lys-Thr-Lys-Pro-Trp-Phe | Lys-Thr-Lys-Pro-Trp-Phe | 2584 |
| Lys-Thr-Lys-Pro-Trp-Arg-Phe | Lys-Thr-Lys-Pro-Trp-Arg-Phe | Lys-Thr-Lys-Pro-Trp-Arg-Phe | 2585 |
| Lys-Thr-Lys-Pro-Trp-Phe-Phe | Lys-Thr-Lys-Pro-Trp-Phe-Phe | Lys-Thr-Lys-Pro-Trp-Phe-Phe | 2586 |
| Lys-Thr-Lys-Pro-Trp-Tyr-Phe | Lys-Thr-Lys-Pro-Trp-Tyr-Phe | Lys-Thr-Lys-Pro-Trp-Tyr-Phe | 2587 |
| Lys-Thr-Lys-Pro-Trp-His-Phe | Lys-Thr-Lys-Pro-Trp-His-Phe | Lys-Thr-Lys-Pro-Trp-His-Phe | 2588 |
| Lys-Thr-Lys-Pro-Trp-Pro-Phe | Lys-Thr-Lys-Pro-Trp-Pro-Phe | Lys-Thr-Lys-Pro-Trp-Pro-Phe | 2589 |
| Lys-Thr-Lys-Pro-Trp-Lys-Phe | Lys-Thr-Lys-Pro-Trp-Lys-Phe | Lys-Thr-Lys-Pro-Trp-Lys-Phe | 2590 |
| Lys-Thr-Lys-Pro-Gln-Phe | Lys-Thr-Lys-Pro-Gln-Phe | Lys-Thr-Lys-Pro-Gln-Phe | 2591 |
| Lys-Thr-Lys-Pro-Gln-Arg-Phe | Lys-Thr-Lys-Pro-Gln-Arg-Phe | Lys-Thr-Lys-Pro-Gln-Arg-Phe | 2592 |
| Lys-Thr-Lys-Pro-Gln-Phe-Phe | Lys-Thr-Lys-Pro-Gln-Phe-Phe | Lys-Thr-Lys-Pro-Gln-Phe-Phe | 2593 |
| Lys-Thr-Lys-Pro-Gln-Tyr-Phe | Lys-Thr-Lys-Pro-Gln-Tyr-Phe | Lys-Thr-Lys-Pro-Gln-Tyr-Phe | 2594 |
| Lys-Thr-Lys-Pro-Gln-His-Phe | Lys-Thr-Lys-Pro-Gln-His-Phe | Lys-Thr-Lys-Pro-Gln-His-Phe | 2595 |
| Lys-Thr-Lys-Pro-Gln-Pro-Phe | Lys-Thr-Lys-Pro-Gln-Pro-Phe | Lys-Thr-Lys-Pro-Gln-Pro-Phe | 2596 |
| Lys-Thr-Lys-Pro-Gln-Lys-Phe | Lys-Thr-Lys-Pro-Gln-Lys-Phe | Lys-Thr-Lys-Pro-Gln-Lys-Phe | 2597 |
| Lys-Thr-Lys-Pro-Asn-Phe | Lys-Thr-Lys-Pro-Asn-Phe | Lys-Thr-Lys-Pro-Asn-Phe | 2598 |
| Lys-Thr-Lys-Pro-Asn-Arg-Phe | Lys-Thr-Lys-Pro-Asn-Arg-Phe | Lys-Thr-Lys-Pro-Asn-Arg-Phe | 2599 |
| Lys-Thr-Lys-Pro-Asn-Phe-Phe | Lys-Thr-Lys-Pro-Asn-Phe-Phe | Lys-Thr-Lys-Pro-Asn-Phe-Phe | 2600 |
| Lys-Thr-Lys-Pro-Asn-Tyr-Phe | Lys-Thr-Lys-Pro-Asn-Tyr-Phe | Lys-Thr-Lys-Pro-Asn-Tyr-Phe | 2601 |

TABLE 1-continued

| X-OH | X-OCH₃ | X-NH₂ | SEQ ID NO |
|---|---|---|---|
| Lys-Thr-Lys-Pro-Asn-His-Phe | Lys-Thr-Lys-Pro-Asn-His-Phe | Lys-Thr-Lys-Pro-Asn-His-Phe | 2602 |
| Lys-Thr-Lys-Pro-Asn-Pro-Phe | Lys-Thr-Lys-Pro-Asn-Pro-Phe | Lys-Thr-Lys-Pro-Asn-Pro-Phe | 2603 |
| Lys-Thr-Lys-Pro-Asn-Lys-Phe | Lys-Thr-Lys-Pro-Asn-Lys-Phe | Lys-Thr-Lys-Pro-Asn-Lys-Phe | 2604 |
| Lys-Thr-Lys-Pro-Tyr-Phe | Lys-Thr-Lys-Pro-Tyr-Phe | Lys-Thr-Lys-Pro-Tyr-Phe | 2605 |
| Lys-Thr-Lys-Pro-Tyr-Arg-Phe | Lys-Thr-Lys-Pro-Tyr-Arg-Phe | Lys-Thr-Lys-Pro-Tyr-Arg-Phe | 2606 |
| Lys-Thr-Lys-Pro-Tyr-Phe-Phe | Lys-Thr-Lys-Pro-Tyr-Phe-Phe | Lys-Thr-Lys-Pro-Tyr-Phe-Phe | 2607 |
| Lys-Thr-Lys-Pro-Tyr-Tyr-Phe | Lys-Thr-Lys-Pro-Tyr-Tyr-Phe | Lys-Thr-Lys-Pro-Tyr-Tyr-Phe | 2608 |
| Lys-Thr-Lys-Pro-Tyr-His-Phe | Lys-Thr-Lys-Pro-Tyr-His-Phe | Lys-Thr-Lys-Pro-Tyr-His-Phe | 2609 |
| Lys-Thr-Lys-Pro-Tyr-Pro-Phe | Lys-Thr-Lys-Pro-Tyr-Pro-Phe | Lys-Thr-Lys-Pro-Tyr-Pro-Phe | 2610 |
| Lys-Thr-Lys-Pro-Tyr-Lys-Phe | Lys-Thr-Lys-Pro-Tyr-Lys-Phe | Lys-Thr-Lys-Pro-Tyr-Lys-Phe | 2611 |
| Lys-Thr-Lys-Pro-Arg-Phe | Lys-Thr-Lys-Pro-Arg-Phe | Lys-Thr-Lys-Pro-Arg-Phe | 2612 |
| Lys-Thr-Lys-Pro-Arg-Arg-Phe | Lys-Thr-Lys-Pro-Arg-Arg-Phe | Lys-Thr-Lys-Pro-Arg-Arg-Phe | 2613 |
| Lys-Thr-Lys-Pro-Arg-Phe-Phe | Lys-Thr-Lys-Pro-Arg-Phe-Phe | Lys-Thr-Lys-Pro-Arg-Phe-Phe | 2614 |
| Lys-Thr-Lys-Pro-Arg-Tyr-Phe | Lys-Thr-Lys-Pro-Arg-Tyr-Phe | Lys-Thr-Lys-Pro-Arg-Tyr-Phe | 2615 |
| Lys-Thr-Lys-Pro-Arg-His-Phe | Lys-Thr-Lys-Pro-Arg-His-Phe | Lys-Thr-Lys-Pro-Arg-His-Phe | 2616 |
| Lys-Thr-Lys-Pro-Arg-Pro-Phe | Lys-Thr-Lys-Pro-Arg-Pro-Phe | Lys-Thr-Lys-Pro-Arg-Pro-Phe | 2617 |
| Lys-Thr-Lys-Pro-Arg-Lys-Phe | Lys-Thr-Lys-Pro-Arg-Lys-Phe | Lys-Thr-Lys-Pro-Arg-Lys-Phe | 2618 |
| Gly-Thr-Lys-Pro-Phe | Gly-Thr-Lys-Pro-Phe | Gly-Thr-Lys-Pro-Phe | 2619 |
| Gly-Thr-Lys-Pro-Arg-Phe | Gly-Thr-Lys-Pro-Arg-Phe | Gly-Thr-Lys-Pro-Arg-Phe | 2620 |
| Gly-Thr-Lys-Pro-Phe-Phe | Gly-Thr-Lys-Pro-Phe-Phe | Gly-Thr-Lys-Pro-Phe-Phe | 2621 |
| Gly-Thr-Lys-Pro-Tyr-Phe | Gly-Thr-Lys-Pro-Tyr-Phe | Gly-Thr-Lys-Pro-Tyr-Phe | 2622 |
| Gly-Thr-Lys-Pro-Gly-Phe | Gly-Thr-Lys-Pro-Gly-Phe | Gly-Thr-Lys-Pro-Gly-Phe | 2623 |
| Gly-Thr-Lys-Pro-His-Phe | Gly-Thr-Lys-Pro-His-Phe | Gly-Thr-Lys-Pro-His-Phe | 2624 |
| Gly-Thr-Lys-Pro-Lys-Phe | Gly-Thr-Lys-Pro-Lys-Phe | Gly-Thr-Lys-Pro-Lys-Phe | 2625 |
| Gly-Thr-Lys-Pro-Gly-Phe | Gly-Thr-Lys-Pro-Gly-Phe | Gly-Thr-Lys-Pro-Gly-Phe | 2626 |
| Gly-Thr-Lys-Pro-Gly-Arg-Phe | Gly-Thr-Lys-Pro-Gly-Arg-Phe | Gly-Thr-Lys-Pro-Gly-Arg-Phe | 2627 |
| Gly-Thr-Lys-Pro-Gly-Phe-Phe | Gly-Thr-Lys-Pro-Gly-Phe-Phe | Gly-Thr-Lys-Pro-Gly-Phe-Phe | 2628 |
| Gly-Thr-Lys-Pro-Gly-Tyr-Phe | Gly-Thr-Lys-Pro-Gly-Tyr-Phe | Gly-Thr-Lys-Pro-Gly-Tyr-Phe | 2629 |
| Gly-Thr-Lys-Pro-Gly-His-Phe | Gly-Thr-Lys-Pro-Gly-His-Phe | Gly-Thr-Lys-Pro-Gly-His-Phe | 2630 |
| Gly-Thr-Lys-Pro-Gly-Pro-Phe | Gly-Thr-Lys-Pro-Gly-Pro-Phe | Gly-Thr-Lys-Pro-Gly-Pro-Phe | 2631 |
| Gly-Thr-Lys-Pro-Gly-Lys-Phe | Gly-Thr-Lys-Pro-Gly-Lys-Phe | Gly-Thr-Lys-Pro-Gly-Lys-Phe | 2632 |
| Gly-Thr-Lys-Pro-Asp-Phe | Gly-Thr-Lys-Pro-Asp-Phe | Gly-Thr-Lys-Pro-Asp-Phe | 2633 |
| Gly-Thr-Lys-Pro-Asp-Arg-Phe | Gly-Thr-Lys-Pro-Asp-Arg-Phe | Gly-Thr-Lys-Pro-Asp-Arg-Phe | 2634 |
| Gly-Thr-Lys-Pro-Asp-Phe-Phe | Gly-Thr-Lys-Pro-Asp-Phe-Phe | Gly-Thr-Lys-Pro-Asp-Phe-Phe | 2635 |
| Gly-Thr-Lys-Pro-Asp-Tyr-Phe | Gly-Thr-Lys-Pro-Asp-Tyr-Phe | Gly-Thr-Lys-Pro-Asp-Tyr-Phe | 2636 |
| Gly-Thr-Lys-Pro-Asp-His-Phe | Gly-Thr-Lys-Pro-Asp-His-Phe | Gly-Thr-Lys-Pro-Asp-His-Phe | 2637 |

TABLE 1-continued

| X-OH | X-OCH₃ | X-NH₂ | SEQ ID NO |
|---|---|---|---|
| Gly-Thr-Lys-Pro-Asp-Pro-Phe | Gly-Thr-Lys-Pro-Asp-Pro-Phe | Gly-Thr-Lys-Pro-Asp-Pro-Phe | 2638 |
| Gly-Thr-Lys-Pro-Asp-Lys-Phe | Gly-Thr-Lys-Pro-Asp-Lys-Phe | Gly-Thr-Lys-Pro-Asp-Lys-Phe | 2639 |
| Gly-Thr-Lys-Pro-Trp-Phe | Gly-Thr-Lys-Pro-Trp-Phe | Gly-Thr-Lys-Pro-Trp-Phe | 2640 |
| Gly-Thr-Lys-Pro-Trp-Arg-Phe | Gly-Thr-Lys-Pro-Trp-Arg-Phe | Gly-Thr-Lys-Pro-Trp-Arg-Phe | 2641 |
| Gly-Thr-Lys-Pro-Trp-Phe-Phe | Gly-Thr-Lys-Pro-Trp-Phe-Phe | Gly-Thr-Lys-Pro-Trp-Phe-Phe | 2642 |
| Gly-Thr-Lys-Pro-Trp-Tyr-Phe | Gly-Thr-Lys-Pro-Trp-Tyr-Phe | Gly-Thr-Lys-Pro-Trp-Tyr-Phe | 2643 |
| Gly-Thr-Lys-Pro-Trp-His-Phe | Gly-Thr-Lys-Pro-Trp-His-Phe | Gly-Thr-Lys-Pro-Trp-His-Phe | 2644 |
| Gly-Thr-Lys-Pro-Trp-Pro-Phe | Gly-Thr-Lys-Pro-Trp-Pro-Phe | Gly-Thr-Lys-Pro-Trp-Pro-Phe | 2645 |
| Gly-Thr-Lys-Pro-Trp-Lys-Phe | Gly-Thr-Lys-Pro-Trp-Lys-Phe | Gly-Thr-Lys-Pro-Trp-Lys-Phe | 2646 |
| Gly-Thr-Lys-Pro-Gln-Phe | Gly-Thr-Lys-Pro-Gln-Phe | Gly-Thr-Lys-Pro-Gln-Phe | 2647 |
| Gly-Thr-Lys-Pro-Gln-Arg-Phe | Gly-Thr-Lys-Pro-Gln-Arg-Phe | Gly-Thr-Lys-Pro-Gln-Arg-Phe | 2648 |
| Gly-Thr-Lys-Pro-Gln-Phe-Phe | Gly-Thr-Lys-Pro-Gln-Phe-Phe | Gly-Thr-Lys-Pro-Gln-Phe-Phe | 2649 |
| Gly-Thr-Lys-Pro-Gln-Tyr-Phe | Gly-Thr-Lys-Pro-Gln-Tyr-Phe | Gly-Thr-Lys-Pro-Gln-Tyr-Phe | 2650 |
| Gly-Thr-Lys-Pro-Gln-His-Phe | Gly-Thr-Lys-Pro-Gln-His-Phe | Gly-Thr-Lys-Pro-Gln-His-Phe | 2651 |
| Gly-Thr-Lys-Pro-Gln-Pro-Phe | Gly-Thr-Lys-Pro-Gln-Pro-Phe | Gly-Thr-Lys-Pro-Gln-Pro-Phe | 2652 |
| Gly-Thr-Lys-Pro-Gln-Lys-Phe | Gly-Thr-Lys-Pro-Gln-Lys-Phe | Gly-Thr-Lys-Pro-Gln-Lys-Phe | 2653 |
| Gly-Thr-Lys-Pro-Asn-Phe | Gly-Thr-Lys-Pro-Asn-Phe | Gly-Thr-Lys-Pro-Asn-Phe | 2654 |
| Gly-Thr-Lys-Pro-Asn-Arg-Phe | Gly-Thr-Lys-Pro-Asn-Arg-Phe | Gly-Thr-Lys-Pro-Asn-Arg-Phe | 2655 |
| Gly-Thr-Lys-Pro-Asn-Phe-Phe | Gly-Thr-Lys-Pro-Asn-Phe-Phe | Gly-Thr-Lys-Pro-Asn-Phe-Phe | 2656 |
| Gly-Thr-Lys-Pro-Asn-Tyr-Phe | Gly-Thr-Lys-Pro-Asn-Tyr-Phe | Gly-Thr-Lys-Pro-Asn-Tyr-Phe | 2657 |
| Gly-Thr-Lys-Pro-Asn-His-Phe | Gly-Thr-Lys-Pro-Asn-His-Phe | Gly-Thr-Lys-Pro-Asn-His-Phe | 2658 |
| Gly-Thr-Lys-Pro-Asn-Pro-Phe | Gly-Thr-Lys-Pro-Asn-Pro-Phe | Gly-Thr-Lys-Pro-Asn-Pro-Phe | 2659 |
| Gly-Thr-Lys-Pro-Asn-Lys-Phe | Gly-Thr-Lys-Pro-Asn-Lys-Phe | Gly-Thr-Lys-Pro-Asn-Lys-Phe | 2660 |
| Gly-Thr-Lys-Pro-Tyr-Phe | Gly-Thr-Lys-Pro-Tyr-Phe | Gly-Thr-Lys-Pro-Tyr-Phe | 2661 |
| Gly-Thr-Lys-Pro-Tyr-Arg-Phe | Gly-Thr-Lys-Pro-Tyr-Arg-Phe | Gly-Thr-Lys-Pro-Tyr-Arg-Phe | 2662 |
| Gly-Thr-Lys-Pro-Tyr-Phe-Phe | Gly-Thr-Lys-Pro-Tyr-Phe-Phe | Gly-Thr-Lys-Pro-Tyr-Phe-Phe | 2663 |
| Gly-Thr-Lys-Pro-Tyr-Tyr-Phe | Gly-Thr-Lys-Pro-Tyr-Tyr-Phe | Gly-Thr-Lys-Pro-Tyr-Tyr-Phe | 2664 |
| Gly-Thr-Lys-Pro-Tyr-His-Phe | Gly-Thr-Lys-Pro-Tyr-His-Phe | Gly-Thr-Lys-Pro-Tyr-His-Phe | 2665 |
| Gly-Thr-Lys-Pro-Tyr-Pro-Phe | Gly-Thr-Lys-Pro-Tyr-Pro-Phe | Gly-Thr-Lys-Pro-Tyr-Pro-Phe | 2666 |
| Gly-Thr-Lys-Pro-Tyr-Lys-Phe | Gly-Thr-Lys-Pro-Tyr-Lys-Phe | Gly-Thr-Lys-Pro-Tyr-Lys-Phe | 2667 |
| Gly-Thr-Lys-Pro-Arg-Phe | Gly-Thr-Lys-Pro-Arg-Phe | Gly-Thr-Lys-Pro-Arg-Phe | 2668 |
| Gly-Thr-Lys-Pro-Arg-Arg-Phe | Gly-Thr-Lys-Pro-Arg-Arg-Phe | Gly-Thr-Lys-Pro-Arg-Arg-Phe | 2669 |
| Gly-Thr-Lys-Pro-Arg-Phe-Phe | Gly-Thr-Lys-Pro-Arg-Phe-Phe | Gly-Thr-Lys-Pro-Arg-Phe-Phe | 2670 |
| Gly-Thr-Lys-Pro-Arg-Tyr-Phe | Gly-Thr-Lys-Pro-Arg-Tyr-Phe | Gly-Thr-Lys-Pro-Arg-Tyr-Phe | 2671 |
| Gly-Thr-Lys-Pro-Arg-His-Phe | Gly-Thr-Lys-Pro-Arg-His-Phe | Gly-Thr-Lys-Pro-Arg-His-Phe | 2672 |
| Gly-Thr-Lys-Pro-Arg-Pro-Phe | Gly-Thr-Lys-Pro-Arg-Pro-Phe | Gly-Thr-Lys-Pro-Arg-Pro-Phe | 2673 |
| Gly-Thr-Lys-Pro-Arg-Lys-Phe | Gly-Thr-Lys-Pro-Arg-Lys-Phe | Gly-Thr-Lys-Pro-Arg-Lys-Phe | 2674 |

BRIEF DESCRIPTION OF THE DRAWINGS

FIG. 1 shows a diagram of Arg-Pro-Gly-Pro (SEQ ID NO: 2676) tetrapeptide synthesis;

FIG. 2 shows a diagram of Pro-Arg-Pro-Gly-Pro (SEQ ID NO: 2675) pentapeptide synthesis;

FIG. 3 shows a diagram of Pro-Gly-Pro (SEQ ID NO: 2677) tripeptide synthesis;

BEST EXAMPLE OF THE INVENTION

Figure 4:
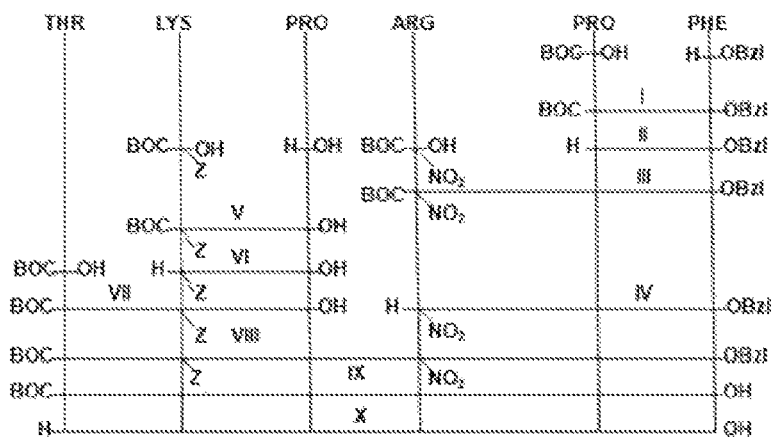
FIG. 4 shows a diagram of Thr-Lys-Pro-Arg-Pro-Phe (SEQ ID NO: 7) hexapeptide synthesis.

The following are the examples illustrating the invention.

Synthesis of peptides with the general formula A-Thr-Lys-Pro-B-C-D-X was performed by methods of peptide chemistry in solution using L-amino acids. Peptide synthesis was carried out by stepwise elongation of the peptide chain, as well as fragment condensation using mixed anhydride method, carbodiimide method with the addition of 1-hydroxybenzotriazole as an auxiliary nucleophile, activated ester method, and mixed anhydride method. All intermediate and final products were isolated and characterized. Evaporation of solutions was conducted using vacuum evaporator at 40° C. Melting points, determined with Boethius apparatus, are given without correction. Identity of the obtained compounds was tested by TLC on Silufol silica gel-coated plates (Czech Republic). Substances were detected by UV light using ninhydrin, Barton's reagent, Pauly reagent, Reindel-Hoppe reagent, and o-tolidine in chlorine environment. Specific rotation was determined by AI-EPO polarimeter. Peptide homogeneity was tested by high performance liquid chromatography (HPLC), and peptide structure was confirmed by mass spectrometric methods. All solvents were correspondingly absolutized. Melting points were not corrected.

Peptides were also obtained by genetic engineering techniques using host cells engineered by known laboratory strains of E. coli, transformed with known commercially available plasmids containing nucleic acid encoding the target peptide.

The examples describe peptide synthesis.

Example 1

Synthesis of Arg-Pro-Gly-Pro Tetrapeptide

Figures 1, 2, 3:
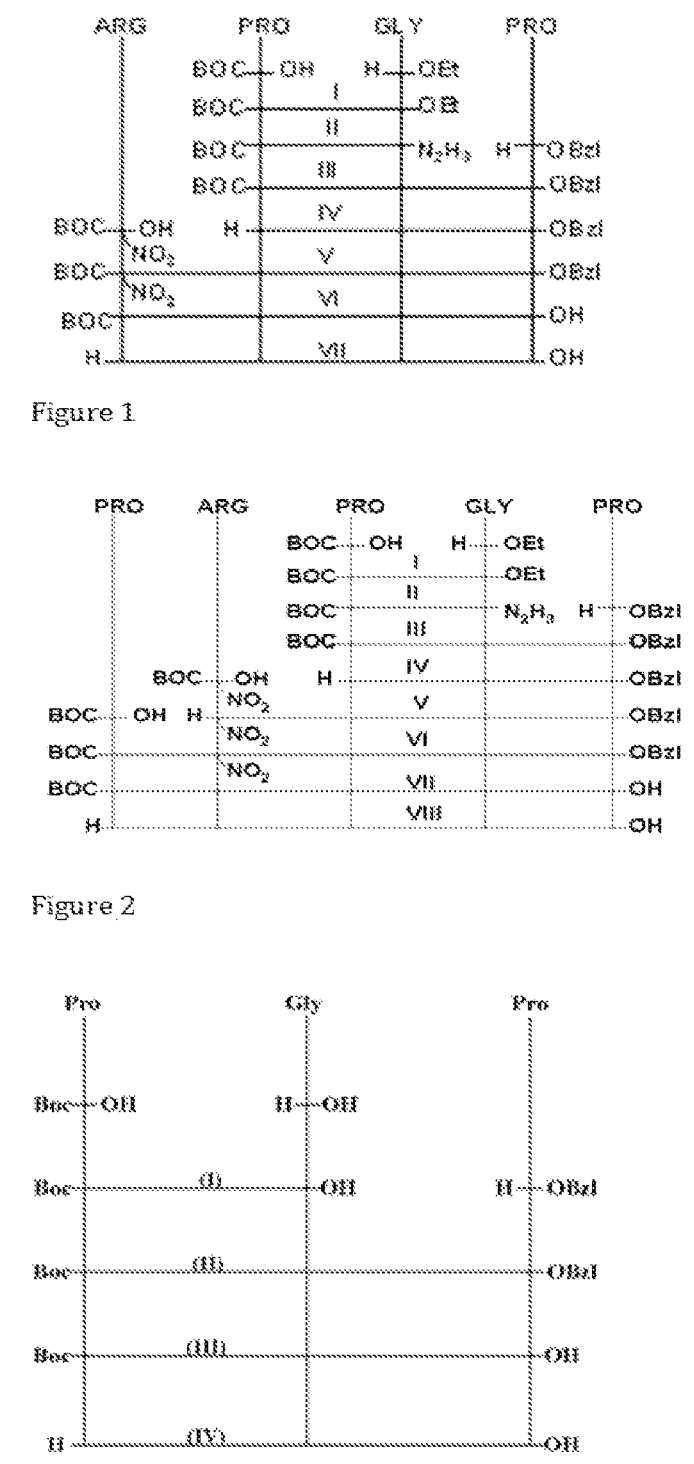

Synthesis of the tetrapeptide was performed according to the diagram shown in FIG. 1.

In synthesis, mixed anhydride method, azide method and carbodiimide method were used. Derivatives of L-amino acids were used for synthesis. Evaporation of solutions was conducted using rotor evaporator at 40° C. Melting points, determined with Boethius apparatus, are given without correction. Identity of the obtained compounds was tested by TLC on Silufol silica gel-coated plates (Czech Republic). Substances were detected by spraying the plate with a solution of ninhydrin and (or) o-tolidine. Substances were detected by spraying the plate with a solution of ninhydrin and (or) o-tolidine. Chromatographic mobility (Rf) values in the following solvent systems are provided: acetone:benzene:acetic acid (50:100:1)—(1); chloroform:methanol (9:1)—(2); hexane:acetone (3:2)—(3); butanol:acetic acid:water (4:1:1)—(4); butanol:acetic acid:pyridine:water (30:6:20:24)—(5); chloroform:methanol:ammonia (6:4:1)—(6); benzene:ethanol (8:2)—(7); Ethyl acetate:acetone:50% acetic acid:water (2:1:1)—(8); chloroform:methanol (14:1)—(9); chloroform:methanol:ammonia (8:1.75:0.25)—(10); chloroform:methanol:ammonia (6.5:3.0:0.5)—(11).

Specific rotation was determined by AI-EPO polarimeter.
Elemental analysis using Carlo-Erba model 1106 analyzer.

I. Boc-Pro-Gly-OEt.

8.3 g (3.45 mmol) of Boc-Pro-OH were dissolved in 50 ml of $CH_2Cl_2$, cooled down to 5° C.; then, 38.45 mmol (5.38 ml) of TEA were added. The reaction mixture was cooled down to −25÷−30° C. At this temperature, 38.45 mmol (4.84 ml) of isobutyl chloroformate were added using a pipette. The reaction mixture temperature was kept in the range of −18÷−20° C. for 20 minutes. Simultaneously, a solution of 5.9 g (42.3 mmol) of 1.1-fold excess of HCl.H-Gly-OEt in 75 ml of chloroform, containing 5.92 ml of TEA. The solution was cooled down to −25° C. and, after formation of mixed anhydride in the first flask, its contents were poured to the ether solution right away. The reaction mixture was incubated for 1 hour at −10° C. and then stirred for 12 hours at 4° C. on a magnetic stirrer. The reaction mixture was evaporated, then 250 ml of ethyl acetate were added; then, ethyl acetate solution was washed 3 times with 25 ml of 0.1N HCl, 3 times with 25 ml $H_2O$, and once with saturated solution of NaCl. The organic layer was dried over $MgSO_4$, filtered and evaporated. The residue was dried under vacuum over $P_2O_5$/KOH and paraffin.

Yield: 10.2 g (30.3 mmol) 78.83%
Rf–0.5 (7); 0.862 (8)
Melting point 68-70° C.

II. Boc-Pro-Gly-$N_2H_2$.

10.2 g of Boc-Pro-Gly-OEt (30.3 mmol) were dissolved in 80 ml of absolute methanol, and 4-fold excess of hydrazine hydrate, viz. 5.88 ml (121.2 mmol), was added. The solution was stirred for 12 hours on a magnetic stirrer at room temperature. The reaction mixture was evaporated, then two times evaporated with ether; then, ether (~5 ml) was poured over the residue and left in a refrigerator overnight (for better crystallization, seeding agent was added). The precipitated crystals were filtered, washed with ether using a filter and dried in a desiccator.

Yield: 6.9 g (20.79 mmol) 68.62%
Rf–0.284 (7); 0.474 (8); 0.189 (9)
Melting point 98-100° C.

III. Boc-Pro-Gly-Pro-OBzl.

58.4 mmol (4-fold excess) of hydrogen chloride in ethyl acetate were added to the solution of Boc-Pro-Gly-$N_2H_3$, containing 4.7 g (14.6 mmol) in 40 ml of DMF, cooled down to −20° C., and, immediately, 1.73 mL (14.6 mmol) of freshly distilled tert-butyl nitrite; then, the reaction mixture was stirred for 30 minutes at −5° C. The reaction mixture was cooled down to −40° C., and solution of 8.2 mL (58.4 mmol) of TEA in 4 mL of DMF, cooled down to −10° C., was added; when the temperature of the reaction mixture had risen to −20° C., 3.7 g (15.3 mmol) of 1.05-fold excess of HCl.H-Pro-OBzl were added to 20 ml of DMF and 2.14 ml of TEA. Then, it was stirred at 4° C. for 24 hours on a magnetic stirrer. The reaction mixture was evaporated, and the residue was dissolved in 200 mL of ethyl acetate and washed 2 times with 20 ml of $H_2O$, 3 times with 20 ml of 10% sodium $KHSO_4$, 3 times with 20 ml of $H_2O$, 3 times with 20 ml of 5% NaHCO3, and 3 times with 20 ml of $H_2O$. Ethyl acetate solution was dried over $MgSO_4$. Then it was evaporated, and a small amount of ether (~10 mL) was added to the residue. Then, it was left in a refrigerator for crystallization. For better product crystallization, seeding agent was added. The precipitated crystals were filtered and washed with a small amount of ether using a filter. Then, they were dried in a desiccator.
Yield: 5.358 g (11.65 mmol) 79.92%
Rf–0.326 (7); 0.947 (8); 0.390 (9)
Melting point 125-126° C.
[α]$_D^{22}$–101.18° (c=0.85; CH$_3$OH).
Elemental analysis: C, 62.89 (62.73); N, 9.21 (9.14); H, 7.52 (7.24).

IV. TFA.H-Pro-Gly-Pro-OBzl.

5.358 g (11.65 mmol) of Boc-Pro-Gly-Pro-OBzl were dissolved in 29.13 ml of methylene chloride; then, 29.13 mL of TFA were added, incubated for 45 minutes at room temperature, evaporated 2 times with absolute ethanol, 2 times with benzene, 2 times with ether and dissolved in benzene; then, hexane was poured over. Hexane was decanted, and the resulted substance was dried under vacuum in a desiccator over KOH, P$_2$O$_5$ and paraffin, while desiccant was changed several times.
Yield: 4.63 g (9.7 mmol) 98%
Rf–0.043 (7); 0.247 (8); 0.018 (9).

V. Boc-Ar(NO2)-Pro-Gly-Pro-OBzl.

3.09 g of Boc-Arg (NO$_2$)—OH (9.7 mmol) were dissolved in 50 mL of THF and 10 ml DMF, 2.07 g (10.67 mmol) of DCC were added, cooled down to 0° C., stirred for 40 minutes; then, a solution of TFA.H-Pro-Gly-Pro-OBzl was added to 50 ml of THF and 4.46 ml (9.7 mmol) of TEA. The reaction mixture was stirred for three days. DCM precipitate was filtered off; the solution was evaporated under vacuum; then, 200 ml of hexane were added to the residue. With this, the desired product was separated as an oil, which was dissolved in 500 mL of ethyl acetate and washed 3 times with 25 ml of 0.1N HCl, three times with 25 ml of H$_2$O, and once with saturated solution of NaCl. The organic layer was dried over MgSO$_4$, filtered and evaporated. The residue was dissolved in ethyl acetate and precipitated with dry ether. The precipitate was filtered and dried under vacuum over P$_2$O$_5$/KOH and paraffin, while desiccant was changed several times.
Yield: 4.76 g (7.9 mmol) 85%
Rf–0.44 (1); 0.8 (11)
Melting point 108-110° C.
[α]$_D^{22}$=–77.8° (c=0.5; CH$_3$COOH).

VI. Boc-Arg-Pro-Gly-Pro.

4.76 g (6.5 mmol) of Boc-Arg(NO$_2$)-Pro-Gly-Pro-OBzl were dissolved in 100 ml of methanol; then 1 ml 1N hydrochloric acid and 4.67 g of catalyst, viz. 10% palladium oxide on neutral aluminum oxide, were added, and hydrogenation in the stream of dry hydrogen at room temperature under 1 atm. was conducted for 6 hours. Then, the catalyst was filtered off and washed on the filter with methanol. Pooled filtrate was evaporated to dryness. The residue was precipitated with ether from the absolute methanol. Then, it was dried under vacuum, while desiccant was changed several times.
Yield: 4.23 g (5.8 mmol) 89%
Rf–0.125 (4); 0.57 (6); 0.37 (5)
Melting point 123-125° C.

VII. Arg-Pro-Gly-Pro.

4.23 g (5.8 mmol) of Boc-Arg-Pro-Gly-Pro-OH were suspended in 10 ml of 2N hydrochloric acid in dioxane and incubated at room temperature for 45 min. Then, dry ether was added, and the precipitate was washed by decantation with dry ether. It was reprecipitated with ether from absolute methanol. The resulting precipitate was dissolved in 7.5 ml of 30% ethanol and applied to Amberlyst A-21 (AcO$^-$ form) column for acetate/hydrochloride salt exchange. Peptide was eluted with 200 ml of 30% ethanol, evaporated to dryness under vacuum and precipitated with absolute ether from methanol.
Yield: 3.69 g (4.93 mmol) 85%
Rf–0.287 (4); 0.145 (5); 0.338 (14)
Melting point 120-122° C.
HPLC results: Column: Supercosil ABZ Plus, size 4.6×250 mm; flow rate 1 mL/min; Eluent A: NH$_4$H$_2$PO$_4$+H$_3$PO$_4$ (50 mM, pH 2.8); eluent B: MeOH
Gradient: 0-20 min (0-40% B); retention time 21.21 min.
Rf–0.24 (6)
Melting point=151° C.
[α]$_D^{22}$=–65.0° (c=0.5 CH$_3$COOH)
HPLC results: Column: Zorbax ODS d=4.6 mm; t=35° C.
Flow rate 1 mL/min; A=50 mM NH$_4$H$_2$PO$_4$ (pH 2.5); B=A+ MeOH (1:1); 10-60% B (in 25 min).
Retention time 16.5 min.

Example 2

Synthesis of Pro-Arg-Pro-Gly-Pro Pentapeptide

Peptide synthesis was performed by classical methods of peptide chemistry using natural L-amino acids according to the diagram shown in FIG. 2.

First, Pro-Gly-Pro tripeptide was produced; then, pentapeptide was obtained by stepwise buildup of the peptide chain from the N-terminus. In synthesis, mixed anhydride method, azide method and carbodiimide method were used.

Chromatographic mobility (Rf) values in the following solvent systems are provided: butanol:acetic acid:water (4:1:1)—(1); chloroform:methanol:ammonia (6:4:1)—(2); acetone:benzene:acetic acid (50:100:1)—(3); chloroform:methanol (9:1)—(4); hexane:acetone (3:2)—(5); butanol:acetic acid:pyridine:water (30:6:20:24)—(6); chloroform:methanol (14:1)—(7).

I. Boc-Pro-Gly-OEt.

8.3 g of Boc-Pro (38.45 mmol) were dissolved in 50 ml of CH$_2$Cl$_2$, cooled down to +5° C., and 38.45 mmol (5.38 ml) of TEA were added. The reaction mixture was cooled down to –25÷–30° C. At this temperature, 38.45 mmol (4.84 ml) of isobutyl chloroformate were added using a pipette. The reaction mixture temperature was kept in the range of –18±–20° C. for 20 minutes. Simultaneously, a solution of 5.9 g (42.3 mmol) of 1.1-fold excess of HCl.H-Gly-OEt in 75 ml of chloroform, containing 5.92 ml of TEA. The solution was cooled down to –25° C. and, after formation of mixed anhydride in the first flask, its contents were poured to the ether solution right away. The reaction mixture was incubated for 1 hour at –10° C. and then stirred for 12 hours at 4° C. on a magnetic stirrer. The reaction mixture was evaporated and 250 ml of ethyl acetate were added to it; the ethyl acetate solution was washed 3 times with 25 ml of 0.1N HCl, 3 times with 25 ml H$_2$O, and once with saturated solution of NaCl. The organic layer was dried over MgSO4, filtered and evaporated. The residue was dried under vacuum over P$_2$O$_5$/KOH and paraffin.
Yield: 10.2 g (30.3 mmol) 78.83%
Rf–0.5 (3); 0.862 (4).

II. Boc-Pro-Gly-N$_2$H$_2$.

10.2 g of Boc-Pro-Gly-OEt (30.3 mmol) were dissolved in 80 ml of absolute methanol, and 4-fold excess of hydrazine hydrate, viz. 5.88 ml (121.2 mmol), was added. The solution was stirred for 12 hours on a magnetic stirrer at room temperature. The reaction mixture was evaporated, then two times evaporated with ether; then, ether (~5 ml) was poured over the residue and left in a refrigerator overnight (for better crystallization, seeding agent was added). The precipitated crystals were filtered, washed with ether using a filter and dried in a desiccator.

Yield: 6.9 g (20.79 mmol) 68.62%

Melting point 98-100° C.

Rf–0.284 (3); 0.474 (4); 0.189 (5).

III. Boc-Pro-Gly-Pro-OBzl.

58.4 mmol (4-fold excess) of hydrogen chloride in ethyl acetate were added to the solution of Boc-Pro-Gly-$N_2H_3$, containing 4.7 g (14.6 mmol) in 40 ml of DMF, cooled down to −20° C., and, immediately, 1.73 mL (14.6 mmol) of freshly distilled tert-butyl nitrite; then, the reaction mixture was stirred for 30 minutes at −5° C. The reaction mixture was cooled down to −40° C., and solution of 8.2 mL (58.4 mmol) of TEA in 4 mL of DMF, cooled down to −10° C., was added; when the temperature of the reaction mixture had risen to −20° C., 3.7 g (15.3 mmol) of 1.05-fold excess of HCl.H-Pro-OBzl were added to 20 ml of DMF and 2.14 ml of TEA. Then, it was stirred at 4° C. for 24 hours on a magnetic stirrer. The reaction mixture was evaporated, and the residue was dissolved in 200 mL of ethyl acetate and washed 2 times with 20 ml of $H_2O$, 3 times with 20 ml of 10% sodium $KHSO_4$, 3 times with 20 ml of $H_2O$, 3 times with 20 ml of 5% $NaHCO_3$, and 3 times with 3 ml of $H_2O$. Ethyl acetate solution was dried over $MgSO_4$. Then it was evaporated, and a small amount of ether (~10 mL) was added to the residue. Then, it was left in a refrigerator. For better product crystallization, seeding agent was added. The precipitated crystals were filtered and washed with a small amount of ether using a filter. Then, they were dried in a desiccator.

Yield: 5.358 g (11.65 mmol) 79.92%

Rf–0.326 (3); 0.947 (4); 0.390 (5)

Melting point 125-126° C.

$[\alpha]_D^{22}=-101.2°$ (c=0.85; $CH_3OH$)

Elemental analysis: C, 62.89 (62.73); N, 9.21 (9.14); H, 7.52 (7.24).

IV. TFA.H-Pro-Gly-Pro-OBzl.

5.358 g (11.65 mmol) of Boc-Pro-Gly-Pro-OBzl were dissolved in 29.13 ml of methylene chloride; 29.13 mL of TFA were added, incubated for 45 minutes at room temperature, evaporated 2 times with absolute ethanol, 2 times with benzene, 2 times with ether and dissolved in benzene; then, hexane was poured over. Hexane was decanted, and the resulted substance was dried under vacuum in a desiccator over $P_2O_5$/KOH and paraffin.

Yield: 4.63 g (9.7 mmol) 98%

Rf–0.043 (3); 0.247 (4); 0.018 (5).

V. Boc-Arg($NO_2$)-Pro-Gly-Pro-OBzl.

3.09 g (9.7 mmol) of Boc-Arg ($NO_2$) were dissolved in 50 ml of THF and 10 ml DMF; then, 2.07 g (10.67 mmol) of DCC were added, cooled down to 0° C. and stirred for 40 minutes; a solution of TFA.H-Pro-Gly-Pro-OBzl was added to 50 ml of THF and 4.46 ml (9.7 mmol) of TEA. The reaction mixture was stirred for three days. DCM precipitate was filtered off; the solution was evaporated under vacuum; then, 200 ml of hexane were added to the residue. With this, the desired product was separated as an oil, which was dissolved in 500 mL of ethyl acetate and washed 3 times with 25 ml of 0.1N HCl, three times with ml of $H_2O$, and once with saturated solution of NaCl. The organic layer was dried over MgSO4, filtered and evaporated. The residue was dried under vacuum over $P_2O_5$/KOH and paraffin.

Yield: 4.76 g (7.9 mmol) 85%

Rf–0.44 (1); 0.8 (6)

Melting point 108-110° C.

VI. TFA-Arg($NO_2$)-Pro-Gly-Pro-OBzl.

4.76 g (7.9 mmol) of Boc-Arg ($NO_2$)-Pro-Gly-Pro-OBzl were dissolved in 20 ml of methylene chloride, 20 mL of TFA were added, incubated for 45 minutes at room temperature, evaporated 2 times with absolute ethanol, 2 times with benzene, 2 times with ether, then dissolved in benzene; then, hexane was poured over. Hexane was decanted, and the resulted substance was dried under vacuum in a desiccator over $P_2O_5$/KOH and paraffin.

The yield is quantitative.

Rf–0.16 (1); 0.27 (6).

VII. BOC-Pro-Arg($NO_2$)-Pro-Gly-OBzl.

1.7 g (7.9 mmol) of Boc-Pro were dissolved in 20 mL of THF, and 1.07 g (7.9 mmol) of BT were added, cooled down to 0° C.; 1.8 g of DCC in 50 ml of THF were added. In 40 min, a solution of TFA-Arg($NO_2$)-Pro-Gly-Pro-OBzl (7.9 mmol) in 50 mL of THF and 1.1 mL (7.9 mmol) of TEA were added to the reaction mixture. It was stirred for 2 hours at 0° C. and for 2 days at room temperature; then, DCM was filtered off, evaporated under vacuum, dissolved in 500 mL of ethyl acetate and treated similarly to Boc-Pro-Arg($NO_2$)-Pro-Gly-Pro-OBzl.

Yield: 4.07 g (67.8%)

Rf–0.42 (1); 0.72 (6); 0.31 (7)

Melting point 147-148° C.

VIII. Boc-Pro-Arg-Pro-Gly-Pro.

4.07 g (6.5 mmol) were dissolved in 100 ml of methanol; 1 ml of 1N hydrochloric acid and 0.85 g of catalyst, viz. 10% palladium oxide on neutral aluminum oxide, were added, and hydrogenation in the stream of dry hydrogen at room temperature under 1 atm. was conducted for 6 hours. Then, the catalyst was filtered off and washed on the filter with methanol. Pooled filtrate was evaporated to dryness. The residue was precipitated with ether from the absolute methanol.

Yield: 3.02 g (5.8 mmol) 89%

Rf–0.125 (1), 0.57 (2), 0.37 (6).

IX. Pro-Arg-Pro-Gly-Pro.

3.02 g (5.8 mmol) of Boc-Pro-Arg-Pro-Gly-Pro were suspended in 10 ml of 2N hydrochloric acid in dioxane and were incubated at room temperature for 45 min. Then, dry ether was added, and the precipitate was washed by decantation with dry ether. It was reprecipitated with ether from absolute methanol. The resulting precipitate was dissolved in 7.5 ml of 30% ethanol and applied to Amberlyst A-21 ($Aco^-$-form) column for acetate/hydrochloride salt exchange. Peptide was eluted with 200 ml of 30% ethanol, evaporated to dryness under vacuum and precipitated with absolute ether from methanol.

Yield: 2.27 g (75%)

Rf–0.2 (2); 0.1 (6)

Melting point 180-185° C.

$[\alpha]_D^{20}=-105°$ (c=0.4; $CH_3COOH$).

Amino acid composition versus arginine: Pro 2.78 (3); Gly 1.1 (1).

HPLC results: Column: Supercosil ABZ Plus, size 4.6×250 mm; flow rate 1 mL/min; Eluent A: $NH_4H_2PO_4+H_3PO_4$ (50 mM, pH 2.8); eluent B: MeOH Gradient: 0-20 min (0-40% B); retention time 10.13 min.

Example 3

Synthesis of Pro-Gly-Pro Tripeptide

The synthesis of Pro-Gly-Pro tripeptide was carried out according to the diagram shown in FIG. 3. Synthesis of Pro- Gly-Pro tripeptide was carried out using modern protecting groups and methods of peptide bond formation in solution. Mixed anhydride method with PivCl was used for peptide bond formation. tert-butyloxycarbonyl protection (Boc) was used for protection of amino groups, and benzyl ester (OBzl) was recruited for protection of carboxyl group. Stepwise approach to peptide chain elongation was used.

Derivatives of L-amino acids were used for synthesis. Evaporation of solutions was conducted using vacuum evaporator at 40° C. Melting points, determined with Boethius apparatus, are given without correction.

Identity of the obtained compounds was tested by TLC on Silufol silica gel-coated plates (Czech Republic). Substances were detected by spraying the plate with a solution of ninhydrin and (or) o-tolidine. Chromatographic mobility (Rf) values in the following solvent systems are provided: (ethyl acetate:acetone:50% acetic acid:water (2:1:1); benzene:ethanol (8:2); chloroform:methanol:ammonia (6:4:1); chloroform:methanol:acetic acid (42:7:1); acetone:benzene:acetic acid (50:100:1); chloroform:methanol (9:1); hexane:acetone (3:2); butanol:acetic acid:water (4:1:1); butanol:acetic acid:pyridine:water (30:6:20:24); hexane:ethyl acetate (4:1); chloroform:methanol:ammonia (8:1.75:0.25); (isopropanol:formic acid:water) (20:5:1); (chloroform:methanol:ammonia) (7:2.5:0.5); methanol. Specific rotation was determined by AI-EPO polarimeter). Elemental analysis using Carlo-Erba model 1106 analyzer.

I. Production of Boc-Pro-Gly-OH.

1. 10.75 g (50 mmol) of Boc-Pro were dissolved in 150 ml of acetonitrile, cooled down to −5° C.; then, 7.7 ml (50 mmol) of triethylamine (TEA) were added to the solution, and it was cooled down to −20° C., while stirring on a magnetic stirrer. 6.8 ml (55 mmol) of pivaloyl chloride (PivCl) were added to the cooled solution, stirred on a magnetic stirrer for 20 minutes at −10° C. and then cooled down to −30° C.; then, precooled solution of Gly was added. Simultaneously, Gly solution was prepared 2. 4.5 g of Gly (60 mmol, 1.2-fold excess) were dissolved in 35 ml of water and 60 ml of acetonitrile, 8.4 ml (60 mmol) of triethylamine were added. The mixture was cooled down to −10° C. and added to the solution in the first flask after 20 minutes. The reaction mixture was incubated for 1 hour at −10° C. and stirred for 2 hours at 18-20° C. on a magnetic stirrer. The reaction mixture was evaporated on a rotary evaporator. About 50 mL of water were added to the residue. The aqueous solution was acidified with a 3-fold excess of NaHSO$_4$ (24.84 g) to pH=3 and extracted 5 times with 100 ml of ethyl acetate. Pooled ethyl acetate solution was washed with H$_2$O (50 mL), 10% solution of KHSO$_4$ (50 mL), H$_2$O (50 mL), and saturated NaCl (50 mL). Ethyl acetate solution was dried over MgSO4. Dried ethyl acetate was filtered and evaporated. Dry ether was added to the residue. Upon the addition of ether to the flask, it precipitated the product, which was filtered and washed with dry ether using a filter. The resulted substance was dried under vacuum in a desiccator over KOH, P2O5 and paraffin, while desiccant was changed several times.

Product M.W. 272.3
Yield: 5.97 g (21.74 mmol); (43.5%)
Melting point 70° C.
Rf−0.863 (acetone-benzene-acetic acid) (50:100:1);
0.746 (benzene-ethanol) (8:2); 0.903 (chloroform:methanol) (9:1);
0.847 (Ethyl acetate:acetone:50% acetic acid:water) (2:1:1).

II. Production of Boc-Pro-Gly-OBzl.

1. 5.97 g (21.74 mmol) of Boc-Pro-Gly-OH were dissolved in 100 ml of acetonitrile, cooled down to −5° C.; then, 1.1- fold excess (3.35 ml, 23.9 mmol) of triethylamine (TEA) was added to the solution, and it was cooled down to −20° C., while stirring on a magnetic stirrer. 1.1-fold excess (2.34 ml, 23.9 mmol) of pivaloyl chloride (PivCl) was added to the cooled solution, stirred on a magnetic stirrer for 20 minutes at −10° C. and then cooled down to −30° C.; then, precooled solution of HCl.Pro-OBzl was added. Simultaneously, HCl.Pro-OBzl was prepared.

2. 6.3 g of HCl.Pro-OBzl (26.1 mmol, 1.2 excess) were dissolved in 50 ml of acetonitrile, 4.0 ml (28.71 mmol; 1.1-fold excess) of triethylamine were added. The mixture was cooled down to −10° C. and added to the solution in the first flask after 20 minutes. The reaction mixture was incubated for 1 hour at −10° C. and stirred for 2 hours at 18-20° C. on a magnetic stirrer. The reaction mixture was evaporated. 300 ml of ethyl acetate were added to the evaporated residue. Ethyl acetate solution was washed with H$_2$O (3 times with 25 mL), 10% solution KHSO$_4$ (3 times with 25 ml) H$_2$O (3 times with 25 ml), 5% NaHCO$_3$ (3 times with 25 ml) H$_2$O (3 times 25 mL), and saturated solution of NaCl (once with 25 mL). Ethyl acetate solution was dried over MgSO$_4$. Dried ethyl acetate was filtered and evaporated. About 100 ml of dry ether were added to the residue. Upon the addition of ether to the flask, it precipitated the product, which was filtered and washed with dry ether using a filter. The resulted substance was dried under vacuum in a desiccator over KOH, P$_2$O$_5$ and paraffin, while desiccant was changed several times.

Product M.W. 459.82
Yield: 8.12 g (17.66 mmol); (81.23%)
Melting point 125-126° C.
Rf−0.326 (acetone:benzene:acetic acid) (50:100:1)
0.390 (hexane:acetone) (3:2)
0.947 (chloroform:methanol) (9:1)
0.716 (methanol)
0.620 (benzene:ethanol) (8:2)

III. Production of Boc-Pro-Gly-Pro-OH.

8 g (17.4 mmol) of Boc-Pro-Gly-Pro-OBzl were dissolved in 100 ml of methanol, 0.5 ml of CH$_3$COOH and palladium black were added, while stirring on a magnetic stirrer, and hydrogen was passed through for 2 hours. The solution was filtered, evaporated, evaporated 3 times with benzene and 2 times with ethyl acetate. Then, it was precipitated with ether hexane from acetone, and the precipitate formed in the flask was dried in a desiccator over P$_2$O$_5$/KOH and paraffin.

Product M.W. 369.39
Yield: 6.3 g (17.05 mmol) 98%
Melting point 99-100° C.
Rf: 0.560 (chloroform-methanol) (9:1)
0.812 (chloroform-methanol-acetic acid) (42:7:1)
0.187 (acetone:benzene:acetic acid) (50:100:1)
0.164 (hexane:acetone) (3:2)

IV. Production of Pro-Gly-Pro.

40.6 ml of methylene chloride and 40.6 ml of TFA were added to 6.0 g (16.24 mmol) of Boc-Pro-Gly-Pro-OH and incubated for 45 minutes at room temperature; after removal of the protecting group, the solution was evaporated 2 times with absolute methanol, 2 times with benzene and 2 times with ether. It was precipitated with ether from acetone. The residue was dried under vacuum over P$_2$O$_5$, KOH and paraffin. The dried product was reprecipitated with dry diethyl ether from absolute MeOH.

Product M.W. 381.39
Yield: 5.6 g (14.72 mmol) (90.62%)

The resulting precipitate of TFA.Pro-Gly-Pro-OH was dissolved in 10 ml of 30% ethanol; then, 25 mL of Amberlyst A-21 (CH$_3$COO$^-$) ion-exchange resin was added for exchange of trifluoroacetate to acetate salt and stirred on a magnetic stirrer for 45 minutes; then, it was washed with 150 ml of 30% ethanol, evaporated to dryness under vacuum and precipitated with dry diethyl ether from absolute methanol. The resulting precipitate was filtered off and dried in a desiccator under vacuum over $P_2O_5$, KOH and paraffin, while desiccant was changed several times.

Product M.W. 328.34
Yield: 4.54 g (13.84 mmol) (94%)
Melting point 143-145° C.
$[\alpha]_D^{22}$ –31.5° (c 1, MeOH)
Rf: 0.59 (chloroform:methanol:ammonia) (6:4:1)
0.52 (chloroform:methanol:ammonia) (4:4.5:1.5)
0.524 (ethanol:ammonia) (7:3)

Example 4

Synthesis of Thr-Lys-Pro-Arg-Pro-Phe Hexapeptide

Synthesis of Thr-Lys-Pro-Arg-Pro-Phe hexapeptide was performed according to the diagram shown in FIG. 4.

Synthesis of Thr-Lys-Pro-Arg-Pro-Phe hexapeptide was carried out using modern protecting groups and methods of peptide bond formation in solution. TBA salt method, activated ester method, carbodiimide method and mixed anhydride method were used for peptide bond formation. Both stepwise and blockwise approaches were used.

Example 5

Synthesis of Thr-Lys-Pro-Arg-Pro Pentapeptide

Figure 5:
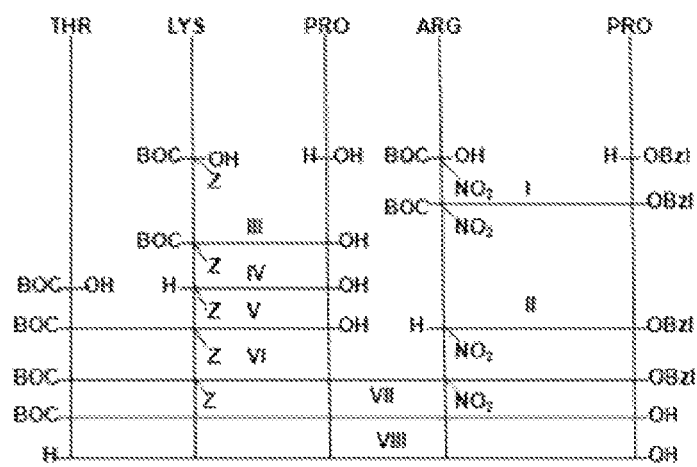
FIG. 5 shows a diagram of Thr-Lys-Pro-Arg-Pro (SEQ ID NO: 6) pentapeptide synthesis.

Synthesis of Thr-Lys-Pro-Arg-Pro pentapeptide was performed according to the diagram shown in FIG. 5.

Synthesis of Thr-Lys-Pro-Arg-Pro pentapeptide was carried out using modern protecting groups and methods of peptide bond formation in solution. TBA salt method, activated ester method and carbodiimide method were used for peptide bond formation. Both stepwise and blockwise approaches were used.

Example 6

Synthesis of Thr-Lys Dipeptide

Figure 6:
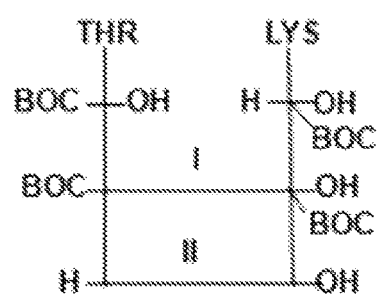
FIG. 6 shows a diagram of Thr-Lys (SEQ ID NO: 2678) dipeptide synthesis.

Synthesis of Thr-Lys dipeptide was performed according to the diagram shown in FIG. 6.

Synthesis of Thr-Lys dipeptide was carried out using modern protecting groups and methods of peptide bond formation in solution. TBA salt method, was used for peptide bond formation.

Derivatives of both protected and free L-amino acids were used for synthesis of the peptides described in Examples 7-9. The solvents used in peptide synthesis, were correspondingly absolutized. Peptide homogeneity was tested by high performance liquid chromatography (HPLC) using Millichrome A-02 microcolumn liquid chromatographic system. The synthesized peptides were characterized by mass spectrometry using Bruker mass spectrometer (®Bruker Daltonik GmbH).

Example 7

Synthesis of Thr-Lys-Pro-Phe Tetrapeptide

Figure 7:
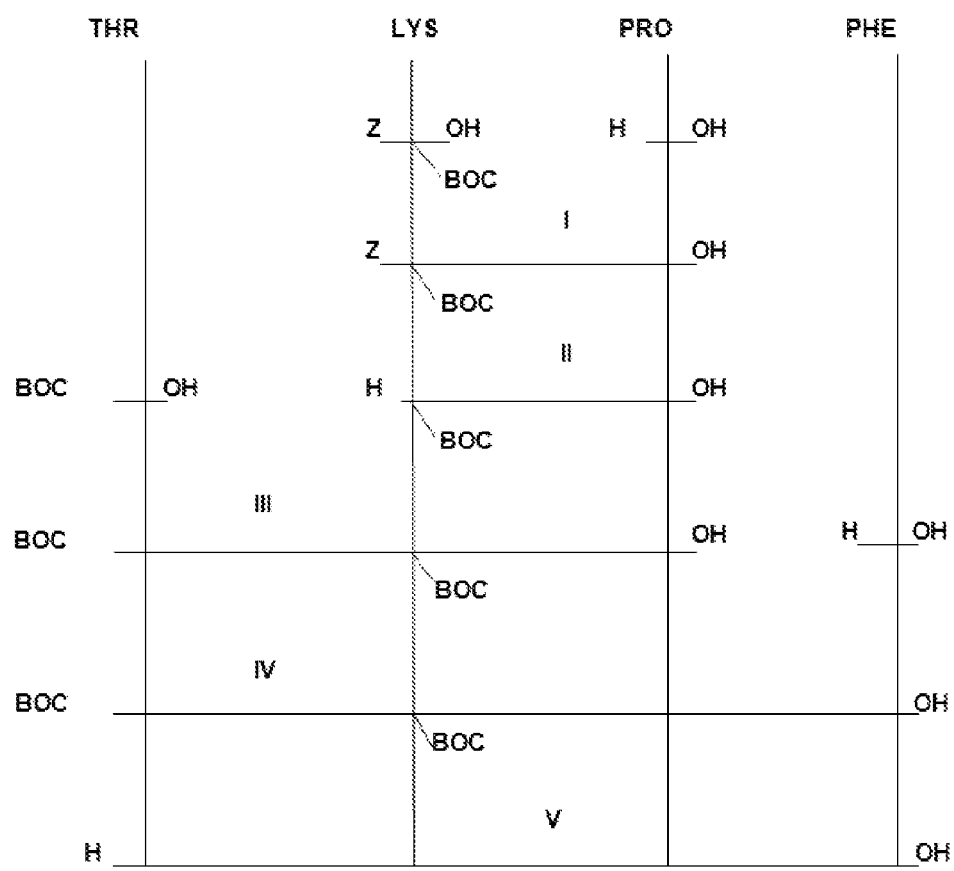
FIG. 7 shows a diagram of Thr-Lys-Pro-Phe (SEQ ID NO: 2679) tetrapeptide synthesis.

The synthesis of Thr-Lys-Pro-Phe tetrapeptide was carried out according to the diagram shown in FIG. 7.

Synthesis of Thr-Lys-Pro-Phe tetrapeptide was carried out using modern protecting groups and methods of peptide bond formation in solution. TBA salt method and activated ester method were used for peptide bond formation. Stepwise approach to peptide chain elongation was used.

Derivatives of both protected and free L-amino acids were used for synthesis. Evaporation of solutions was conducted using vacuum evaporator at 40° C. Melting points, determined with Boethius apparatus, are given without correction. Identity of the obtained compounds was tested by TLC on Silufol silica gel-coated plates (Czech Republic). Substances were detected by spraying the plate with a solution of ninhydrin and (or) o-tolidine. Chromatographic mobility (Rf) values in the following solvent systems are provided: (butanol:acetic acid:water) (4:1:1); (benzene-ethanol) (8:2); (chloroform:methanol) (9:1); (isopropanol:formic acid:water) (20:5:1); (chloroform-methanol-acetic acid) (42:7:1); (chloroform:methanol:ammonia) (8:1.75:0.25); (acetone-benzene-acetic acid) (50:100:1); (chloroform:methanol:ammonia) (6:4:1); (chloroform:methanol:ammonia) (44.5:1.5); (butanol:acetic acid:pyridine:water) (30:6:20:24).

I. Production of Z-Lys(Boc)-Pro-OH.

13% solution of TBA (98 ml) was added to 46.32 mmol (5.34 g) of Pro and evaporated two times with ethanol, two times with ethanol/benzene mixture, and 2 times with benzene. 300 ml of absolute ethyl acetate were added; the reaction mixture was cooled down to 0° C., and 23.16 mmol (12.66 g) of previously synthesized Z-Lys (Boc)-OPfp were added and stirred on a magnetic stirrer for 1 hour. The reaction mass was evaporated, and 40 ml of water were added to the evaporation residue. The aqueous solution was washed 3 times with 80 ml of ether. After washing with ether, the aqueous solution was acidified with citric acid to pH 3. After acidification, aqueous solution was extracted with ethyl acetate 3 times in 40 ml aliquots. Pooled ethyl acetate after extraction was washed 3 times with 20 ml of water, 3 times with 20 ml of 10% solution of $KHSO_4$, and 3 times with 20 ml of water. Ethyl acetate solution was dried over $MgSO_4$. Then, it was filtered and evaporated on a rotary evaporator. The resulted substance was precipitated with hexane from ethyl acetate. Hexane was decanted, and the resulted substance was dried under vacuum in a desiccator over KOH, $P_2O_5$ and paraffin, repeatedly changing desiccant.

Yield: 9.68 g (20.26 mmol); (87.51%).
Melting point 76-77° C.
Rf–0.705 (butanol:acetic acid:water) (4:1:1);
0.560 (benzene-ethanol) (8:2);
0.476 (chloroform:methanol) (9:1);
0.813 (isopropanol:formic acid:water) (20:5:1);
0.297 (acetone-benzene-acetic acid) (50:100:1).

I. Production of H-Lys(Boc)-Pro-OH.

300 ml of absolute methanol, 2 ml of acetic acid, and palladium black were added to 9.68 g (20.26 mmol) of Z-Lys (Boc)-Pro-OH, and hydrogenation was performed in the stream of dry hydrogen at room temperature under 1 atm for 8 hours. Then, the catalyst was filtered off and washed on the filter with methanol. Pooled filtrate was evaporated to dryness. The residue was precipitated with ether from the absolute methanol. Then, it was dried under vacuum, while desiccant was changed several times.

Yield: 6.38 g (18.58 mmol); (91.87%)
Melting point 98-99° C.
Rf–0.110 (chloroform-methanol-acetic acid) (42:7:1);
0.166 (butanol:acetic acid:water) (4:1:1);
0.235 (chloroform:methanol:ammonia) (8:1.75:0.25);
0.494 (isopropanol:formic acid:water) (20:5:1) (2:1:1).

III. Production of Boc-Thr-Lys-Boc)-Pro-OH.

13% solution of TBA (39.4 ml) was added to 18.58 mmol (6.38 g) of Lys (Boc)-Pro-OH and evaporated 2 times with ethanol, 2 times with ethanol/benzene mixture and 2 times with benzene. 250 ml of absolute ethyl acetate were added; the reaction mixture was cooled down to 0° C., and 9.2 mmol (3.74 g) of previously synthesized Boc-Thr-OPfp were added and stirred on a magnetic stirrer for 1 hour. The reaction mass was evaporated, and 40 ml of water were added to the evaporation residue. The aqueous solution was washed 3 times with 80 ml of ether. After washing with ether, the aqueous solution was acidified with 18.58 mmol (3.95 g) of citric acid to pH 3. After acidification, aqueous solution was extracted with ethyl acetate 3 times in 40 ml aliquots. Pooled ethyl acetate after extraction was washed 3 times with 20 ml of water, 3 times with 20 ml of 10% solution of $KHSO_4$, and 3 times with 20 ml of water. Ethyl acetate solution was dried over $MgSO_4$.

Then, it was filtered and evaporated on a rotary evaporator. The resulted substance was precipitated with hexane from ethyl acetate. Hexane was decanted, and the resulted substance was dried under vacuum in a desiccator over KOH, $P_2O_5$ and paraffin, while desiccant was changed several times.
Yield: 3.32 g (6.1 mmol); (66.26%) Melting point 105-107° C.
Rf–0.297 (acetone-benzene-acetic acid) (50:100:1);
0.234 (chloroform:methanol) (9:1); 0.560 (benzene-ethanol) (8:2).

IV. Production of Boc-Thr-Lys(Boc)-Pro-Phe-OH.
  1. Production of Boc-Thr-Lys(Boc)-Pro-OSu.
  3.53 mmol (0.38 g) of hydroxysuccinimide were added to 1.66 g (3.05 mmol) of Boc-Thr-Lys(Boc)-Pro in 50 ml of absolute ethyl acetate, and the resulting solution was cooled down to 0° C., while stirring on a magnetic stirrer; then, 0.76 g (3.53 mmol) DCC (dicyclohexylcarbodiimide) were added and stirred on a magnetic stirrer at room temperature for 2 hours. After reaction stopped, the resulting reaction mixture was filtered off and the precipitate was discarded. 200 ml of absolute ethyl acetate were added to the resulting solution. Pooled ethyl acetate was washed 2 times with 20 ml of saturated solution of NaCl, two times with 20 ml of 10% sodium $KHSO_4$, 2 times with 20 ml of saturated solution of NaCl, 2 times with 20 ml of 5% $NaHCO_3$, and 2 times with 20 ml of saturated solution of NaCl. Ethyl acetate solution was dried over $MgSO_4$. Then, it was filtered and evaporated on a rotary evaporator. The resulted substance was precipitated with ether and hexane from ethyl acetate. The precipitate was filtered and dried under vacuum over KOH, $P_2O_5$ and paraffin, while desiccant was changed several times.
Yield: 1.52 g (2.37 mmol) 77.74%.
Rf–0.560 (benzene-ethanol) (8:2); 0.457 (chloroform:methanol) (9:1).

2. After preparation, 1.52 g (2.37 mmol) of Boc-Thr-Lys (Boc)-Pro-OSu were dissolved in 25 ml of dimethylformamide and added to the prepared solution, containing 0.392 g (2.37 mmol) of L-Phe in 25 ml of dimethylformamide. The solution was stirred on a magnetic stirrer at room temperature. The reaction mixture was evaporated on a rotary evaporator and precipitated with ether from benzene. The precipitate was filtered and dried under vacuum over $P_2O_5$/KOH and paraffin, while desiccant was changed several times.
Yield: 1.03 g (1.64 mmol) 69.0%.
Rf–0.063 (isopropanol:formic acid:water) (20:5:1) (2:1:1).
0.745 (chloroform:methanol:ammonia) (8:1.75:0.25);

V. Production of H-Thr-Lys-Pro-Phe-OH.
  1.03 g (1.64 mmol) of Boc-Thr-Lys (Boc)-Pro-Phe-OH were added to 8.2 mL of methylene chloride and 8.2 ml of TFA, then the mixture was incubated for 45 minutes at room temperature, and, after removal of protecting groups, the solution was evaporated 2 times with absolute methanol, 2 times with benzene, and 2 times with ether. It was precipitated with ether from methanol. The residue was dried under vacuum over $P_2O_5$, KOH and paraffin. The resulting precipitate was dissolved in 5 ml of 30% ethanol and applied to Amberlyst A-21 ($AcO^-$-form) column for acetate/hydrochloride salt exchange. Peptide was eluted with 100 ml of 30% ethanol, evaporated to dryness under vacuum and precipitated with absolute ether from absolute methanol. The resulting precipitate was filtered and dried in a desiccator under vacuum over $P_2O_5$, KOH and paraffin, while desiccant was changed several times.
Yield: 0.7 g (1.43 mmol) (87%).
Melting point 129-131° C.
Rf: –0.201 (butanol:acetic acid:pyridine:water) (30:6:20:24);
0.156 (chloroform:methanol:ammonia) (4:4.5:1.5).

Chromatographic and mass spectrometric analysis of peptide sequences, described in Examples 1-7, is shown in Table 2.

TABLE 2

| No | Peptide | SEQ ID NO | MW | Chromatographic characteristics Tr, min | Purity, % | $*[M + H]^+$ | Mass spectrometric characteristics Fragmentation of the molecular ion peak** |
|---|---|---|---|---|---|---|---|
| 1 | Thr-Lys-Pro-Arg-Pro | 6 | 597 | 8.01 | 97 | 598 | 369(100), 272(31), 580(29) |
| 2 | Thr-Lys-Pro-Arg-Pro-Phe | 7 | 744 | 14.8 | 96 | 745 | 516(100)0.263(59), 327(38) |
| 3 | Pro-Arg-Pro-Gly-Pro | 2675 | 522 | 9.14 | 89 | 523 | 25(100)0.425(27), 407(11) |
| 4 | Thr-Lys-Pro-Arg | 4 | 500 | 5.72 | 94 | 501 | 457(100)0.272(55), 484(47), |
| 5 | Arg-Pro-Gly-Pro | 2676 | 425 | 6.82 | 85 | 426 | 408(100), 293(54), 254(24) |
| 6 | Pro-Gly-Pro | 2677 | 269 | 5.42 | >98 | 270 | 173(100), 155(98), 116(75) |

TABLE 2-continued

| No | Peptide | SEQ ID NO | MW | Chromatographic characteristics Tr, min | Purity, % | *[M + H]⁺ | Mass spectrometric characteristics Fragmentation of the molecular ion peak** |
|---|---|---|---|---|---|---|---|
| 7 | Thr-Lys-Pro | 5 | 344 | 4.15 | 93 | 345 | 230(100), 129(19), 212(16) |
| 8 | Thr-Lys | 2678 | 247 | 1.77 | 95 | 248 | 230(100), 129(78), 84(30) |
| 9 | Thr-Lys-Pro-Phe | 2679 | 500 | 5.72 | 94 | 501 | 457(100) 0.272(55), 484(47) |

Note.
*Molecular peak corresponding to [M + H]⁺
**Most intense ions formed in the fragmentation of the molecular ion peak at the energy of collisions with helium atoms of 35 eV.

Table 2 shows the data of high performance liquid chromatography (HPLC) using Millichrome A-02 microcolumn liquid chromatographic system and mass spectrometric characteristics of synthesized peptides obtained using Thermo-Electron LCQ Advantage MAX mass spectrometer.

Developed chromatographic conditions allow to easily obtain chromatographically homogeneous product.

Chromatographic conditions for analysis of peptides.
Chromatograph: Milichrom-A02
Column: Prontosil 120-5C18aq, 2*75 mm
Eluent A: 0.2M LiClO4+5 mM HClO$_4$
eluent B: methanol.

Table 3 presents gradient shape for separation of the synthesized peptides.

TABLE 3

| Time | % B |
|---|---|
| 0 | 5 |
| 16.5 | 80 |

Flow rate: 150 μl/min
Set of wavelengths: 210, 220, 230, 240 nm
Mass Spectrometry Conditions
Equipment: ThermoElectron LCQ Advantage MAX
Ion source: electrospray; direct introduction of peptide solution with a concentration of 10 μg/ml in 0.1% acetic acid at a flow rate of 5 μl/min Molecular ion fragmentation at 35 eV by ion collisions (He)

Source temperature: 250° C.
Ionization potential 3.5 kV

Example 8

Identification of Pharmacophore Position

To identify pharmacophore, fragments of the parent peptide Selank were synthesized: Thr-Lys; Thr-Lys-Pro; Pro-Gly-Pro; Arg-Pro-Gly-Pro; Pro-Arg-Pro-Gly-Pro; and efficacy tests were conducted in vivo using relevant pre-clinical model (Lordosis test).

We studied the efficacy of the following group of peptides: Thr-Lys; Thr-Lys-Pro; Pro-Gly-Pro; Arg-Pro-Gly-Pro; Pro-Arg-Pro-Gly-Pro in the dose of 100 μg/rat in relation to sexual behavior of female rats. Sexual behavior was recorded in ovariectomized hormonally stimulated females in direct contact with the sexually active male, or when such a contact was impossible. It was found that Thr-Lys-Pro peptide increased the intensity of proceptive behavior in females from 14±4 to 29±6 acts during monitoring (p=0.028, Wilcoxon test). The effect on the lordosis reaction in females had the same trend (p=0.09): the number of lordoses under the action of Thr-Lys-Pro peptide increased from 0.73±0.12 to 0.97±0.12. These results indicate the intensification of sexual motivation on the background of Thr-Lys-Pro peptide action. The effect is specific and manifested in an adequate behavioral situation. Results of efficacy studies of the following peptides: Thr-Lys; Thr-Lys-Pro; Pro-Gly-Pro; Arg-Pro-Gly-Pro; and Pro-Arg-Pro-Gly-Pro; in the model of lordosis are shown in Table 4

TABLE 4

| Group | SEQ ID NO | Progesterone, mg/rat | Test product, μg/rat | Number of acts of proceptive behavior | Percentage of lordoses |
|---|---|---|---|---|---|
| Negative Control | | 0.5 | 0 | 14 ± 4 | 0.73 ± 0.12 |
| Thr-Lys | 2678 | 0.5 | 100 | 13 ± 4 | 0.70 ± 0.02 |

TABLE 4-continued

| Group | SEQ ID NO | Progesterone, mg/rat | Test product, μg/rat | Number of acts of proceptive behavior | Percentage of lordoses |
|---|---|---|---|---|---|
| Thr-Lys-Pro | 5 | 0.5 | 100 | 29 ± 6 | 0.97 ± 0.12 |
| Pro-Gly-Pro | 2677 | 0.5 | 100 | 13 ± 5 | 0.74 ± 0.09 |
| Arg-Pro-Gly-Pro | 2676 | 0.5 | 100 | 15 ± 4 | 0.69 ± 0.14 |
| Pro-Arg-Pro-Gly-Pro | 2675 | 0.5 | 100 | 14 ± 6 | 0.73 ± 0.14 |
| Positive Control | | 1.0 | 0 | 22 ± 11 | 0.98 ± 0.09 |

Table 4 proves that Thr-Lys-Pro tripeptide is the pharmacophore; furthermore, the smaller sequence, i.e. Thr-Lys dipeptide, does not function, as results from the Table 4.

Example 9

Pharmacophore Test

To test the pharmacophore, peptides based on it were synthesized, viz. Thr-Lys-Pro tripeptide, Thr-Lys-Pro-Arg (SEQ ID NO: 4) and Thr-Lys-Pro-Phe (SEQ ID NO: 2679) tetrapeptides, Thr-Lys-Pro-Arg-Pro (SEQ ID NO: 6) pentapeptide, and Thr-Lys-Pro-Arg-Pro-Phe (SEQ ID NO: 7) hexapeptide, corresponding to the general formula A-Thr-Lys-Pro-B-C-D-X, efficacy test were conducted on the in vivo, using relevant pre-clinical models (lordosis test).

We studied the efficacy of the following group of peptides: Thr-Lys-Pro (SEQ ID NO: 5); Thr-Lys-Pro-Arg (SEQ ID NO: 4); Thr-Lys-Pro-Arg-Pro (SEQ ID NO: 6); and Thr-Lys-Pro-Arg-Pro-Phe (SEQ ID NO: 7); at a dose of 100 μg/rat in relation to sexual behavior of female rats. Sexual behavior was recorded in ovariectomized hormonally stimulated females in direct contact with the sexually active male, or when such a contact was impossible. It was found that peptides from the group, including Thr-Lys-Pro (SEQ ID NO: 5), Thr-Lys-Pro-Arg-Pro (SEQ ID NO: 6), and Thr-Lys-Pro-Arg-Pro-Phe (SEQ ID NO: 7), increased the intensity of proceptive behavior in females from 14±4 to 26±4-36±6 acts during monitoring (p=0.028, Wilcoxon test). At the same time, Thr-Lys-Pro-Arg (SEQ ID NO: 4) and Thr-Lys-Pro-Phe (SEQ ID NO: 2679) do not affect the intensity of proceptive behavior of females and do not increase the number of lordoses, and the basic parameters of Thr-Lys-Pro-Arg (SEQ ID NO: 4) and Thr-Lys-Pro-Phe (SEQ ID NO: 2679) tetrapeptides remain at the level of negative control. The effect on the lordosis reaction in females had the same trend (p=0.09). In the absence of direct contact of partners, peptide action was manifested. The results indicate the intensification of sexual motivation on the background of Thr-Lys-Pro (SEQ ID NO: 5), Thr-Lys-Pro-Arg-Pro (SEQ ID NO: 6), Thr-Lys-Pro-Arg-Pro-Phe (SEQ ID NO: 7) peptide action and lack of sexual motivation effect in Thr-Lys-Pro-Arg (SEQ ID NO: 4) and Thr-Lys-Pro-Phe (SEQ ID NO: 2679) tetrapeptides. The effect is specific and manifested in an adequate behavioral situation. Results of efficacy studies of the following peptides: Thr-Lys-Pro; Thr-Lys-Pro-Arg (SEQ ID NO: 4); Thr-Lys-Pro-Phe (SEQ ID NO: 2679); Thr-Lys-Pro-Arg-Pro (SEQ ID NO: 6); Thr-Lys-Pro-Arg-Pro-Phe (SEQ ID NO: 7); in the model of lordosis are shown in Table 5.

TABLE 5

| Group | SEQ ID NO | Progesterone mg/rat | Test product, μg/rat | Number of acts of proceptive behavior | Percentage of lordoses |
|---|---|---|---|---|---|
| Negative Control | | 0.5 | 0 | 14 ± 4 | 0.73 ± 0.12 |
| Thr-Lys-Pro | 5 | 0.5 | 100 | 28 ± 4 | 0.96 ± 0.12 |
| Thr-Lys-Pro-Arg | 4 | 0.5 | 100 | 14 ± 4 | 0.72 ± 0.02 |
| Thr-Lys-Pro-Phe | 2679 | 0.5 | 100 | 13 ± 5 | 0.73 ± 0.09 |
| Thr-Lys-Pro-Arg-Pro | 6 | 0.5 | 100 | 36 ± 6 | 0.99 ± 0.09 |
| Thr-Lys-Pro-Arg-Pro-Phe | 7 | 0.5 | 100 | 26 ± 4 | 0.94 ± 0.14 |
| Positive Control | | 1.0 | 0 | 22 ± 11 | 0.98 + 0.09 |

INDUSTRIAL APPLICABILITY

The invention relates to the field of biochemistry, in particular, to a method for producing peptides exhibiting high activity and capable of stimulating self-healing in the organs where a disturbance occurred. In particular, the invention allows to expand the range of tools for stimulation of sexual function and treatment of sexual dysfunction, while reducing the duration of course therapy and the costs of medications.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09409947B2). An electronic copy of the "Sequence Listing" will also be available from the USPTO upon request and payment of the fee set forth in 37 CFR 1.19(b)(3).

The invention claimed is:

1. A pharmaceutical composition comprising a peptide consisting of formula:

A-Thr-Lys-Pro-B-C-D-X, wherein:
  A is absent, Met, Met(O), Thr, Ala, His, Phe, Lys, Gly;
  B is absent, Gly, Asp, Trp, Gln, Asn, Tyr, Pro, Arg;
  C is absent, Arg, Phe, Tyr, Gly, His, Pro;
  D is absent, Val, Tyr, Trp, Phe, His;
  X is a carboxy terminal OH, OCH$_3$, or NH$_2$ group,
provided that (i) when A is present, at least one of B, C, or D is also present, or when B is present, then C and/or D is also present and (ii) the peptide is not a tetrapeptide and is not Thr-Lys-Pro-X (SEQ ID NO: 5), Phe-Thr-Lys-Pro-Gly-X (SEQ ID NO: 1), Thr-Lys-Pro-Pro-Arg-X (SEQ ID NO: 2), Thr-Thr-Lys-Pro-Arg-X (SEQ ID NO: 607), Lys-Thr-Lys-Pro-Arg-X (SEQ ID NO: 772), Thr-Lys-Pro-Gly-Pro-X (SEQ ID NO: 460), Thr-Lys-Pro-Gly-Arg-X (SEQ ID NO: 456), Thr-Lys-Pro-Arg-Tyr (SEQ ID NO: 494), or Thr-Lys-Pro-Arg-Gly-X (SEQ ID NO: 3), wherein said peptide is present in the composition in an amount effective for stimulating sexual or reproductive function.

2. The pharmaceutical composition of claim 1, wherein said peptide is produced by expression in a recombinant microorganism.

3. The pharmaceutical composition of claim 1, wherein said peptide is produced by chemical synthesis.

4. A pharmaceutical composition comprising a peptide consisting of the formula Thr-Lys-Pro-Arg-Pro-X (SEQ ID NO: 6), wherein X is a carboxy terminal OH, OCH$_3$, or NH$_2$ group, and wherein said peptide is present in the composition in an amount effective for stimulating sexual or reproductive function.

5. The pharmaceutical composition of claim 4, wherein said peptide is produced by expression in a recombinant microorganism.

6. The pharmaceutical composition of claim 4, wherein said peptide is produced by chemical synthesis.

7. A pharmaceutical composition comprising a peptide consisting of the formula Thr-Lys-Pro-Arg-Pro-Phe-X (SEQ ID NO: 7), wherein X is a carboxy terminal OH, OCH$_3$, or NH$_2$ group, and wherein said peptide is present in the composition in an amount effective for stimulating sexual or reproductive function.

8. The pharmaceutical composition of claim 7, wherein said peptide is produced by expression in a recombinant microorganism.

9. The pharmaceutical composition of claim 7, wherein said peptide is produced by chemical synthesis.

10. A pharmaceutical composition comprising a peptide consisting of the formula Thr-Lys-Pro-B-C-X, wherein B is Arg, Gln, or Asn, and C is Pro, Gly, or Phe, wherein X is a carboxy terminal OH, OCH$_3$, or NH$_2$ group, wherein said peptide is not Thr-Lys-Pro-Arg-Gly-X (SEQ ID NO: 3), and wherein said peptide is present in the composition in an amount effective for stimulating sexual or reproductive function.

11. The pharmaceutical composition of claim 10, wherein said peptide is produced by expression in a recombinant microorganism.

12. The pharmaceutical composition of claim 10 wherein said peptide is produced by chemical synthesis.

13. A pharmaceutical composition comprising a peptide consisting of the formula A-Thr-Lys-Pro-B-C-X, wherein:
  A is Met, Thr, Ala, His, Phe, Lys, or Gly;
  B is Arg, Gln, or Asn, and
  C is Pro, Gly, or Phe,
wherein X is a carboxy terminal OH, OCH$_3$, or NH$_2$ group, and wherein said peptide is present in the composition in an amount effective for stimulating sexual or reproductive function.

14. The pharmaceutical composition of claim 13, wherein said peptide is produced by expression in a recombinant microorganism.

15. The pharmaceutical composition of claim 13, wherein said peptide is produced by chemical synthesis.

16. A pharmaceutical composition comprising a peptide consisting of the formula A-Thr-Lys-Pro-B-C-D-X, wherein:
  A is Met, Thr, Ala, His, Phe, Lys, or Gly;
  B is Arg, Gln, or Asn;
  C is Pro, Gly, or Phe, and
  D is Val, Gly, Tyr, Trp, Phe, or His,
wherein X is a carboxy terminal OH, OCH$_3$, or NH$_2$ group, and wherein said peptide is present in the composition in an amount effective for stimulating sexual or reproductive function.

17. The pharmaceutical composition of claim 16, wherein said peptide is produced by expression in a recombinant microorganism.

18. The pharmaceutical composition of claim 16, wherein said peptide is produced by chemical synthesis.

19. A method for stimulating sexual or reproductive function in a mammal in need thereof comprising administering to said mammal the pharmaceutical composition of claim 1.

20. The method of claim 19, wherein the mammal has a reproductive or sexual dysfunction.

21. A method for treating a reproductive or sexual dysfunction in a mammal in need of such treatment comprising administering to said mammal the pharmaceutical composition of claim 1.

22. A method for stimulating sexual or reproductive function in a mammal in need thereof comprising administering to said mammal the pharmaceutical composition of claim 4.

23. The method of claim 22, wherein the mammal has a reproductive or sexual dysfunction.

24. A method for treating a reproductive or sexual dysfunction in a mammal in need of such treatment comprising administering to said mammal the pharmaceutical composition of claim 4.

25. A method for stimulating sexual or reproductive function in a mammal in need thereof comprising administering to said mammal the pharmaceutical composition of claim 7.

26. The method of claim 25, wherein the mammal has a reproductive or sexual dysfunction.

27. A method for treating a reproductive or sexual dysfunction in a mammal in need of such treatment comprising administering to said mammal the pharmaceutical composition of claim 7.

28. A method for stimulating sexual or reproductive function in a mammal in need thereof comprising administering to said mammal the pharmaceutical composition of claim 10.

29. The method of claim 28, wherein the mammal has a reproductive or sexual dysfunction.

30. A method for treating a reproductive or sexual dysfunction in a mammal in need of such treatment comprising administering to said mammal the pharmaceutical composition of claim 10.

31. A method for stimulating sexual or reproductive function in a mammal in need thereof comprising administering to said mammal the pharmaceutical composition of claim 13.

32. The method of claim 31, wherein the mammal has a reproductive or sexual dysfunction.

33. A method for treating a reproductive or sexual dysfunction in a mammal in need of such treatment comprising administering to said mammal the pharmaceutical composition of claim 13.

34. A method for stimulating sexual or reproductive function in a mammal in need thereof comprising administering to said mammal the pharmaceutical composition of claim 16.

35. The method of claim 34, wherein the mammal has a reproductive or sexual dysfunction.

36. A method for treating a reproductive or sexual dysfunction in a mammal in need of such treatment comprising administering to said mammal the pharmaceutical composition of claim 16.

* * * * *